US011471462B2

(12) United States Patent
Hoch et al.

(10) Patent No.: US 11,471,462 B2
(45) Date of Patent: Oct. 18, 2022

(54) COMPOSITIONS AND METHODS FOR DETECTING AND TREATING DIABETES

(71) Applicants: THE BROAD INSTITUTE, INC., Cambridge, MA (US); PRESIDENT AND FELLOWS OF HARVARD COLLEGE, Cambridge, MA (US); INSTITUTO CARLOS SLIM DE LA SALUD, A.C., Mexico City (MX)

(72) Inventors: Eitan Hoch, Cambridge, MA (US); Suzanne Beth Rosenberg Jacobs, Cambridge, MA (US); Victor Rusu, Cambridge, MA (US); Liping Zhao, Cambridge, MA (US); Jose M. Mercader Bigas, Cambridge, MA (US)

(73) Assignees: THE BROAD INSTITUTE, INC., Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 16/312,775

(22) PCT Filed: Jun. 27, 2017

(86) PCT No.: PCT/US2017/039431
§ 371 (c)(1),
(2) Date: Dec. 21, 2018

(87) PCT Pub. No.: WO2018/005445
PCT Pub. Date: Jan. 4, 2018

(65) Prior Publication Data
US 2019/0350938 A1 Nov. 21, 2019

Related U.S. Application Data

(60) Provisional application No. 62/355,190, filed on Jun. 27, 2016, provisional application No. 62/458,832, filed on Feb. 14, 2017.

(51) Int. Cl.
*A61K 31/5377* (2006.01)
*A61K 31/4436* (2006.01)
(Continued)

(52) U.S. Cl.
CPC ...... *A61K 31/5377* (2013.01); *A61K 31/4436* (2013.01); *A61K 38/177* (2013.01); *G01N 33/6803* (2013.01)

(58) Field of Classification Search
CPC ............ A61K 31/5377; A61K 31/4436; A61K 31/436
See application file for complete search history.

(56) References Cited

U.S. PATENT DOCUMENTS 6,306,663 B1 10/2001 Kenten et al.
2012/0015841 A1 1/2012 Shekdar et al.
(Continued)

FOREIGN PATENT DOCUMENTS

WO 2014176281 A1 10/2014
WO 2015089486 A2 6/2015
WO 2015179436 A1 11/2015

OTHER PUBLICATIONS

Hara et al., "Genetic architecture of type 2 diabetes," Biochemical and Biophysical Research Communications, Elsevier, Amsterdam, NL, Aug. 8, 2014; vol. 452, No. 2, pp. 213-220 (8 pages).
(Continued)

*Primary Examiner* — San Ming R Hui
(74) *Attorney, Agent, or Firm* — Melissa Hunter-Ensor; Leslie Serunian; Greenberg Traurig, LLP

(57) ABSTRACT

The invention features compositions and methods that are useful for increasing the level or activity of SLC16A11 in a subject, there by treating or preventing type 2 diabetes in the subject.

36 Claims, 94 Drawing Sheets

Specification includes a Sequence Listing.

(51) Int. Cl.
*A61K 38/17* (2006.01)
*G01N 33/68* (2006.01)

(56) References Cited

U.S. PATENT DOCUMENTS

| | | |
|---|---|---|
| 2014/0194388 A1 | 7/2014 | Proia et al. |
| 2014/0242088 A1 | 8/2014 | Garcia-Echeverria et al. |
| 2014/0335091 A1 | 11/2014 | Forgie et al. |
| 2015/0176027 A1 | 6/2015 | Gao et al. |
| 2016/0010076 A1 | 1/2016 | Joung et al. |

OTHER PUBLICATIONS

Partial European Search Report, dated Feb. 13, 2020, in corresponding European Patent Application No. 17821057.1 (19 pages).
Hara et al., "Genome-Wide Association Study Identifies Three Novel Loci for Type 2 Diabetes," Human Molecular Genetics, Aug. 14, 2013, vol. 23, No. 1, pp. 239-246.
Scheuner et al., "The Unfolded Protein Response: A Pathway That Links Insulin Demand with β-Cell Failure and Diabetes," Endocrine Reviews, May 1, 2008, vol. 29, Issue 3, pp. 317-333.
Tooley et al., "New Roles for Old Modifications: Emerging Roles of N-Terminal Post-Translational Modifications in Development and Disease," Protein Science, Sep. 26, 2014, vol. 23, Issue 12, pp. 1641-1649.
The SIGMA Type 2 Diabetes Consortium, "Sequence Variants in SLC16A11 are a Common Risk Factor for Type 2 Diabetes in Mexico," Nature, Dec. 25, 2013, vol. 506, No. 7486, pp. 97-101.
Newman et al., "Ketone Bodies as Signaling Metabolites," Trends in Endocrinology & Metabolism, Oct. 18, 2013, vol. 25, No. 1 pp. 42-52.
International Search Report and Written Opinion for corresponding PCT/US2017/039431, dated Sep. 7, 2017 (28 pages).
Extended European Search Report, dated Jun. 25, 2020, issued in corresponding European Patent Application No. 17821057.1 (15 pages).
Ciechanover, Aaron, "N-Terminal Ubiquitination," Methods in Molecular Biology, Ubiquitin-Proteasome Protocols, 2005, vol. 301, pp. 255-270 (16 pages).
Estrada et al., "Association of a Low-Frequency Variant in HNF1A With Type 2 Diabetes in a Latino Population," Journal of the American Medical Association (JAMA Network), Jun. 11, 2014, vol. 311, No. 22, pp. 2305-2314 (10 pages).
Halestrap et al., "The SLC16 gene family—from monocarboxylate transporters (MCTs) to aromatic amino acid transporters and beyond," Pflügers Archiv—European Journal of Physiology, Feb. 2004, vol. 447, Iss. 5, pp. 619-628 (10 pages).
Halestrap, Andrew P., "The SLC16 gene family—structure, role and regulation in health and disease," Molecular Aspects of Medicine, 2013, vol. 34, No. 2-3, pp. 337-349 (13 pages).
Hilton et al., "Epigenome editing by a CRISPR-Cas9-based acetyltransferase activates genes from promoters and enhancers," Nature Biotechnology, May 2015, vol. 33, No. 5, pp. 510-517 (10 pages).
Hugo et al., "A monocarboxylate transporter required for hepatocyte secretion of ketone bodies during fasting," Genes & Development, 2012, vol. 26, pp. 282-293 (13 pages).
Konermann et al., "Genome-scale transcriptional activation by an engineered CRISPR-Cas9 complex," Nature, Jan. 29, 2015, vol. 517, pp. 583-588 (18 pages).
Maurano et al., "Systematic Localization of Common Disease-Associated Variation in Regulatory DNA," Science, Sep. 7, 2012, vol. 337, No. 6099, pp. 1190-1195 (15 pages).
Muoio et al., "Molecular and metabolic mechanisms of insulin resistance and β-cell failure in type 2 diabetes," Nature Reviews Molecular Cell Biology, 2008, vol. 9, No. 3, pp. 193-205 (13 pages).
Ng et al., "Meta-Analysis of Genome-Wide Association Studies in African Americans Provides Insights into the Genetic Architecture of Type 2 Diabetes," PLoS Genetics, Aug. 2014, vol. 10, Iss. 8, e1004517 (14 pages).
Perry et al., "The role of hepatic lipids in hepatic insulin resistance and type 2 diabetes," Nature, Jun. 5, 2014, vol. 510, No. 7503, pp. 84-91 (22 pages).
Pochini et al., "Membrane transporters for the special amino acid glutamine: structure/funotion relationships and relevance to human health," Frontiers in Chemistry, Aug. 11, 2014, vol. 2, Article 61, pp. 1-23 (23 pages).
Rink et al., "Cytoplasmic pH and Free Mg2+ in Lymphocytes," The Journal of Cell Biology, 1982, vol. 95, pp. 189-196 (8 pages).
Rychlewski et al., "Comparison of sequences profiles. Strategies for structural predictions using sequence information," Protein Science, 2000, vol. 9, pp. 232-241 (10 pages).
Sali et al., "Comparative Protein Modelling by Satisfaction of Spatial Restraints," Journal of Molecular Biology, 1993, vol. 234, pp. 779-815 (37 pages).
Sanjana et al., "Improved vectors and genome-wide libraries for CRISPR screening," Nature Methods, Aug. 2014, vol. 11, No. 8, pp. 783-784 (5 pages).
Shalem et al., "Genome-Scale CRISPR-Cas9 Knockout Screening in Human Cells," Science, Jan. 3, 2014, vol. 343, No. 6166, pp. 84-87 (10 pages).
SIGMA Type 2 Diabetes Consortium, "Sequence variants in SLC16A11 are a common risk factor for type 2 diabetes in Mexico," Nature, Feb. 6, 2014, vol. 506, No. 7486, pp. 97-101 (25 pages).
Traurig et al., "Analysis of SLC16A11 Variants in 12,811 American Indians: Genotype-Obesity Interaction for Type 2 Diabetes and an Association with RNASEK Expression," Diabetes, Feb. 2016, vol. 65, pp. 510-519 (10 pages).
Von Grotthuss et al., "Application of 3D-Jury, GRDB, and Verify3D in Fold Recognition," Proteins: Structure, Function, and Genetics, 2003, vol. 53, Suppl. 6, pp. 418-423 (6 pages).
Zhang et al., "A Simple Statistical Parameter for Use in Evaluation and Validation of High Throughput Screening Assays," Journal of Biomolecular Screening, 1999, vol. 4, No. 2, pp. 67-73 (7 pages).
Examination Report dated Jul. 8, 2021 in corresponding European Patent Application No. 17821057.1 (12 pages).

FIG. 1A
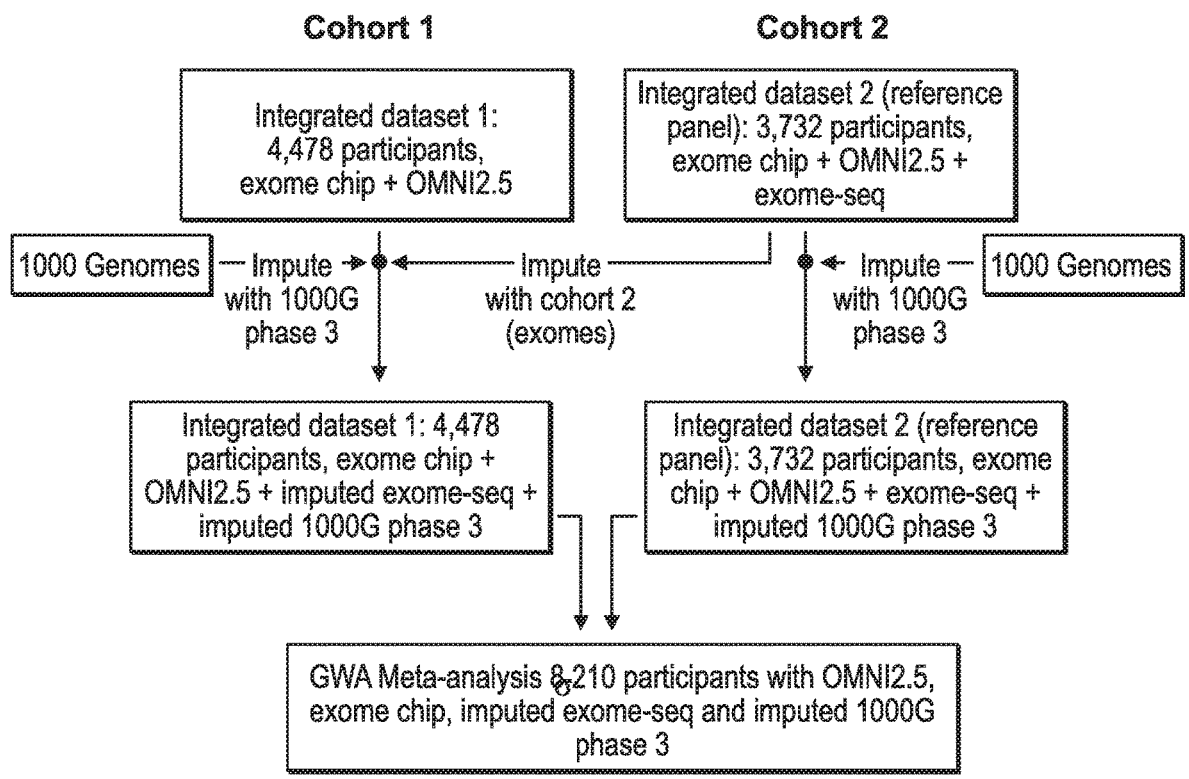
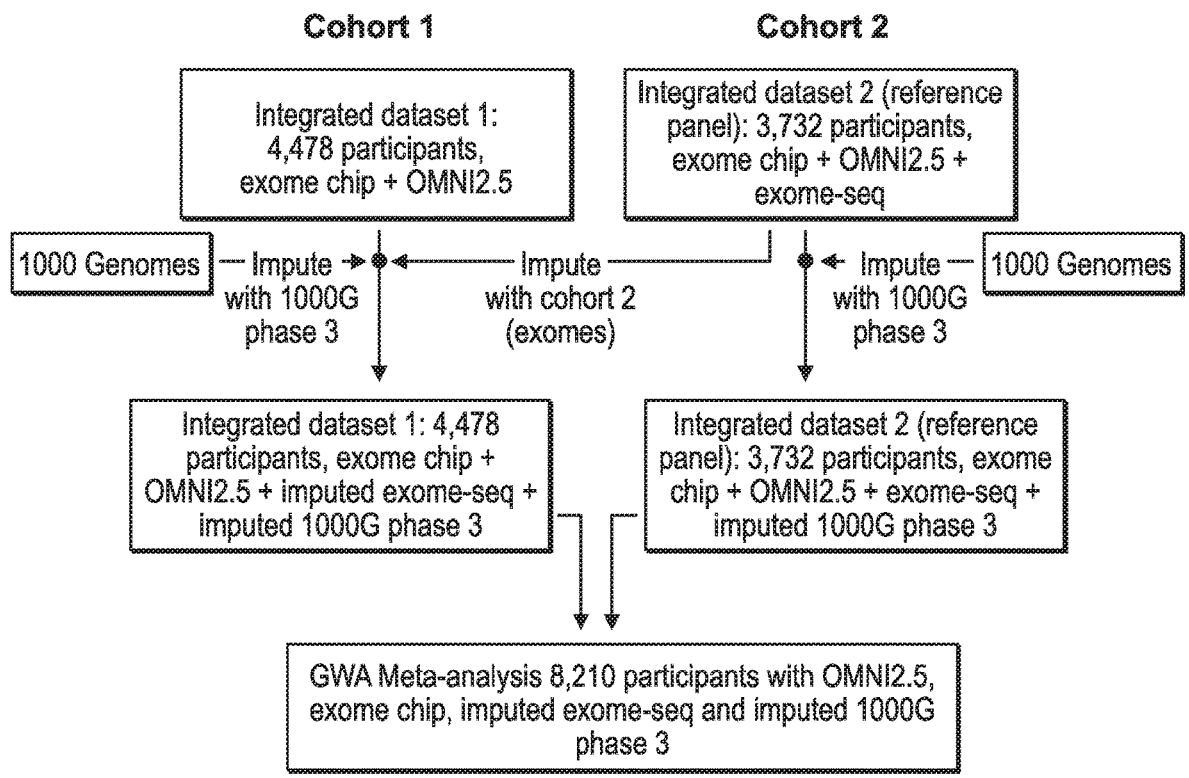

FIG. 2A-1 (top panel)
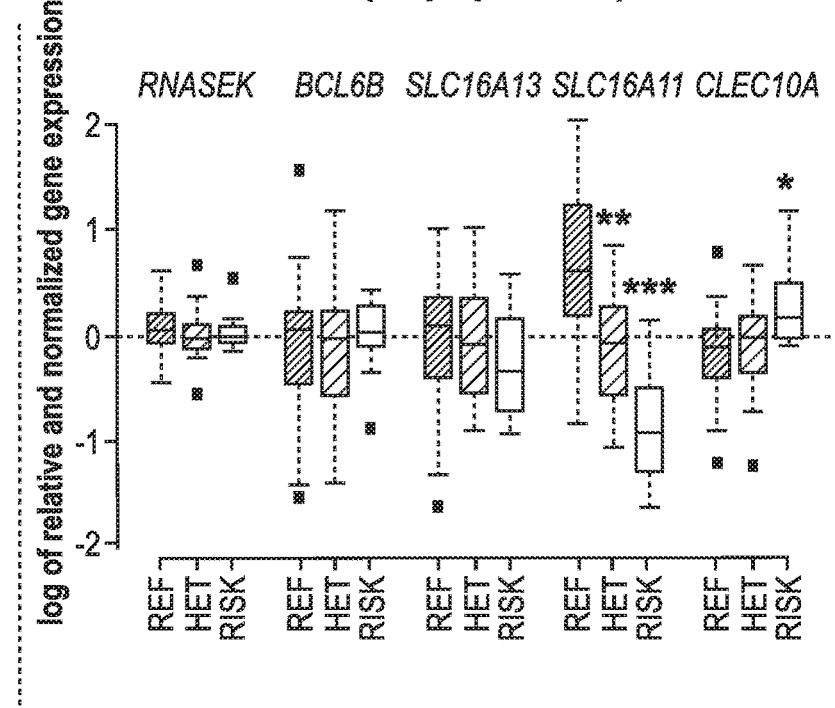
FIG. 2A-2 (bottom panel)
Liver eQTL analysis - 2nd probe
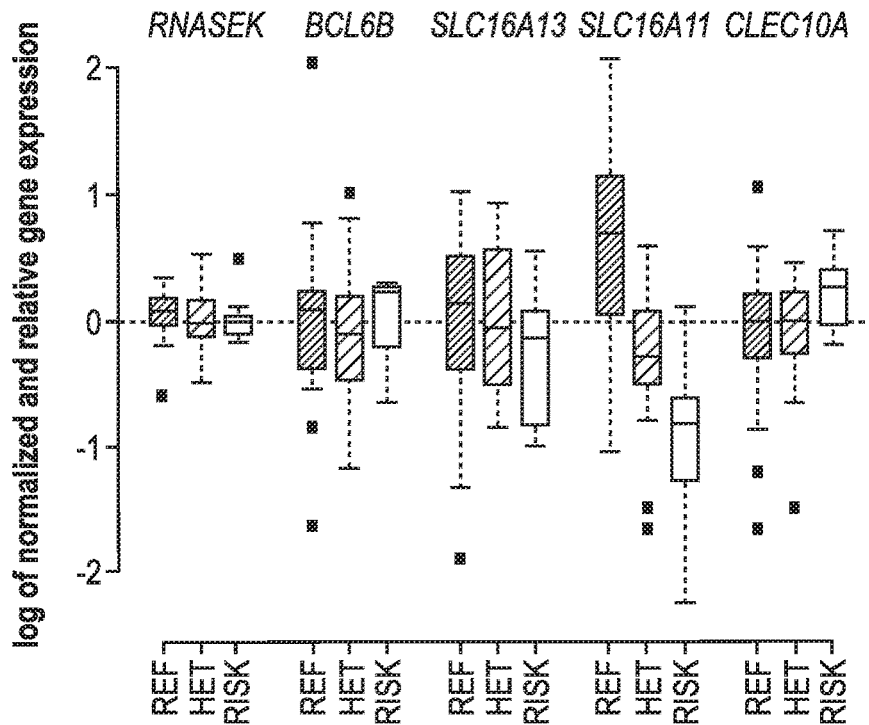

FIG. 2B-1 (top panel)
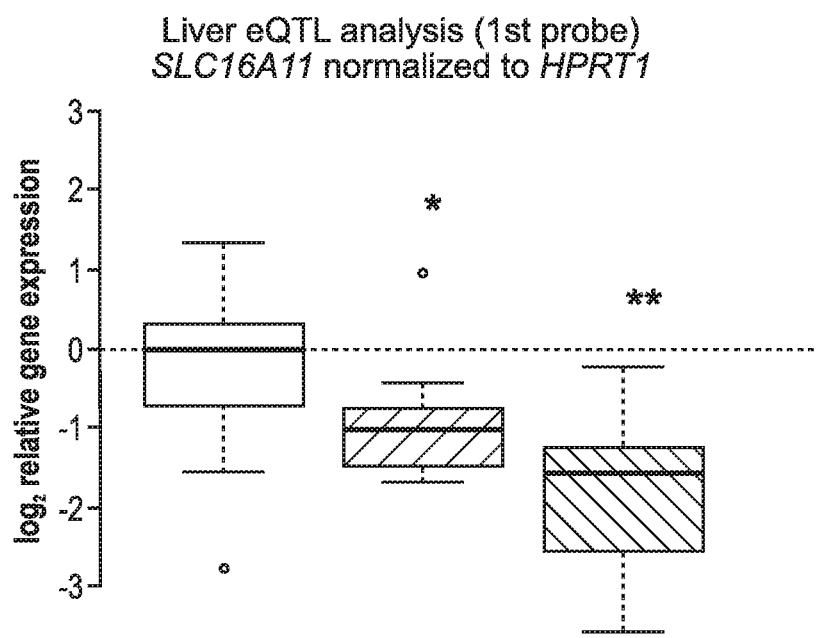
FIG. 2B-2 (bottom panel)
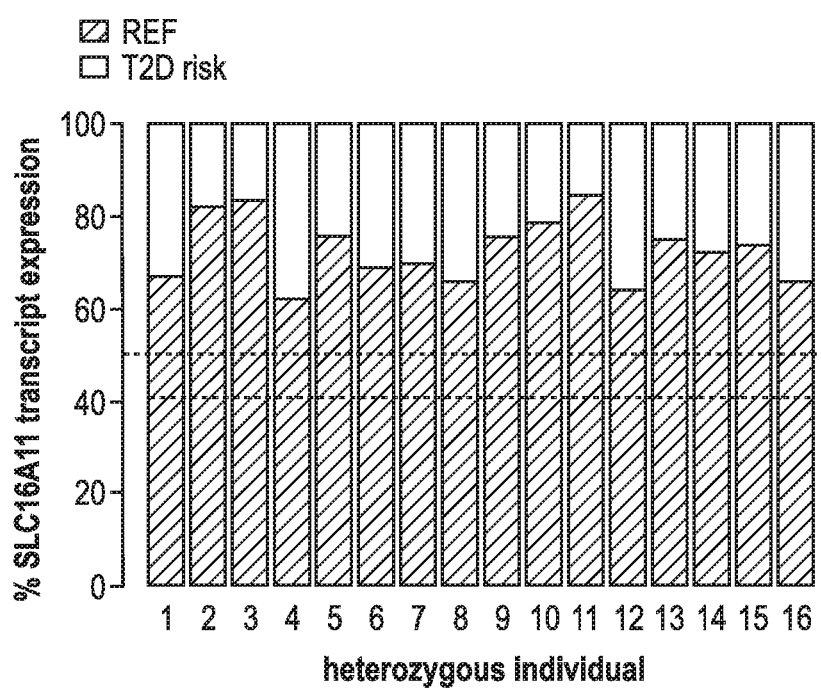

FIG. 2C-1 (top panel)
Visceral Adipose eQTL analysis
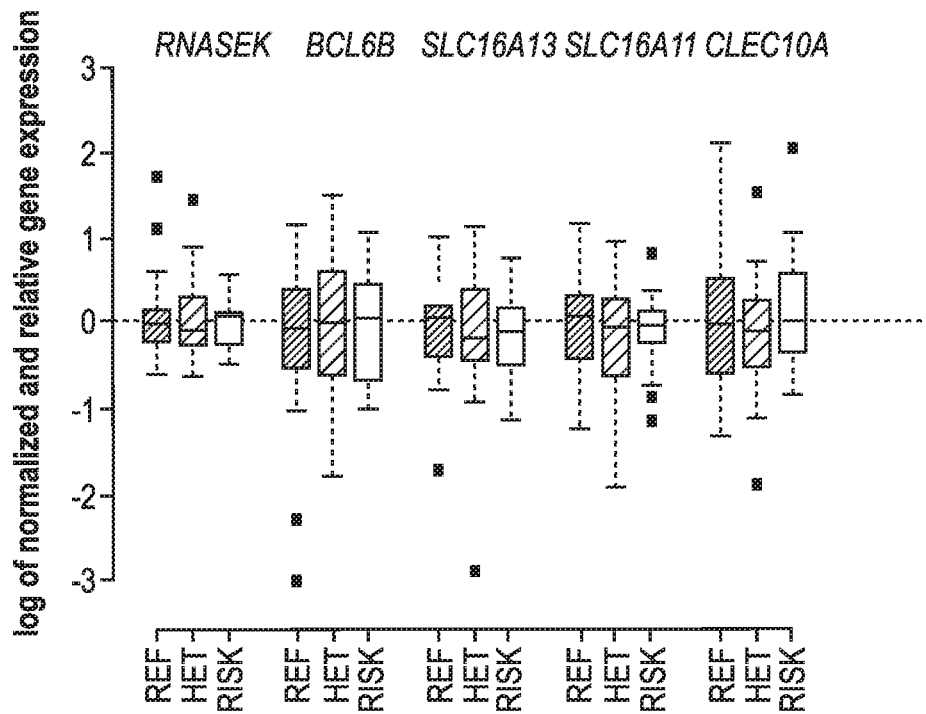
FIG. 2C-2 (bottom panel)
liver
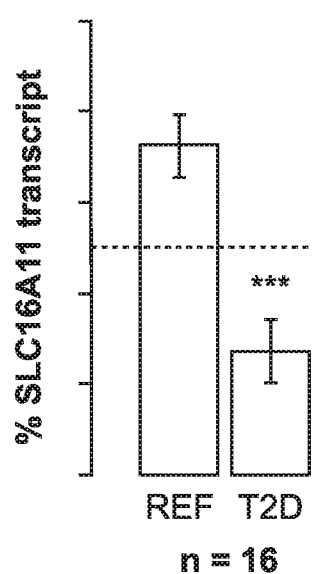

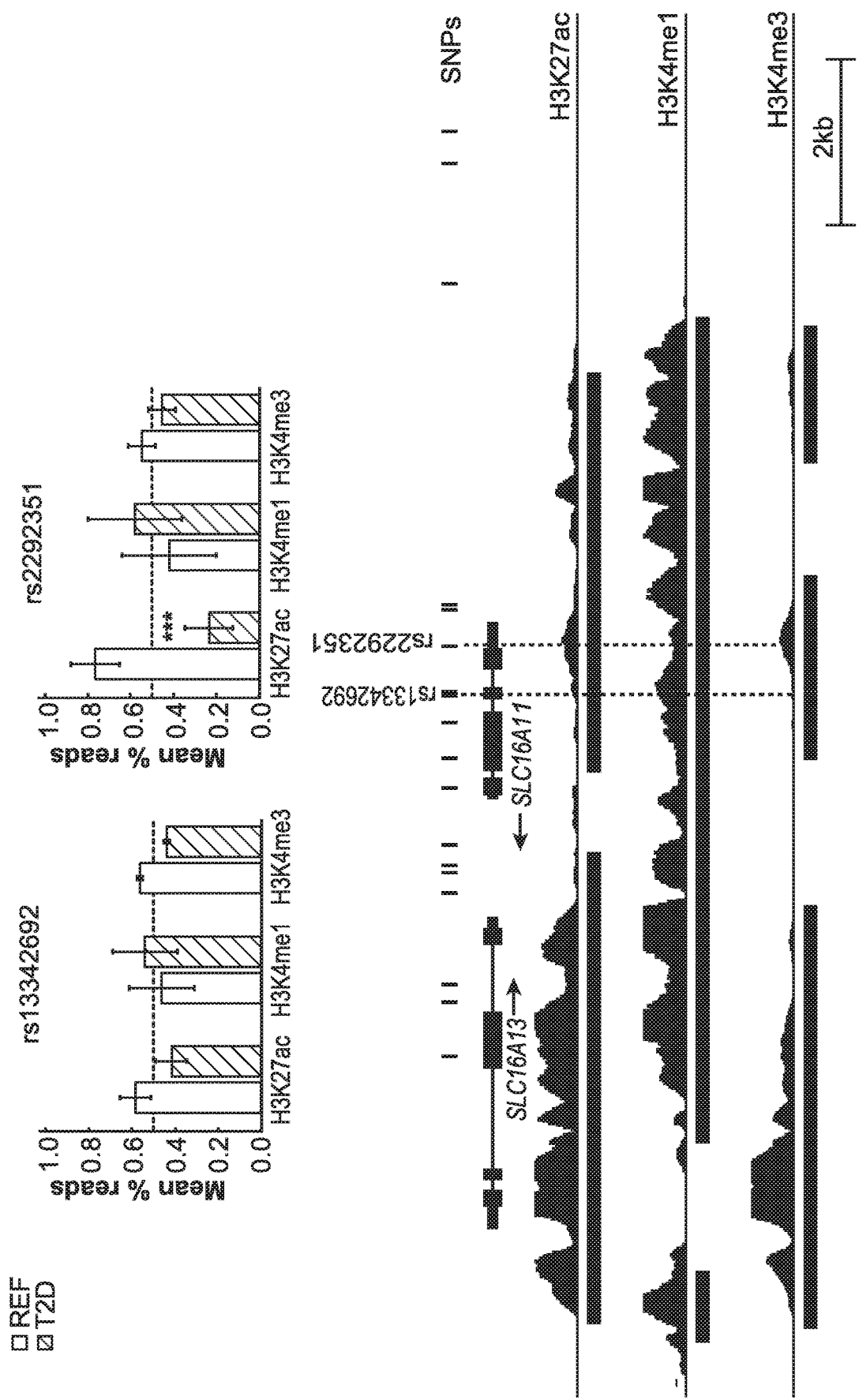
FIG. 2E-1 (top panel)

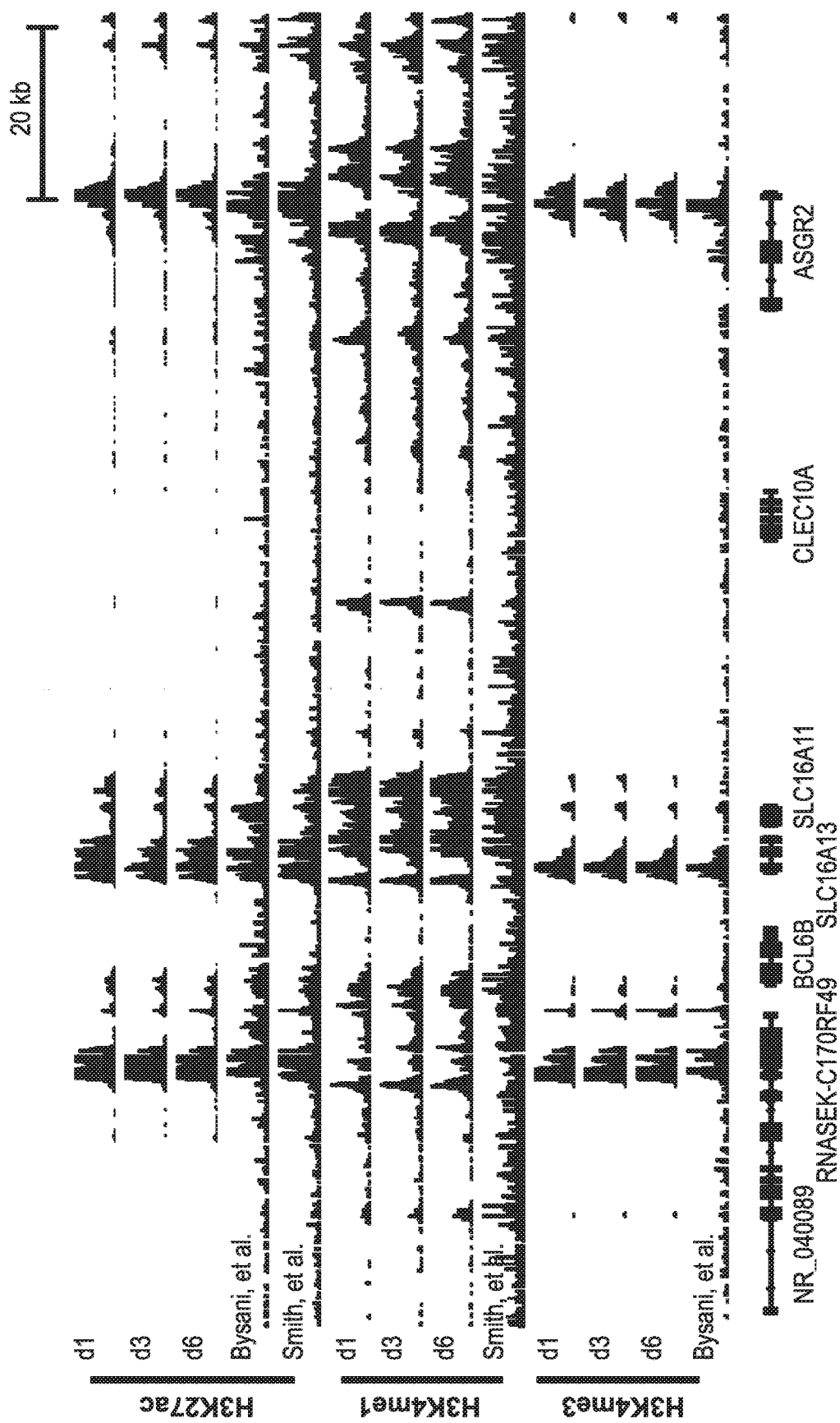
FIG. 2E-2 (bottom panel)

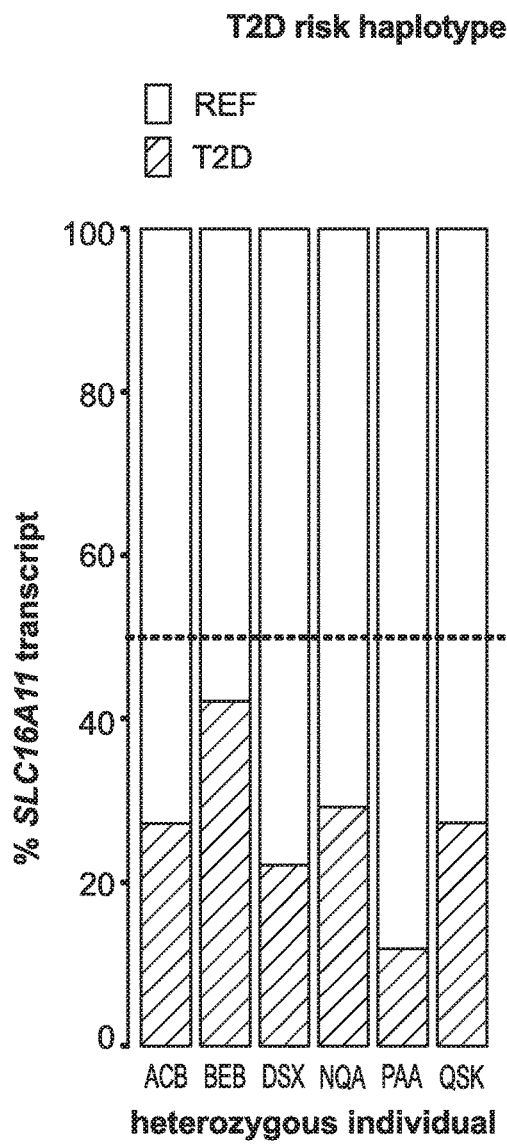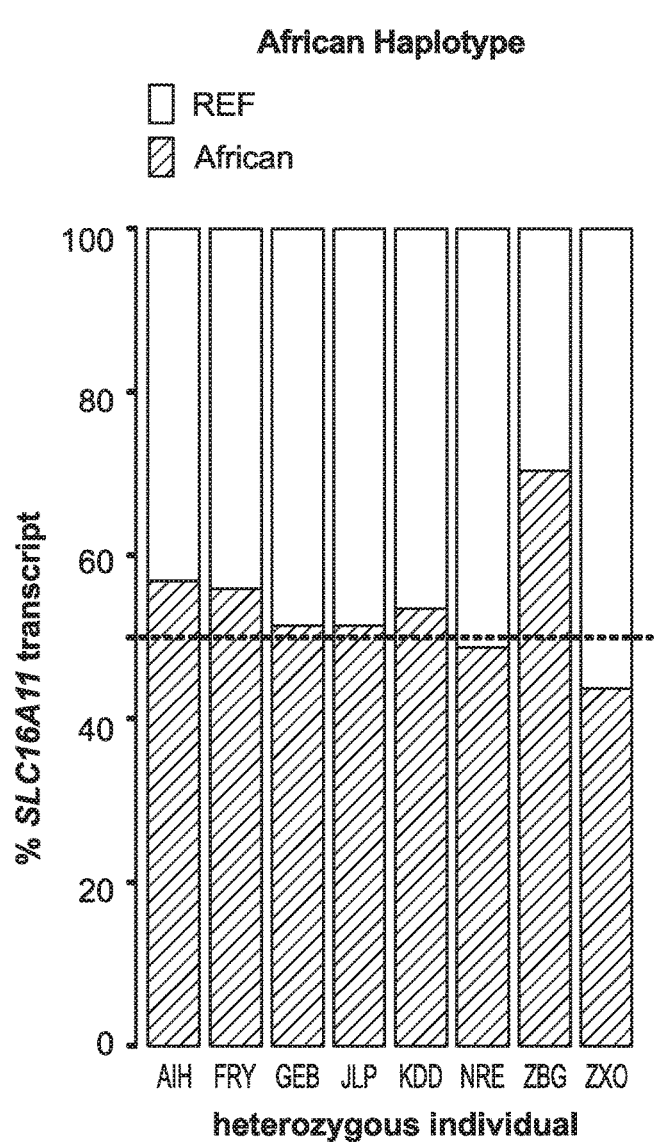

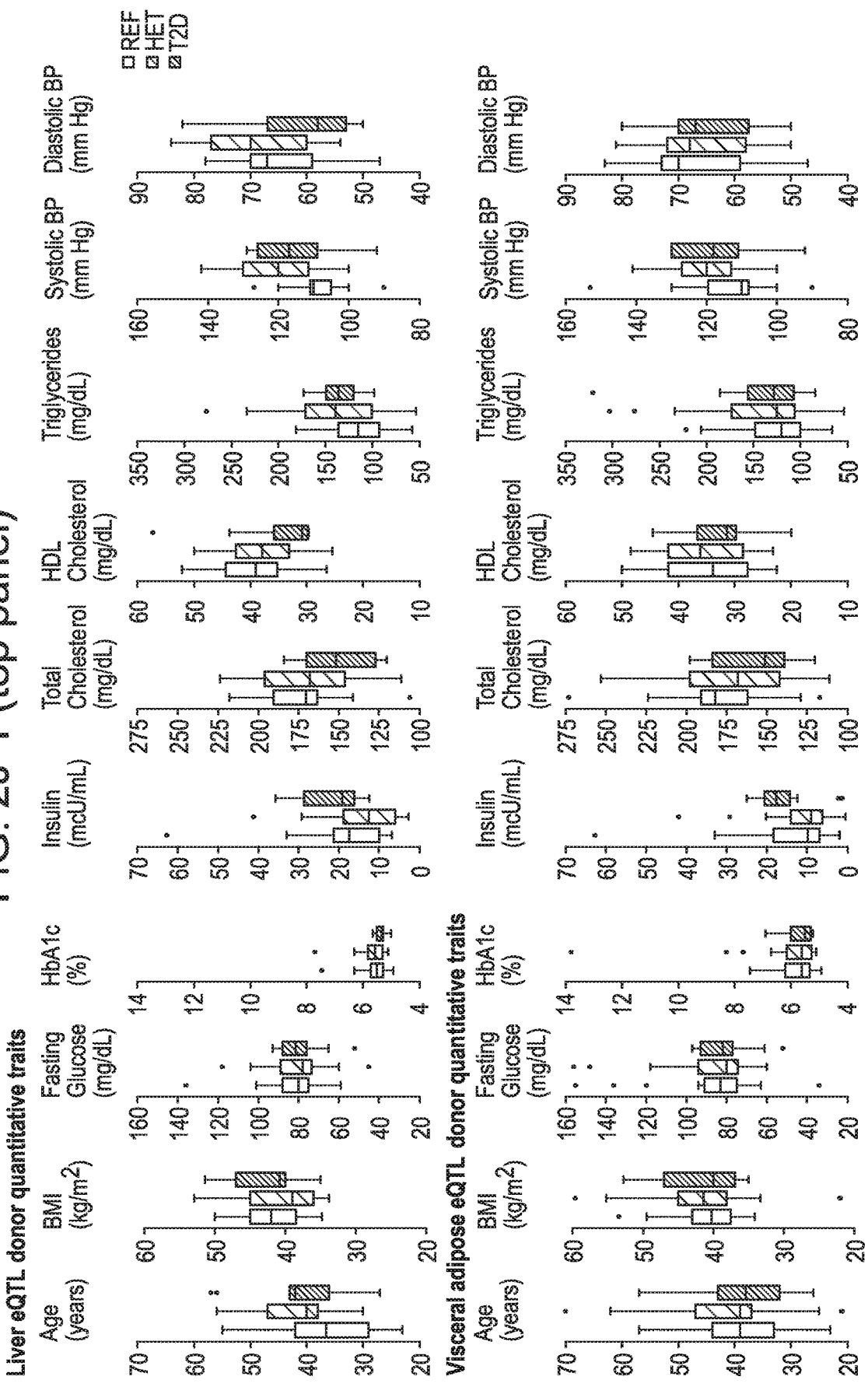
FIG. 2J-1 (top panel)

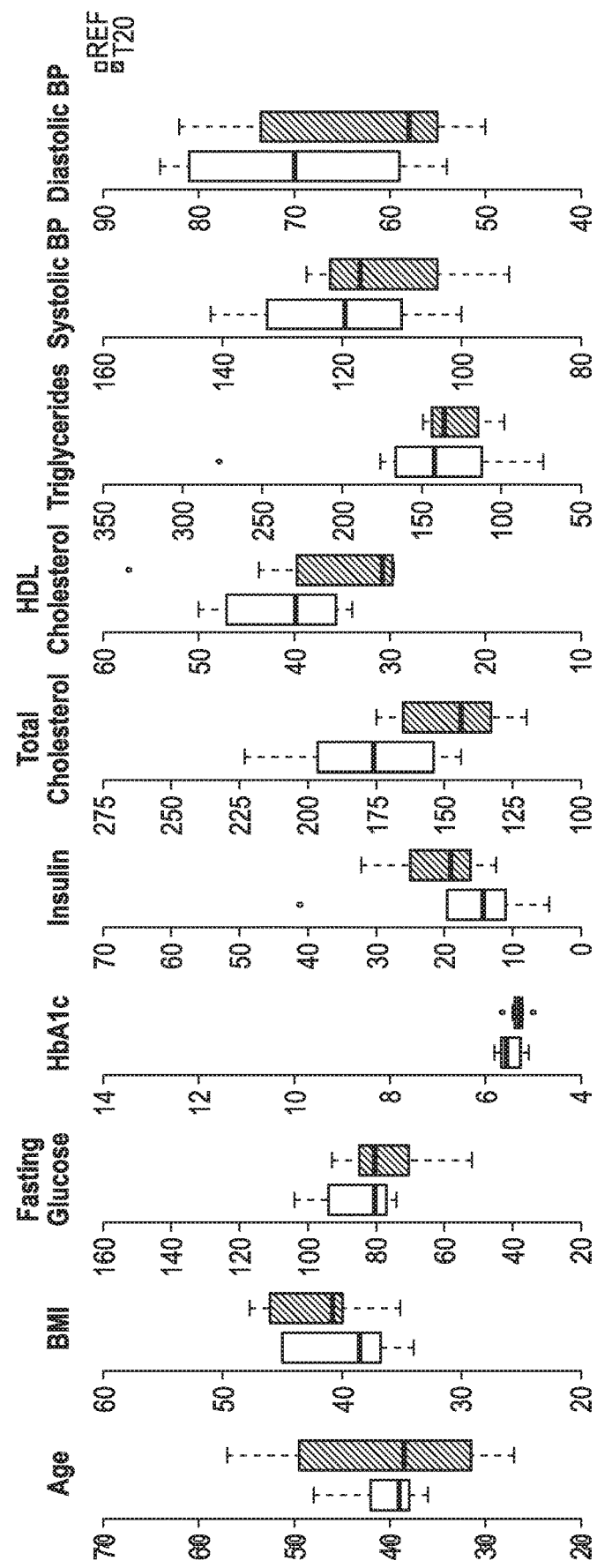
FIG. 2J-2 (bottom panel)

FIG. 3A-1 (top panel)

| | TMD 1 | TMD 8 |
|---|---|---|
| Category I | | |
| SLC16A11 | PPDGGWVVAAAAFAINGLSYGLLRSLGLAFPDL | VVAVAAMGDAGARLVCGWLADQGW |
| SLC16A1  | PPDGGWAVVIGAFISIGFSYAFPKSITVFFKEI | LLSILAFVDMVARPSMGLVANTKP |
| SLC16A3  | APDGGWNAVLFGCFVITGFSYAFPKAVSVFFKEL | LLTILGFIDIFARPAAGFVAGLGK |
| SLC16A7  | PPDGGWIVVGAAFISIGFSYAFPKAVTVFFKEI | LLSVMAFVDMFARPSVGLIANSKY |
| SLC16A8  | PPDGGWVLGACFVVTGFAYGFPKAVSVFFRAL | LLSIVGFVDIVARPACCGALAGLAR |
| Category III | | |
| SLC16A2  | PPEGGFGWVVFAATWCNGSIFGIHNSVGILYSML | LLVCIGATSGLGRLVSGHISDSIP |
| SLC16A10 | PPEGGWLVMLAAMWCNGSVFGIQNACGVLFVSM | VLMCIGVTSGVGRLLFGRIADYVP |
| SLC16A13 | PPDGGWNVVVLSAFFQSALVFGVLRSFGVFFVEF | LLSVVAISDLVGRVVSGWLGDAVP |
| SLC16A6  | VPDGGWAVVSFFFVEVFTYGIIKTFGVFFENDL | LLSTMAIAEVFGRIGAGFVLNREP |
| SLC16A12 | PPDGGWMIVAGCFLVTICTRAVTRCISIFFVEF | LMSILGVIDIGNITFGWLTDRRC |
| SLC16A4  | TLDGGWMIVIHFFLVNVFVMGMTKTFAIFFVVE | LVSVAGILETVSQIISGWVADQNW |
| SLC16A5  | RADGSWAWVLLATMVTQGLTLGFPTCIGIFFTEL | LISIIGFSNIFLRPLAGLMAGRPA |
| SLC16A9  | SPDGGWGWVIVFVSFLTQFLCYGSPLAVGVLIEW | LISIIGIMTAVGKLLLGILADFKW |
| SLC16A14 | NIDGGWAWMMVLSSFFVHILIMGSQMALGVLNVEW | LTSIIAIVHIFGKVILGVIADLPC |

FIG. 3A-2 (bottom panel)

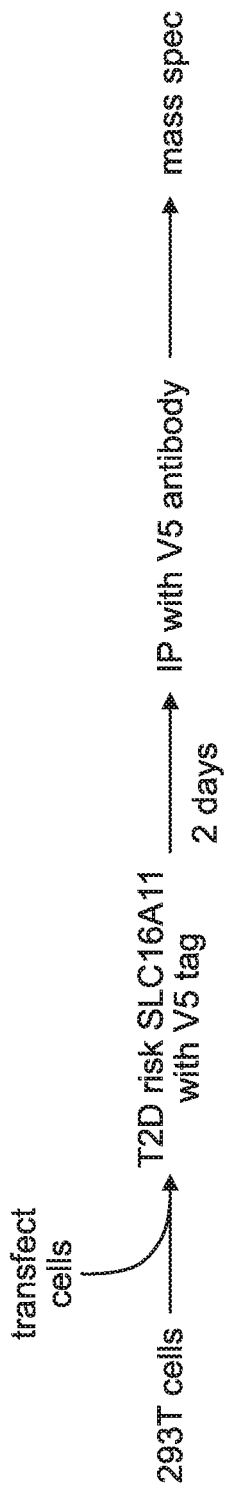

293T cells → transfect cells → T2D risk SLC16A11 with V5 tag → 2 days → IP with V5 antibody → mass spec

| 1 | MPAPQRKHRR | GGFSHRCFPT | PQTAMTPQPA | GPPDGGWGWV | VAAAAFAING | LSYGLLRSLG | LAFPDLAEHF | DRSAQDTAWI | 80 |
|---|---|---|---|---|---|---|---|---|---|
| 81 | SALALAVQQA | ASPVGSALST | RWGARPVVMV | GGILASLGFV | FSAFASGLLH | LYLGLGLLAG | FGWALVFAPA | LGTLSRYFSR | 160 |
| 161 | RRVLAVGLAL | TGNGASSLLL | APALQLLLDT | FGWRGALLLL | GAITLHLTPC | GALLLPLVLP | GDPPAPPRSP | LAALGLSLFT | 240 |
| 241 | RRAFSIFALG | TALVGGGYFV | PYVHLAPHAL | DRGLGGYGAA | LVVAVAAMGD | AGARLVCGWL | ADQGWVPLPR | LLAVFGALTG | 320 |
| 321 | LGLWVVGLVP | VVGGEESWGS | PLLAAAVAYG | LSAGSYAPLV | FGVLPGLVGV | GGVVQATGLV | MMLMSLGGLL | GPPLSGFLRD | 400 |
| 401 | ETGDFTASFL | LSGSLILSGS | FIYIGLPRAL | PSCGPASPPA | TPTPETGELL | PAPQAVLLSP | GGPGSTLDTT | CLPTFLYKVV | 480 |
| 481 | GKPIPNPLLG | LDST | | | | | | | 494 |

The matched peptides cover 78% (390/494 amino acids) of the tagged protein.

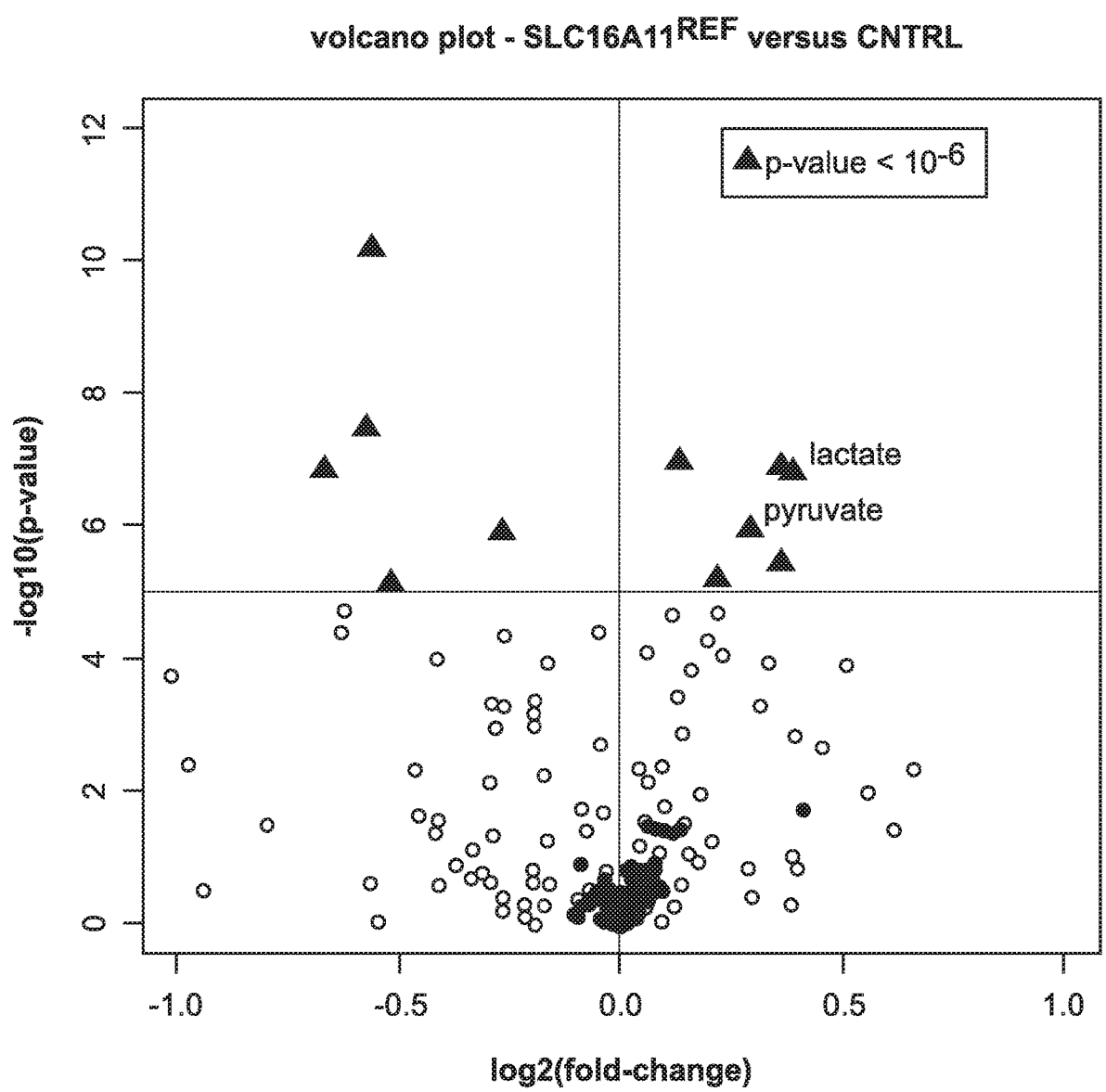

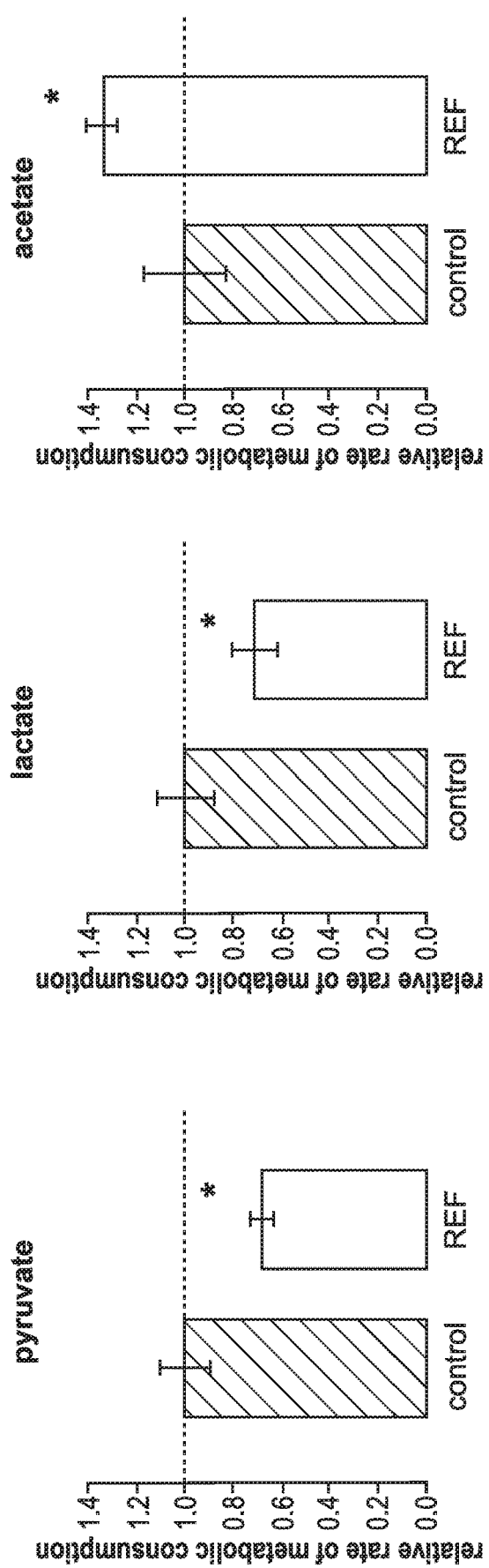

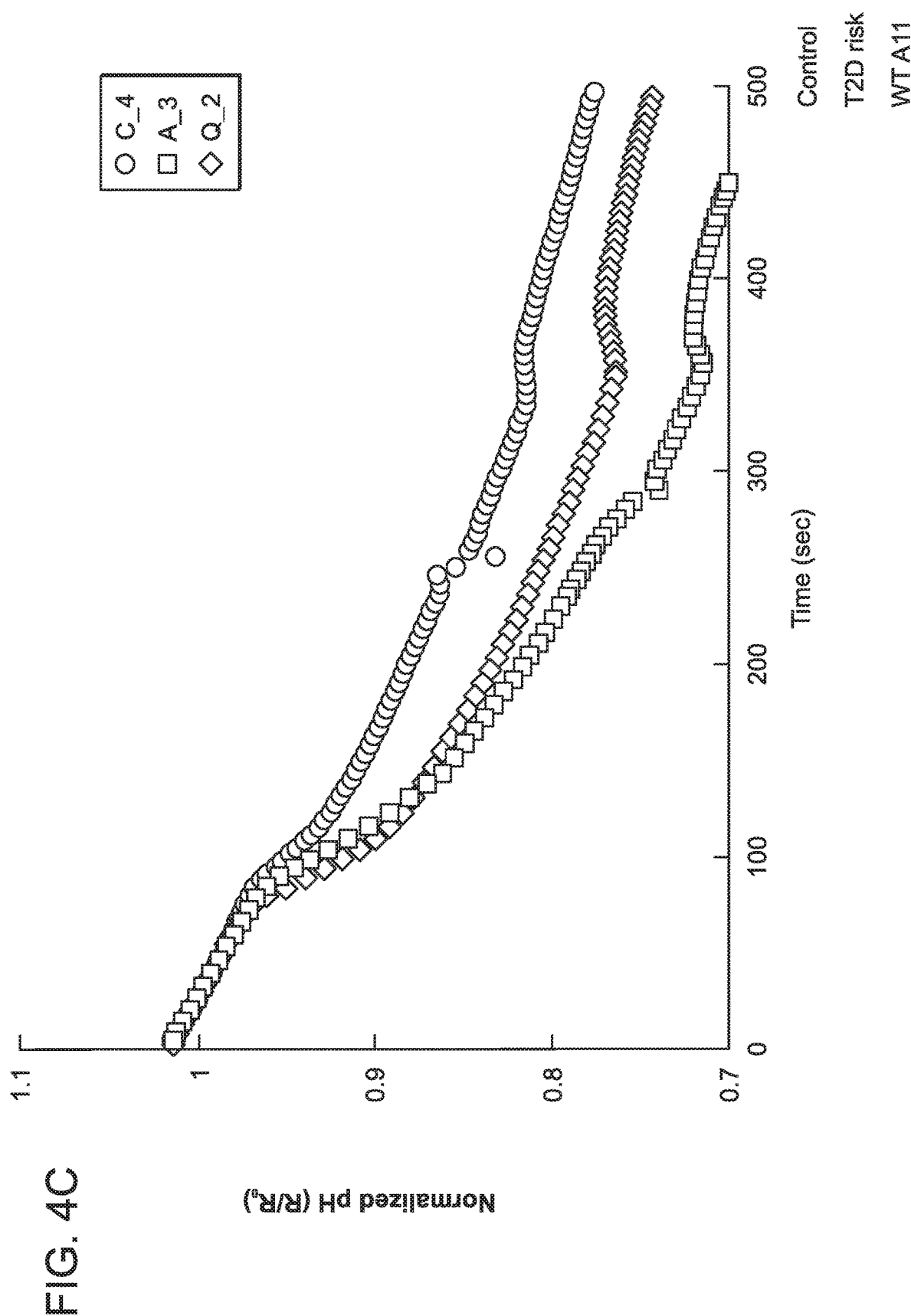

FIG. 4D (top panel)
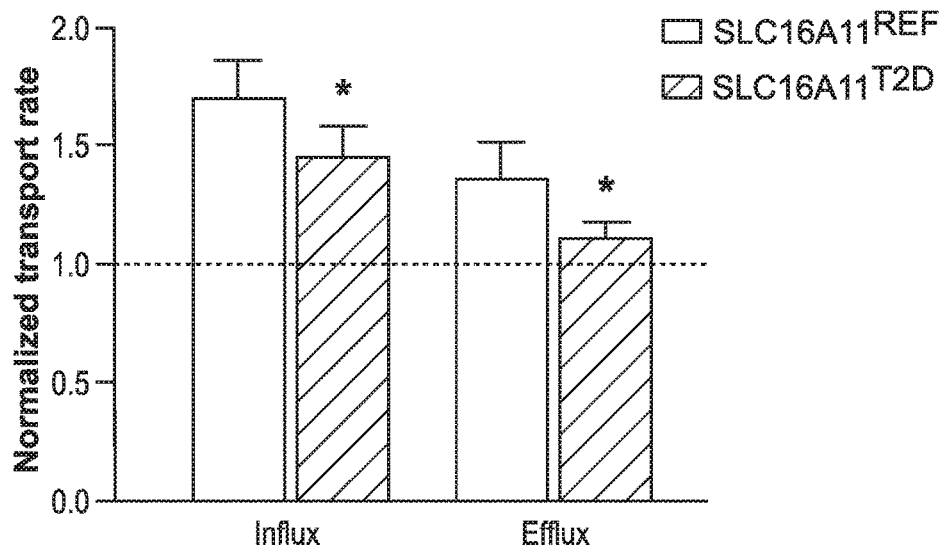
FIG. 4D (bottom panel)
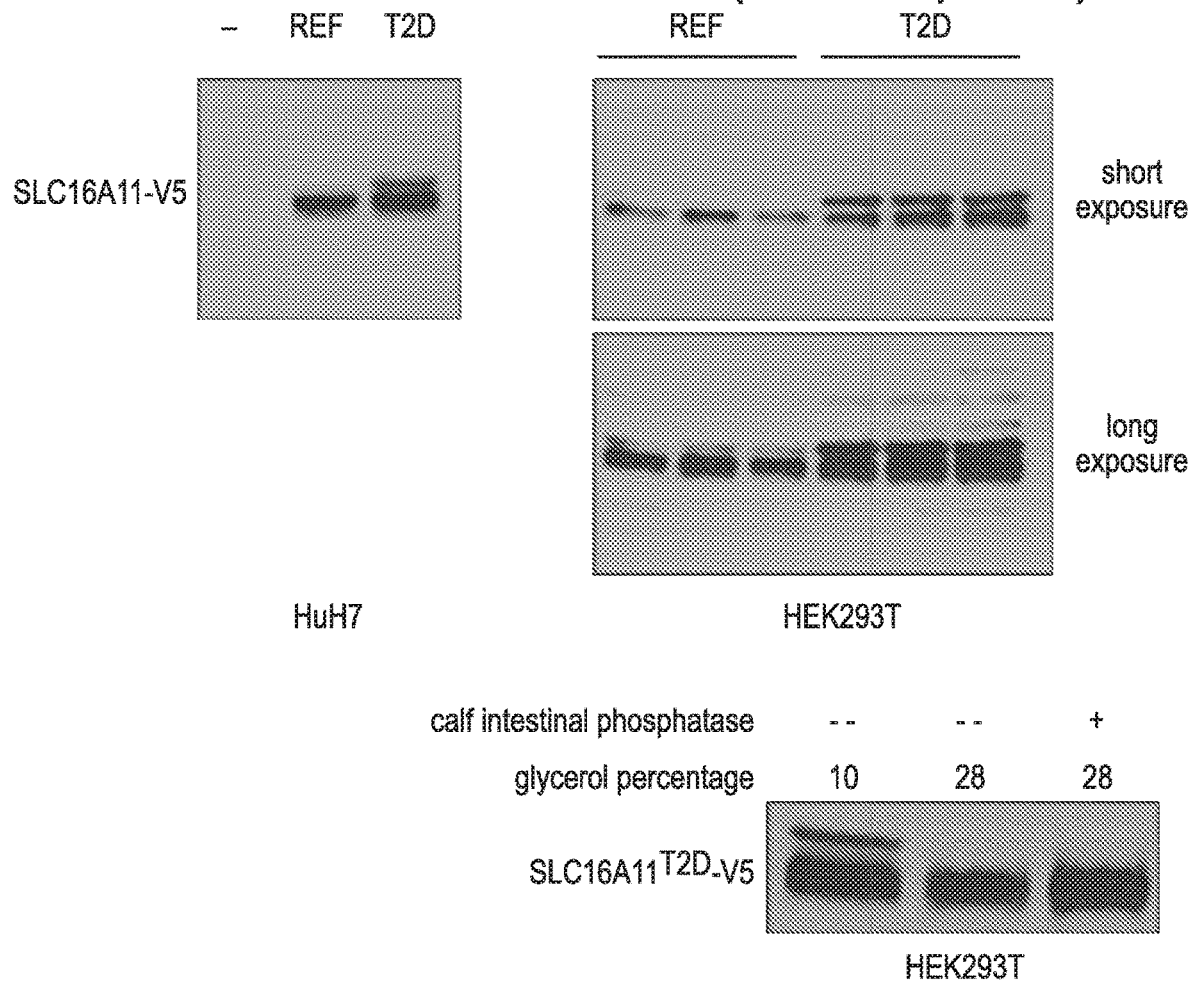

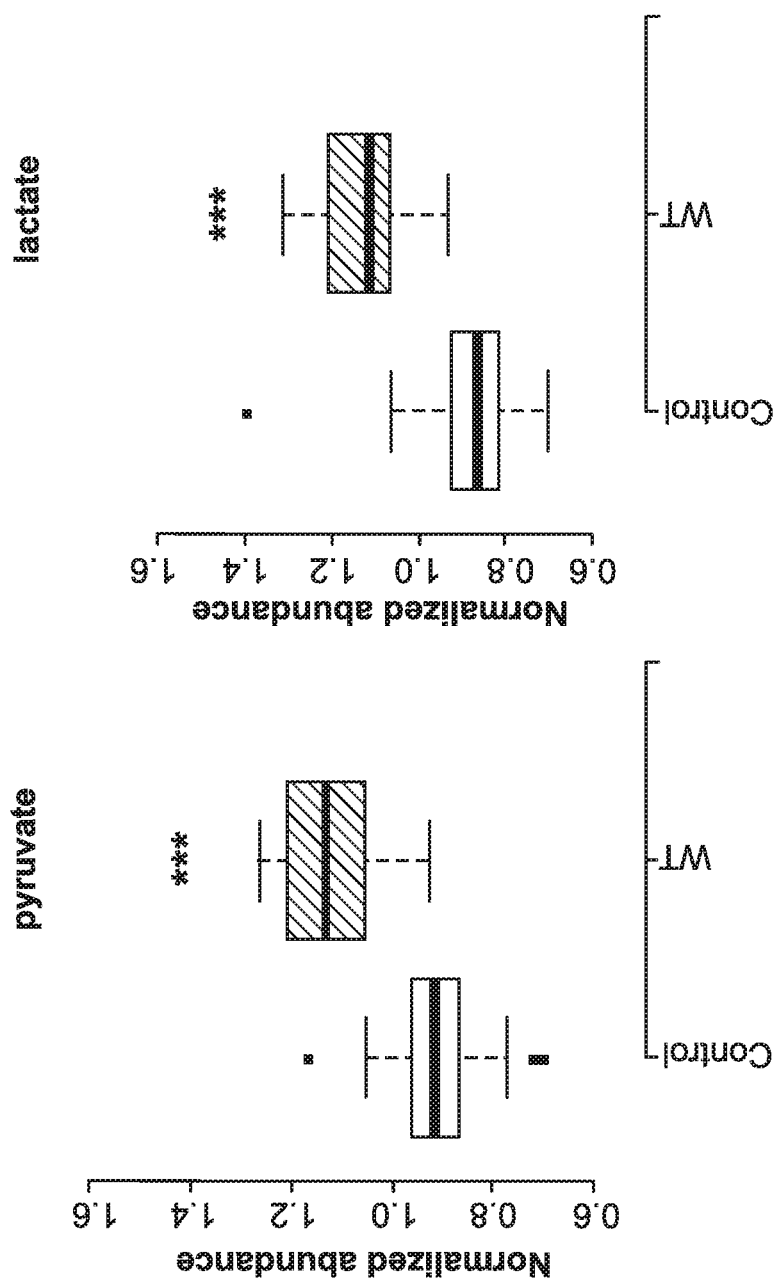

FIG. 5A (top panel)
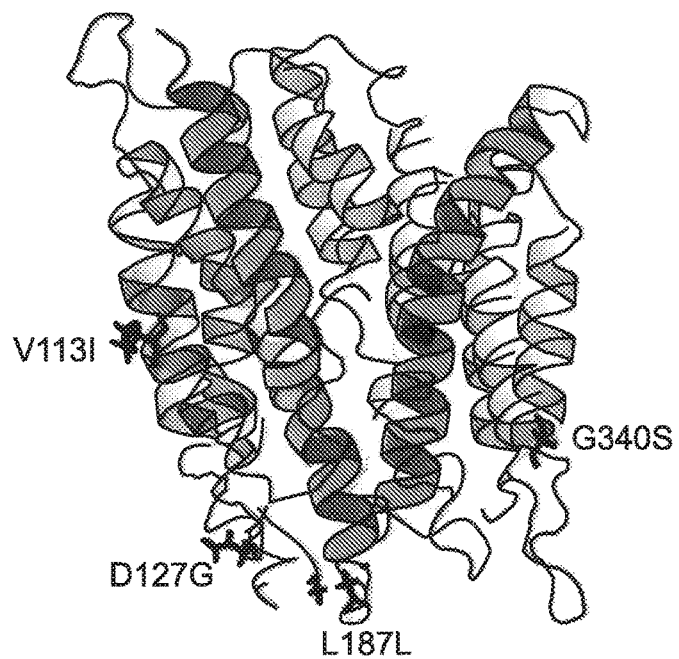
FIG. 5A (bottom panel)
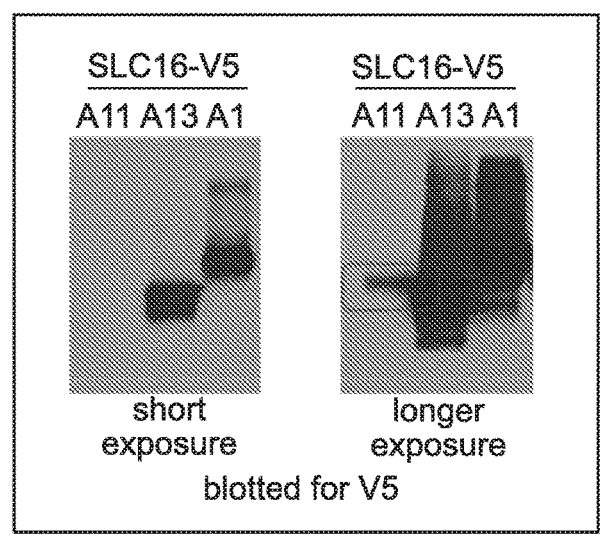

FIG. 5B (top panel)
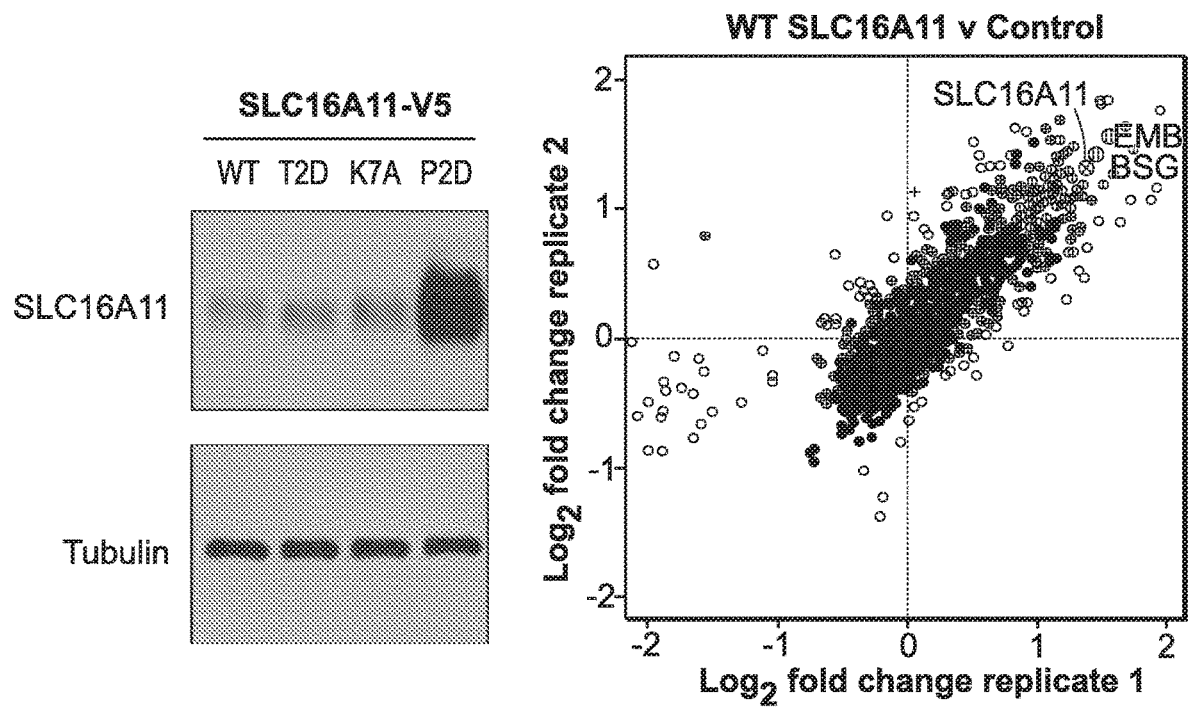
FIG. 5B (bottom panel)
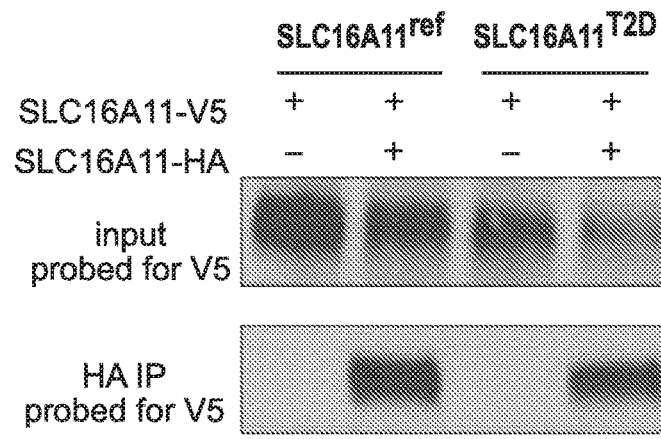

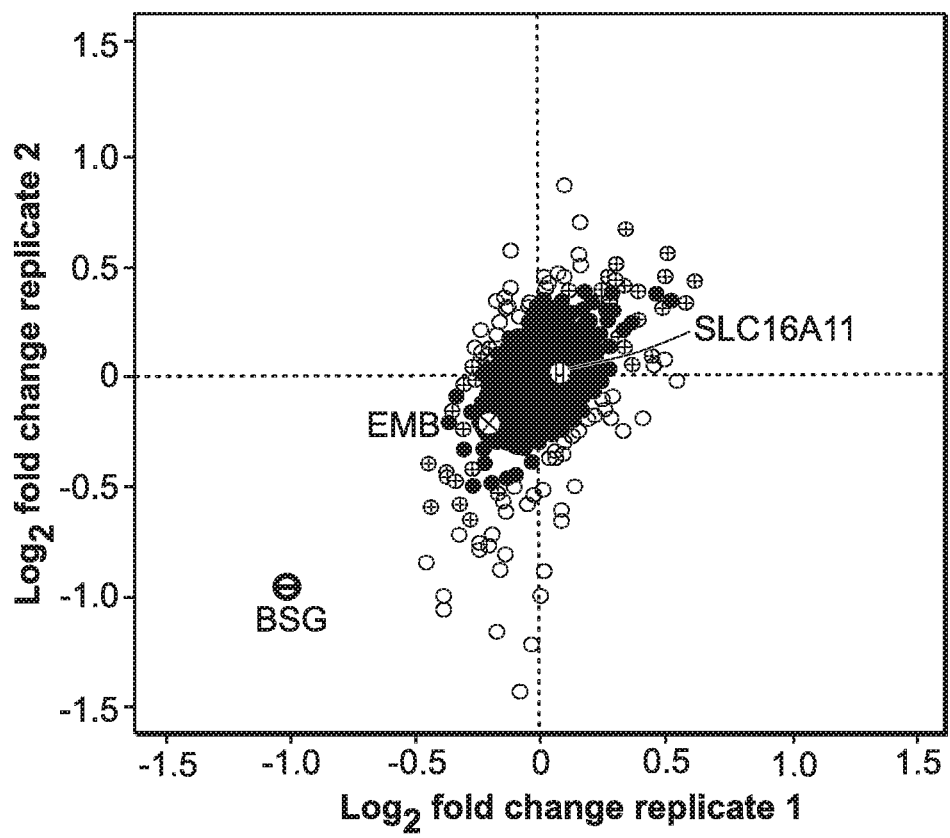

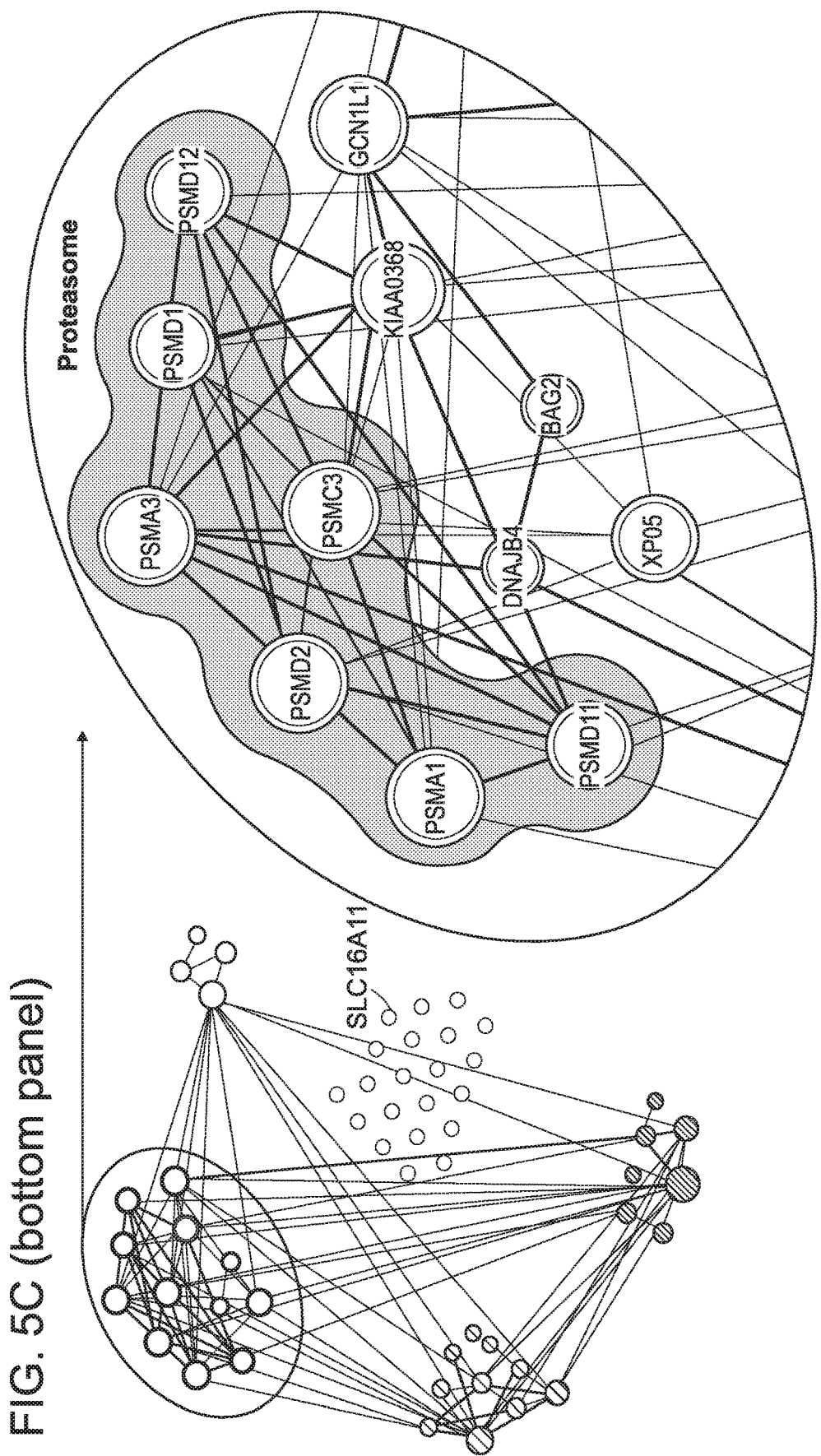
FIG. 5C (bottom panel)

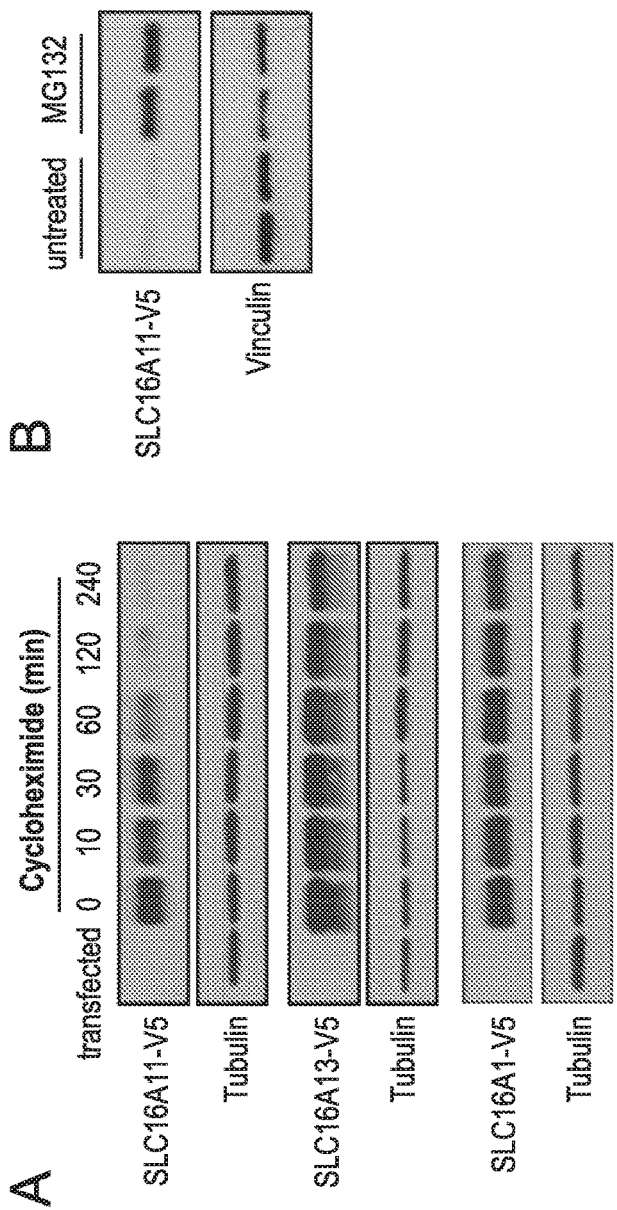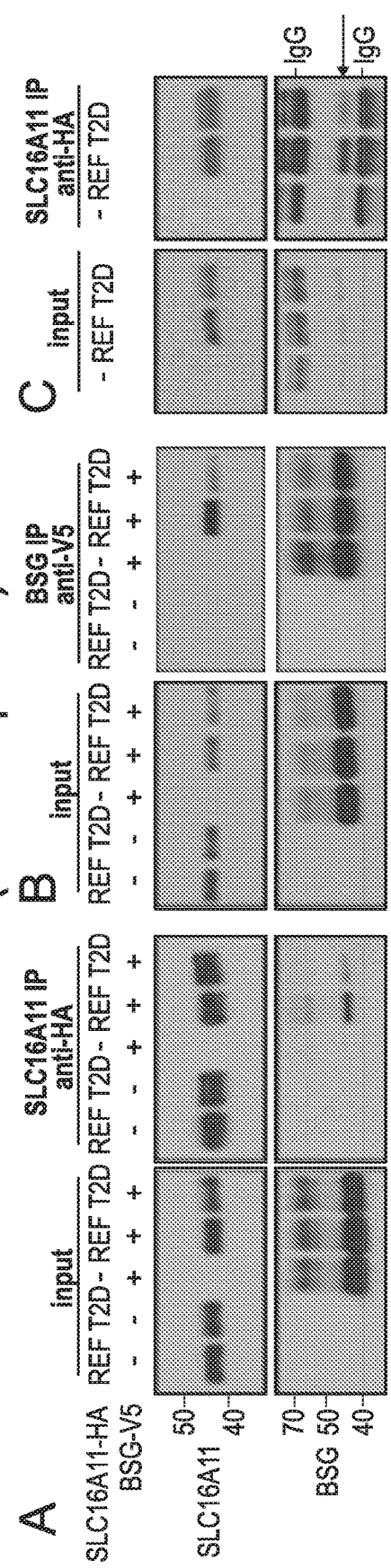
FIG. 5D (top panel)
FIG. 5D (bottom panel)

FIG. 5E (top panel)
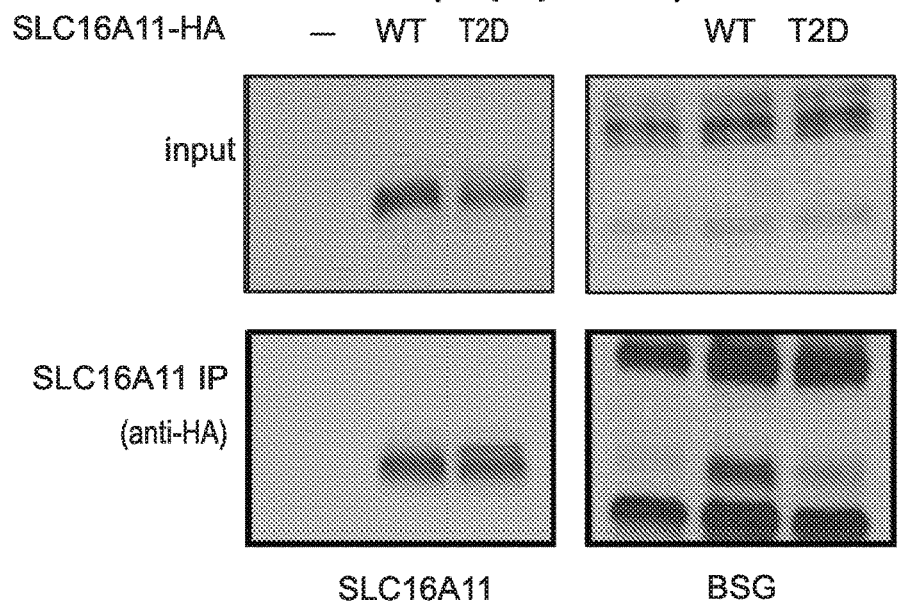
FIG. 5E (bottom panel)
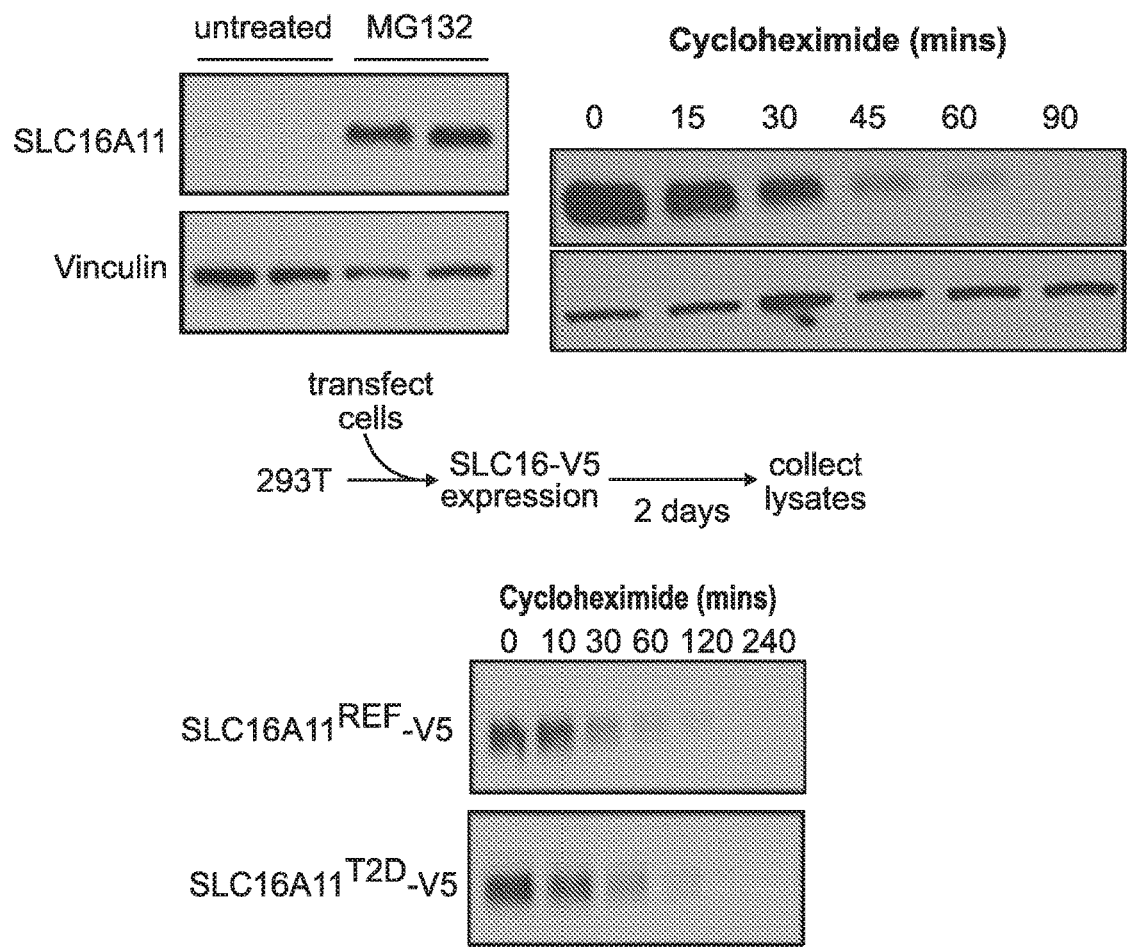

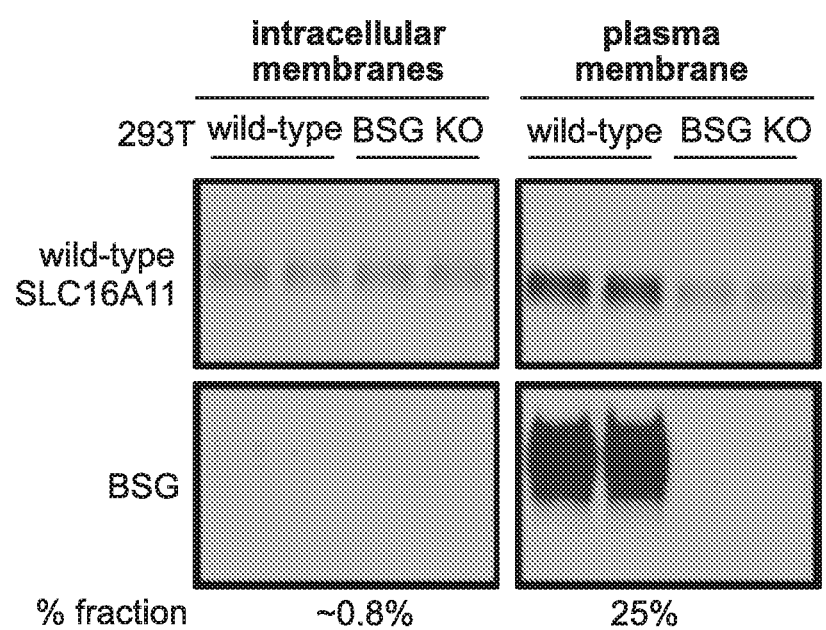

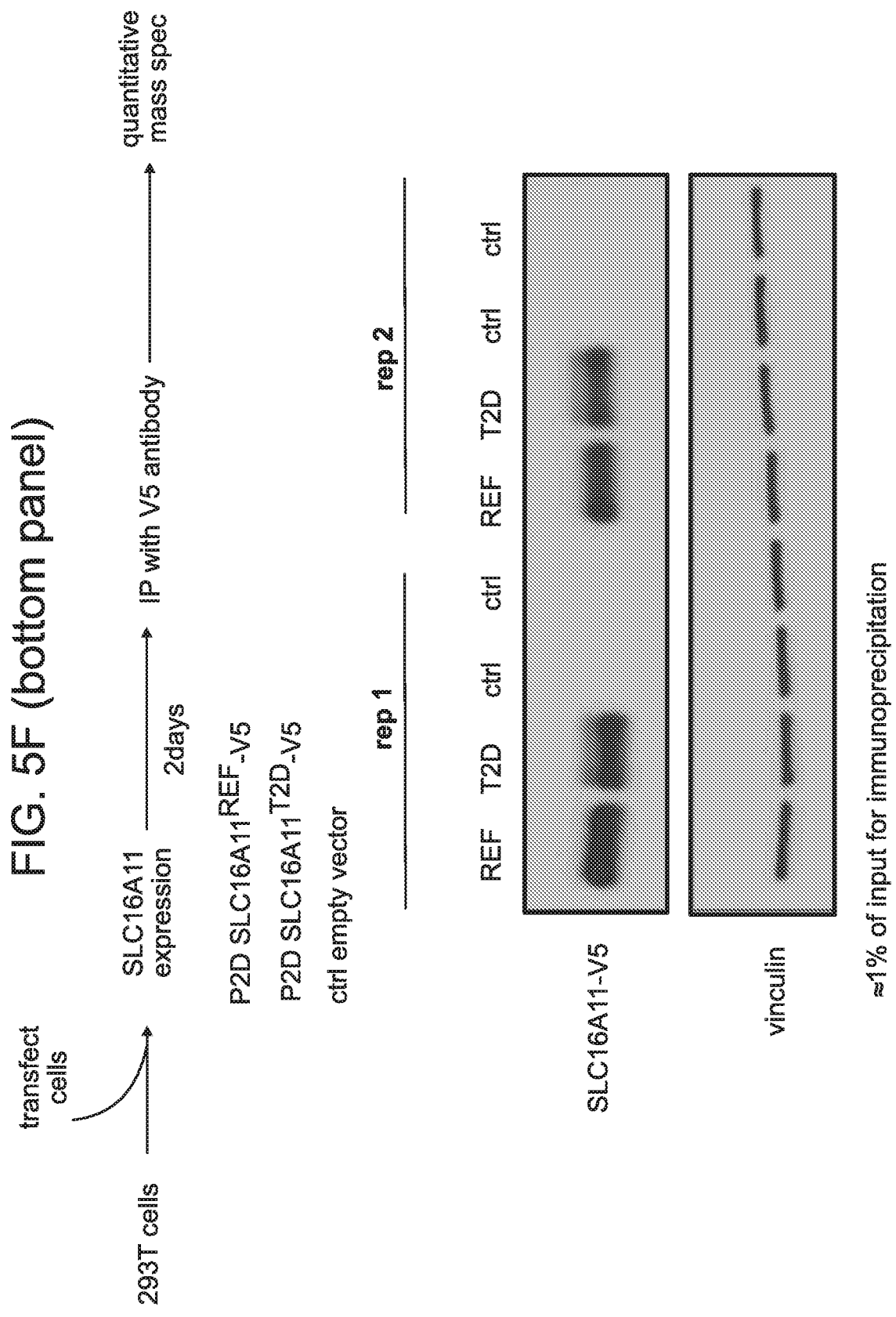

FIG. 5G (top panel)
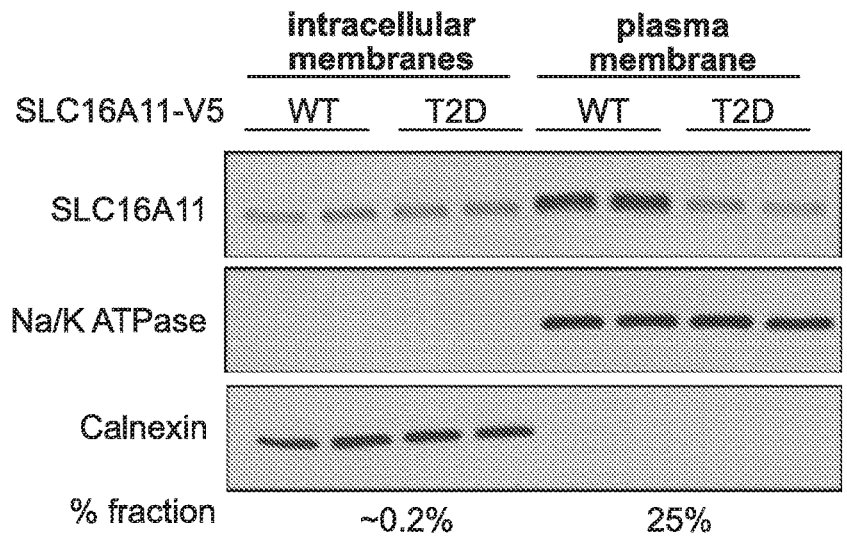
FIG. 5G (bottom panel)
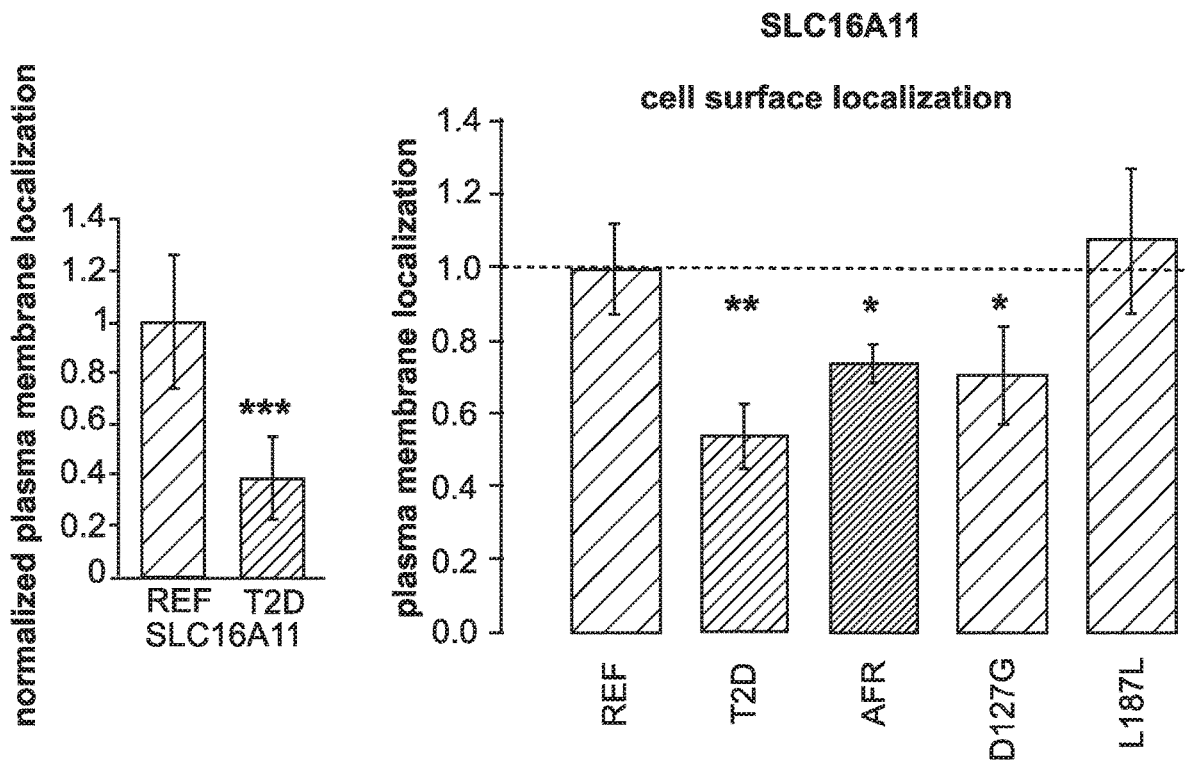

(FIGS. 5I-A, 5I-B and 5I-C)

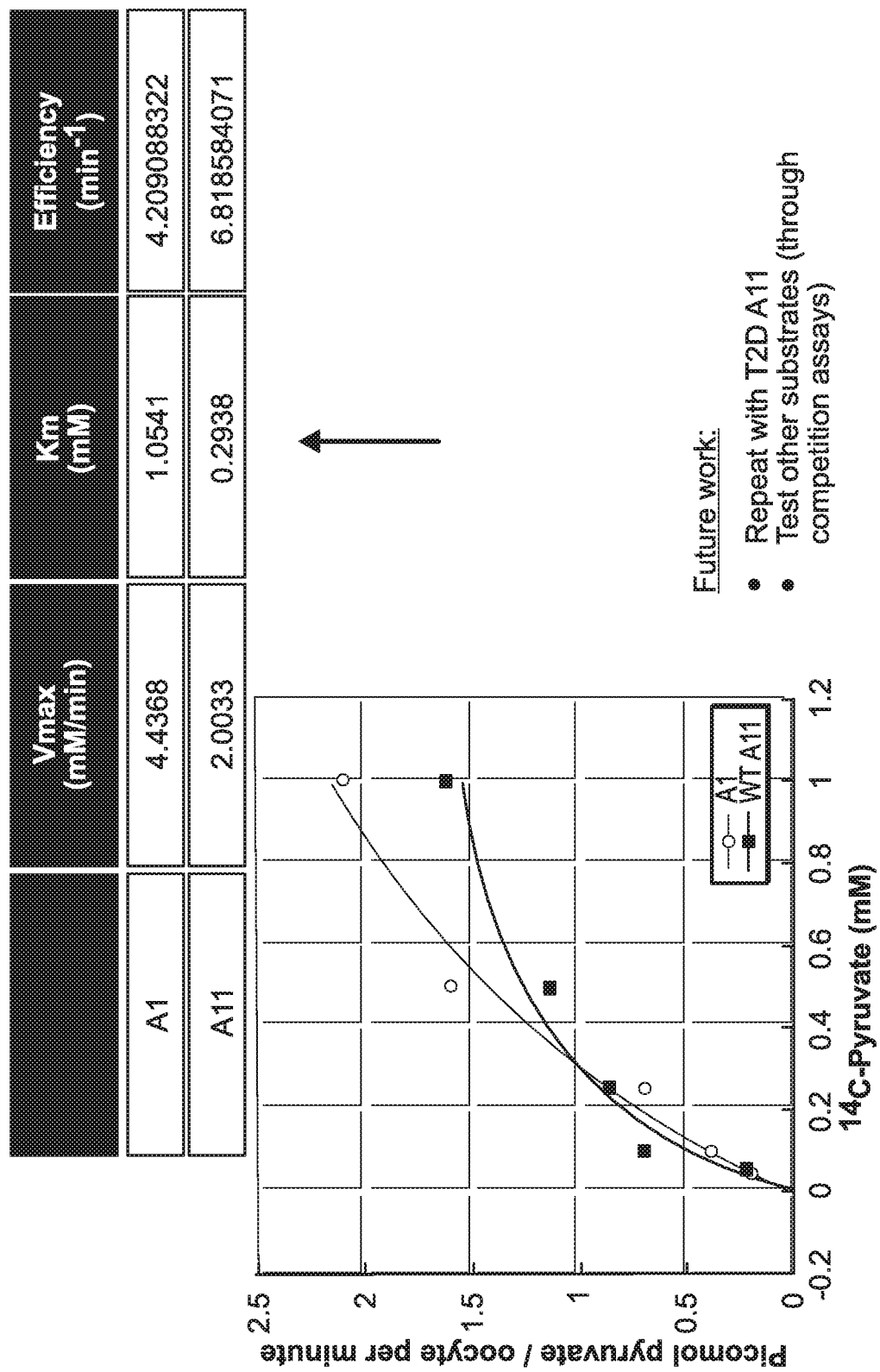
FIG. 8B  SLC16A11 has higher affinity to pyruvate and greater translocation efficiency

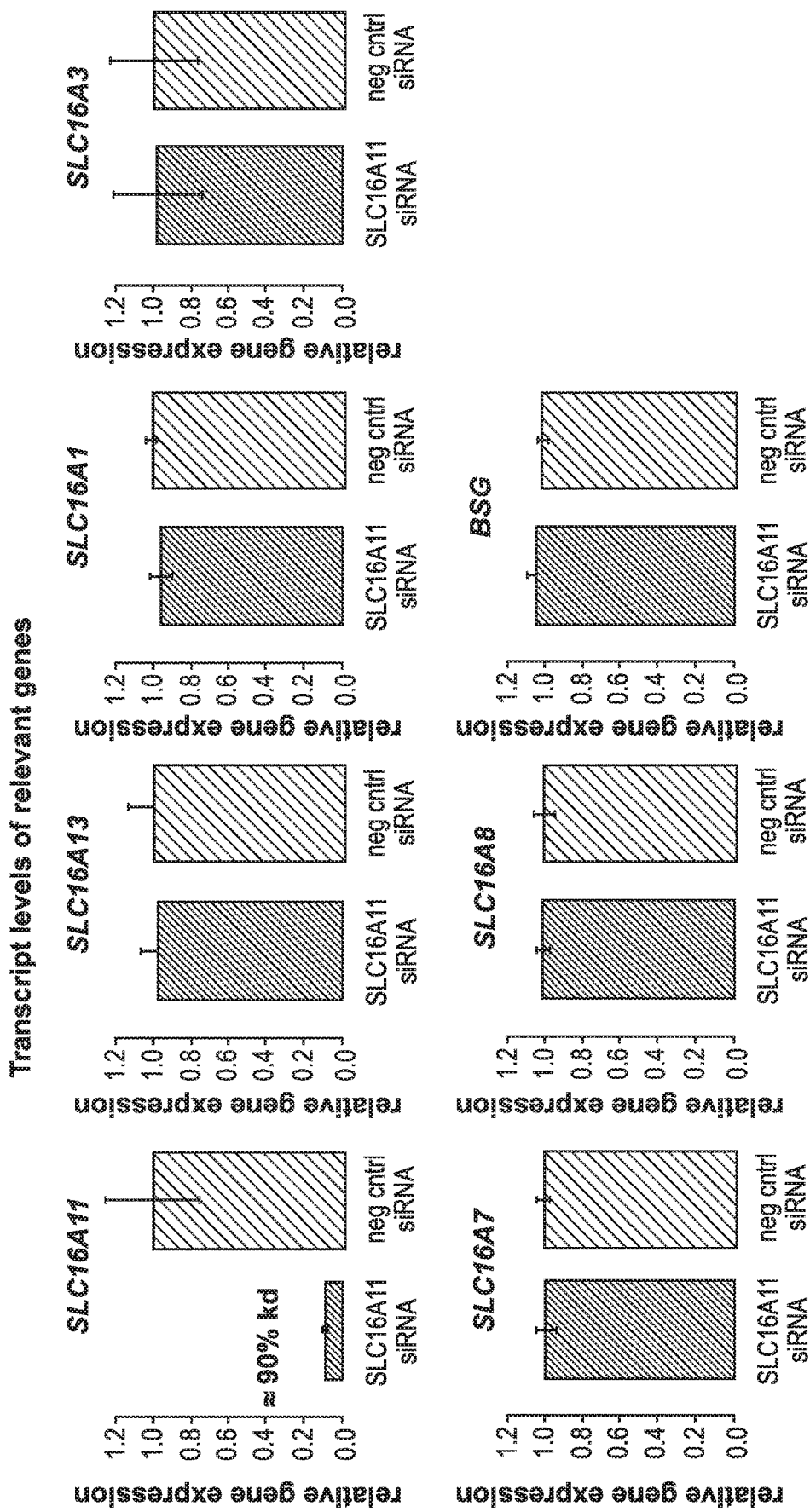
FIG. 9B (top panel)

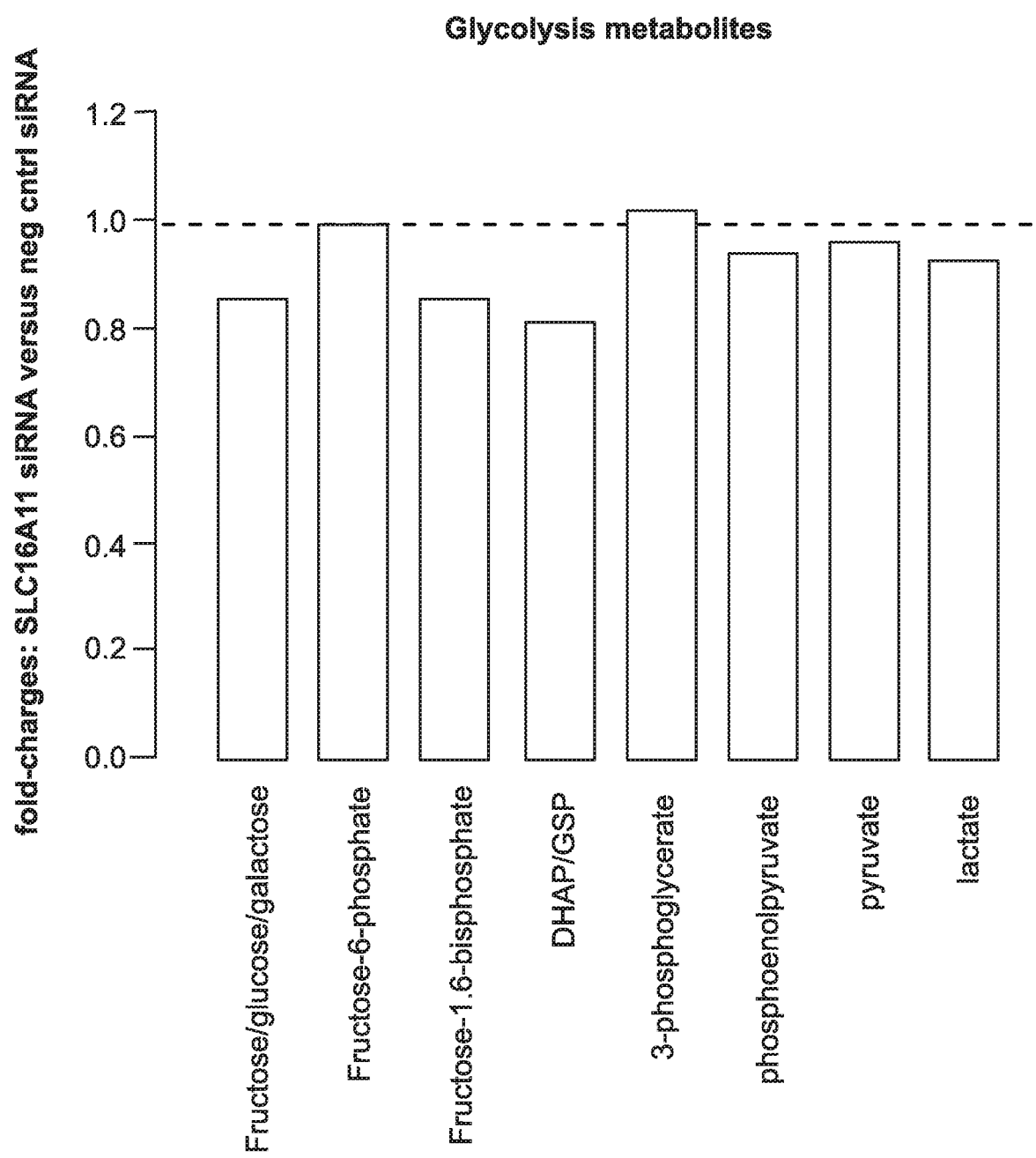
FIG. 9B (bottom panel)

FIG. 9C

Slc16a11 KO models
(65/71 pups carried a mutation)

| Genotype | # Het Mice |
|---|---|
| wild-type | 6 |
| deletion of 2 bp | 3 ← |
| deletion of 4 bp | 2 ← |
| deletion of 5 bp | 19 ← |
| deletion of 14 bp | 4 |
| deletion of 19 bp | 8 ← |
| deletion of 32 bp | 6 |
| deletion of 36 bp | 2 |
| deletion of 92 bp | 9 |
| insertion of 1 bp | 12 |

Slc16a13 KO models
(92/98 pups carried a mutation)

| Genotype | # Het Mice |
|---|---|
| wild-type | 6 |
| deletion of 1 bp | 1 |
| deletion of 2 bp | 6 ← |
| deletion of 3 bp | 5 |
| deletion of 5 bp | 3 |
| deletion of 6 bp | 19 |
| deletion of 7 bp | 4 ← |
| deletion of 8 bp | 8 ← |
| deletion of 9 bp | 8 |
| deletion of 13 bp | 5 ← |
| deletion of 16 bp | 2 |
| deletion of 19 bp | 2 |
| deletion of 77 bp | 3 |
| insertion of 1 bp | 24 |
| insertion of 4 bp | 2 |

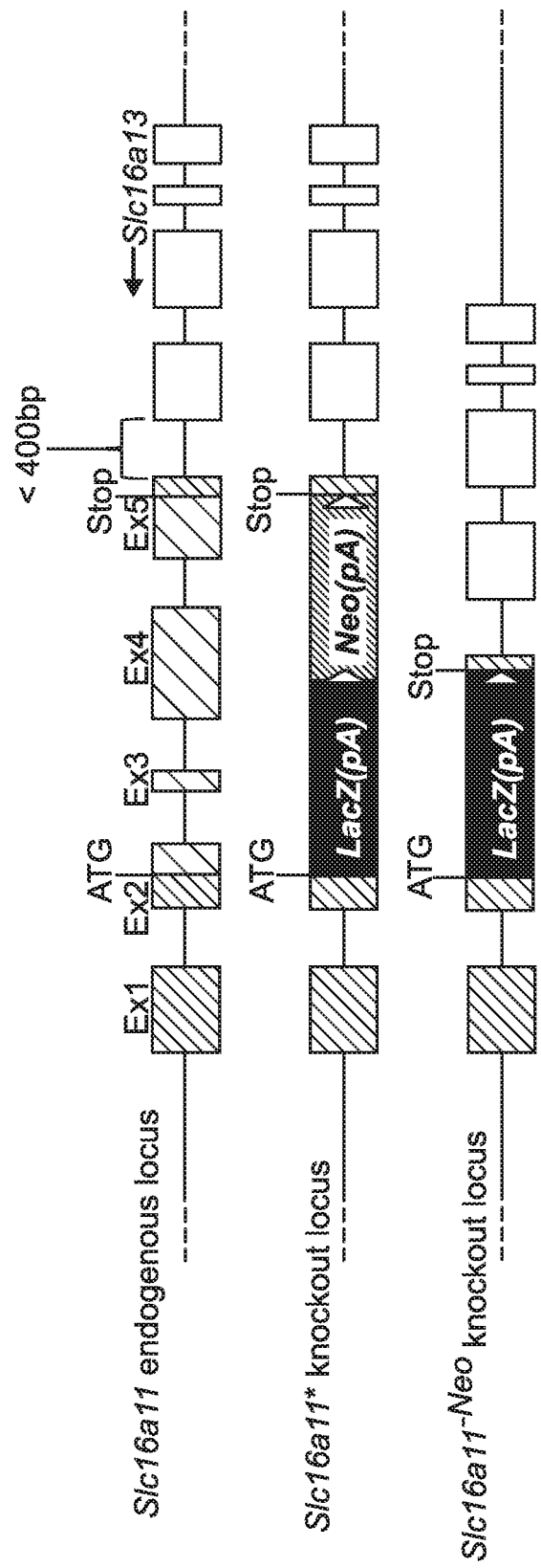
FIG. 9D (top panel)

FIG. 9D (middle panel)
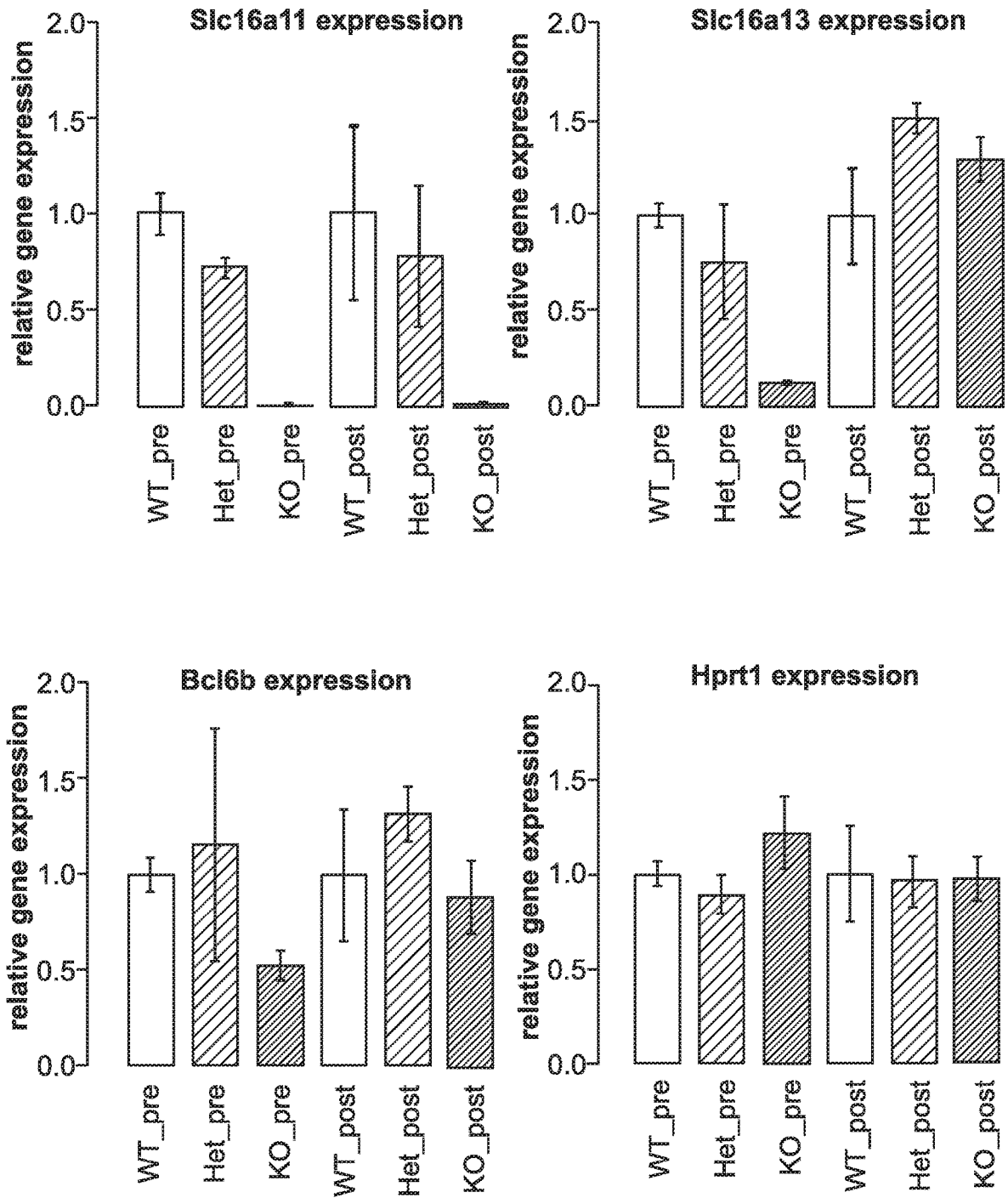

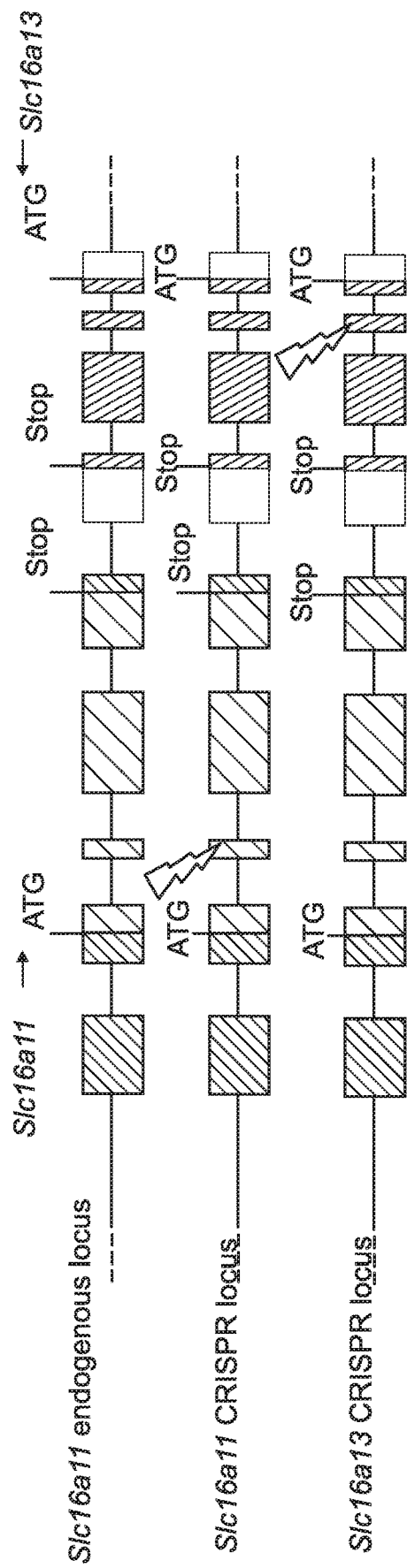
FIG. 9D (bottom panel)

FIG. 9E (top panel)
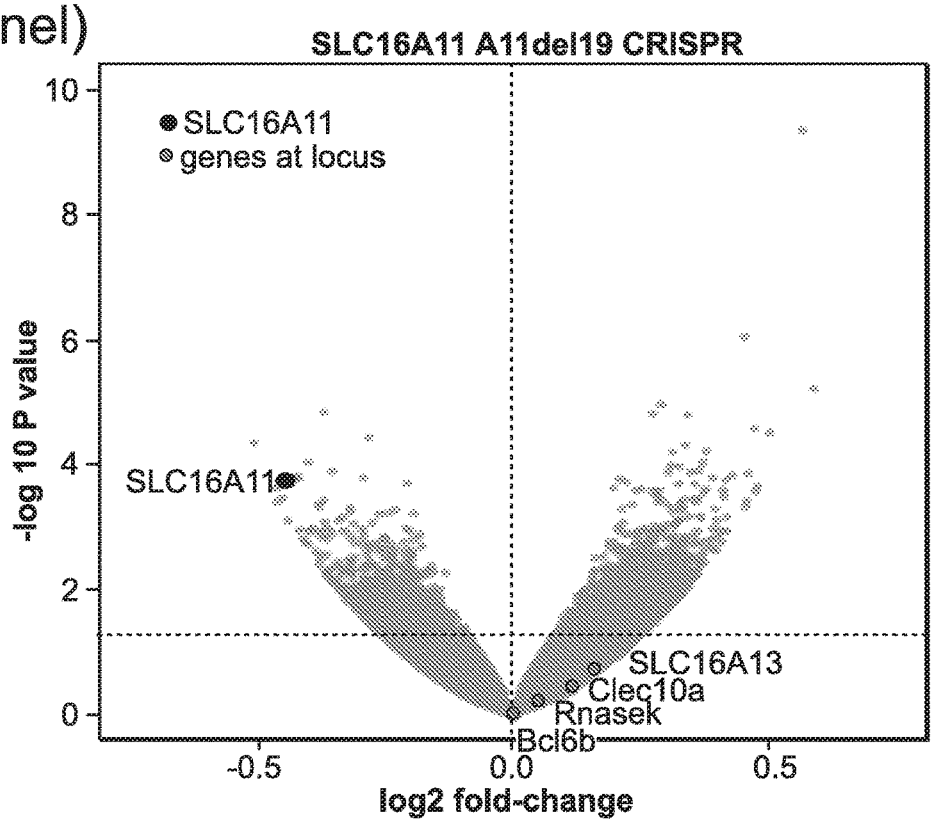
FIG. 9E (bottom panel)
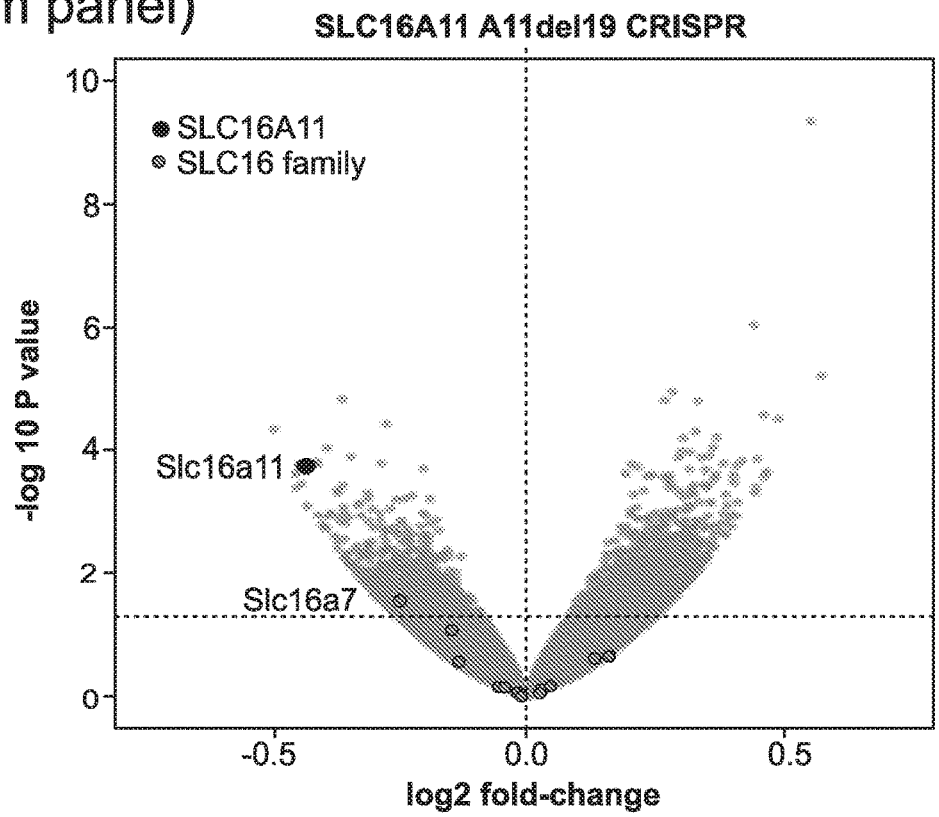

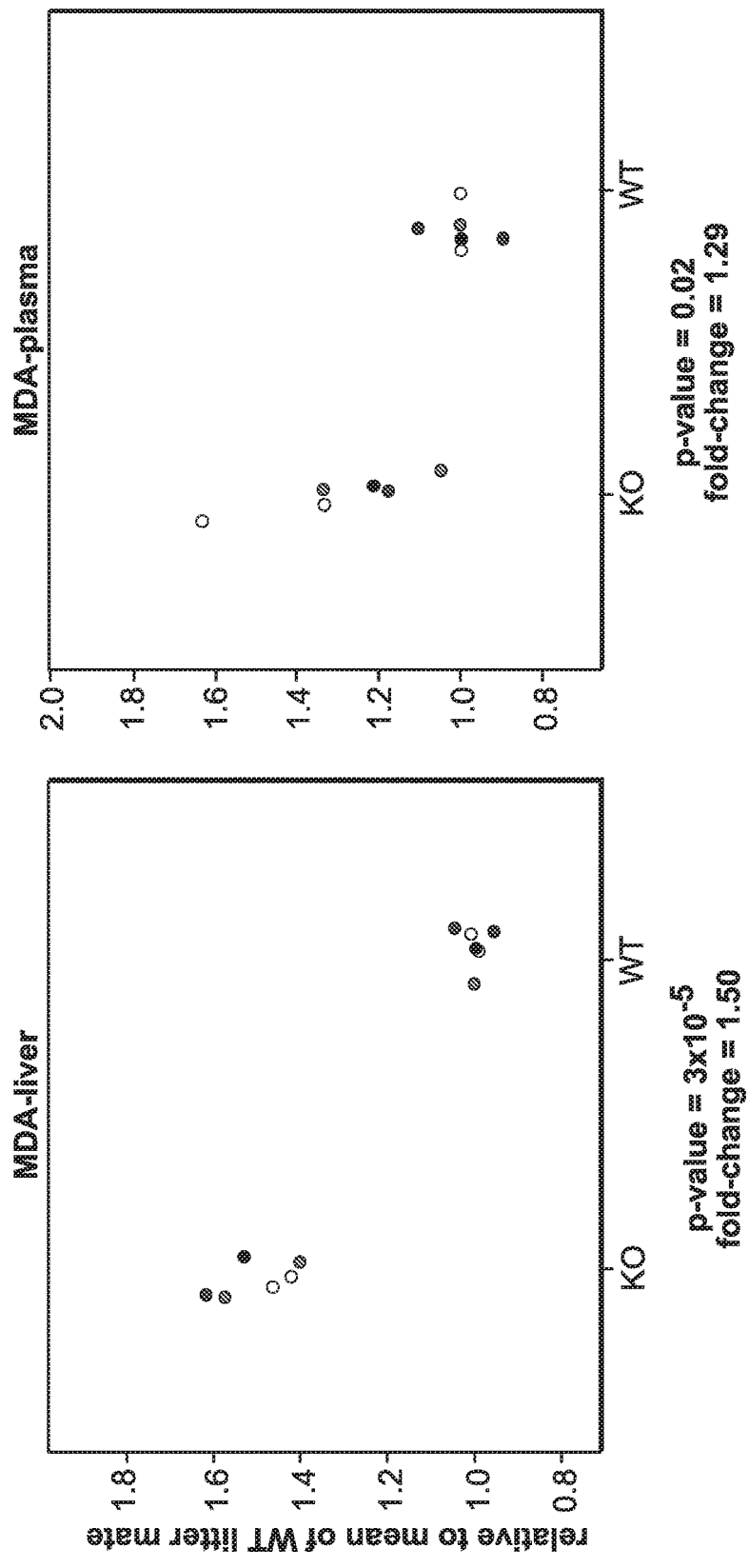

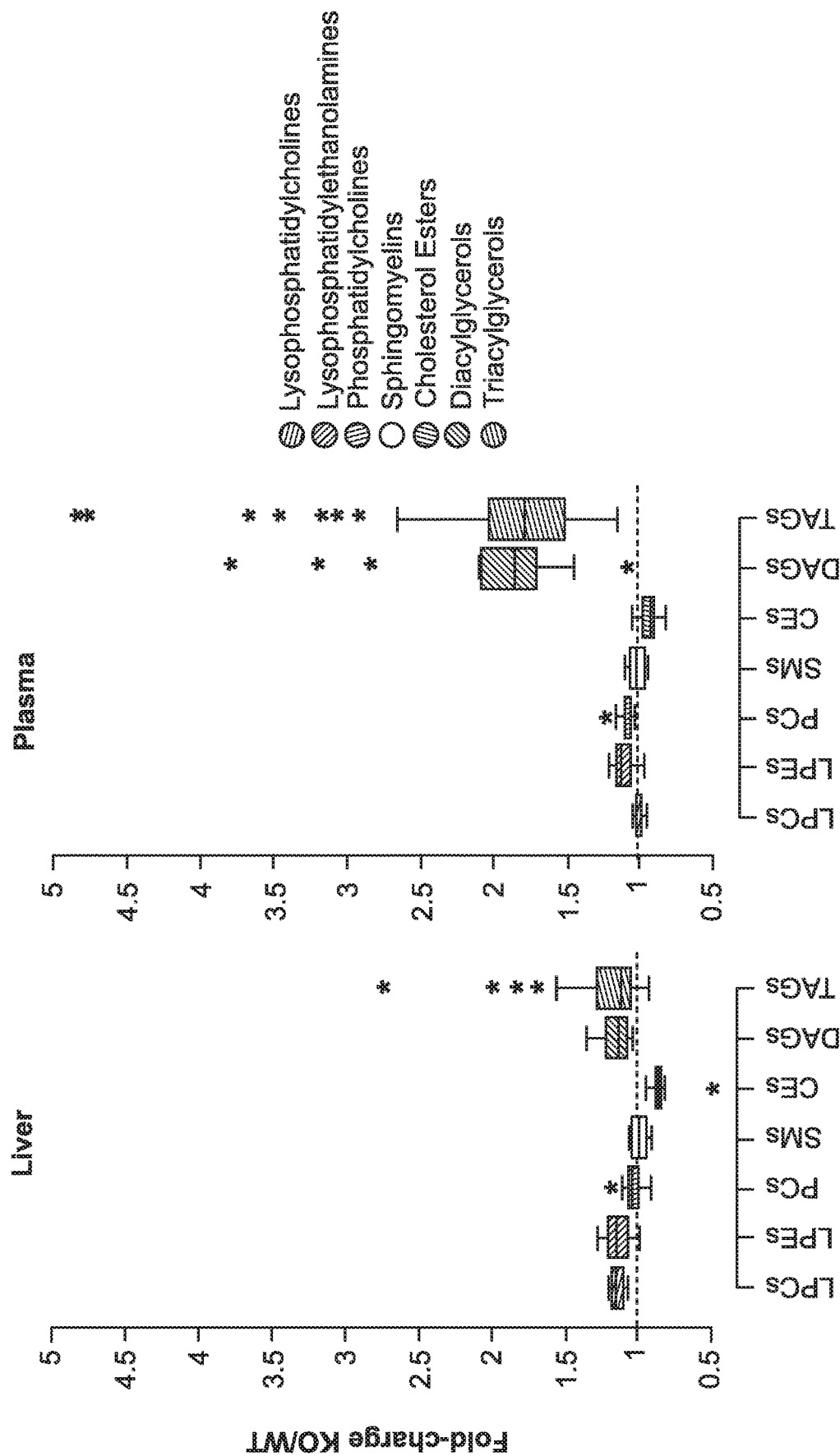

FIG. 9K-2A

Pathway Enrichment Analysis – Intracellular (48h)

GSEA Pre-ranked analysis
55 KEGG metabolic pathways
15 Lipid classes

| NAME | SIZE | NES | p-value | FDR |
|---|---|---|---|---|
| CARNITINES | 19 | 3.24 | 0.00 | 0.00 |
| TAGS | 65 | 3.18 | 0.00 | 0.00 |
| LPCS | 11 | -2.53 | 0.00 | 0.00 |
| PYRIMIDINE METABOLISM | 11 | 2.27 | 0.00 | 0.00 |
| PE PLASMALOGENS | 7 | 2.11 | 0.00 | 0.01 |
| DAGS | 15 | 2.03 | 0.00 | 0.01 |
| PCS | 21 | -1.98 | 0.00 | 0.04 |
| PC PLASMALOGENS | 13 | -1.77 | 0.01 | 0.09 |
| ARGININE & PROLINE METABOLISM | 15 | -1.53 | 0.05 | 0.25 |
| LPES | 8 | -1.46 | 0.09 | 0.27 |
| GLYOXYLATE & DICARBOXYLATE METABOLISM | 10 | 1.32 | 0.16 | 0.38 |
| SMS | 9 | 1.17 | 0.27 | 0.40 |
| STARCH & SUCROSE METABOLISM | 5 | 1.18 | 0.27 | 0.43 |
| PURINE METABOLISM | 11 | 1.20 | 0.24 | 0.44 |
| CES | 8 | 1.10 | 0.34 | 0.45 |
| CITRIC ACID CYCLE | 7 | 1.22 | 0.20 | 0.47 |
| AMINOACYL-TRNA BIOSYNTHESIS | 18 | -1.28 | 0.19 | 0.48 |
| PES | 14 | 1.00 | 0.42 | 0.50 |
| CYSTEINE & METHIONINE METABOLISM | 5 | 1.01 | 0.44 | 0.53 |
| NICOTINATE & NICOTINAMIDE METABOLISM | 6 | -1.21 | 0.23 | 0.54 |
| GLYCINE SERINE & THREONINE METABOLISM | 11 | 0.92 | 0.56 | 0.58 |
| GLYCOLYSIS | 6 | -0.90 | 0.58 | 0.76 |
| ALANINE ASPARTATE & GLUTAMATE METABOLISM | 7 | 0.75 | 0.79 | 0.78 |
| BETA-ALANINE METABOLISM | 6 | -0.91 | 0.56 | 0.81 |
| PHENYLALANINE METABOLISM | 5 | -0.79 | 0.69 | 0.82 |
| NITROGEN METABOLISM | 6 | -0.81 | 0.70 | 0.86 |
| CYANOAMINO ACID METABOLISM | 7 | -0.91 | 0.55 | 0.89 |
| GALACTOSE METABOLISM | 6 | -0.95 | 0.51 | 0.90 |
| GLUTATHIONE METABOLISM | 7 | -0.96 | 0.50 | 0.97 |
| BUTANOATE METABOLISM | 5 | -0.54 | 0.97 | 0.97 |
| PHENYLALANINE TYROSINE & TRYPTOPHAN BIOSYNTHESIS | 6 | -0.57 | 0.95 | 1.00 |

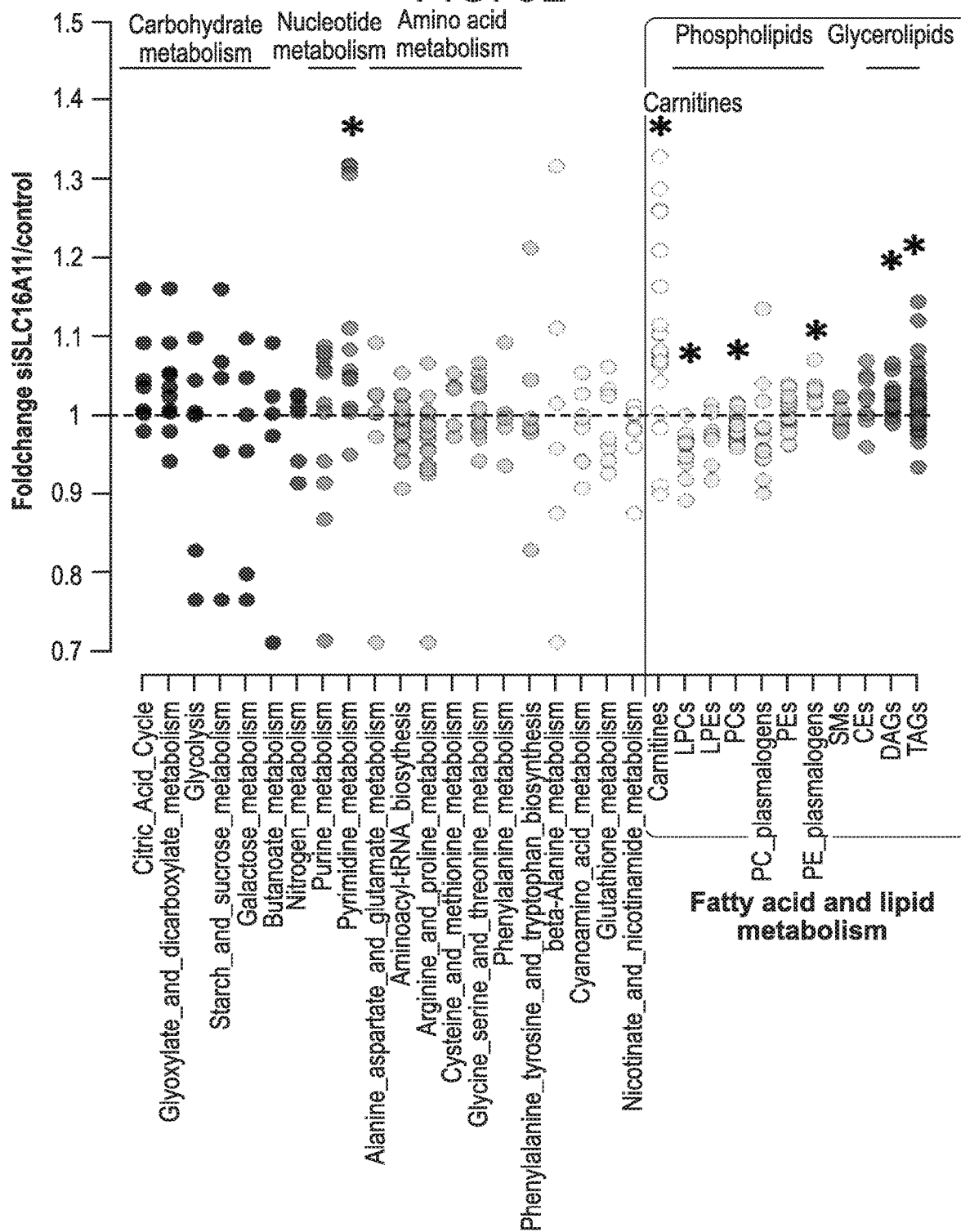

FIG. 9N

Pathway Enrichment Analysis - Extracellular (24)
  GSEA Pre-ranked analysis
  55 KEGG metabolic pathways
  15 Lipid classes

| NAME | SIZE | NES | p-value | FDR |
|---|---|---|---|---|
| TAGS | 58 | 2.58 | 0.00 | 0.00 |
| CES | 12 | -1.36 | 0.10 | 0.37 |
| VALINE LEUCINE & ISOLAEUCINE DEGRADATION | 5 | 1.31 | 0.16 | 0.42 |
| LPES | 9 | -1.72 | 0.03 | 0.43 |
| PCS | 19 | -1.36 | 0.10 | 0.44 |
| PRIMARY BILE ACID BIOSYNTHESIS | 5 | -1.25 | 0.19 | 0.48 |
| GLYOXYLATE & DICARBOXYLATE METABOLISM | 12 | 1.32 | 0.16 | 0.49 |
| TYROSINE METABOLISM | 5 | -1.38 | 0.10 | 0.49 |
| GLYCINE SERINE & THREONINE METABOLISM | 11 | 1.52 | 0.07 | 0.54 |
| CITRIC ACID CYCLE | 8 | 1.20 | 0.22 | 0.54 |
| BUTANOATE METABOLISM | 6 | -1.41 | 0.10 | 0.59 |
| DAGS | 14 | 1.39 | 0.09 | 0.60 |
| AMINOACYL-TRNA BIOSYNTHESIS | 18 | 1.32 | 0.16 | 0.61 |
| GALACTOSE METABOLISM | 5 | 1.09 | 0.32 | 0.61 |
| PC PLASMALOGENS | 12 | -1.10 | 0.31 | 0.62 |
| TAURINE & HYOITAURINE METABOLISM | 6 | -1.06 | 0.39 | 0.63 |
| PANTOTHENATE & COA BIOSYNTHESIS | 5 | -1.13 | 0.29 | 0.63 |
| SMS | 9 | 1.03 | 0.37 | 0.64 |
| CYANOAMINO ACID METABOLISM | 7 | 1.00 | 0.44 | 0.65 |
| PURINE METABOLISM | 11 | 1.09 | 0.36 | 0.68 |
| TRYPTOPHAN METABOLISM | 5 | -0.97 | 0.48 | 0.74 |
| PYRIMIDINE METABOLISM | 12 | -0.93 | 0.52 | 0.75 |
| ALANINE ASPARTATE & GLUTAMATE METABOLISM | 8 | -1.44 | 0.10 | 0.76 |
| CYCTEINE & METHIONINE METABOLISM | 6 | -0.85 | 0.63 | 0.77 |
| LPCS | 11 | -0.87 | 0.61 | 0.80 |
| ARGININE & PROLINE METABOLISM | 13 | -0.76 | 0.77 | 0.88 |
| PHENYLALANINE METABOLISM | 6 | -0.71 | 0.85 | 0.88 |
| BETA-ALANINE METABOLISM | 6 | -0.63 | 0.91 | 0.92 |
| PES | 12 | 0.49 | 0.99 | 0.99 |
| CARNITINES | 11 | 0.60 | 0.95 | 1.00 |
| NICOTINATE & NICOTINAMIDE METABOLISM | 6 | 0.70 | 0.81 | 1.00 |
| PHENYLALANINE TYROSINE & TRYPTOPHAN BIOSYNTHESIS | 5 | 0.67 | 0.88 | 1.00 |
| NITROGEN METABOLISM | 5 | 0.61 | 0.91 | 1.00 |

FIG. 13A
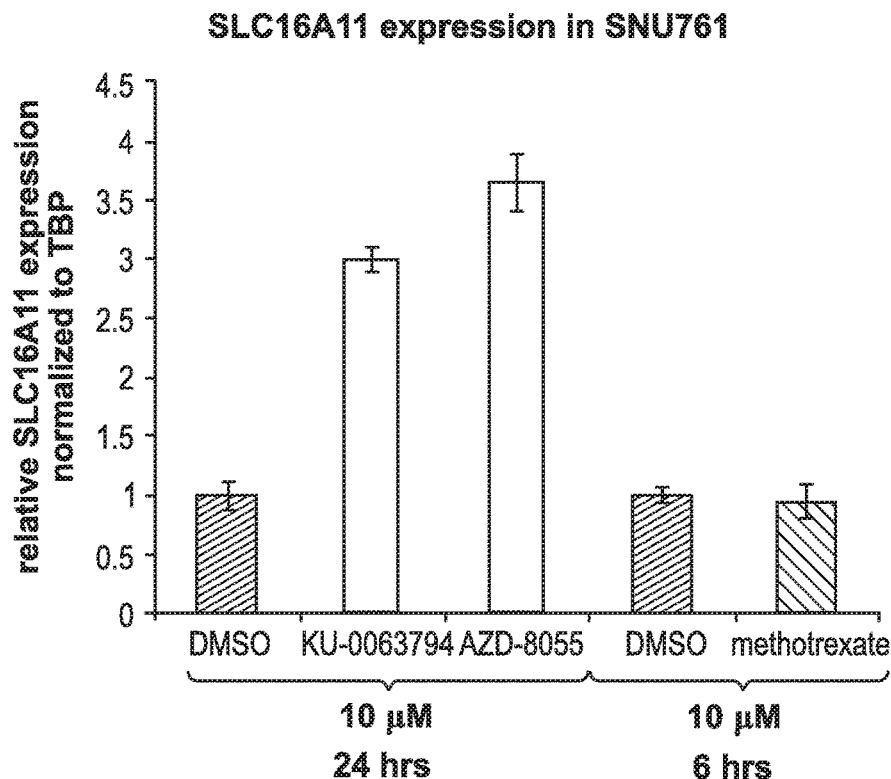
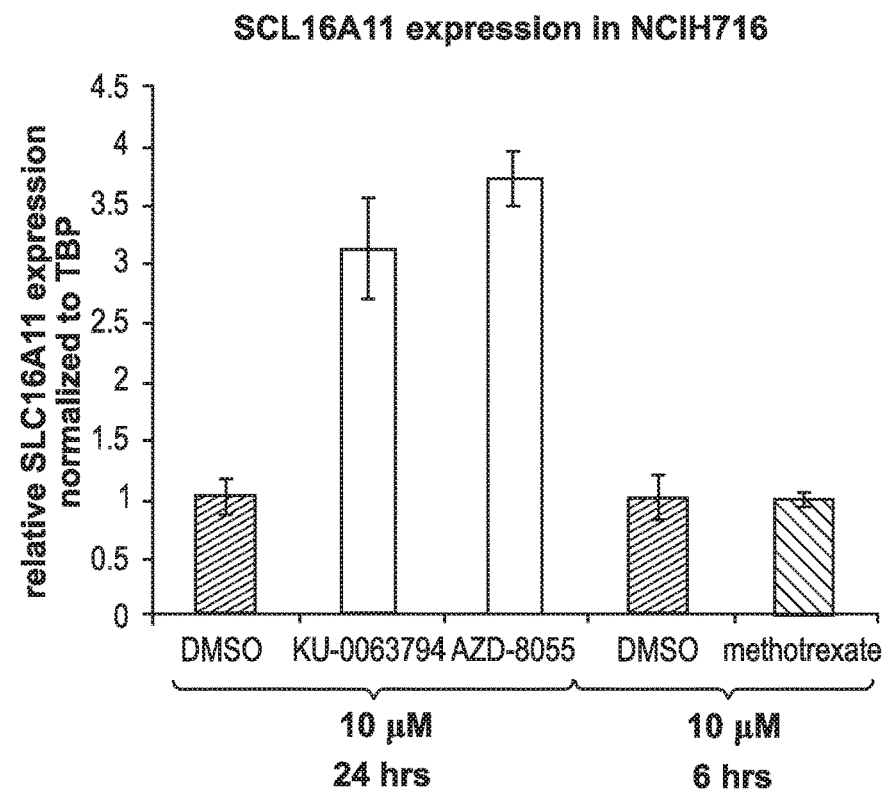

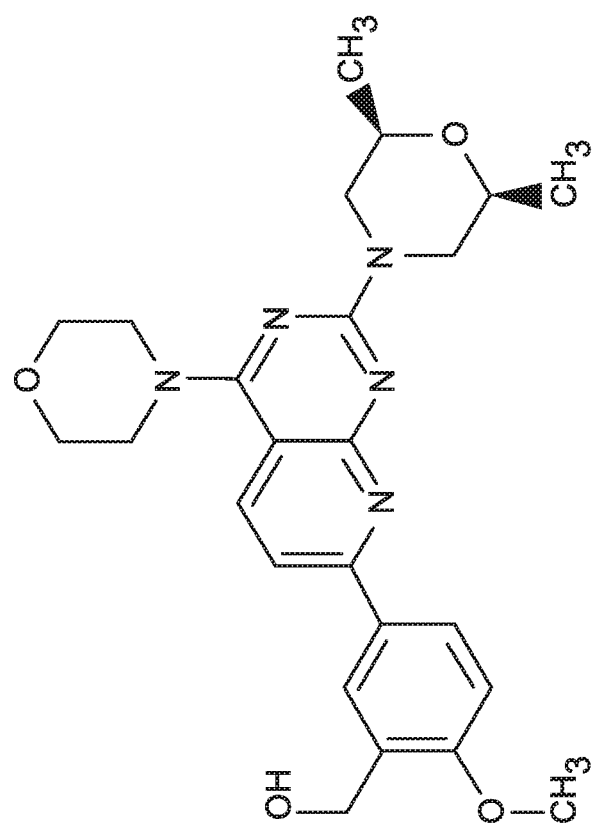
KU-0063794
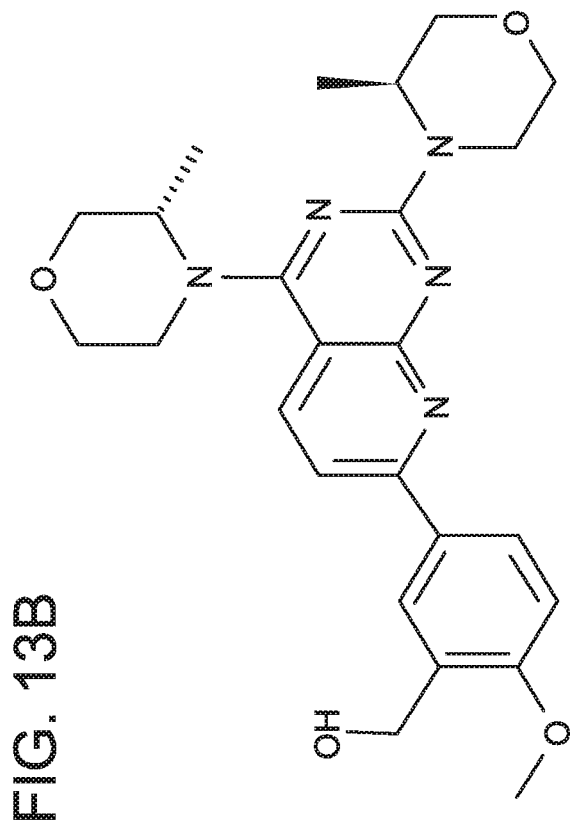
AZD 8055
FIG. 13B

FIG. 16 (top panel)
AZD8055
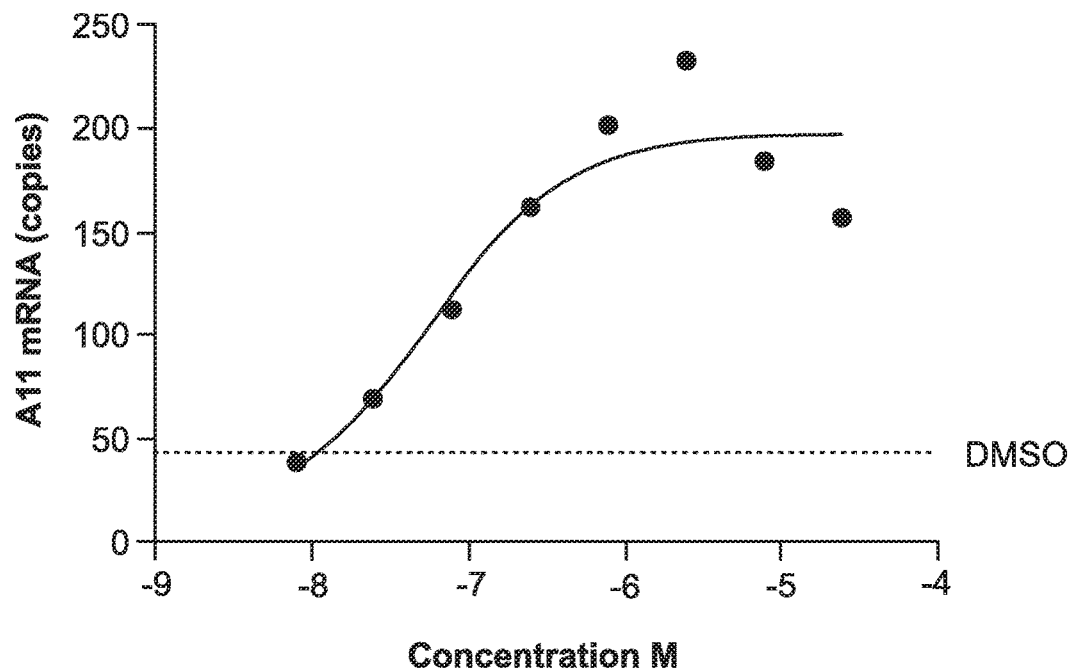
FIG. 16 (bottom panel)
AZD8055
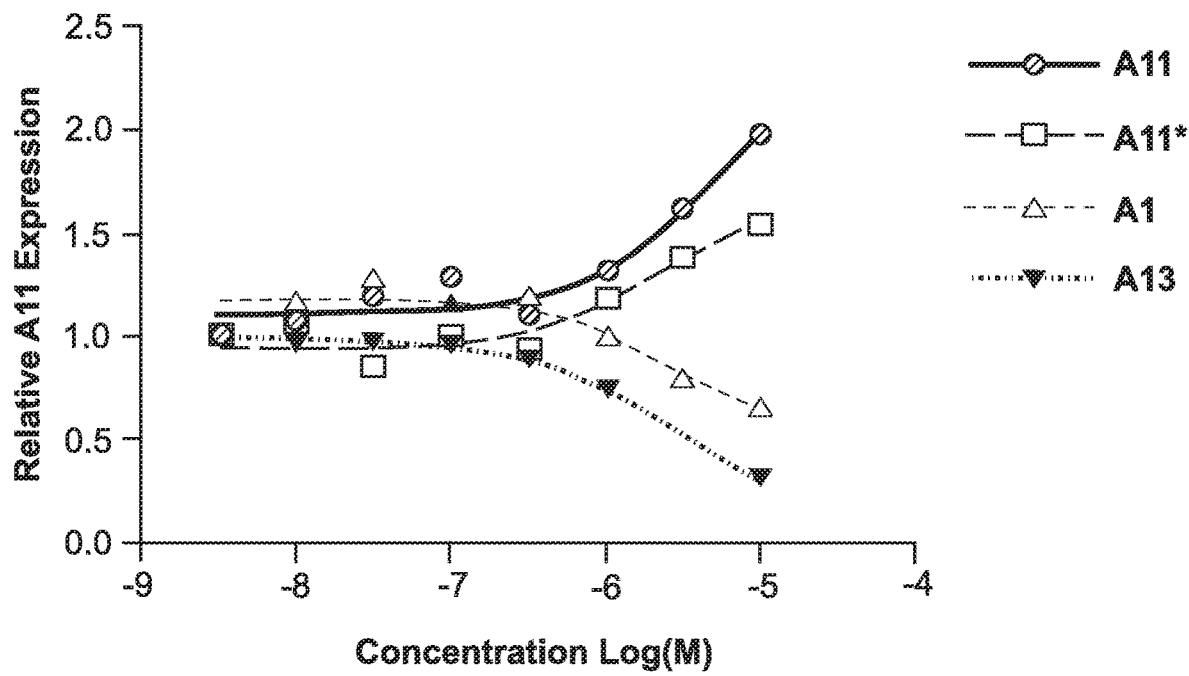

FIG. 22
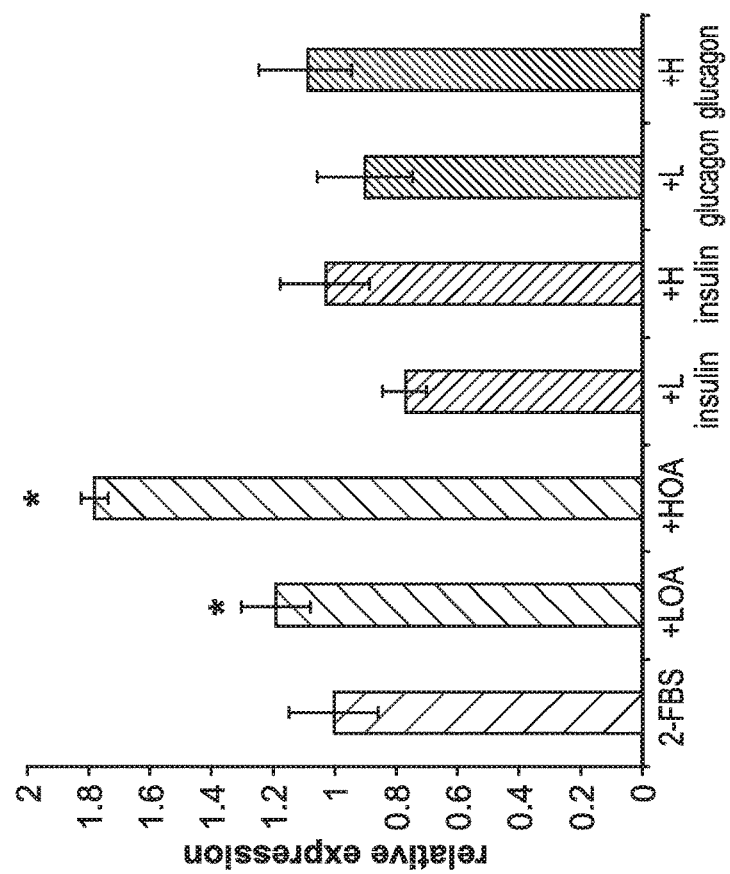
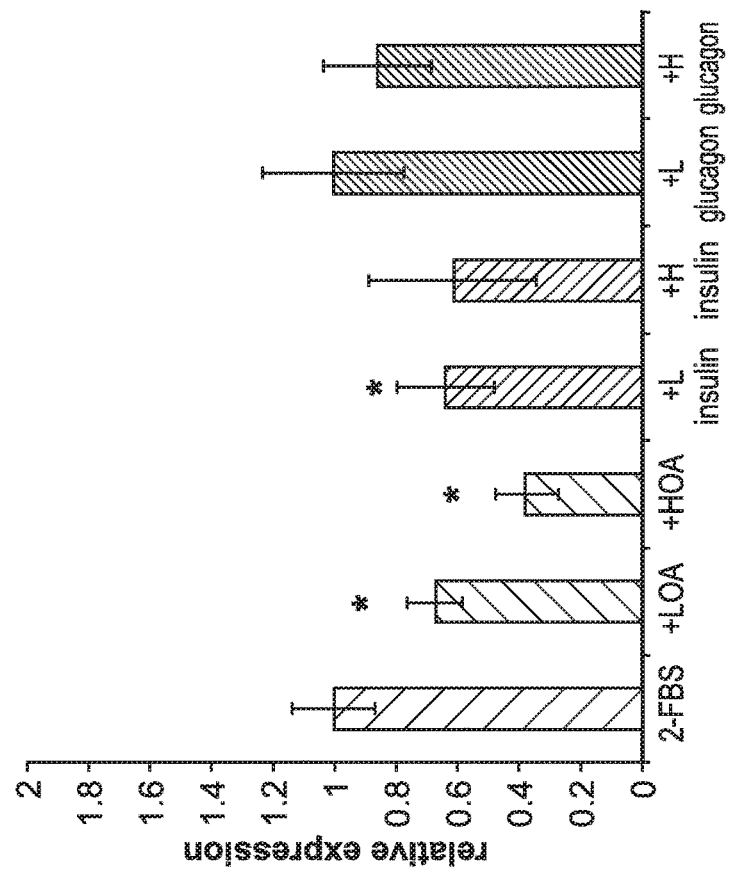

FIG. 24-1 rs77086571 *[Homo sapiens]*
CACACAACCCCAGGCCCGGGGGAG[C/G/T]GGGGAGCGGCGAGAAATGAATGCAG
(SEQ ID NO: 109)
Chromosome: 17:7044074
Gene: SLC16A11 (GeneView)
Functional Consequence: missense, upstream variant 2KB rs74577409 *[Homo sapiens]*
GCCCTACTCACACGCATGCACCTGC[C/G]GCCTGCTGCGCGCAGGGGAGACACG
(SEQ ID NO: 110)
Chromosome: 17:7044134
Gene: SLC16A11 (GeneView)
Functional Consequence: upstream variant 2KB, utr variant 5 prime rs2292351
CGGGCCCACCCCGGGCGAGCAGCCA[C/G]AGGCTGGATCTCAGGGATGCCAGCT
(SEQ ID NO: 111)
Chromosome: 17:7043602
Gene: SLC16A11 (GeneView)
Functional Consequence: intron variant, utr variant 5 prime rs13342232
CGCCCCGCCAGCCGAAAGTATCGAG[A/G]AGAAGCTGCAAGGCGGGCGCCAGGA
(SEQ ID NO: 112)
Chromosome: 17:7042621
Gene: SLC16A11 (GeneView)
Functional Consequence: downstream variant 500B, synonymous codon rs13342692
CAGGCCGAGGTAGAGATGCAGCAGA[C/T]CGCTGGCGAAAGCCGAGAAGACGAA
(SEQ ID NO: 113)
Chromosome: 17:7042968
Gene: SLC16A11 (GeneView)
Functional Consequence: missense rs117767867
AAGACGAAGCCCAGCGAGGCGAGGA[C/T]GCCCCCAACCATCACCACGGGGCGG
(SEQ ID NO: 114)
Chromosome: 17:7043011
Gene: SLC16A11 (GeneView)
Functional Consequence: missense

FIG. 24-2 rs75418188
GCCACAGCCGCGGCCAGCAGGGGAC[A/C/T]CCCCCAGCTCTCTTCGCCGCCCACC
(SEQ ID NO: 115)
Chromosome: 17:7042164
Gene: SLC16A11 (GeneView)
Functional Consequence: missense rs17203120
TGTTTGGGAAACAAAACTGTCCCTT[G/T]GAGATAAAATCAAATAAGAAAATTG
(SEQ ID NO: 116)
Chromosome: 17:7040670 rs145952323
CTCCTAAAAATACAAAAATTAGCCG[C/G]GTGTGTTGGCGTGTGCCTGTAGTTG
(SEQ ID NO: 117)
Chromosome: 17:7041030 rs75493593
GGAAGCAGCTCCCCCGTCTCTGGGG[C/G/T]AGGCGTGGCTGGAGGGGAGGCTGGA
(SEQ ID NO: 118)
Chromosome: 17:7041768
Gene: SLC16A11 (GeneView)
Functional Consequence: missense rs75075014
GCCGAATGGAGTCATGCCTGGAAGT[A/G]GAGGAGAGTGTCCAGGAGCTCCGAT
(SEQ ID NO:119)
Chromosome: 17:7040770 rs78972129
TGGTGTAGTACAGTACACAGCCTGC[A/G]TGGCCAACCATAGCATCCCTGAAAT
(SEQ ID NO: 120)
Chromosome: 17:7039011
Gene: SLC16A13 (GeneView)
Functional Consequence: intron variant rs76070643
TTTTCCAGTGGCTGCTCAGCCACTA[C/T]GCCTGGAGGGGGTCCCTGCTGCTGG
(SEQ ID NO: 121)
Chromosome: 17:7038306
Gene: SLC16A13 (GeneView)
Functional Consequence: synonymous codon

FIG. 24-3 rs77552976
AGGAACCTGGCTGGACCTAACAGCA[C/T]GGCAGCCCTTTCCCACCTGGCTACC
(SEQ ID NO: 122)
Chromosome: 17:7048293 rs58223767
GGCCAGGATGGTCTCGAACTCCTGA[C/T]CTTGTGATCCACCCCCCCCCCCCT
(SEQ ID NO: 123)
Chromosome: 17:7040410
Gene: SLC16A13 (GeneView)
Functional Consequence: downstream variant 500B rs4630597
CCTACTGGGCCCCAAACCAGGTATC[C/T]GAGGCACCTGGTCAAAGTTCTGCTG
(SEQ ID NO: 124)
Chromosome: 17:7039227
Gene: SLC16A13 (GeneView)
Functional Consequence: intron variant rs113748381
CTAACCTCGTGATCTGCCCGCCTCG[A/G]CCTCCCAAAGTGCTGGGATTACAGG
(SEQ ID NO: 125)
Chromosome: 17:7049836 rs73239895
CATGGGAACTCCTGCCGGAGGTTCT[C/T]GGGGCCTCTGGAGTCTGCAGCCTCA
(SEQ ID NO: 126)
Chromosome: 17:7050239

SEQUENCE LISTING

<160> NUMBER OF SEQ ID NOS: 126

<210> SEQ ID NO 1
<211> LENGTH: 6
<212> TYPE: PRT
<213> ORGANISM: Unknown
<220> FEATURE:
<223> OTHER INFORMATION: Description of Unknown:
      Solute Carrier Family 16 conserved sequence
<220> FEATURE:
<221> NAME/KEY: MOD_RES
<222> LOCATION: (1)..(1)
<223> OTHER INFORMATION: Asp or Glu
<220> FEATURE:
<221> NAME/KEY: MOD_RES
<222> LOCATION: (3)..(3)
<223> OTHER INFORMATION: Gly or Ser
<220> FEATURE:
<221> NAME/KEY: MOD_RES
<222> LOCATION: (4)..(4)
<223> OTHER INFORMATION: Trp or Phe
<220> FEATURE:
<221> NAME/KEY: MOD_RES
<222> LOCATION: (5)..(5)
<223> OTHER INFORMATION: Gly or Ala

<400> SEQUENCE: 1

Xaa Gly Xaa Xaa Xaa Trp
1               5

<210> SEQ ID NO 2
<211> LENGTH: 16
<212> TYPE: PRT
<213> ORGANISM: Unknown
<220> FEATURE:
<223> OTHER INFORMATION: Description of Unknown:
      Solute Carrier Family 16 conserved sequence
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Arg or Lys
<220> FEATURE:
<221> NAME/KEY: MOD_RES
<222> LOCATION: (6)..(6)
<223> OTHER INFORMATION: Arg or Leu
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Gly or Ala
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid

<400> SEQUENCE: 2

Tyr Phe Xaa Lys Xaa Xaa Xaa Leu Ala Xaa Xaa Xaa Ala Xaa Ala Gly
1               5                   10                  15

-continued

```
<210> SEQ ID NO 3
<211> LENGTH: 471
<212> TYPE: PRT
<213> ORGANISM: Homo sapiens

<400> SEQUENCE: 3

Met Pro Ala Pro Gln Arg Lys His Arg Arg Gly Gly Phe Ser His Arg
1               5                   10                  15

Cys Phe Pro Thr Pro Gln Thr Ala Met Thr Pro Gln Pro Ala Gly Pro
                20                  25                  30

Pro Asp Gly Gly Trp Gly Trp Val Val Ala Ala Ala Phe Ala Ile
            35                  40                  45

Asn Gly Leu Ser Tyr Gly Leu Leu Arg Ser Leu Gly Leu Ala Phe Pro
    50                  55                  60

Asp Leu Ala Glu His Phe Asp Arg Ser Ala Gln Asp Thr Ala Trp Ile
65                  70                  75                  80

Ser Ala Leu Ala Leu Ala Val Gln Gln Ala Ala Ser Pro Val Gly Ser
                85                  90                  95

Ala Leu Ser Thr Arg Trp Gly Ala Arg Pro Val Val Met Val Gly Gly
                100                 105                 110

Val Leu Ala Ser Leu Gly Phe Val Phe Ser Ala Phe Ala Ser Asp Leu
            115                 120                 125

Leu His Leu Tyr Leu Gly Leu Gly Leu Leu Ala Gly Phe Gly Trp Ala
    130                 135                 140

Leu Val Phe Ala Pro Ala Leu Gly Thr Leu Ser Arg Tyr Phe Ser Arg
145                 150                 155                 160

Arg Arg Val Leu Ala Val Gly Leu Ala Leu Thr Gly Asn Gly Ala Ser
                165                 170                 175

Ser Leu Leu Leu Ala Pro Ala Leu Gln Leu Leu Leu Asp Thr Phe Gly
            180                 185                 190

Trp Arg Gly Ala Leu Leu Leu Gly Ala Ile Thr Leu His Leu Thr
    195                 200                 205

Pro Cys Gly Ala Leu Leu Leu Pro Leu Val Leu Pro Gly Asp Pro Pro
210                 215                 220

Ala Pro Pro Arg Ser Pro Leu Ala Ala Leu Gly Leu Ser Leu Phe Thr
225                 230                 235                 240

Arg Arg Ala Phe Ser Ile Phe Ala Leu Gly Thr Ala Leu Val Gly Gly
                245                 250                 255

Gly Tyr Phe Val Pro Tyr Val His Leu Ala Pro His Ala Leu Asp Arg
            260                 265                 270

Gly Leu Gly Gly Tyr Gly Ala Ala Leu Val Val Ala Val Ala Ala Met
    275                 280                 285

Gly Asp Ala Gly Ala Arg Leu Val Cys Gly Trp Leu Ala Asp Gln Gly
290                 295                 300

Trp Val Pro Leu Pro Arg Leu Leu Ala Val Phe Gly Ala Leu Thr Gly
305                 310                 315                 320

Leu Gly Leu Trp Val Gly Leu Val Pro Val Gly Gly Glu Glu
                325                 330                 335

Ser Trp Gly Gly Pro Leu Leu Ala Ala Ala Val Ala Tyr Gly Leu Ser
            340                 345                 350

Ala Gly Ser Tyr Ala Pro Leu Val Phe Gly Val Leu Pro Gly Leu Val
    355                 360                 365

Gly Val Gly Gly Val Val Gln Ala Thr Gly Leu Val Met Met Leu Met
370                 375                 380
```

```
Ser Leu Gly Gly Leu Leu Gly Pro Pro Leu Ser Gly Phe Leu Arg Asp
385                 390                 395                 400

Glu Thr Gly Asp Phe Thr Ala Ser Phe Leu Leu Ser Gly Ser Leu Ile
            405                 410                 415

Leu Ser Gly Ser Phe Ile Tyr Ile Gly Leu Pro Arg Ala Leu Pro Ser
        420                 425                 430

Cys Gly Pro Ala Ser Pro Pro Ala Thr Pro Pro Glu Thr Gly Glu
        435                 440                 445

Leu Leu Pro Ala Pro Gln Ala Val Leu Leu Ser Pro Gly Gly Pro Gly
    450                 455                 460

Ser Thr Leu Asp Thr Thr Cys
465                 470

<210> SEQ ID NO 4
<211> LENGTH: 1803
<212> TYPE: DNA
<213> ORGANISM: Homo sapiens

<400> SEQUENCE: 4
atctctgttt accgagagag cccgtccaag ttgggctcca tcgctgccct cgctcccctt      60
cggggccccc gcccgcctgg aagcagaga gaaagccggg cccagccctt cctcacccct     120
cccctccccg caccgcccgg agaggtcggg taagggggaa ggagtgtgcg tgggacgggg    180
aacctcgggc ctggggatct ggctgtcccc gtccccgtac ctcgcgcgga cccgggagtt    240
ccagccctag gccaggctcc ggctccctcc gccccgcgcc atcgcgctcg gagtgacggg    300
cccaccccgg gcgagcagcc agaggctgga tctcagggat gccagctccc agcggaagc    360 acaggcgtgg aggcttctct cacagatgtt tccccacccc gcagacggcg atgaccccc    420 agcccgccga accccggat gggggctggg gctggtggt ggcggccgca gccttcgcga    480
taaacgggct gtcctacggg ctgctgcgct cgctgggcct tgccttccct gaccttgccg    540
agcactttga ccgaagcgcc caggacactg cgtggatcag cgccctggcc ctggccgtgc    600
agcaggcagc cagccccgtg ggcagcgccc tgagcacgcg ctgggggggcc cgccccgtgg    660 tgatggttgg gggcgtcctc gcctcgctgg gcttcgtctt ctcggctttc gccagcgatc    720
tgctgcatct ctacctcggc ctgggcctcc tcgctggctt tggttgggcc ctggtgttcg    780
cccccgccct aggcacccct cgcgttact tctcccgccg tcgagtcttg gcggtggggc    840
tggcgctcac cggcaacggg gcctcctcgc tgctcctggc gcccgccttg cagcttcttc    900
tcgatacttt cggctggcgg ggcgctctgc tcctcctcgg cgcgatcacc ctccacctca    960 cccctgtgg cgccctgctg ctacccctgg tccttcctgg agaccccca gccccaccgc    1020 gtagtcccct agctgccctc ggcctgagtc tgttcacacg ccgggccttc tcaatctttg    1080
ctctaggcac agccctggtt gggggcgggt acttcgttcc ttacgtgcac ttggctcccc    1140
acgctttaga ccggggcctg gggggatacg gagcagcgct ggtggtggcc gtggctgcga    1200
tgggggatgc gggcgcccgg ctggtctgcg ggtggctgg agaccaaggc tgggtgcccc    1260
tcccgcggct gctggccgta ttcggggctc tgactgggct ggggctgtgg gtggtggggc    1320
tggtgcccgt ggtgggcggc gaagagagct ggggggggtcc cctgctggcc gcggctgtgg    1380
cctatgggct gagcgcgggg agttacgccc cgctggtttt cggtgtactc cccgggctgg    1440
tgggcgtcgg aggtgtggtg caggccacag gctggtggat gatgctgatg agcctcgggg    1500
ggctcctggg ccctcccctg tcaggcttcc taagggatga gacaggagac ttcaccgcct    1560 cttttcctcct gtctggttct tgatcctct ccggcagctt catctacata gggttgccca    1620
```

-continued

```
gggcgctgcc ctcctgtggt ccagcctccc ctccagccac gcctccccca gagacggggg   1680
agctgcttcc cgctcccag gcagtcttgc tgtccccagg aggccctggc tccactctgg    1740
acaccacttg ttgattattt tcttgtttga gcccctcccc caataaagaa tttttatcgg   1800
gtt                                                                 1803
```

<210> SEQ ID NO 5
<211> LENGTH: 2549
<212> TYPE: PRT
<213> ORGANISM: Homo sapiens

<400> SEQUENCE: 5

```
Met Leu Gly Thr Gly Pro Ala Ala Thr Thr Ala Ala Thr Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Met Glu Glu
        275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335
```

```
Ser Ser His Gln Gly Leu Met Gly Phe Gly Thr Ser Pro Ser Pro Ala
        340                 345                 350
Lys Ser Thr Leu Val Glu Ser Arg Cys Cys Arg Asp Leu Met Glu Glu
        355                 360                 365
Lys Phe Asp Gln Val Cys Gln Trp Val Leu Lys Cys Arg Asn Ser Lys
        370                 375                 380
Asn Ser Leu Ile Gln Met Thr Ile Leu Asn Leu Leu Pro Arg Leu Ala
385                 390                 395                 400
Ala Phe Arg Pro Ser Ala Phe Thr Asp Thr Gln Tyr Leu Gln Asp Thr
                405                 410                 415
Met Asn His Val Leu Ser Cys Val Lys Lys Glu Lys Glu Arg Thr Ala
                420                 425                 430
Ala Phe Gln Ala Leu Gly Leu Leu Ser Val Ala Val Arg Ser Glu Phe
                435                 440                 445
Lys Val Tyr Leu Pro Arg Val Leu Asp Ile Ile Arg Ala Ala Leu Pro
        450                 455                 460
Pro Lys Asp Phe Ala His Lys Arg Gln Lys Ala Met Gln Val Asp Ala
465                 470                 475                 480
Thr Val Phe Thr Cys Ile Ser Met Leu Ala Arg Ala Met Gly Pro Gly
                485                 490                 495
Ile Gln Gln Asp Ile Lys Glu Leu Leu Glu Pro Met Leu Ala Val Gly
                500                 505                 510
Leu Ser Pro Ala Leu Thr Ala Val Leu Tyr Asp Leu Ser Arg Gln Ile
        515                 520                 525
Pro Gln Leu Lys Lys Asp Ile Gln Asp Gly Leu Leu Lys Met Leu Ser
        530                 535                 540
Leu Val Leu Met His Lys Pro Leu Arg His Pro Gly Met Pro Lys Gly
545                 550                 555                 560
Leu Ala His Gln Leu Ala Ser Pro Gly Leu Thr Thr Leu Pro Glu Ala
                565                 570                 575
Ser Asp Val Gly Ser Ile Thr Leu Ala Leu Arg Thr Leu Gly Ser Phe
                580                 585                 590
Glu Phe Glu Gly His Ser Leu Thr Gln Phe Val Arg His Cys Ala Asp
        595                 600                 605
His Phe Leu Asn Ser Glu His Lys Glu Ile Arg Met Glu Ala Ala Arg
        610                 615                 620
Thr Cys Ser Arg Leu Leu Thr Pro Ser Ile His Leu Ile Ser Gly His
625                 630                 635                 640
Ala His Val Val Ser Gln Thr Ala Val Gln Val Val Ala Asp Val Leu
                645                 650                 655
Ser Lys Leu Leu Val Val Gly Ile Thr Asp Pro Asp Pro Asp Ile Arg
                660                 665                 670
Tyr Cys Val Leu Ala Ser Leu Asp Glu Arg Phe Asp Ala His Leu Ala
        675                 680                 685
Gln Ala Glu Asn Leu Gln Ala Leu Phe Val Ala Leu Asn Asp Gln Val
        690                 695                 700
Phe Glu Ile Arg Glu Leu Ala Ile Cys Thr Val Gly Arg Leu Ser Ser
705                 710                 715                 720
Met Asn Pro Ala Phe Val Met Pro Phe Leu Arg Lys Met Leu Ile Gln
                725                 730                 735
Ile Leu Thr Glu Leu Glu His Ser Gly Ile Gly Arg Ile Lys Glu Gln
                740                 745                 750
```

```
Ser Ala Arg Met Leu Gly His Leu Val Ser Asn Ala Pro Arg Leu Ile
        755                 760                 765

Arg Pro Tyr Met Glu Pro Ile Leu Lys Ala Leu Ile Leu Lys Leu Lys
    770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
            805                 810                 815

Val Asp Glu Leu Phe Ile Ile Ile Met Asp Met Leu Gln Asp Ser Ser
        820                 825                 830

Leu Leu Ala Lys Arg Gln Val Ala Leu Trp Thr Leu Gly Gln Leu Val
            835                 840                 845

Ala Ser Thr Gly Tyr Val Val Glu Pro Tyr Arg Lys Tyr Pro Thr Leu
        850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
            885                 890                 895

Tyr Lys His Lys Val Asn Ile Gly Met Ile Asp Gln Ser Arg Asp Ala
        900                 905                 910

Ser Ala Val Ser Leu Ser Glu Ser Lys Ser Ser Gln Asp Ser Ser Asp
        915                 920                 925

Tyr Ser Thr Ser Glu Met Leu Val Asn Met Gly Asn Leu Pro Leu Asp
        930                 935                 940

Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
            965                 970                 975

Phe Ile Phe Lys Ser Leu Gly Leu Lys Cys Val Gln Phe Leu Pro Gln
        980                 985                 990

Val Met Pro Thr Phe Leu Asn Val Ile Arg Val Cys Asp Gly Ala Ile
        995                 1000                1005

Arg Glu Phe Leu Phe Gln Gln Leu Gly Met Leu Val Ser Phe Val
    1010                1015                1020

Lys Ser His Ile Arg Pro Tyr Met Asp Glu Ile Val Thr Leu Met
    1025                1030                1035

Arg Glu Phe Trp Val Met Asn Thr Ser Ile Gln Ser Thr Ile Ile
    1040                1045                1050

Leu Leu Ile Glu Gln Ile Val Val Ala Leu Gly Gly Glu Phe Lys
    1055                1060                1065

Leu Tyr Leu Pro Gln Leu Ile Pro His Met Leu Arg Val Phe Met
    1070                1075                1080

His Asp Asn Ser Pro Gly Arg Ile Val Ser Ile Lys Leu Leu Ala
    1085                1090                1095

Ala Ile Gln Leu Phe Gly Ala Asn Leu Asp Asp Tyr Leu His Leu
    1100                1105                1110

Leu Leu Pro Pro Ile Val Lys Leu Phe Asp Ala Pro Glu Ala Pro
    1115                1120                1125

Leu Pro Ser Arg Lys Ala Ala Leu Glu Thr Val Asp Arg Leu Thr
    1130                1135                1140

Glu Ser Leu Asp Phe Thr Asp Tyr Ala Ser Arg Ile Ile His Pro
    1145                1150                1155

Ile Val Arg Thr Leu Asp Gln Ser Pro Glu Leu Arg Ser Thr Ala
```

|      |      |      |      | 1160 |      |      |      |      | 1165 |      |      |      |      | 1170 |
|---|---|---|---|---|---|---|---|---|---|---|---|---|---|---|

Met Asp Thr Leu Ser Ser Leu Val Phe Gln Leu Gly Lys Lys Tyr
             1175             1180                 1185

Gln Ile Phe Ile Pro Met Val Asn Lys Val Leu Val Arg His Arg
             1190             1195                 1200

Ile Asn His Gln Arg Tyr Asp Val Leu Ile Cys Arg Ile Val Lys
             1205             1210                 1215

Gly Tyr Thr Leu Ala Asp Glu Glu Asp Pro Leu Ile Tyr Gln
             1220             1225                 1230

His Arg Met Leu Arg Ser Gly Gln Gly Asp Ala Leu Ala Ser Gly
             1235             1240                 1245

Pro Val Glu Thr Gly Pro Met Lys Lys Leu His Val Ser Thr Ile
             1250             1255                 1260

Asn Leu Gln Lys Ala Trp Gly Ala Ala Arg Arg Val Ser Lys Asp
             1265             1270                 1275

Asp Trp Leu Glu Trp Leu Arg Arg Leu Ser Leu Glu Leu Leu Lys
             1280             1285                 1290

Asp Ser Ser Ser Pro Ser Leu Arg Ser Cys Trp Ala Leu Ala Gln
             1295             1300                 1305

Ala Tyr Asn Pro Met Ala Arg Asp Leu Phe Asn Ala Ala Phe Val
             1310             1315                 1320

Ser Cys Trp Ser Glu Leu Asn Glu Asp Gln Gln Asp Glu Leu Ile
             1325             1330                 1335

Arg Ser Ile Glu Leu Ala Leu Thr Ser Gln Asp Ile Ala Glu Val
             1340             1345                 1350

Thr Gln Thr Leu Leu Asn Leu Ala Glu Phe Met Glu His Ser Asp
             1355             1360                 1365

Lys Gly Pro Leu Pro Leu Arg Asp Asp Asn Gly Ile Val Leu Leu
             1370             1375                 1380

Gly Glu Arg Ala Ala Lys Cys Arg Ala Tyr Ala Lys Ala Leu His
             1385             1390                 1395

Tyr Lys Glu Leu Glu Phe Gln Lys Gly Pro Thr Pro Ala Ile Leu
             1400             1405                 1410

Glu Ser Leu Ile Ser Ile Asn Asn Lys Leu Gln Gln Pro Glu Ala
             1415             1420                 1425

Ala Ala Gly Val Leu Glu Tyr Ala Met Lys His Phe Gly Glu Leu
             1430             1435                 1440

Glu Ile Gln Ala Thr Trp Tyr Glu Lys Leu His Glu Trp Glu Asp
             1445             1450                 1455

Ala Leu Val Ala Tyr Asp Lys Lys Met Asp Thr Asn Lys Asp Asp
             1460             1465                 1470

Pro Glu Leu Met Leu Gly Arg Met Arg Cys Leu Glu Ala Leu Gly
             1475             1480                 1485

Glu Trp Gly Gln Leu His Gln Gln Cys Cys Glu Lys Trp Thr Leu
             1490             1495                 1500

Val Asn Asp Glu Thr Gln Ala Lys Met Ala Arg Met Ala Ala Ala
             1505             1510                 1515

Ala Ala Trp Gly Leu Gly Gln Trp Asp Ser Met Glu Glu Tyr Thr
             1520             1525                 1530

Cys Met Ile Pro Arg Asp Thr His Asp Gly Ala Phe Tyr Arg Ala
             1535             1540                 1545

Val Leu Ala Leu His Gln Asp Leu Phe Ser Leu Ala Gln Gln Cys
             1550             1555                 1560

Ile Asp Lys Ala Arg Asp Leu Leu Asp Ala Glu Leu Thr Ala Met
1565                1570                1575

Ala Gly Glu Ser Tyr Ser Arg Ala Tyr Gly Ala Met Val Ser Cys
1580                1585                1590

His Met Leu Ser Glu Leu Glu Glu Val Ile Gln Tyr Lys Leu Val
1595                1600                1605

Pro Glu Arg Arg Glu Ile Ile Arg Gln Ile Trp Trp Glu Arg Leu
1610                1615                1620

Gln Gly Cys Gln Arg Ile Val Glu Asp Trp Gln Lys Ile Leu Met
1625                1630                1635

Val Arg Ser Leu Val Val Ser Pro His Glu Asp Met Arg Thr Trp
1640                1645                1650

Leu Lys Tyr Ala Ser Leu Cys Gly Lys Ser Gly Arg Leu Ala Leu
1655                1660                1665

Ala His Lys Thr Leu Val Leu Leu Leu Gly Val Asp Pro Ser Arg
1670                1675                1680

Gln Leu Asp His Pro Leu Pro Thr Val His Pro Gln Val Thr Tyr
1685                1690                1695

Ala Tyr Met Lys Asn Met Trp Lys Ser Ala Arg Lys Ile Asp Ala
1700                1705                1710

Phe Gln His Met Gln His Phe Val Gln Thr Met Gln Gln Gln Ala
1715                1720                1725

Gln His Ala Ile Ala Thr Glu Asp Gln Gln His Lys Gln Glu Leu
1730                1735                1740

His Lys Leu Met Ala Arg Cys Phe Leu Lys Leu Gly Glu Trp Gln
1745                1750                1755

Leu Asn Leu Gln Gly Ile Asn Glu Ser Thr Ile Pro Lys Val Leu
1760                1765                1770

Gln Tyr Tyr Ser Ala Ala Thr Glu His Asp Arg Ser Trp Tyr Lys
1775                1780                1785

Ala Trp His Ala Trp Ala Val Met Asn Phe Glu Ala Val Leu His
1790                1795                1800

Tyr Lys His Gln Asn Gln Ala Arg Asp Glu Lys Lys Lys Leu Arg
1805                1810                1815

His Ala Ser Gly Ala Asn Ile Thr Asn Ala Thr Thr Ala Ala Thr
1820                1825                1830

Thr Ala Ala Thr Ala Thr Thr Thr Ala Ser Thr Glu Gly Ser Asn
1835                1840                1845

Ser Glu Ser Glu Ala Glu Ser Thr Glu Asn Ser Pro Thr Pro Ser
1850                1855                1860

Pro Leu Gln Lys Lys Val Thr Glu Asp Leu Ser Lys Thr Leu Leu
1865                1870                1875

Met Tyr Thr Val Pro Ala Val Gln Gly Phe Phe Arg Ser Ile Ser
1880                1885                1890

Leu Ser Arg Gly Asn Asn Leu Gln Asp Thr Leu Arg Val Leu Thr
1895                1900                1905

Leu Trp Phe Asp Tyr Gly His Trp Pro Asp Val Asn Glu Ala Leu
1910                1915                1920

Val Glu Gly Val Lys Ala Ile Gln Ile Asp Thr Trp Leu Gln Val
1925                1930                1935

Ile Pro Gln Leu Ile Ala Arg Ile Asp Thr Pro Arg Pro Leu Val
1940                1945                1950

```
Gly Arg Leu Ile His Gln Leu Leu Thr Asp Ile Gly Arg Tyr His
1955                1960                1965

Pro Gln Ala Leu Ile Tyr Pro Leu Thr Val Ala Ser Lys Ser Thr
1970                1975                1980

Thr Thr Ala Arg His Asn Ala Ala Asn Lys Ile Leu Lys Asn Met
1985                1990                1995

Cys Glu His Ser Asn Thr Leu Val Gln Gln Ala Met Met Val Ser
2000                2005                2010

Glu Glu Leu Ile Arg Val Ala Ile Leu Trp His Glu Met Trp His
2015                2020                2025

Glu Gly Leu Glu Glu Ala Ser Arg Leu Tyr Phe Gly Glu Arg Asn
2030                2035                2040

Val Lys Gly Met Phe Glu Val Leu Glu Pro Leu His Ala Met Met
2045                2050                2055

Glu Arg Gly Pro Gln Thr Leu Lys Glu Thr Ser Phe Asn Gln Ala
2060                2065                2070

Tyr Gly Arg Asp Leu Met Glu Ala Gln Glu Trp Cys Arg Lys Tyr
2075                2080                2085

Met Lys Ser Gly Asn Val Lys Asp Leu Thr Gln Ala Trp Asp Leu
2090                2095                2100

Tyr Tyr His Val Phe Arg Arg Ile Ser Lys Gln Leu Pro Gln Leu
2105                2110                2115

Thr Ser Leu Glu Leu Gln Tyr Val Ser Pro Lys Leu Leu Met Cys
2120                2125                2130

Arg Asp Leu Glu Leu Ala Val Pro Gly Thr Tyr Asp Pro Asn Gln
2135                2140                2145

Pro Ile Ile Arg Ile Gln Ser Ile Ala Pro Ser Leu Gln Val Ile
2150                2155                2160

Thr Ser Lys Gln Arg Pro Arg Lys Leu Thr Leu Met Gly Ser Asn
2165                2170                2175

Gly His Glu Phe Val Phe Leu Leu Lys Gly His Glu Asp Leu Arg
2180                2185                2190

Gln Asp Glu Arg Val Met Gln Leu Phe Gly Leu Val Asn Thr Leu
2195                2200                2205

Leu Ala Asn Asp Pro Thr Ser Leu Arg Lys Asn Leu Ser Ile Gln
2210                2215                2220

Arg Tyr Ala Val Ile Pro Leu Ser Thr Asn Ser Gly Leu Ile Gly
2225                2230                2235

Trp Val Pro His Cys Asp Thr Leu His Ala Leu Ile Arg Asp Tyr
2240                2245                2250

Arg Glu Lys Lys Lys Ile Leu Leu Asn Ile Glu His Arg Ile Met
2255                2260                2265

Leu Arg Met Ala Pro Asp Tyr Asp His Leu Thr Leu Met Gln Lys
2270                2275                2280

Val Glu Val Phe Glu His Ala Val Asn Asn Thr Ala Gly Asp Asp
2285                2290                2295

Leu Ala Lys Leu Leu Trp Leu Lys Ser Pro Ser Ser Glu Val Trp
2300                2305                2310

Phe Asp Arg Arg Thr Asn Tyr Thr Arg Ser Leu Ala Val Met Ser
2315                2320                2325

Met Val Gly Tyr Ile Leu Gly Leu Gly Asp Arg His Pro Ser Asn
2330                2335                2340

Leu Met Leu Asp Arg Leu Ser Gly Lys Ile Leu His Ile Asp Phe
```

```
                2345                2350                2355
Gly Asp Cys Phe Glu Val Ala Met Thr Arg Glu Lys Phe Pro Glu
    2360                2365                2370
Lys Ile Pro Phe Arg Leu Thr Arg Met Leu Thr Asn Ala Met Glu
    2375                2380                2385
Val Thr Gly Leu Asp Gly Asn Tyr Arg Ile Thr Cys His Thr Val
    2390                2395                2400
Met Glu Val Leu Arg Glu His Lys Asp Ser Val Met Ala Val Leu
    2405                2410                2415
Glu Ala Phe Val Tyr Asp Pro Leu Leu Asn Trp Arg Leu Met Asp
    2420                2425                2430
Thr Asn Thr Lys Gly Asn Lys Arg Ser Arg Thr Arg Thr Asp Ser
    2435                2440                2445
Tyr Ser Ala Gly Gln Ser Val Glu Ile Leu Asp Gly Val Glu Leu
    2450                2455                2460
Gly Glu Pro Ala His Lys Lys Thr Gly Thr Thr Val Pro Glu Ser
    2465                2470                2475
Ile His Ser Phe Ile Gly Asp Gly Leu Val Lys Pro Glu Ala Leu
    2480                2485                2490
Asn Lys Lys Ala Ile Gln Ile Ile Asn Arg Val Arg Asp Lys Leu
    2495                2500                2505
Thr Gly Arg Asp Phe Ser His Asp Asp Thr Leu Asp Val Pro Thr
    2510                2515                2520
Gln Val Glu Leu Leu Ile Lys Gln Ala Thr Ser His Glu Asn Leu
    2525                2530                2535
Cys Gln Cys Tyr Ile Gly Trp Cys Pro Phe Trp
    2540                2545

<210> SEQ ID NO 6
<211> LENGTH: 8733
<212> TYPE: DNA
<213> ORGANISM: Homo sapiens

<400> SEQUENCE: 6
gctcccggct tagaggacag cggggaaggc gggcggtggg gcaggggggcc tgaagcggcg    60 gtaccggtgc tggcggcggc agctgaggcc ttggccgaag ccgcgcgaac ctcagggcaa   120
gatgcttgga accggacctg ccgccgccac caccgctgcc accacatcta gcaatgtgag   180
cgtcctgcag cagtttgcca gtggcctaaa gagccggaat gaggaaacca gggccaaagc   240
cgccaaggag ctccagcact atgtcaccat ggaactccga gagatgagtc aagaggagtc   300
tactcgcttc tatgaccaac tgaaccatca cattttttgaa ttggtttcca gctcagatgc   360
caatgagagg aaaggtggca tcttggccat agctagcctc ataggagtgg aagtgggaa    420 tgccacccga attggcagat tgccaactga tcttcggaac ctcctcccct ccaatgaccc   480
agttgtcatg gaaatggcat ccaaggccat tggccgtctt gccatggcag ggacacttt    540 taccgctgag tacgtggaat tgaggtgaa gcgagccctg aatggctggg tgctgaccg    600 caatgagggc cggagacatg cagctgtcct ggttctccgt gagctggcca tcagcgtccc   660
taccttcttc ttccagcaag tgcaacccct ctttgacaac attttttgtgg ccgtgtggga   720 ccccaaacag gccatccgtg agggagctgt agccgccctt cgtgcctgtc tgattctcac   780
aacccagcgt gagccgaagg agatgcagaa gcctcagtgg tacaggcaca catttgaaga   840
agcagagaag ggatttgatg agaccttggc caaagagaag ggcatgaatc gggatgatcg   900
```

```
gatccatgga gccttgttga tccttaacga gctggtccga atcagcagca tggagggaga    960
gcgtctgaga gaagaaatgg aagaaatcac acagcagcag ctggtacacg acaagtactg   1020
caaagatctc atgggcttcg gaacaaaacc tcgtcacatt accccttca ccagtttcca    1080
ggctgtacag ccccagcagt caaatgcctt ggtggggctg ctggggtaca gctctcacca   1140
aggcctcatg ggatttggga cctcccccag tccagctaag tccaccctgg tggagagccg   1200
gtgttgcaga gacttgatgg aggagaaatt tgatcaggtg tgccagtggg tgctgaaatg   1260
caggaatagc aagaactcgc tgatccaaat gacaatcctt aatttgttgc cccgcttggc   1320
tgcattccga ccttctgcct tcacagatac ccagtatctc caagatacca tgaaccatgt   1380
cctaagctgt gtcaagaagg agaaggaacg tacagcggcc ttccaagccc tggggctact   1440
ttctgtggct gtgaggtctg agtttaaggt ctatttgcct cgcgtgctgg acatcatccg   1500
agcggccctg cccccaaagg acttcgccca taagaggcag aaggcaatgc aggtggatgc   1560
cacagtcttc acttgcatca gcatgctggc tcgagcaatg gggccaggca tccagcagga   1620
tatcaaggag ctgctggagc ccatgctggc agtgggacta agccctgccc tcactgcagt   1680
gctctacgac ctgagccgtc agattccaca gctaaagaag gacattcaag atgggctact   1740
gaaaatgctg tccctggtcc ttatgcacaa accccttcgc cacccaggca tgcccaaggg   1800
cctggcccat cagctggcct ctcctggcct cacgaccctc cctgaggcca gcgatgtggg   1860
cagcatcact cttgccctcc gaacgcttgg cagctttgaa tttgaaggcc actctctgac   1920
ccaatttgtt cgccactgtg cggatcattt cctgaacagt gagcacaagg agatccgcat   1980
ggaggctgcc cgcacctgct cccgcctgct cacaccctcc atccacctca tcagtggcca   2040
tgctcatgtg gttagccaga ccgcagtgca agtggtggca gatgtgctta gcaaactgct   2100
cgtagttggg ataacagatc ctgaccctga cattcgctac tgtgtcttgg cgtccctgga   2160
cgagcgcttt gatgcacacc tggcccaggc ggagaacttg caggccttgt tgtggctct    2220
gaatgaccag gtgtttgaga tccgggagct ggccatctgc actgtgggcc gactcagtag   2280
catgaaccct gcctttgtca tgcctttcct gcgcaagatg ctcatccaga ttttgacaga   2340
gttggagcac agtgggattg aagaatcaa agagcagagt gcccgcatgc tggggcacct    2400
ggtctccaat gcccccgac tcatccgccc ctacatggag cctattctga aggcattaat    2460
tttgaaactg aaagatccag accctgatcc aaacccaggt gtgatcaata atgtcctggc   2520
aacaatagga gaattggcac aggttagtgg cctggaaatg aggaaatggg ttgatgaact   2580
ttttattatc atcatggaca tgctccagga ttcctctttg ttggccaaaa ggcaggtggc   2640
tctgtggacc ctgggacagt tggtggccag cactggctat gtagtagagc cctacaggaa   2700
gtaccctact ttgcttgagg tgctactgaa ttttctgaag actgagcaga accagggtac   2760
acgcagagag gccatccgtg tgttagggct tttaggggct ttggatcctt acaagcacaa   2820
agtgaacatt ggcatgatag accagtcccg ggatgcctct gctgtcagcc tgtcagaatc   2880
caagtcaagt caggattcct ctgactatag cactagtgaa atgctggtca acatgggaaa   2940
cttgcctctg gatgagttct acccagctgt gtccatggtg ccctgatgc ggatcttccg    3000
agaccagtca ctctctcatc atcacaccat ggttgtccag gccatcacct tcatcttcaa   3060
gtccctggga ctcaaatgtg tgcagttcct gccccaggtc atgcccacgt tccttaacgt   3120
cattcgagtc tgtgatgggg ccatccggga attttgttc cagcagctgg gaatgttggt    3180
gtcctttgtg aagagccaca tcagaccctta tatggatgaa atagtcaccc tcatgagaga   3240
attctgggtc atgaacacct caattcagag cacgatcatt cttctcattg agcaaattgt   3300
```

```
ggtagctctt gggggtgaat ttaagctcta cctgccccag ctgatcccac acatgctgcg    3360
tgtcttcatg catgacaaca gcccaggccg cattgtctct atcaagttac tggctgcaat    3420
ccagctgttt ggcgccaacc tggatgacta cctgcattta ctgctgcctc ctattgttaa    3480
gttgtttgat gccctgaag ctccactgcc atctcgaaag gcagcgctag agactgtgga    3540
ccgcctgacg gagtccctgg atttcactga ctatgcctcc cggatcattc accctattgt    3600
tcgaacactg gaccagagcc cagaactgcg ctccacagcc atggcacgc tgtcttcact    3660 tgttttcag ctggggaaga agtaccaaat tttcattcca atggtgaata aagttctggt    3720
gcgacaccga atcaatcatc agcgctatga tgtgctcatc tgcagaattg tcaagggata    3780
cacacttgct gatgaagagg aggatccttt gatttaccag catcggatgc ttaggagtgg    3840
ccaaggggat gcattggcta gtggaccagt ggaaacagga cccatgaaga aactgcacgt    3900
cagcaccatc aacctccaaa aggcctgggg cgctgccagg agggtctcca agatgactg    3960 gctggaatgg ctgagacggc tgagcctgga gctgctgaag gactcatcat cgccctccct    4020
gcgctcctgc tgggccctgg cacaggccta aacccgatg gccagggatc tcttcaatgc    4080
tgcatttgtg tcctgctggt ctgaactgaa tgaagatcaa caggatgagc tcatcagaag    4140
catcgagttg gccctcacct cacaagacat cgctgaagtc acacagaccc tcttaaactt    4200
ggctgaattc atggaacaca gtgacaaggg cccctgcca ctgagagatg acaatggcat    4260
tgttctgctg ggtgagagag ctgccaagtg ccgagcatat gccaaagcac tacactacaa    4320
agaactggag ttccagaaag gccccacccc tgccattcta gaatctctca tcagcattaa    4380
taataagcta cagcagccgg aggcagcggc cggagtgtta gaatatgcca tgaaacactt    4440
tggagagctg gagatccagg ctacctggta tgagaaactg cacgagtggg aggatgccct    4500
tgtggcctat gacaagaaaa tggacaccaa caaggacgac ccagagctga tgctgggccg    4560
catgcgctgc ctcgaggcct tgggggaatg gggtcaactc caccagcagt gctgtgaaaa    4620
gtggaccctg gttaatgatg agacccaagc caagatggcc cggatggctg ctgcagctgc    4680
atggggttta ggtcagtggg acagcatgga agaatacacc tgtatgatcc ctcgggacac    4740
ccatgatggg gcatttata gagctgtgct ggcactgcat caggacctct tctccttggc    4800
acaacagtgc attgacaagg ccagggacct gctggatgct gaattaactg cgatggcagg    4860
agagagttac agtcgggcat atggggccat ggtttcttgc cacatgctgt ccgagctgga    4920
ggaggttatc cagtacaaac ttgtccccga gcgacgagag atcatccgcc agatctggtg    4980
ggagagactg cagggctgcc agcgtatcgt agaggactgg cagaaaatcc ttatggtgcg    5040
gtcccttgtg gtcagccctc atgaagacat gagaacctgg ctcaagtatg caagcctgtg    5100
cggcaagagt ggcaggctgg ctcttgctca taaaacttta gtgttgctcc tgggagttga    5160
tccgtctcgg caacttgacc atcctctgcc aacagttcac cctcaggtga cctatgccta    5220
catgaaaaac atgtggaaga gtgcccgcaa gatcgatgcc ttccagcaca tgcagcattt    5280
tgtccagacc atgcagcaac aggcccagca tgccatcgct actgaggacc agcagcataa    5340
gcaggaactg cacaagctca tggccccgatg cttcctgaaa cttggagagt ggcagctgaa    5400
tctacagggc atcaatgaga gcacaatccc caaagtgctg cagtactaca gcgccgccac    5460
agagcacgac cgcagctggt acaaggcctg gcatgcgtgg gcagtgatga acttcgaagc    5520
tgtgctacac tacaaacatc agaaccaagc ccgcgatgaa aagaagaaac tgcgtcatgc    5580
cagcggggcc aacatcacca cgccaccac tgccgccacc acggccgcca ctgccaccac    5640
```

```
cactgccagc accgagggca gcaacagtga gagcgaggcc gagagcaccg agaacagccc      5700 cacccccatcg ccgctgcaga agaaggtcac tgaggatctg tccaaaaccc tcctgatgta    5760
cacggtgcct gccgtccagg gcttcttccg ttccatctcc ttgtcacgag gcaacaacct     5820
ccaggataca ctcagagttc taccttatg gtttgattat ggtcactggc cagatgtcaa      5880
tgaggcctta gtggagggg tgaaagccat ccagattgat acctggctac aggttatacc      5940
tcagctcatt gcaagaattg atacgccag acccttggtg ggacgtctca ttcaccagct      6000
tctcacagac attggtcggt accaccccca ggccctcatc tacccactga cagtggcttc     6060
taagtctacc acgacagccc ggcacaatgc agccaacaag attctgaaga acatgtgtga    6120
gcacagcaac ccctggtcc agcaggccat gatggtgagc gaggagctga tccgagtggc     6180
catcctctgg catgagatgt ggcatgaagg cctggaagag gcatctcgtt tgtactttgg    6240
ggaaaggaac gtgaaaggca tgtttgaggt gctggagccc ttgcatgcta tgatggaacg    6300
gggcccccag actctgaagg aaacatcctt taatcaggcc tatggtcgag atttaatgga    6360
ggcccaagag tggtgcagga agtacatgaa atcagggaat gtcaaggacc tcacccaagc    6420
ctgggacctc tattatcatg tgttccgacg aatctcaaag cagctgcctc agctcacatc     6480
cttagagctg caatatgttt ccccaaaact tctgatgtgc cgggaccttg aattggctgt    6540
gccaggaaca tatgacccca accagccaat cattcgcatt cagtccatag caccgtcttt    6600
gcaagtcatc acatccaagc agaggccccg gaaattgaca cttatgggca gcaacggaca    6660
tgagtttgtt ttccttctaa aaggccatga agatctgcgc caggatgagc gtgtgatgca    6720
gctcttcggc ctggttaaca cccttctggc caatgaccca acatctcttc ggaaaaacct    6780
cagcatccag agatacgctg tcatcccttt atcgaccaac tcgggcctca ttggctgggt    6840 tcccactgt gacacactgc acgccctcat ccgggactac agggagaaga agaagatcct     6900
tctcaacatc gagcatcgca tcatgttgcg gatggctccg gactatgacc acttgactct     6960
gatgcagaag gtgaggtgt ttgagcatgc cgtcaataat acagctgggg acgacctggc     7020
caagctgctg tggctgaaaa gccccagctc cgaggtgtgg tttgaccgaa gaaccaatta    7080
tacccgttct ttagcggtca tgtcaatggt tgggtatatt ttaggcctgg gagatagaca    7140
cccatccaac ctgatgctgg accgtctgag tgggaagatc ctgcacattg actttgggga    7200
ctgctttgag gttgctatga cccgagagaa gtttccagag aagattccat ttagactaac    7260
aagaatgttg accaatgcta tggaggttac aggcctggat ggcaactaca gaatcacatg    7320
ccacacagtg atggaggtgc tgcgagagca caaggacagt gtcatggccg tgctggaagc    7380 cttttgtctat gaccccttgc tgaactggag gctgatggac acaaatacca aaggcaacaa    7440
gcgatcccga acgaggacgg attcctactc tgctggccag tcagtcgaaa ttttggacgg    7500
tgtggaactt ggagagccag cccataagaa aacgggacc acagtgccag aatctattca    7560
ttctttcatt ggagacggtt tggtgaaacc agaggcccta aataagaaag ctatccagat    7620
tattaacagg gttcgagata agctcactgg tcggacttc tctcatgatg acactttgga    7680
tgttccaacg caagttgagc tgctcatcaa acaagcgaca tcccatgaaa acctctgcca    7740
gtgctatatt ggctggtgcc cttttctggta actggaggcc cagatgtgcc catcacgttt    7800
tttctgaggc ttttgtactt tagtaaatgc ttccactaaa ctgaaaccat ggtgagaaag    7860
tttgactttg ttaaatattt tgaaatgtaa atgaaaagaa ctactgtata ttaaaagttg    7920
gtttgaacca actttctagc tgctgttgaa gaatatattg tcagaaacac aaggcttgat    7980
ttggttccca ggacagtgaa acatagtaat accacgtaaa tcaagccatt catttttgggg   8040
```

-continued

```
aacagaagat ccataacttt agaaatacgg gttttgactt aactcacaag agaactcatc    8100
ataagtactt gctgatggaa gaatgaccta gttgctcctc tcaacatggg tacagcaaac    8160
tcagcacagc caagaagcct caggtcgtgg agaacatgga ttaggatcct agactgtaaa    8220
gacacagaag atgctgacct cacccctgcc acctatccca agacctcact ggtctgtgga    8280
cagcagcaga atgtttgca agataggcca aaatgagtac aaaaggtctg tcttccatca     8340
gacccagtga tgctgcgact cacacgcttc aattcaagac ctgaccgcta gtagggaggt    8400
ttattcagat cgctggcagc ctcggctgag cagatgcaca gagggatca ctgtgcagtg     8460 ggaccaccct cactggcctt ctgcagcagg gttctgggat gttttcagtg gtcaaaatac    8520
tctgtttaga gcaagggctc agaaaacaga aatactgtca tggaggtgct gaacacaggg    8580
aaggtctggt acatattgga aattatgagc agaacaaata ctcaactaaa tgcacaaagt    8640
ataaagtgta gccatgtcta gacaccatgt tgtatcagaa taattttgt gccaataaat     8700 gacatcagaa ttttaaacat atgtaaaaaa aaa                                 8733
```

<210> SEQ ID NO 7
<211> LENGTH: 476
<212> TYPE: PRT
<213> ORGANISM: Homo sapiens

<400> SEQUENCE: 7

```
Met Ala Val Pro Phe Val Glu Asp Trp Asp Leu Val Gln Thr Leu Gly
1               5                   10                  15

Glu Gly Ala Tyr Gly Glu Val Gln Leu Ala Val Asn Arg Val Thr Glu
            20                  25                  30

Glu Ala Val Ala Val Lys Ile Val Asp Met Lys Arg Ala Val Asp Cys
        35                  40                  45

Pro Glu Asn Ile Lys Lys Glu Ile Cys Ile Asn Lys Met Leu Asn His
    50                  55                  60

Glu Asn Val Val Lys Phe Tyr Gly His Arg Arg Glu Gly Asn Ile Gln
65                  70                  75                  80

Tyr Leu Phe Leu Glu Tyr Cys Ser Gly Gly Glu Leu Phe Asp Arg Ile
                85                  90                  95

Glu Pro Asp Ile Gly Met Pro Glu Pro Asp Ala Gln Arg Phe Phe His
            100                 105                 110

Gln Leu Met Ala Gly Val Val Tyr Leu His Gly Ile Gly Ile Thr His
        115                 120                 125

Arg Asp Ile Lys Pro Glu Asn Leu Leu Leu Asp Glu Arg Asp Asn Leu
    130                 135                 140

Lys Ile Ser Asp Phe Gly Leu Ala Thr Val Phe Arg Tyr Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Arg Glu Phe His Ala Glu Pro Val Asp Val Trp
            180                 185                 190

Ser Cys Gly Ile Val Leu Thr Ala Met Leu Ala Gly Glu Leu Pro Trp
        195                 200                 205

Asp Gln Pro Ser Asp Ser Cys Gln Glu Tyr Ser Asp Trp Lys Glu Lys
    210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Asn Pro Ser Ala Arg Ile Thr Ile
```

```
                   245                 250                 255
Pro Asp Ile Lys Lys Asp Arg Trp Tyr Asn Lys Pro Leu Lys Lys Gly
            260                 265                 270

Ala Lys Arg Pro Arg Val Thr Ser Gly Gly Val Ser Glu Ser Pro Ser
            275                 280             285

Gly Phe Ser Lys His Ile Gln Ser Asn Leu Asp Phe Ser Pro Val Asn
        290                 295                 300

Ser Ala Ser Ser Glu Glu Asn Val Lys Tyr Ser Ser Ser Gln Pro Glu
305                 310                 315                 320

Pro Arg Thr Gly Leu Ser Leu Trp Asp Thr Ser Pro Ser Tyr Ile Asp
                325                 330                 335

Lys Leu Val Gln Gly Ile Ser Phe Ser Gln Pro Thr Cys Pro Asp His
            340                 345                 350

Met Leu Leu Asn Ser Gln Leu Leu Gly Thr Pro Gly Ser Ser Gln Asn
                355                 360                 365

Pro Trp Gln Arg Leu Val Lys Arg Met Thr Arg Phe Phe Thr Lys Leu
        370                 375                 380

Asp Ala Asp Lys Ser Tyr Gln Cys Leu Lys Glu Thr Cys Glu Lys Leu
385                 390                 395                 400

Gly Tyr Gln Trp Lys Ser Cys Met Asn Gln Val Thr Ile Ser Thr
                405                 410                 415

Thr Asp Arg Arg Asn Asn Lys Leu Ile Phe Lys Val Asn Leu Leu Glu
                420                 425                 430

Met Asp Asp Lys Ile Leu Val Asp Phe Arg Leu Ser Lys Gly Asp Gly
                435                 440                 445

Leu Glu Phe Lys Arg His Phe Leu Lys Ile Lys Gly Lys Leu Ile Asp
            450                 455                 460

Ile Val Ser Ser Gln Lys Ile Trp Leu Pro Ala Thr
465                 470                 475
```

<210> SEQ ID NO 8
<211> LENGTH: 1821
<212> TYPE: DNA
<213> ORGANISM: Homo sapiens

<400> SEQUENCE: 8

```
ggccggacag tccgccgagg tgctcggtgg agtcatggca gtgccctttg tggaagactg      60
ggacttggtg caaaccctgg gagaaggtgc ctatggagaa gttcaacttg ctgtgaatag     120
agtaactgaa gaagcagtcg cagtgaagat tgtagatatg aagcgtgccg tagactgtcc     180
agaaaatatt aagaaagaga tctgtatcaa taaaatgcta atcatgaaa atgtagtaaa      240
attctatggt cacaggagag aaggcaatat ccaatattta tttctggagt actgtagtgg     300
aggagagctt tttgacagaa tagagccaga cataggcatg cctgaaccag atgctcagag     360
attcttccat caactcatgg caggggtggt ttatctgcat ggtattggaa taactcacag     420
ggatattaaa ccagaaaatc ttctgttgga tgaaagggat aacctcaaaa tctcagactt     480
tggcttggca acagtatttc ggtataataa tcgtgagcgt tgttgaaca agatgtgtgg     540
tactttacca tatgttgctc cagaacttct gaagagaaga gaatttcatg cagaaccagt     600
tgatgtttgg tcctgtggaa tagtacttac tgcaatgctc gctggagaat tgccatggga     660
ccaacccagt gacagctgtc aggagtattc tgactggaaa gaaaaaaaaa catacctcaa     720
cccttggaaa aaaatcgatt ctgctcctct agctctgctg cataaaatct tagttgagaa     780
tccatcagca agaattacca ttccagacat caaaaaagat agatggtaca caaaacccct     840
```

```
caagaaaggg gcaaaaaggc cccgagtcac ttcaggtggt gtgtcagagt ctcccagtgg    900
attttctaag cacattcaat ccaatttgga cttctctcca gtaaacagtg cttctagtga    960
agaaaatgtg aagtactcca gttctcagcc agaacccogc acaggtcttt ccttatggga   1020
taccagcccc tcatacattg ataaattggt acaagggatc agcttttccc agcccacatg   1080
tcctgatcat atgcttttga atagtcagtt acttggcacc ccaggatcct cacagaaccc   1140
ctggcagcgg ttggtcaaaa gaatgacacg attctttacc aaattggatg cagacaaatc   1200
ttatcaatgc ctgaaagaga cttgtgagaa gttgggctat caatggaaga aagttgtat    1260 gaatcaggtt actatatcaa caactgatag gagaaacaat aaactcattt tcaaagtgaa   1320
tttgttagaa atggatgata aatattggt tgacttccgg ctttctaagg gtgatggatt    1380
ggagttcaag agacacttcc tgaagattaa agggaagctg attgatattg tgagcagcca   1440
gaaggtttgg cttcctgcca catgatcgga ccatcggctc tggggaatcc tggtgaatat   1500
agtgctgcta tgttgacatt attcttccta gagaagatta tcctgtcctg caaactgcaa   1560
atagtagttc ctgaagtgtt cacttccctg tttatccaaa catcttccaa tttatttgt   1620 ttgttcggca tacaaataat acctatatct taattgtaag caaaactttg gggaaaggat   1680
gaatagaatt catttgatta tttcttcatg tgtgtttagt atctgaattt gaaactcatc   1740
tggtggaaac caagtttcag gggacatgag ttttccagct tttatacaca cgtatctcat   1800
ttttatcaaa acattttgtt t                                             1821
```

<210> SEQ ID NO 9
<211> LENGTH: 543
<212> TYPE: PRT
<213> ORGANISM: Homo sapiens

<400> SEQUENCE: 9

```
Met Ser Arg Glu Ser Asp Val Glu Ala Gln Gln Ser His Gly Ser Ser
1               5                   10                  15

Ala Cys Ser Gln Pro His Gly Ser Val Thr Gln Ser Gln Gly Ser Ser
            20                  25                  30

Ser Gln Ser Gln Gly Ile Ser Ser Ser Thr Ser Thr Met Pro Asn
        35                  40                  45

Ser Ser Gln Ser Ser His Ser Ser Ser Gly Thr Leu Ser Ser Leu Glu
    50                  55                  60

Thr Val Ser Thr Gln Glu Leu Tyr Ser Ile Pro Glu Asp Gln Glu Pro
65                  70                  75                  80

Glu Asp Gln Glu Pro Glu Glu Pro Thr Pro Ala Pro Trp Ala Arg Leu
                85                  90                  95

Trp Ala Leu Gln Asp Gly Phe Ala Asn Leu Glu Cys Val Asn Asp Asn
            100                 105                 110

Tyr Trp Phe Gly Arg Asp Lys Ser Cys Glu Tyr Cys Phe Asp Glu Pro
        115                 120                 125

Leu Leu Lys Arg Thr Asp Lys Tyr Arg Thr Tyr Ser Lys Lys His Phe
    130                 135                 140

Arg Ile Phe Arg Glu Val Gly Pro Lys Asn Ser Tyr Ile Ala Tyr Ile
145                 150                 155                 160

Glu Asp His Ser Gly Asn Gly Thr Phe Val Asn Thr Glu Leu Val Gly
                165                 170                 175

Lys Gly Lys Arg Arg Pro Leu Asn Asn Asn Ser Glu Ile Ala Leu Ser
            180                 185                 190
```

| | | | | | | | | | | |
|---|---|---|---|---|---|---|---|---|---|---|
|Leu|Ser|Arg|Asn|Lys|Val|Phe|Val|Phe|Asp|Leu|Thr|Val|Asp|Asp|
| |  |195|  |  |  |200|  |  |  |205|  |  |  |  |

Leu Ser Arg Asn Lys Val Phe Val Phe Asp Leu Thr Val Asp Asp
                195                 200                 205

Gln Ser Val Tyr Pro Lys Ala Leu Arg Asp Glu Tyr Ile Met Ser Lys
210                 215                 220

Thr Leu Gly Ser Gly Ala Cys Gly Glu Val Lys Leu Ala Phe Glu Arg
225                 230                 235                 240

Lys Thr Cys Lys Lys Val Ala Ile Lys Ile Ile Ser Lys Arg Lys Phe
                245                 250                 255

Ala Ile Gly Ser Ala Arg Glu Ala Asp Pro Ala Leu Asn Val Glu Thr
                260                 265                 270

Glu Ile Glu Ile Leu Lys Lys Leu Asn His Pro Cys Ile Ile Lys Ile
                275                 280                 285

Lys Asn Phe Phe Asp Ala Glu Asp Tyr Tyr Ile Val Leu Glu Leu Met
290                 295                 300

Glu Gly Gly Glu Leu Phe Asp Lys Val Val Gly Asn Lys Arg Leu Lys
305                 310                 315                 320

Glu Ala Thr Cys Lys Leu Tyr Phe Tyr Gln Met Leu Leu Ala Val Gln
                325                 330                 335

Tyr Leu His Glu Asn Gly Ile Ile His Arg Asp Leu Lys Pro Glu Asn
                340                 345                 350

Val Leu Leu Ser Ser Gln Glu Glu Asp Cys Leu Ile Lys Ile Thr Asp
                355                 360                 365

Phe Gly His Ser Lys Ile Leu Gly Glu Thr Ser Leu Met Arg Thr Leu
                370                 375                 380

Cys Gly Thr Pro Thr Tyr Leu Ala Pro Glu Val Leu Val Ser Val Gly
385                 390                 395                 400

Thr Ala Gly Tyr Asn Arg Ala Val Asp Cys Trp Ser Leu Gly Val Ile
                405                 410                 415

Leu Phe Ile Cys Leu Ser Gly Tyr Pro Pro Phe Ser Glu His Arg Thr
                420                 425                 430

Gln Val Ser Leu Lys Asp Gln Ile Thr Ser Gly Lys Tyr Asn Phe Ile
                435                 440                 445

Pro Glu Val Trp Ala Glu Val Ser Glu Lys Ala Leu Asp Leu Val Lys
450                 455                 460

Lys Leu Leu Val Val Asp Pro Lys Ala Arg Phe Thr Thr Glu Glu Ala
465                 470                 475                 480

Leu Arg His Pro Trp Leu Gln Asp Glu Asp Met Lys Arg Lys Phe Gln
                485                 490                 495

Asp Leu Leu Ser Glu Glu Asn Glu Ser Thr Ala Leu Pro Gln Val Leu
                500                 505                 510

Ala Gln Pro Ser Thr Ser Arg Lys Arg Pro Arg Glu Gly Glu Ala Glu
                515                 520                 525

Gly Ala Glu Thr Thr Lys Arg Pro Ala Val Cys Ala Ala Val Leu
530                 535                 540

<210> SEQ ID NO 10
<211> LENGTH: 1542
<212> TYPE: DNA
<213> ORGANISM: Homo sapiens

<400> SEQUENCE: 10
atgtctcggg agtcggatgt tgaggctcag cagtctcatg gcagcagtgc ctgttcacag     60
ccccatggca gcgttaccca gtcccaaggc tcctcctcac agtcccaggg catatccagc    120
tcctctacca gcacgatgcc aaactccagc cagtcctctc actccagctc tgggacactg    180

```
agctccttag agacagtgtc cactcaggaa ctctattcta ttcctgagga ccaagaacct    240
gaggaccaag aacctgagga gcctacccct gcccctgggg ctcgattatg ggcccttcag    300
gatggatttg ccaatcttga atgtgtgaat gacaactact ggtttgggag ggacaaaagc    360
tgtgaatatt gctttgatga accactgctg aaaagaacag ataaataccg aacatacagc    420
aagaaacact tcggattttt cagggaagtg ggtcctaaaa actcttacat tgcatacata    480
gaagatcaca gtggcaatgg aacctttgta aatacagagc ttgtagggaa aggaaaacgc    540
cgtcctttga ataacaattc tgaaattgca ctgtcactaa gcagaaataa agttttgtc     600
tttttgatc tgactgtaga tgatcagtca gtttatccta aggcattaag agatgaatac    660
atcatgtcaa aaactcttgg aagtggtgcc tgtggagagg taaagctggc tttcgagagg    720
aaaacatgta agaaagtagc cataaagatc atcagcaaaa ggaagtttgc tattggttca    780
gcaagagagg cagacccagc tctcaatgtt gaaacagaaa tagaaatttt gaaaagcta     840
aatcatcctt gcatcatcaa gattaaaaac tttttttgatg cagaagatta ttatattgtt    900
ttggaattga tggaaggggg agagctgttt gacaaagtgg tggggaataa acgcctgaaa    960
gaagctacct gcaagctcta tttttaccag atgctcttgg ctgtgcagat tactgatttt   1020
gggcactcca agattttggg agagacctct ctcatgagaa ccttatgtgg aaccccccacc   1080
tacttggcgc ctgaagttct tgtttctgtt gggactgctg ggtataaccg tgctgtggac   1140
tgctggagtt taggagttat tctttttatc tgccttagtg ggtatccacc tttctctgag   1200
cataggactc aagtgtcact gaaggatcag atcaccagtg gaaaatacaa cttcattcct   1260
gaagtctggg cagaagtctc agagaaagct ctggaccttg tcaagaagtt gttggtagtg   1320
gatccaaagg cacgttttac gacagaagaa gccttaagac acccgtggct tcaggatgaa   1380
gacatgaaga gaaagtttca gatcttctg tctgaggaaa atgaatccac agctctaccc   1440
caggttctag cccagccttc tactagtcga aagcggcccc gtgaagggga agccgagggt   1500
gccgagacca caaagcgccc agctgtgtgt gctgctgtgt tg                       1542
```

<210> SEQ ID NO 11
<211> LENGTH: 35
<212> TYPE: PRT
<213> ORGANISM: Homo sapiens

<400> SEQUENCE: 11

```
Pro Pro Asp Gly Gly Trp Gly Trp Val Val Ala Ala Ala Phe Ala
1               5                   10                  15

Ile Asn Gly Leu Ser Tyr Gly Leu Leu Arg Ser Leu Gly Leu Ala Phe
            20                  25                  30

Pro Asp Leu
        35
```

<210> SEQ ID NO 12
<211> LENGTH: 35
<212> TYPE: PRT
<213> ORGANISM: Homo sapiens

<400> SEQUENCE: 12

```
Pro Pro Asp Gly Gly Trp Gly Trp Ala Val Val Ile Gly Ala Phe Ile
1               5                   10                  15

Ser Ile Gly Phe Ser Tyr Ala Phe Pro Lys Ser Ile Thr Val Phe Phe
            20                  25                  30

Lys Glu Ile
```

```
                           35

<210> SEQ ID NO 13
<211> LENGTH: 35
<212> TYPE: PRT
<213> ORGANISM: Homo sapiens

<400> SEQUENCE: 13

Ala Pro Asp Gly Gly Trp Gly Trp Ala Val Leu Phe Gly Cys Phe Val
1               5                   10                  15

Ile Thr Gly Phe Ser Tyr Ala Phe Pro Lys Ala Val Ser Val Phe Phe
            20                  25                  30

Lys Glu Leu
        35

<210> SEQ ID NO 14
<211> LENGTH: 35
<212> TYPE: PRT
<213> ORGANISM: Homo sapiens

<400> SEQUENCE: 14

Pro Pro Asp Gly Gly Trp Gly Trp Ile Val Val Gly Ala Ala Phe Ile
1               5                   10                  15

Ser Ile Gly Phe Ser Tyr Ala Phe Pro Lys Ala Val Thr Val Phe Phe
            20                  25                  30

Lys Glu Ile
        35

<210> SEQ ID NO 15
<211> LENGTH: 35
<212> TYPE: PRT
<213> ORGANISM: Homo sapiens

<400> SEQUENCE: 15

Pro Pro Asp Gly Gly Trp Gly Trp Val Val Leu Gly Ala Cys Phe Val
1               5                   10                  15

Val Thr Gly Phe Ala Tyr Gly Phe Pro Lys Ala Val Ser Val Phe Phe
            20                  25                  30

Arg Ala Leu
        35

<210> SEQ ID NO 16
<211> LENGTH: 35
<212> TYPE: PRT
<213> ORGANISM: Homo sapiens

<400> SEQUENCE: 16

Pro Pro Glu Gly Gly Phe Gly Trp Val Val Val Phe Ala Ala Thr Trp
1               5                   10                  15

Cys Asn Gly Ser Ile Phe Gly Ile His Asn Ser Val Gly Ile Leu Tyr
            20                  25                  30

Ser Met Leu
        35

<210> SEQ ID NO 17
<211> LENGTH: 35
<212> TYPE: PRT
<213> ORGANISM: Homo sapiens

<400> SEQUENCE: 17

Pro Pro Glu Gly Gly Trp Gly Trp Leu Val Met Leu Ala Ala Met Trp
```

```
            1               5                  10                  15
Cys Asn Gly Ser Val Phe Gly Ile Gln Asn Ala Cys Gly Val Leu Phe
                20                  25                  30
Val Ser Met
        35

<210> SEQ ID NO 18
<211> LENGTH: 35
<212> TYPE: PRT
<213> ORGANISM: Homo sapiens

<400> SEQUENCE: 18

Pro Pro Asp Gly Gly Trp Gly Trp Val Val Leu Ser Ala Phe Phe
1               5                  10                  15
Gln Ser Ala Leu Val Phe Gly Val Leu Arg Ser Phe Gly Val Phe Phe
                20                  25                  30
Val Glu Phe
        35

<210> SEQ ID NO 19
<211> LENGTH: 35
<212> TYPE: PRT
<213> ORGANISM: Homo sapiens

<400> SEQUENCE: 19

Val Pro Asp Gly Gly Trp Gly Trp Ala Val Ala Val Ser Phe Phe Phe
1               5                  10                  15
Val Glu Val Phe Thr Tyr Gly Ile Ile Lys Thr Phe Gly Val Phe Phe
                20                  25                  30
Asn Asp Leu
        35

<210> SEQ ID NO 20
<211> LENGTH: 35
<212> TYPE: PRT
<213> ORGANISM: Homo sapiens

<400> SEQUENCE: 20

Pro Pro Asp Gly Gly Trp Gly Trp Met Ile Val Ala Gly Cys Phe Leu
1               5                  10                  15
Val Thr Ile Cys Thr Arg Ala Val Thr Arg Cys Ile Ser Ile Phe Phe
                20                  25                  30
Val Glu Phe
        35

<210> SEQ ID NO 21
<211> LENGTH: 35
<212> TYPE: PRT
<213> ORGANISM: Homo sapiens

<400> SEQUENCE: 21

Thr Leu Asp Gly Gly Trp Gly Trp Met Ile Val Ile His Phe Phe Leu
1               5                  10                  15
Val Asn Val Phe Val Met Gly Met Thr Lys Thr Phe Ala Ile Phe Phe
                20                  25                  30
Val Val Phe
        35

<210> SEQ ID NO 22
<211> LENGTH: 35
```

```
<212> TYPE: PRT
<213> ORGANISM: Homo sapiens

<400> SEQUENCE: 22

Arg Ala Asp Gly Ser Trp Ala Trp Val Val Leu Leu Ala Thr Met Val
1               5                   10                  15

Thr Gln Gly Leu Thr Leu Gly Phe Pro Thr Cys Ile Gly Ile Phe Phe
            20                  25                  30

Thr Glu Leu
        35

<210> SEQ ID NO 23
<211> LENGTH: 35
<212> TYPE: PRT
<213> ORGANISM: Homo sapiens

<400> SEQUENCE: 23

Ser Pro Asp Gly Gly Trp Gly Trp Val Ile Val Phe Val Ser Phe Leu
1               5                   10                  15

Thr Gln Phe Leu Cys Tyr Gly Ser Pro Leu Ala Val Gly Val Leu Tyr
            20                  25                  30

Ile Glu Trp
        35

<210> SEQ ID NO 24
<211> LENGTH: 35
<212> TYPE: PRT
<213> ORGANISM: Homo sapiens

<400> SEQUENCE: 24

Asn Ile Asp Gly Gly Trp Ala Trp Met Met Val Leu Ser Ser Phe Phe
1               5                   10                  15

Val His Ile Leu Ile Met Gly Ser Gln Met Ala Leu Gly Val Leu Asn
            20                  25                  30

Val Glu Trp
        35

<210> SEQ ID NO 25
<211> LENGTH: 494
<212> TYPE: PRT
<213> ORGANISM: Homo sapiens

<400> SEQUENCE: 25

Met Pro Ala Pro Gln Arg Lys His Arg Gly Gly Phe Ser His Arg
1               5                   10                  15

Cys Phe Pro Thr Pro Gln Thr Ala Met Thr Pro Gln Pro Ala Gly Pro
            20                  25                  30

Pro Asp Gly Gly Trp Gly Trp Val Val Ala Ala Ala Phe Ala Ile
            35                  40                  45

Asn Gly Leu Ser Tyr Gly Leu Leu Arg Ser Leu Gly Leu Ala Phe Pro
        50                  55                  60

Asp Leu Ala Glu His Phe Asp Arg Ser Ala Gln Asp Thr Ala Trp Ile
65                  70                  75                  80

Ser Ala Leu Ala Leu Ala Val Gln Gln Ala Ser Pro Val Gly Ser
            85                  90                  95

Ala Leu Ser Thr Arg Trp Gly Ala Arg Pro Val Val Met Val Gly Gly
            100                 105                 110

Ile Leu Ala Ser Leu Gly Phe Val Phe Ser Ala Phe Ala Ser Gly Leu
            115                 120                 125
```

```
Leu His Leu Tyr Leu Gly Leu Gly Leu Leu Ala Gly Phe Gly Trp Ala
        130                 135                 140

Leu Val Phe Ala Pro Ala Leu Gly Thr Leu Ser Arg Tyr Phe Ser Arg
145                 150                 155                 160

Arg Arg Val Leu Ala Val Gly Leu Ala Leu Thr Gly Asn Gly Ala Ser
                165                 170                 175

Ser Leu Leu Leu Ala Pro Ala Leu Gln Leu Leu Asp Thr Phe Gly
        180                 185                 190

Trp Arg Gly Ala Leu Leu Leu Gly Ala Ile Thr Leu His Leu Thr
        195                 200                 205

Pro Cys Gly Ala Leu Leu Leu Pro Leu Val Leu Pro Gly Asp Pro Pro
        210                 215                 220

Ala Pro Pro Arg Ser Pro Leu Ala Ala Leu Gly Leu Ser Leu Phe Thr
225                 230                 235                 240

Arg Arg Ala Phe Ser Ile Phe Ala Leu Gly Thr Ala Leu Val Gly Gly
                245                 250                 255

Gly Tyr Phe Val Pro Tyr Val His Leu Ala Pro His Ala Leu Asp Arg
                260                 265                 270

Gly Leu Gly Gly Tyr Gly Ala Ala Leu Val Val Ala Val Ala Ala Met
        275                 280                 285

Gly Asp Ala Gly Ala Arg Leu Val Cys Gly Trp Leu Ala Asp Gln Gly
        290                 295                 300

Trp Val Pro Leu Pro Arg Leu Leu Ala Val Phe Gly Ala Leu Thr Gly
305                 310                 315                 320

Leu Gly Leu Trp Val Val Gly Leu Val Pro Val Gly Gly Glu Glu
                325                 330                 335

Ser Trp Gly Ser Pro Leu Leu Ala Ala Ala Val Ala Tyr Gly Leu Ser
        340                 345                 350

Ala Gly Ser Tyr Ala Pro Leu Val Phe Gly Val Leu Pro Gly Leu Val
        355                 360                 365

Gly Val Gly Gly Val Val Gln Ala Thr Gly Leu Val Met Met Leu Met
        370                 375                 380

Ser Leu Gly Gly Leu Leu Gly Pro Pro Leu Ser Gly Phe Leu Arg Asp
385                 390                 395                 400

Glu Thr Gly Asp Phe Thr Ala Ser Phe Leu Leu Ser Gly Ser Leu Ile
                405                 410                 415

Leu Ser Gly Ser Phe Ile Tyr Ile Gly Leu Pro Arg Ala Leu Pro Ser
                420                 425                 430

Cys Gly Pro Ala Ser Pro Pro Ala Thr Pro Thr Pro Glu Thr Gly Glu
                435                 440                 445

Leu Leu Pro Ala Pro Gln Ala Val Leu Leu Ser Pro Gly Gly Pro Gly
        450                 455                 460

Ser Thr Leu Asp Thr Thr Cys Leu Pro Thr Phe Leu Tyr Lys Val Val
465                 470                 475                 480

Gly Lys Pro Ile Pro Asn Pro Leu Leu Gly Leu Asp Ser Thr
                485                 490
```

<210> SEQ ID NO 26
<211> LENGTH: 23
<212> TYPE: DNA
<213> ORGANISM: Homo sapiens

<400> SEQUENCE: 26
acaaccccca ggcccggggg agg                                          23

<210> SEQ ID NO 27
<211> LENGTH: 23
<212> TYPE: DNA
<213> ORGANISM: Homo sapiens

<400> SEQUENCE: 27
tctcccctgc gcgcagcagg cgg                                          23

<210> SEQ ID NO 28
<211> LENGTH: 20
<212> TYPE: DNA
<213> ORGANISM: Homo sapiens

<400> SEQUENCE: 28 aaccccagg cccgggggag                                               20

<210> SEQ ID NO 29
<211> LENGTH: 20
<212> TYPE: DNA
<213> ORGANISM: Homo sapiens

<400> SEQUENCE: 29
acctgccgcc tgctgcgcgc                                              20

<210> SEQ ID NO 30
<211> LENGTH: 20
<212> TYPE: DNA
<213> ORGANISM: Homo sapiens

<400> SEQUENCE: 30
agcctctggc tgctcgcccg                                              20

<210> SEQ ID NO 31
<211> LENGTH: 20
<212> TYPE: DNA
<213> ORGANISM: Homo sapiens

<400> SEQUENCE: 31
cttatttgat tttatctcaa                                              20

<210> SEQ ID NO 32
<211> LENGTH: 20
<212> TYPE: DNA
<213> ORGANISM: Homo sapiens

<400> SEQUENCE: 32
caaaaattag ccgggtgtgt                                              20

<210> SEQ ID NO 33
<211> LENGTH: 20
<212> TYPE: DNA
<213> ORGANISM: Homo sapiens

<400> SEQUENCE: 33
ggaagtggag gagagtgtcc                                              20

<210> SEQ ID NO 34
<211> LENGTH: 20
<212> TYPE: DNA
<213> ORGANISM: Homo sapiens

<400> SEQUENCE: 34

```
gatgctatgg ttggccacgc                                          20

<210> SEQ ID NO 35
<211> LENGTH: 20
<212> TYPE: DNA
<213> ORGANISM: Homo sapiens

<400> SEQUENCE: 35
gaaagggctg ccgtgctgtt                                          20

<210> SEQ ID NO 36
<211> LENGTH: 20
<212> TYPE: DNA
<213> ORGANISM: Homo sapiens

<400> SEQUENCE: 36
tcaggagttc gagaccatcc                                          20

<210> SEQ ID NO 37
<211> LENGTH: 20
<212> TYPE: DNA
<213> ORGANISM: Homo sapiens

<400> SEQUENCE: 37
ggtgcctcag atacctggtt                                          20

<210> SEQ ID NO 38
<211> LENGTH: 20
<212> TYPE: DNA
<213> ORGANISM: Homo sapiens

<400> SEQUENCE: 38
gcctcggcct cccaaagtgc                                          20

<210> SEQ ID NO 39
<211> LENGTH: 20
<212> TYPE: DNA
<213> ORGANISM: Homo sapiens

<400> SEQUENCE: 39
actcctgccg gaggttctcg                                          20

<210> SEQ ID NO 40
<211> LENGTH: 20
<212> TYPE: DNA
<213> ORGANISM: Homo sapiens

<400> SEQUENCE: 40
gattttcact cttgttgccc                                          20

<210> SEQ ID NO 41
<211> LENGTH: 20
<212> TYPE: DNA
<213> ORGANISM: Homo sapiens

<400> SEQUENCE: 41
tgatgaaacc tggccgggca                                          20

<210> SEQ ID NO 42
<211> LENGTH: 20
<212> TYPE: DNA
<213> ORGANISM: Homo sapiens

<400> SEQUENCE: 42
```
tctgccaatc ttggctctgt                                                       20

<210> SEQ ID NO 43
<211> LENGTH: 20
<212> TYPE: DNA
<213> ORGANISM: Homo sapiens

<400> SEQUENCE: 43
tggtgctaag gggcacacac                                                       20

<210> SEQ ID NO 44
<211> LENGTH: 20
<212> TYPE: DNA
<213> ORGANISM: Homo sapiens

<400> SEQUENCE: 44
tgaaagtaag tcaatcatgg                                                       20

<210> SEQ ID NO 45
<211> LENGTH: 20
<212> TYPE: DNA
<213> ORGANISM: Homo sapiens

<400> SEQUENCE: 45
tagaaccagc ttctaggttc                                                       20

<210> SEQ ID NO 46
<211> LENGTH: 20
<212> TYPE: DNA
<213> ORGANISM: Homo sapiens

<400> SEQUENCE: 46
tcacgcgcgg cttgccggat                                                       20

<210> SEQ ID NO 47
<211> LENGTH: 20
<212> TYPE: DNA
<213> ORGANISM: Homo sapiens

<400> SEQUENCE: 47
gtacataatt caatccccgt                                                       20

<210> SEQ ID NO 48
<211> LENGTH: 20
<212> TYPE: DNA
<213> ORGANISM: Homo sapiens

<400> SEQUENCE: 48
ctatttccac gcgttggcgg                                                       20

<210> SEQ ID NO 49
<211> LENGTH: 20
<212> TYPE: DNA
<213> ORGANISM: Homo sapiens

<400> SEQUENCE: 49
tgttctcagg aacgttgccg                                                       20

<210> SEQ ID NO 50
<211> LENGTH: 20
<212> TYPE: DNA
<213> ORGANISM: Homo sapiens

```
<400> SEQUENCE: 50
ttacaggctt gcaccgcgcc                                              20

<210> SEQ ID NO 51
<211> LENGTH: 20
<212> TYPE: DNA
<213> ORGANISM: Homo sapiens

<400> SEQUENCE: 51
acggaaactg gcgcgctcca                                              20

<210> SEQ ID NO 52
<211> LENGTH: 20
<212> TYPE: DNA
<213> ORGANISM: Homo sapiens

<400> SEQUENCE: 52
gcgggattta ggcattgttg                                              20

<210> SEQ ID NO 53
<211> LENGTH: 20
<212> TYPE: DNA
<213> ORGANISM: Homo sapiens

<400> SEQUENCE: 53
tggcagtccc cgcgtcacgt                                              20

<210> SEQ ID NO 54
<211> LENGTH: 20
<212> TYPE: DNA
<213> ORGANISM: Homo sapiens

<400> SEQUENCE: 54
tggctctggg tgctgaaacg                                              20

<210> SEQ ID NO 55
<211> LENGTH: 20
<212> TYPE: DNA
<213> ORGANISM: Homo sapiens

<400> SEQUENCE: 55
ggctgcgtgt tagtggcttc                                              20

<210> SEQ ID NO 56
<211> LENGTH: 20
<212> TYPE: DNA
<213> ORGANISM: Homo sapiens

<400> SEQUENCE: 56
tcgccgctcc ccctccccc                                               20

<210> SEQ ID NO 57
<211> LENGTH: 20
<212> TYPE: DNA
<213> ORGANISM: Homo sapiens

<400> SEQUENCE: 57
ccctgcgcgc agcaggcggc                                              20

<210> SEQ ID NO 58
<211> LENGTH: 20
<212> TYPE: DNA
<213> ORGANISM: Homo sapiens
```

```
<400> SEQUENCE: 58
caccccgggc gagcagccag                                               20

<210> SEQ ID NO 59
<211> LENGTH: 20
<212> TYPE: DNA
<213> ORGANISM: Homo sapiens

<400> SEQUENCE: 59
ttatttgatt ttatctcaaa                                               20

<210> SEQ ID NO 60
<211> LENGTH: 20
<212> TYPE: DNA
<213> ORGANISM: Homo sapiens

<400> SEQUENCE: 60
caggcacacg ccaacacacc                                               20

<210> SEQ ID NO 61
<211> LENGTH: 20
<212> TYPE: DNA
<213> ORGANISM: Homo sapiens

<400> SEQUENCE: 61
ggagtcatgc ctggaagtgg                                               20

<210> SEQ ID NO 62
<211> LENGTH: 20
<212> TYPE: DNA
<213> ORGANISM: Homo sapiens

<400> SEQUENCE: 62
agtacagtac acagcctgcg                                               20

<210> SEQ ID NO 63
<211> LENGTH: 20
<212> TYPE: DNA
<213> ORGANISM: Homo sapiens

<400> SEQUENCE: 63
cctggctgga cctaacagca                                               20

<210> SEQ ID NO 64
<211> LENGTH: 20
<212> TYPE: DNA
<213> ORGANISM: Homo sapiens

<400> SEQUENCE: 64
gatccacccc ccccccccct                                               20

<210> SEQ ID NO 65
<211> LENGTH: 20
<212> TYPE: DNA
<213> ORGANISM: Homo sapiens

<400> SEQUENCE: 65
aaccaggtat ctgaggcacc                                               20

<210> SEQ ID NO 66
<211> LENGTH: 20
<212> TYPE: DNA
```

<213> ORGANISM: Homo sapiens

<400> SEQUENCE: 66
gcactttggg aggccgaggc                                       20

<210> SEQ ID NO 67
<211> LENGTH: 20
<212> TYPE: DNA
<213> ORGANISM: Homo sapiens

<400> SEQUENCE: 67
aggccccgag aacctccggc                                       20

<210> SEQ ID NO 68
<211> LENGTH: 20
<212> TYPE: DNA
<213> ORGANISM: Homo sapiens

<400> SEQUENCE: 68
ttcactcttg ttgcccaggc                                       20

<210> SEQ ID NO 69
<211> LENGTH: 20
<212> TYPE: DNA
<213> ORGANISM: Homo sapiens

<400> SEQUENCE: 69
gtgagccacc gtgcccggcc                                       20

<210> SEQ ID NO 70
<211> LENGTH: 20
<212> TYPE: DNA
<213> ORGANISM: Homo sapiens

<400> SEQUENCE: 70
gaaacctaca gagccaagat                                       20

<210> SEQ ID NO 71
<211> LENGTH: 20
<212> TYPE: DNA
<213> ORGANISM: Homo sapiens

<400> SEQUENCE: 71
tgctcatttt cctctgcact                                       20

<210> SEQ ID NO 72
<211> LENGTH: 20
<212> TYPE: DNA
<213> ORGANISM: Homo sapiens

<400> SEQUENCE: 72
atgattgact tactttcatc                                       20

<210> SEQ ID NO 73
<211> LENGTH: 20
<212> TYPE: DNA
<213> ORGANISM: Homo sapiens

<400> SEQUENCE: 73
tccttcctga acctagaagc                                       20

<210> SEQ ID NO 74
<211> LENGTH: 20

<212> TYPE: DNA
<213> ORGANISM: Homo sapiens

<400> SEQUENCE: 74
tgggacgcgg ggtgtacgga                                               20

<210> SEQ ID NO 75
<211> LENGTH: 20
<212> TYPE: DNA
<213> ORGANISM: Homo sapiens

<400> SEQUENCE: 75
gcggcgagaa atgaatgcag                                               20

<210> SEQ ID NO 76
<211> LENGTH: 20
<212> TYPE: DNA
<213> ORGANISM: Homo sapiens

<400> SEQUENCE: 76
attgatatcc gagatttacc                                               20

<210> SEQ ID NO 77
<211> LENGTH: 20
<212> TYPE: DNA
<213> ORGANISM: Homo sapiens

<400> SEQUENCE: 77
tgggtgaatc acctgacgtc                                               20

<210> SEQ ID NO 78
<211> LENGTH: 20
<212> TYPE: DNA
<213> ORGANISM: Homo sapiens

<400> SEQUENCE: 78
tatcactggg gtgtccgggc                                               20

<210> SEQ ID NO 79
<211> LENGTH: 20
<212> TYPE: DNA
<213> ORGANISM: Homo sapiens

<400> SEQUENCE: 79
cgggagcccc gcgtcctcat                                               20

<210> SEQ ID NO 80
<211> LENGTH: 20
<212> TYPE: DNA
<213> ORGANISM: Homo sapiens

<400> SEQUENCE: 80
catgcgtaag gaggggcgtt                                               20

<210> SEQ ID NO 81
<211> LENGTH: 20
<212> TYPE: DNA
<213> ORGANISM: Homo sapiens

<400> SEQUENCE: 81
gactctcttg ctttaatgag                                               20

<210> SEQ ID NO 82

```
<211> LENGTH: 20
<212> TYPE: DNA
<213> ORGANISM: Homo sapiens

<400> SEQUENCE: 82
ggaattgcaa ggccctgttg                                              20

<210> SEQ ID NO 83
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aggcagccag ccc                                                     13

<210> SEQ ID NO 84
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ccgaggtaga gatgcag                                                 17

<210> SEQ ID NO 85
<211> LENGTH: 16
<212> TYPE: DNA
<213> ORGANISM: Homo sapiens

<400> SEQUENCE: 85
tttcgccagc gatctg                                                  16

<210> SEQ ID NO 86
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
tcgccagcgg tctg                                                    14

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
agtcctaacc tcgcttggct                                              20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 88
gcagcccaat actcaggtat                                               20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tggatgttgg ccgtgcccat                                               20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
cacctgtcac tgactgggcc                                               20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tggatgttgg ccgtgcccat                                               20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cacctgtcac tgactgggcc                                               20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
agtcctaacc tcgcttggct                                               20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
```
gcagcccaat actcaggtat                                          20

<210> SEQ ID NO 95
<211> LENGTH: 24
<212> TYPE: PRT
<213> ORGANISM: Homo sapiens

<400> SEQUENCE: 95

Val Val Ala Val Ala Ala Met Gly Asp Ala Gly Ala Arg Leu Val Cys
1               5                   10                  15

Gly Trp Leu Ala Asp Gln Gly Trp
            20

<210> SEQ ID NO 96
<211> LENGTH: 24
<212> TYPE: PRT
<213> ORGANISM: Homo sapiens

<400> SEQUENCE: 96

Leu Leu Ser Ile Leu Ala Phe Val Asp Met Val Ala Arg Pro Ser Met
1               5                   10                  15

Gly Leu Val Ala Asn Thr Lys Pro
            20

<210> SEQ ID NO 97
<211> LENGTH: 24
<212> TYPE: PRT
<213> ORGANISM: Homo sapiens

<400> SEQUENCE: 97

Leu Leu Thr Ile Leu Gly Phe Ile Asp Ile Phe Ala Arg Pro Ala Ala
1               5                   10                  15

Gly Phe Val Ala Gly Leu Gly Lys
            20

<210> SEQ ID NO 98
<211> LENGTH: 24
<212> TYPE: PRT
<213> ORGANISM: Homo sapiens

<400> SEQUENCE: 98

Leu Leu Ser Val Met Ala Phe Val Asp Met Phe Ala Arg Pro Ser Val
1               5                   10                  15

Gly Leu Ile Ala Asn Ser Lys Tyr
            20

<210> SEQ ID NO 99
<211> LENGTH: 24
<212> TYPE: PRT
<213> ORGANISM: Homo sapiens

<400> SEQUENCE: 99

Leu Leu Ser Ile Val Gly Phe Val Asp Ile Val Ala Arg Pro Ala Cys
1               5                   10                  15

Gly Ala Leu Ala Gly Leu Ala Arg
            20

<210> SEQ ID NO 100
<211> LENGTH: 24
<212> TYPE: PRT
<213> ORGANISM: Homo sapiens

<400> SEQUENCE: 100

Leu Leu Val Cys Ile Gly Ala Thr Ser Gly Leu Gly Arg Leu Val Ser
1               5                   10                  15

Gly His Ile Ser Asp Ser Ile Pro
            20

<210> SEQ ID NO 101
<211> LENGTH: 24
<212> TYPE: PRT
<213> ORGANISM: Homo sapiens

<400> SEQUENCE: 101

Val Leu Met Cys Ile Gly Val Thr Ser Gly Val Gly Arg Leu Leu Phe
1               5                   10                  15

Gly Arg Ile Ala Asp Tyr Val Pro
            20

<210> SEQ ID NO 102
<211> LENGTH: 24
<212> TYPE: PRT
<213> ORGANISM: Homo sapiens

<400> SEQUENCE: 102

Leu Leu Ser Val Val Ala Ile Ser Asp Leu Val Gly Arg Val Val Ser
1               5                   10                  15

Gly Trp Leu Gly Asp Ala Val Pro
            20

<210> SEQ ID NO 103
<211> LENGTH: 24
<212> TYPE: PRT
<213> ORGANISM: Homo sapiens

<400> SEQUENCE: 103

Leu Leu Ser Thr Met Ala Ile Ala Glu Val Phe Gly Arg Ile Gly Ala
1               5                   10                  15

Gly Phe Val Leu Asn Arg Glu Pro
            20

<210> SEQ ID NO 104
<211> LENGTH: 24
<212> TYPE: PRT
<213> ORGANISM: Homo sapiens

<400> SEQUENCE: 104

Leu Met Ser Ile Leu Gly Val Ile Asp Ile Ile Gly Asn Ile Thr Phe
1               5                   10                  15

Gly Trp Leu Thr Asp Arg Arg Cys
            20

<210> SEQ ID NO 105
<211> LENGTH: 24
<212> TYPE: PRT
<213> ORGANISM: Homo sapiens

<400> SEQUENCE: 105

Leu Val Ser Val Ala Gly Ile Leu Glu Thr Val Ser Gln Ile Ile Ser
1               5                   10                  15

Gly Trp Val Ala Asp Gln Asn Trp
            20

<210> SEQ ID NO 106
<211> LENGTH: 24
<212> TYPE: PRT
<213> ORGANISM: Homo sapiens

<400> SEQUENCE: 106

Leu Ile Ser Ile Ile Gly Phe Ser Asn Ile Phe Leu Arg Pro Leu Ala
1               5                   10                  15

Gly Leu Met Ala Gly Arg Pro Ala
            20

<210> SEQ ID NO 107
<211> LENGTH: 24
<212> TYPE: PRT
<213> ORGANISM: Homo sapiens

<400> SEQUENCE: 107

Leu Ile Ser Ile Ile Gly Ile Met Thr Ala Val Gly Lys Leu Leu Leu
1               5                   10                  15

Gly Ile Leu Ala Asp Phe Lys Trp
            20

<210> SEQ ID NO 108
<211> LENGTH: 24
<212> TYPE: PRT
<213> ORGANISM: Homo sapiens

<400> SEQUENCE: 108

Leu Thr Ser Ile Ile Ala Ile Val His Ile Phe Gly Lys Val Ile Leu
1               5                   10                  15

Gly Val Ile Ala Asp Leu Pro Cys
            20

<210> SEQ ID NO 109
<211> LENGTH: 51
<212> TYPE: DNA
<213> ORGANISM: Homo sapiens

<400> SEQUENCE: 109
cacacaaccc ccaggcccgg gggagbgggg agcggcgaga aatgaatgca g        51

<210> SEQ ID NO 110
<211> LENGTH: 51
<212> TYPE: DNA
<213> ORGANISM: Homo sapiens

<400> SEQUENCE: 110
gccctactca cacgcatgca cctgcsgcct gctgcgcgca ggggagacac g         51

<210> SEQ ID NO 111
<211> LENGTH: 51
<212> TYPE: DNA
<213> ORGANISM: Homo sapiens

<400> SEQUENCE: 111
cgggcccacc ccgggcgagc agccasaggc tggatctcag ggatgccagc t         51

<210> SEQ ID NO 112
<211> LENGTH: 51
<212> TYPE: DNA
<213> ORGANISM: Homo sapiens

<400> SEQUENCE: 112
cgccccgcca gccgaaagta tcgagragaa gctgcaaggc gggcgccagg a        51

<210> SEQ ID NO 113
<211> LENGTH: 51
<212> TYPE: DNA
<213> ORGANISM: Homo sapiens

<400> SEQUENCE: 113
caggccgagg tagagatgca gcagaycgct ggcgaaagcc gagaagacga a        51

<210> SEQ ID NO 114
<211> LENGTH: 51
<212> TYPE: DNA
<213> ORGANISM: Homo sapiens

<400> SEQUENCE: 114
aagacgaagc ccagcgaggc gaggaygccc ccaaccatca ccacggggcg g        51

<210> SEQ ID NO 115
<211> LENGTH: 51
<212> TYPE: DNA
<213> ORGANISM: Homo sapiens

<400> SEQUENCE: 115
gccacagccg cggccagcag gggachcccc cagctctctt cgccgcccac c        51

<210> SEQ ID NO 116
<211> LENGTH: 51
<212> TYPE: DNA
<213> ORGANISM: Homo sapiens

<400> SEQUENCE: 116
tgtttgggaa acaaaactgt cccttkgaga taaaatcaaa taagaaaatt g        51

<210> SEQ ID NO 117
<211> LENGTH: 51
<212> TYPE: DNA
<213> ORGANISM: Homo sapiens

<400> SEQUENCE: 117
ctcctaaaaa tacaaaaatt agccgsgtgt gttggcgtgt gcctgtagtt g        51

<210> SEQ ID NO 118
<211> LENGTH: 51
<212> TYPE: DNA
<213> ORGANISM: Homo sapiens

<400> SEQUENCE: 118
ggaagcagct cccccgtctc tggggbaggc gtggctggag gggaggctgg a        51

<210> SEQ ID NO 119
<211> LENGTH: 51
<212> TYPE: DNA
<213> ORGANISM: Homo sapiens

<400> SEQUENCE: 119
gccgaatgga gtcatgcctg gaagtrgagg agagtgtcca ggagctccga t        51

<210> SEQ ID NO 120
<211> LENGTH: 51
<212> TYPE: DNA
<213> ORGANISM: Homo sapiens

<400> SEQUENCE: 120

```
tggtgtagta cagtacacag cctgcrtggc caaccatagc atccctgaaa t            51
```

<210> SEQ ID NO 121
<211> LENGTH: 51
<212> TYPE: DNA
<213> ORGANISM: Homo sapiens

<400> SEQUENCE: 121

```
ttttccagtg gctgctcagc cactaygcct ggaggggtc cctgctgctg g             51
```

<210> SEQ ID NO 122
<211> LENGTH: 51
<212> TYPE: DNA
<213> ORGANISM: Homo sapiens

<400> SEQUENCE: 122

```
aggaacctgg ctggacctaa cagcayggca gcccttccc acctggctac c             51
```

<210> SEQ ID NO 123
<211> LENGTH: 51
<212> TYPE: DNA
<213> ORGANISM: Homo sapiens

<400> SEQUENCE: 123

```
ggccaggatg gtctcgaact cctgaycttg tgatccaccc ccccccccc t             51
```

<210> SEQ ID NO 124
<211> LENGTH: 51
<212> TYPE: DNA
<213> ORGANISM: Homo sapiens

<400> SEQUENCE: 124

```
cctactgggc cccaaaccag gtatcygagg cacctggtca aagttctgct g            51
```

<210> SEQ ID NO 125
<211> LENGTH: 51
<212> TYPE: DNA
<213> ORGANISM: Homo sapiens

<400> SEQUENCE: 125

```
ctaacctcgt gatctgcccg cctcgrcctc ccaaagtgct gggattacag g            51
```

<210> SEQ ID NO 126
<211> LENGTH: 51
<212> TYPE: DNA
<213> ORGANISM: Homo sapiens

<400> SEQUENCE: 126

```
catgggaact cctgccggag gttctyrggg cctctggagt ctgcagcctc a            51
```

COMPOSITIONS AND METHODS FOR DETECTING AND TREATING DIABETES

CROSS-REFERENCE TO RELATED APPLICATIONS

This application is the U.S. national phase application, pursuant to 35 U.S.C. § 371, of PCT International Application No.: PCT/US2017/039431, filed Jun. 27, 2017, designating the United States and published in English, which claims priority under 35 U.S.C. § 119(e) to U.S. Provisional Application No. 62/458,832, filed Feb. 14, 2017, and to U.S. Provisional Patent Application No. 62/355,190, filed Jun. 27, 2016, the entire contents of each of which are hereby incorporated by reference.

SEQUENCE LISTING

The application contains a Sequence Listing which has been submitted electronically in ASCII format and is hereby incorporated by reference in its entirety. The ASCII copy, created on Jul. 24, 2017, is named 167741_013402PCT_SL.TXT and is 82,064 bytes in size.

BACKGROUND OF THE INVENTION

Type 2 diabetes (T2D) afflicts ~415M people worldwide, with a disproportionate impact on populations of Mexican and Latin American ancestry. Type 2 or noninsulin-dependent diabetes mellitus (NIDDM) is characterized by resistance to insulin action on glucose uptake in peripheral tissues, especially skeletal muscle and adipocytes, impaired insulin action to inhibit hepatic glucose production, and dysregulated insulin secretion. In most cases, type 2 diabetes is a polygenic disease with complex inheritance patterns that is also influenced by environmental factors, including diet, physical activity, and age. The prevalence of type 2 diabetes in Mexican and Latin American populations is roughly twice that of U.S. non-Hispanic whites. Methods of treating and preventing type 2 diabetes, particularly in Mexican and Latin American populations, are urgently required.

SUMMARY OF THE INVENTION

The invention features compositions and methods that are useful for increasing the level or activity of SLC16A11 in subjects having or having a propensity to develop type 2 diabetes, including, but not limited to, carriers of the SLC16A11 risk haplotype, thereby treating or preventing type 2 diabetes in those subjects. The invention further provides methods of treating or preventing type 2 diabetes by increasing the activity or level of a wild-type SLC16A11 protein in a cell of the subject.

In an aspect, the invention provides a method of increasing the expression of a SLC16A11 polypeptide or a polynucleotide encoding the polypeptide in a cell, in which the method comprises contacting a cell with an agent that is a mechanistic target of rapamycin (mTOR) inhibitor.

In an aspect, the method provides a method of increasing the expression of a SLC16A11 polypeptide or a polynucleotide encoding the polypeptide, in which the method comprises contacting an adipocyte or hepatocyte with an agent selected from the group consisting of [5-[2-(2,6-dimethyl-morpholin-4-yl)-4-morpholin-4-ylpyrido[2,3-d]pyrimidin-7-yl]-2-methoxyphenyl]methanol (KU-0063794), [5-[2,4-Bis((3S)-3-methylmorpholin-4-yl)pyrido[2,3-d]pyrimidin-7-yl]-2-methoxyphenyl]methanol (AZD-8055), 2-methyl-2-[4-(3-methyl-2-oxo-8-quinolin-3-ylimidazo[4,5-c]quinolin-1-yl)phenyl]propanenitrile (NVP-BEZ235), 3-(6-morpholin-4-yl-8-oxa-3,5,10-triazatricyclo[7.4.0.0$^{2,7}$] trideca-1 (9),2(7),3,5,10,12-hexaen-4-yl)phenol (PI-103), methyl 4-[6-[4-(methoxycarbonylamino)phenyl]-4-morpholin-4-ylpyrazolo[3,4-d]pyrimidin-1-yl]piperidine-1-carboxylate (WYE-354), trans-4-[4-amino-5-(7 methoxy-1H-indol-2-yl)imidazo[5,1-f][1,2,4]triazin-7-yl]-cyclohexanecarboxylic acid (OSI-027), and deforolimus.

In embodiments of the foregoing aspects, the agent is KU-0063794 or AZD-8055. In other embodiments of the foregoing aspects, the agent increases SLC16A11 transcript levels by at least about 2-fold or 3-fold relative to the levels present in a reference cell.

In another aspect, the invention provides a method of inhibiting mTOR in a cell, in which the method comprises contacting a cell expressing mTOR with an agent selected from the group consisting of KU-0063794, AZD-8055, NVP-BEZ235, PI-103, WYE-354, OSI-027, and deforolimus. In an embodiment, the agent is KU-0063794 or AZD-8055. In an embodiment, the agent inhibits mTORC1 and mTORC2. In an embodiment, the cell is a hepatocyte, adipocyte, thyroid cell or salivary gland cell.

In embodiments of the foregoing aspects, the cell is in vitro or in vivo.

In another aspect, the invention provides a method of increasing the expression of a SLC16A11 polypeptide or a polynucleotide encoding the polypeptide in a diabetic subject, in which the method comprises administering to a subject with type 2 diabetes an effective amount of an agent selected from the group consisting of KU-0063794, AZD-8055, NVP-BEZ235, PI-103, WYE-354, OSI-027, and deforolimus, In another aspect, the invention provides a method of inhibiting mTOR in a diabetic subject, the method comprising administering to a subject with type 2 diabetes an agent selected from the group consisting of KU-0063794, AZD-8055, NVP-BEZ235, PI-103, WYE-354, OSI-027, and deforolimus.

In yet another aspect of the invention, a method of treating or preventing type 2 diabetes in a subject is provided, in which the method comprises administering to a subject with type 2 diabetes an effective amount of an agent selected from the group consisting of KU-0063794, AZD-8055, NVP-BEZ235, PI-103, WYE-354, OSI-027, and deforolimus.

In another embodiment, the invention provides a method of increasing the expression of a SLC16A11 polypeptide or a polynucleotide encoding the polypeptide, in which the method comprises contacting a cell with an agent that is a Checkpoint Kinase (CHK) inhibitor. In an embodiment, the CHK inhibitor is 3-[(aminocarbonyl) amino]-5-(3-fluoro-phenyl)-N-(3S)-3-piperidinyl-2-thiophenecarboxamide (AZD-7762). In an embodiment, the agent increases SLC16A11 transcript levels by at least about 3-fold, 4-fold, or 5-fold relative to the levels present in a reference cell.

In embodiments of the foregoing aspects, the cell is a hepatocyte, adipocyte, thyroid cell or salivary gland cell. In embodiments of the foregoing aspects, the cell is in vitro or in vivo. In an embodiment of the foregoing aspects, the subject is identified as a carrier of the SLC16A11 risk haplotype. In an embodiment of the foregoing aspects, the subject is identified as having an SLC16A11 protein comprising an amino acid alteration selected from the group consisting of V113I, D127G, L187L, G340S, or P443T.

In another aspect, the invention provides a non-human mammal having an engineered genome comprising a loss-of-function alteration in a gene encoding a SLC16A11 polypeptide. In an embodiment, the non-human mammal is a rodent. In an embodiment, the genome comprises a deletion that results in a truncated Slc16a11 protein. In an embodiment, the genome comprises Slc16a11 del19.

In another aspect, the invention provides a method of treating or preventing type 2 diabetes in a subject, in which the method comprises recombinantly expressing a wild-type SLC16A11 protein in a cell of a subject.

In another aspect, the invention provides a method of replacing a SLC16A11 gene in a subject, in which the method comprises contacting a cell in the subject with Cas9 and a SLC16A11-specific guide RNA.

In another aspect, the invention provides a method of activating SLC16A11 transcription, in which the method comprises contacting a cell with a sgRNA plasmid comprising a SLC16A11-specific targeting sequence, a MS2-effector plasmid, and a dCas9 plasmid, thereby activating transcription of SLC16A11. In an embodiment, the dCas9 plasmid comprises NLS-dCas9-VP64, the MS2-effector plasmid comprises MS2-p65-and HSF1, and the SLC16A11-specific targeting sequence targets sequences proximal to SLC16A11. In an embodiment, the cell is an adipocyte, hepatocyte, myocyte, pancreatic cell, thyroid cell, salivary gland cell, and their progenitor cells, or any other cell type that expresses SLC16A11. In an embodiment, Cas9 and/or guide RNA are provided to the cell through expression from one or more expression vectors coding therefor, for example, a viral vector, such as an adeno-associated viral vector, or a non-viral vector. In another embodiment, Cas9 is provided to the cell as naked plasmid DNA or chemically-modified mRNA. In another embodiment, the cell is contacted with a single-stranded oligonucleotide to effect homology directed repair. In another embodiment, the Cas9, SLC16A11 guide RNA and/or single-stranded SLC16A11 oligonucleotide are delivered directly to liver, thyroid, salivary gland, and/or muscle tissue. In another embodiment, the Cas9, SLC16A11 guide RNA and/or single-stranded SLC16A11 oligonucleotide are delivered systemically. In an embodiment, the subject is selected as a carrier of the SLC16A11 risk haplotype. In an embodiment, the cell is contacted in vitro or in vivo.

In another aspect, the invention provides an expression vector comprising a nucleic acid sequence encoding a wild-type SLC16A11 polypeptide.

In another aspect, the invention provides a host cell comprising an expression vector comprising a nucleic acid sequence encoding a wild-type SLC16A11 polypeptide. In an embodiment, the host cell is a prokaryotic or eukaryotic cell. In an embodiment, the host cell is a mammalian cell.

In another aspect, the invention provides a viral vector encoding a SLC16A11 polypeptide.

In another aspect, the invention provides an adeno-associated viral (AAV) vector encoding a SLC16A11 polypeptide, wherein the polypeptide is operably linked to a promoter positioned for expression in a mammalian cell.

In another of its aspects, the invention provides a method of treating or preventing type 2 diabetes in a subject in need thereof, in which the method comprises contacting a cell of the subject with a vector encoding a SLC16A11 polypeptide, and expressing the SLC16A11 polypeptide in the cell, thereby treating or preventing type 2 diabetes in the subject. In an embodiment, the subject is identified as having the SLC16A11 risk haplotype. In an embodiment, the targeted sequence is rs77086571 or rs74577409.

In another of its aspects, the invention provides a method of stabilizing or enhancing expression levels of SLC16A11 protein in a cell, in which the method comprises contacting the cell with an agent that blocks or inhibits ubiquitination of the SLC16A11 protein at its N-terminus, thereby stabilizing or enhancing expression levels of the SLC16A11 protein in the cell. In another of its aspects, the invention provides a method of treating, ameliorating, or preventing type 2 diabetes in a subject, in which the method comprises administering to a subject in need thereof an agent that blocks or inhibits ubiquitination of the N-terminus of the SLC16A11 polypeptide in a cell, thereby stabilizing and enhancing the expression level of the SLC16A11 polypeptide by preventing proteosomal degradation, so as to treat, ameliorate, or prevent type 2 diabetes in the subject. In embodiments of the foregoing methods, the longevity of SLC16A11 polypeptide expression is increased in the cell. In embodiments of the methods, the agent is a protein, polypeptide, or peptide. In an embodiment of the methods, the agent is an antibody or an antigen binding fragment thereof that specifically binds to the N-terminus of the SLC16A11 polypeptide. In an embodiment of the methods, the agent is a small molecule compound. In an embodiment of the methods, a proline residue at position 2 of the N-terminus of the SLC16A11 protein is blocked or inhibited by the agent, for example, a small molecule, or an antibody or an antigen binding fragment thereof. In an embodiment of the methods, the agent is reversibly bound to the N-terminus of the SLC16A11 protein.

In another aspect, the invention provides a SLC16A11 protein having bound at its N-terminus an agent that blocks or inhibits ubiquitination of the protein at the N-terminus. In an embodiment, the agent is a protein or a peptide. In an embodiment, the agent is a small molecule compound. In an embodiment, the agent blocks or masks a proline residue at position 2 of the N-terminus of the SLC16A11 protein. In an embodiment, the agent is reversibly bound to the N-terminus of the protein.

In another aspect, the invention provides a SLC16A11 protein stabilized or enhanced by the methods of the foregoing aspects.

Compositions and articles defined by the invention were isolated or otherwise manufactured. Other features and advantages of the invention will be apparent from the detailed description herein, and from the claims.

Definitions

Unless defined otherwise, all technical and scientific terms used herein have the meaning commonly understood by a person of ordinary skill in the art to which this invention belongs. The following references provide one of ordinary skill in the art with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "Solute Carrier Family 16 member" is meant a protein having 12 transmembrane (TM) helical domains with cytoplasmic N- and C-termini, a large intracellular loop between TM6 and TM7, and two highly conserved sequences; [D/E]G[G/S][W/F][G/A]W (SEQ ID NO.: 1) and YFxK[R/K][R/L]xLAx[G/A]xAxAG (SEQ ID NO.: 2) and having transport activity. Exemplary SLC16 family members and their substrates are reviewed in Pochini et al. Front Chem. 2014 Aug. 11; 2:61. doi: 10.3389/fchem.2014.00061. eCollection 2014; also reviewed by Andrew P. Halestrap. Mol Aspects Med. 2013, April-June; 34(2-3):337-49. doi: 10.1016/j.mam.2012.05.003.

Exemplary SLC16 family members and their substrates are provided in Table 1:

TABLE 1

SLC16 - The monocarboxylate transporter family. For detailed information about the SLC gene tables, please visit http://www.bioparadigms.org.

| Human gene name | Protein name | Aliases | Predominant substrates | Transport type/ coupling ions | Tissue distribution and cellular/ subcellular expression | Link to disease[a] | Human gene locus | Sequence Accession ID | Splice variants and their specific features |
|---|---|---|---|---|---|---|---|---|---|
| SLC16A1 | MCT1 | MOT1 | Lactate, pyruvate, ketone bodies | C/H$^+$ or E/ monocarboxylate | Ubiquitous except β cell of endocrine pancreas | Exercise-induced hyperinsulinaemia hypoglycaemia[G] | 1p12 | NM_003051 | Splice variants in non-coding region |
| SLC16A2 | MCT8 | MOT8 XPCT MCT7 | T2, rT3, T3, T4 | F | Most tissues including liver, heart, brain, thymus, intestine, ovary, prostate, pancreas, placenta, lung kidney, skeletal muscle | Allan-Herndon-Dudley syndrome | Xq13.2 | NM_006517 | |
| SLC16A3 | MCT4 | MOT4 MCT3 | Lactate, ketone bodies | C/H$^+$ | Skeletal muscle, chondrocytes, leukocytes, testis, lung, ovary, placenta, heart | | 17q25.3 | NM_004207 | Splice variants in non-coding region |
| SLC16A4 | MCT5 | MOT5 MCT4 | O | | Brain, muscle, liver, kidney, lung, ovary, placenta, heart | | 1p13.3 | NM_004696 | Multiple splice variants listed in ENSG00000168679 |
| SLC16A5 | MCT6 | MOT6 MCT5 | ? Bumetanide Probenecid nateglinide | | Kidney, muscle, brain, heart, pancreas, prostate, lung, placenta | | 17q25.1 | NM_004695 | Several splice variants listed in ENSG00000170190 |
| SLC16A6 | MCT7 | MOT7 MCT6 | O | | Brain, pancreas, muscle, prostate | | 17q24.2 | NM_004694 | |
| SLC16A7 | MCT2 | MOT2 | Pyruvate, lactate, ketone bodies | C/H$^+$ | High expression in testis, moderate to low in spleen, heart, kidney, pancreas, skeletal muscle, brain and leukocyte | | 12q13 | NM_004731 | Multiple splice variants listed in ENSG00000118596 |
| SLC16A8 | MCT3 | MOT3 REMP | Lactate | C/H$^+$ (pH dependent but cotransport not confirmed experimentally) | Retinal pigment epithelium, choroid plexus | | 22q112.3-q13.2 | NM_013356 | Several splice variants listed in ENSG00000100156 |
| SLC16A9 | MCT9 | MOT9 | | O | Endometrium, testis, ovary, breast, brain, kidney, spleen adrenal, retina | | 10q21.1 | NM_194298 | Several splice variants listed in ENSG00000165449 |
| SLC16A10 | TAT1, MCT10 | MOT10 | Aromatic amino acids, T3, T4 | F | Kidney (basolateral), intestine, muscle, placenta, heart | | 6q21-q22 | NM_018593 | Several splice variants listed in ENSG00000112394 |

TABLE 1-continued

SLC16 - The monocarboxylate transporter family. For detailed information about the SLC gene tables, please visit http://www.bioparadigms.org.

| Human gene name | Protein name | Aliases | Predominant substrates | Transport type/ coupling ions | Tissue distribution and cellular/ subcellular expression | Link to disease[a] | Human gene locus | Sequence Accession ID | Splice variants and their specific features |
|---|---|---|---|---|---|---|---|---|---|
| SLC16A11 | MCT11 | MOT11 | | O | Skin, lung, ovary, breast, lung, pancreas, retinal pigment epithelium, choroid plexus | | 17p13.1 | NM_153357 | Two splice variants listed in ENSG00000174326 |
| SLC16A12 | MCT12 | MOT12 | | O | Kidney, retina, lung testis | Juvenile cataracts with microcornea and renal glucosuria | 10q23.31 | NM_213606 | Several splice variants listed in ENSG00000152779 |
| SLC16A13 | MCT13 | MOT13 | | O | Breast, bone marrow stem cells | | 17p13.1 | NM_201566 | |
| SLC16A14 | MCT14 | MOT14 | | O | Brain, heart, muscle, ovary, prostate, breast, lung, pancreas liver, spleen, thymus | | 2q36.3 | NM_152257 | Several splice variants listed in ENSG00000163053 |

By "Solute carrier family 16 member 11 (SLC16A11) polypeptide," also termed monocarboxylate transporter (MCT) 11, is meant a monocarboxylate transporter polypeptide having at least about 85% amino acid identity to the sequence provided at NCBI Reference sequence NP_699188.1, or a fragment thereof capable of transporting a substrate across a biological membrane. See also review articles Pochini et al. Front Chem. 2014 Aug. 11; 2:61. doi: 10.3389/fchem.2014.00061. eCollection 2014; also reviewed by Andrew P. Halestrap. Mol Aspects Med. 2013 April-June; 34(2-3):337-49. doi: 10.1016/j.mam.2012.05.003.

An exemplary SLC16A11 amino acid sequence is provided below:
Monocarboxylate transporter 11 [*Homo sapiens*]
NCBI Reference Sequence: NP_699188.1

In particular embodiments, the SLC16A11 polypeptide comprises one or more of the following alterations: V113I, D127G, L187L, G340S, P443T. In one embodiment, an SLC16A11 polypeptide having the sequence of NP_699188 is a wild-type SLC16A11 polypeptide.

By "monocarboxylate transporter activity" is meant the transport of a substrate[s] across a biological membrane by a transporter that has been defined bioinformatically as a member of the SLC16 family. In one embodiment, the monocarboxylate transporter transports pyruvate and/or lactate across a cell membrane.

By "SLC16A11 polynucleotide" is meant a nucleic acid molecule encoding a SLC16A11 polypeptide. An exemplary SLC16A11 polynucleotide sequence is provided at NCBI Reference Sequence: NM_153357, and reproduced herein below.

```
                                              (SEQ ID NO.: 3)
  1  mpapqrkhrr ggfshrcfpt pqtamtpqpa gppdggwgwv vaaaafaing lsygllrslg 61  lafpdlaehf drsaqdtawi salalavqqa aspvgsalst rwgarpvvmv ggvlaslgfv 121  fsafasdllh lylglgllag fgwalvfapa lgtlsryfsr rrvlavglal tngasslll 181  apalqllldt fgwrgalll gaitlhltpc galllplvlp gdppapprsp laalglslft 241  rrafsifalg talvgggyfv pyvhlaphal drglggygaa lvvavaamgd agarlvcgwl 301  adqgwvplpr llavfgaltg lglwvvglvp vvggeeswgg pllaaavayg lsagsyaplv 361  fgvlpglvgv ggvvqatglv mmlmslggll gpplsgflrd etgdftasfl lsgslilsgs 421  fiyiglpral pscgpasppa tpppetgell papqavllsp ggpgstldtt c
```

(SEQ ID NO.: 4)

```
   1 atctctgttt accgagagag cccgtccaag ttgggctcca tcgctgccct cgctcccctt
  61 cggggccccc gcccgcctgg gaagcagaga gaaagccggg cccagccctt cctcaccctt
 121 cccctccccg caccgcccgg agaggtcggg taaggggga ggagtgtgcg tgggacgggg
 181 aacctcgggc ctggggatct ggctgtcccc gtcccgtac ctcgcgcgga cccgggagtt
 241 ccagccctag gccaggctcc ggctccctcc gccccgcgcc atcgcgctcg gagtgacggg
 301 cccaccccgg gcgagcagcc agaggctgga tctcagggat gccagctccc cagcggaagc
 361 acaggcgtgg aggcttctct cacagatgtt tccccacccc gcagacggcg atgacccccc
 421 agcccgccgg accccggat gggggctggg gctgggtggt ggcggccgca gccttcgcga
 481 taaacgggct gtcctacggg ctgctgcgct cgctgggcct tgccttccct gaccttgccg
 541 agcactttga ccgaagcgcc caggacactg cgtggatcag cgccctggcc ctggccgtgc
 601 agcaggcagc cagccccgtg ggcagcgccc tgagcacgcg ctgggggggcc cgccccgtgg
 661 tgatggttgg gggcgtcctc gcctcgctgg gcttcgtctt ctcggctttc gccagcgatc
 721 tgctgcatct ctacctcggc ctgggcctcc tcgctggctt tggttgggcc ctggtgttcg
 781 cccccgccct aggcaccctc tcgcgttact tctcccgccg tcgagtcttg gcggtggggc
 841 tggcgctcac cggcaacggg gcctcctcgc tgctcctggc gcccgccttg cagcttcttc
 901 tcgatacttt cggctggcgg ggcgctctgc tcctcctcgg cgcgatcacc ctccacctca
 961 ccccctgtgg cgccctgctg ctacccctgg tccttcctgg agaccccca gccccaccgc
1021 gtagtcccct agctgccctc ggcctgagtc tgttcacacg ccgggccttc tcaatctttg
1081 ctctaggcac agccctggtt gggggcgggt acttcgttcc ttacgtgcac ttggctcccc
1141 acgctttaga ccggggcctg gggggatacg gagcagcgct ggtggtggcc gtggctgcga
1201 tgggggatgc gggcgcccgg ctggtctgcg ggtggctggc agaccaaggc tgggtgcccc
1261 tcccgcggct gctggccgta ttcggggctc tgactgggct ggggctgtgg gtggtggggc
1321 tggtgcccgt ggtgggcggc gaagagagct gggggggtcc cctgctggcc gcggctgtgg
1381 cctatgggct gagcgcgggg agttacgccc cgctggtttt cggtgtactc cccgggctgg
1441 tgggcgtcgg aggtgtggtg caggccacag ggctggtgat gatgctgatg agcctcgggg
1501 ggctcctggg ccctcccctg tcaggcttcc taagggatga gacaggagac ttcaccgcct
1561 ctttcctcct gtctggttct ttgatcctct ccggcagctt catctacata gggttgccca
1621 gggcgctgcc ctcctgtggt ccagcctccc ctccagccac gcctccccca gagacggggg
1681 agctgcttcc cgctccccag gcagtcttgc tgtccccagg aggccctggc tccactctgg
1741 acaccacttg ttgattattt tcttgtttga gcccctcccc caataaagaa tttttatcgg
1801 gtt
```

By "SLC16A11 risk haplotype" is meant a set of alterations in the sequence of one chromosome that is inherited from a parent that is associated with type 2 diabetes.

By "T2D risk SLC16A11" is meant the SLC16A11 polypeptide containing one or more T2D-associated coding alterations in SLC16A11. In particular embodiments, the SLC16A11 polypeptide comprises one or more of V113I, D127G, L187L, G340S, and P443T.

By "mechanistic target of rapamycin (mTOR) Pathway Inhibitor" is meant an agent that reduces the activity of an mTOR cell signaling pathway.

By "mechanistic target of rapamycin (mTOR) inhibitor" is meant an agent that reduces or eliminates the biological function or activity of an mTOR polypeptide. Exemplary biological activities or functions of an mTOR polypeptide include serine/threonine protein kinase and tyrosine protein kinase activity, as well as regulation of cellular metabolism, growth, and proliferation. Examples of an mTOR inhibitor include, without limitation, AZD-8055, KU-0063794, tipifarnib-P2, calpeptin, MEK1-2-inhibitor, Fostamatinib, NVP-BEZ235, PP-30, PD-0325901, PIK-90, BMS-536924, PI-828, PI-103, KIN001-244, serdemetan, PP-2, WYE-354, methotrexate, U0126, U-0126, NU-7026, OSI-027, Selumetinib, deforolimus, and PAC-1. In other embodiments, the mTOR inhibitor is Apitolisib (GDC-0980, RG7422), BEZ235 (e.g., NVP-BEZ235, Dactolisib), BGT226 (NVP-BGT226), CC-223, Chrysophanic acid, CH5132799, CZ415, Deforolimus (AP23573, MK-8669, Ridaforolimus), Everolimus (RAD001), ETP-46464, GDC-0349, Gedatolisib (PF-05212384, PKI-587), GSK1059615, INK 128 (MLN0128), Omipalisib (GSK2126458, GSK458), OSI-027, Palomid 529 (P529), PF-04691502, PI-103, PP121, Sirolimus, Tacrolimus (FK506), Temsirolimus (CCI-779, NSC 683864), Torin 1, Torin 2, Torkinib (PP242), Vistusertib (AZD-2014), Voxtalisib (XL765, SAR245409), WAY-600, WYE-125132 (WYE-132), WYE-354, WYE-687, XL388, and Zotarolimus (ABT-578).

By "mechanistic target of rapamycin (mTOR) polypeptide" is meant a polypeptide or a fragment thereof having at least about 85% amino acid identity to NCBI Accession No. NP_004949.1 Exemplary biological activities or functions of an mTOR polypeptide include serine/threonine protein kinase and tyrosine protein kinase activity, as well as regulation of cellular metabolism, growth, and proliferation. The sequence of an exemplary mTOR at NCBI Accession No. NP_004949.1 is shown below:

```
                                                            (SEQ ID NO.: 5)
   1 mlgtgpaaat taattssnvs vlqqfasglk srneetraka akelqhyvtm elremsqees
  61 trfydqlnhh ifelvsssda nerkggilai asligveggn atrigrfany lrnllpsndp
 121 vvmemaskai grlamagdtf taeyvefevk ralewlgadr negrrhaavl vlrelaisvp
 181 tfffqqvgpf fdnifvavwd pkqairegav aalraclilt tqrepkemqk pqwyrhtfee
 241 aekgfdetla kekgmnrddr ihgallilne lvrissmege rlreemeeit qqqlvhdkyc
 301 kdlmgfgtkp rhitpftsfq avqpqqsnal vgllgysshq glmgfgtsps pakstivesr
 361 ccrdlmeekf dqvcqwvlkc rnsknsliqm tilnllprla afrpsaftdt qylqdtmnhv
 421 lscvkkeker taafgalgll svavrsefkv ylprvldiir aalppkdfah krqkamqvda
 481 tvftcismla ramgpgiqqd ikellepmla vglspaltav lydlsrqipq lkkdiqdgll
 541 kmlslvlmhk plrhpgmpkg lahglaspgl ttlpeasdvg sitlalrtlg sfefeghslt
 601 qfvrhcadhf lnsehkeirm eaartcsrll tpsihlisgh ahvvsqtavq vvadvlskll
 661 vvgitdpdpd irycvlasld erfdahlaqa enlqalfval ndqvfeirel aictvgrlss
 721 mnpafvmpfl rkmliqilte lehsgigrik eqsarmlghl vsnaprlirp ymepilkali
 781 lklkdpdpdp npgvinnvla tigelaqvsg lemrkwvdel fiiimdmlqd ssllakrqva
 841 lwtlgqlvas tgyvvepyrk yptllevlln flkteqnqgt rreairvlgl lgaldpykhk
 901 vnigmidqsr dasayslses kssqdssdys tsemlvnmgn lpldefypav smvalmrifr
 961 dqslshhhtm vvqaitfifk slglkcvqfl pqvmptflnv irvcdgaire flfqqlgmlv
1021 sfvkshirpy mdeivtlmre fwvmntsiqs tiilliegiv valggefkly lpgliphmlr
1081 vfmhdnspgr ivsikllaai qlfganlddy lhllllppivk lfdapeaplp srkaaletvd
1141 rltesldftd yasriihpiv rtldqspelr stamdtlssl vfqlgkkyqi fipmvnkvlv
1201 rhrinhqryd vlicrivkgy tladeeedpl iyqhrmlrsg qgdalasgpv etgpmkklhv
1261 stinlqkawg aarrvskddw lewlrrlsle llkdssspsl rscwalaqay npmardlfna
1321 afvscwseln edqqdelirs ielaltsqdi aevtqtllnl aefmehsdkg plplrddngi
1381 vllgeraakc rayakalhyk elefqkgptp aileslisin nklqqpeaaa gvleyamkhf
1441 geleiqatwy eklhewedal vaydkkmdtn kddpelmlgr mrclealgew gqlhqqccek
1501 wtlvndetqa kmarmaaaaa wglgqwdsme eytcmiprdt hdgafyravl alhqdlfsla
1561 qqcidkardl ldaeltamag esysraygam vschmlsele evigyklype rreiirqiww
1621 erlqgcqriv edwqkilmvr slvvsphedm rtwlkyaslc gksgrlalah ktlvlllgvd
1681 psrqldhplp tvhpqvtyay mknmwksark idafqhmqhf vqtmqqqaqh aiatedqqhk
1741 qelhklmarc flklgewqln lqginestip kvlqyysaat ehdrswykaw hawavmnfea
1801 vlhykhqnqa rdekkklrha sganitnatt aattaatatt tastegsnse seaestensp
1861 tpsplqkkvt edlsktllmy tvpavgqffr sislsrgnnl qdtlrvltlw fdyghwpdvn
1921 ealvegvkai qidtwlqvip qliaridtpr plvgrlihql ltdigryhpq aliypltvas
1981 kstttarhna ankilknmce hsntivqqam mvseelirva ilwhemwheg leeasrlyfg
```

-continued

```
2041  ernvkgmfev leplhammer gpqtlketsf nqaygrdlme aqeworkymk sgnvkdltqa 2101  wdlyyhvfrr iskqlpqlts lelgyvspkl lmcrdlelav pgtydpnqpi iriqsiapsl 2161  qvitskqrpr kltlmgsngh efvfllkghe dlrqdervmq lfglvntlla ndptslrknl 2221  siqryavipl stnsgligwv phcdtlhali rdyrekkkil lniehrimlr mapdydhltl 2281  mqkvevfeha vnntagddla kllwlkspss evwfdrrtny trslavmsmv gyilglgdrh 2341  psnlmldrls gkilhidfgd cfevamtrek fpekipfrlt rmltnamevt gldgnyritc 2401  htvmevlreh kdsvmavlea fvydpllnwr lmdtntkgnk rsrtrtdsys agqsveildg 2461  velgepahkk tgttvpesih sfigdglvkp ealnkkaiqi inrvrdkltg rdfshddtld 2521  vptqvellik qatshenlcq cyigwcpfw
```

By "mechanistic target of rapamycin (mTOR) polynucleotide" is meant a polynucleotide encoding any mTOR polypeptide. An exemplary mTOR polynucleotide sequence is provided at NCBI Accession No. NM_004958.3. The sequence is provided below:

```
                                                      (SEQ ID NO.: 6)
   1  gctcccggct tagaggacag cggggaaggc gggcggtggg gcaggggggcc tgaagcggcg 61  gtaccggtgc tggcggcggc agctgaggcc ttggccgaag ccgcgcgaac ctcagggcaa 121  gatgcttgga accggacctg ccgccgccac caccgctgcc accacatcta gcaatgtgag 181  cgtcctgcag cagtttgcca gtggcctaaa gagccggaat gaggaaacca gggccaaagc 241  cgccaaggag ctccagcact atgtcaccat ggaactccga gagatgagtc aagaggagtc 301  tactcgcttc tatgaccaac tgaaccatca cattttttgaa ttggtttcca gctcagatgc 361  caatgagagg aaaggtggca tcttggccat agctagcctc ataggagtgg aaggtgggaa 421  tgccacccga attggcagat tgccaactta tcttcggaac ctcctcccct ccaatgaccc 481  agttgtcatg gaaatggcat ccaaggccat tggccgtctt gccatggcag ggacacttt 541  taccgctgag tacgtggaat ttgaggtgaa gcgagccctg aatggctgg gtgctgaccg 601  caatgagggc cggagacatg cagctgtcct ggttctccgt gagctggcca tcagcgtccc 661  taccttcttc ttccagcaag tgcaacccct ctttgacaac attttttgtgg ccgtgtggga 721  ccccaaacag gccatccgtg agggagctgt agccgcccct cgtgcctgtc tgattctcac 781  aacccagcgt gagccgaagg agatgcagaa gcctcagtgg tacaggcaca catttgaaga 841  agcagagaag ggatttgatg agaccttggc caaagagaag ggcatgaatc gggatgatcg 901  gatccatgga gccttgttga tccttaacga gctggtccga atcagcagca tggagggaga 961  gcgtctgaga gaagaaatgg aagaaatcac acagcagcag ctggtacacg acaagtactg 1021  caaagatctc atgggcttcg gaacaaaacc tcgtcacatt accccttca ccagttttcca 1081  ggctgtacag ccccagcagt caaatgcctt ggtgggggctg ctggggtaca gctctcacca 1141  aggcctcatg ggatttggga cctcccccag tccagctaag tccaccctgg tggagagccg 1201  gtgttgcaga gacttgatgg aggagaaatt tgatcaggtg tgccagtggg tgctgaaatg 1261  caggaatagc aagaactcgc tgatccaaat gacaatcctt aatttgttgc ccgcttggc 1321  tgcattccga ccttctgcct tcacagatac ccagtatctc caagataca tgaaccatgt 1381  cctaagctgt gtcaagaagg agaaggaacg tacagcggcc ttccaagccc tggggctact 1441  ttctgtggct gtgaggtctg agtttaaggt ctatttgcct cgcgtgctgg acatcatccg 1501  agcggccctg ccccccaaagg acttcgccca taagaggcag aaggcaatgc aggtggatgc 1561  cacagtcttc acttgcatca gcatgctggc tcgagcaatg gggccaggca tccagcagga
```

-continued

```
1621 tatcaaggag ctgctggagc ccatgctggc agtgggacta agccctgccc tcactgcagt
1681 gctctacgac ctgagccgtc agattccaca gctaaagaag gacattcaag atgggctact
1741 gaaaatgctg tccctggtcc ttatgcacaa accccttcgc cacccaggca tgcccaaggg
1801 cctggcccat cagctggcct ctcctggcct cacgaccctc cctgaggcca gcgatgtggg
1861 cagcatcact cttgccctcc gaacgcttgg cagctttgaa tttgaaggcc actctctgac
1921 ccaatttgtt cgccactgtg cggatcattt cctgaacagt gagcacaagg agatccgcat
1981 ggaggctgcc cgcacctgct cccgcctgct cacaccctcc atccacctca tcagtggcca
2041 tgctcatgtg gttagccaga ccgcagtgca agtggtggca gatgtgctta gcaaactgct
2101 cgtagttggg ataacagatc ctgaccctga cattcgctac tgtgtcttgg cgtccctgga
2161 cgagcgcttt gatgcacacc tggcccaggc ggagaacttg caggccttgt tgtggctct
2221 gaatgaccag gtgtttgaga tccgggagct ggccatctgc actgtgggcc gactcagtag
2281 catgaaccct gcctttgtca tgcctttcct gcgcaagatg ctcatccaga ttttgacaga
2341 gttggagcac agtgggattg aagaatcaa agagcagagt gcccgcatgc tggggcacct
2401 ggtctccaat gcccccgac tcatccgccc tacatggag cctattctga aggcattaat
2461 tttgaaactg aaagatccag accctgatcc aaacccaggt gtgatcaata atgtcctggc
2521 aacaatagga gaattggcac aggttagtgg cctggaaatg aggaaatggg ttgatgaact
2581 ttttattatc atcatggaca tgctccagga ttcctctttg ttggccaaaa ggcaggtggc
2641 tctgtggacc ctgggacagt tggtggccag cactggctat gtagtagagc cctacaggaa
2701 gtaccctact ttgcttgagg tgctactgaa ttttctgaag actgagcaga accagggtac
2761 acgcagagag gccatccgtg tgttagggct tttaggggct ttggatcctt acaagcacaa
2821 agtgaacatt ggcatgatag accagtcccg ggatgcctct gctgtcagcc tgtcagaatc
2881 caagtcaagt caggattcct ctgactatag cactagtgaa atgctggtca acatgggaaa
2941 cttgcctctg gatgagttct acccagctgt gtccatggtg gccctgatgc ggatcttccg
3001 agaccagtca ctctctcatc atcacaccat ggttgtccag gccatcacct tcatcttcaa
3061 gtccctggga ctcaaatgtg tgcagttcct gccccaggtc atgcccacgt tccttaacgt
3121 cattcgagtc tgtgatgggg ccatccggga attttttgttc cagcagctgg gaatgttggt
3181 gtcctttgtg aagagccaca tcagaccctta tatggatgaa atagtcaccc tcatgagaga
3241 attctgggtc atgaacacct caattcagag cacgatcatt cttctcattg agcaaattgt
3301 ggtagctctt gggggtgaat ttaagctcta cctgccccag ctgatcccac acatgctgcg
3361 tgtcttcatg catgacaaca gcccaggccg cattgtctct atcaagttac tggctgcaat
3421 ccagctgttt ggcgccaacc tggatgacta cctgcattta ctgctgcctc ctattgttaa
3481 gttgtttgat gcccctgaag ctccactgcc atctcgaaag gcagcgctag agactgtgga
3541 ccgcctgacg gagtccctgg atttcactga ctatgcctcc cggatcattc accctattgt
3601 tcgaacactg accagagcc cagaactgcg ctccacagcc atggacacgc tgtcttcact
3661 tgttttttcag ctggggaaga gtaccaaat tttcattcca atggtgaata agttctggt
3721 gcgacaccga atcaatcatc agcgctatga tgtgctcatc tgcagaattg tcaagggata
3781 cacacttgct gatgaagagg aggatccttt gatttaccag catcggatgc ttaggagtgg
3841 ccaaggggat gcattggcta gtggaccagt ggaaacagga cccatgaaga aactgcacgt
3901 cagcaccatc aacctccaaa aggcctgggg cgctgccagg agggtctcca agatgactg
3961 gctggaatgg ctgagacggc tgagcctgga gctgctgaag gactcatcat cgccctccct
```

-continued

```
4021 gcgctcctgc tgggccctgg cacaggccta aacccgatg gccagggatc tcttcaatgc
4081 tgcatttgtg tcctgctggt ctgaactgaa tgaagatcaa caggatgagc tcatcagaag
4141 catcgagttg gccctcacct cacaagacat cgctgaagtc acacagaccc tcttaaactt
4201 ggctgaattc atggaacaca gtgacaaggg ccccctgcca ctgagagatg acaatggcat
4261 tgttctgctg ggtgagagag ctgccaagtg ccgagcatat gccaaagcac tacactacaa
4321 agaactggag ttccagaaag ccccaccccc tgccattcta gaatctctca tcagcattaa
4381 taataagcta cagcagccgg aggcagcggc cggagtgtta aatatgcca tgaaacactt
4441 tggagagctg gagatccagg ctacctggta tgagaaactg cacgagtggg aggatgccct
4501 tgtggcctat gacaagaaaa tggacaccaa caaggacgac ccagagctga tgctgggccg
4561 catgcgctgc ctcgaggcct tgggggaatg gggtcaactc caccagcagt gctgtgaaaa
4621 gtggaccctg gttaatgatg agacccaagc caagatggcc cggatggctg ctgcagctgc
4681 atggggttta ggtcagtggg acagcatgga agaatacacc tgtatgatcc ctcgggacac
4741 ccatgatggg gcattttata gagctgtgct ggcactgcat caggacctct tctccttggc
4801 acaacagtgc attgacaagg ccagggacct gctggatgct gaattaactg cgatggcagg
4861 agagagttac agtcgggcat atggggccat ggtttcttgc cacatgctgt ccgagctgga
4921 ggaggttatc cagtacaaac ttgtccccga gcgacgagag atcatccgcc agatctggtg
4981 ggagagactg cagggctgcc agcgtatcgt agaggactgg cagaaaatcc ttatggtgcg
5041 gtcccttgtg gtcagccctc atgaagacat gagaacctgg ctcaagtatg caagcctgtg
5101 cggcaagagt ggcaggctgg ctcttgctca taaaacttta gtgttgctcc tgggagttga
5161 tccgtctcgg caacttgacc atcctctgcc aacagttcac cctcaggtga cctatgccta
5221 catgaaaaac atgtggaaga gtgcccgcaa gatcgatgcc ttccagcaca tgcagcattt
5281 tgtccagacc atgcagcaac aggcccagca tgccatcgct actgaggacc agcagcataa
5341 gcaggaactc acaagctca tggcccgatg cttcctgaaa cttggagagt ggcagctgaa
5401 tctacagggc atcaatgaga gcacaatccc caaagtgctg cagtactaca gcgccgccac
5461 agagcacgac cgcagctggt acaaggcctg gcatgcgtgg gcagtgatga acttcgaagc
5521 tgtgctacac tacaaacatc agaaccaagc ccgcgatgag aagaagaaac tgcgtcatgc
5581 cagcgggggcc aacatcacca acgccaccac tgccgccacc acggccgcca ctgccaccac
5641 cactgccagc accgagggca gcaacagtga gagcgaggcc gagagcaccg agaacagccc
5701 cacccccatcg ccgctgcaga agaaggtcac tgaggatctg tccaaaaccc tcctgatgta
5761 cacggtgcct gccgtccagg gcttcttccg ttccatctcc ttgtcacgag caacaacct
5821 ccaggataca ctcagagttc tcaccttatg gtttgattat ggtcactggc cagatgtcaa
5881 tgaggcctta gtggaggggg tgaaagccat ccagattgat acctggctac aggttatacc
5941 tcagctcatt gcaagaattg atacgcccag acccttggtg ggacgtctca ttcaccagct
6001 tctcacagac attggtcggt accacccca ggccctcatc tacccactga cagtggcttc
6061 taagtctacc acgacagccc ggcacaatgc agccaacaag attctgaaga acatgtgtga
6121 gcacagcaac accctggtcc agcaggccat gatggtgagc gaggagctga tccgagtggc
6181 catcctctgg catgagatgt ggcatgaagg cctggaagag gcatctcgtt tgtactttgg
6241 ggaaaggaac gtgaaaggca tgtttgaggt gctggagccc ttgcatgcta tgatggaacg
6301 gggcccccag actctgaagg aaacatcctt taatcaggcc tatggtcgag atttaatgga
6361 ggcccaagag tggtgcagga agtacatgaa atcagggaat gtcaaggacc tcacccaagc
6421 ctgggacctc tattatcatg tgttccgacg aatctcaaag cagctgcctc agctcacatc
```

-continued

```
6481 cttagagctg caatatgttt ccccaaaact tctgatgtgc cgggaccttg aattggctgt 6541 gccaggaaca tatgaccoca accagccaat cattcgcatt cagtccatag caccgtcttt 6601 gcaagtcatc acatccaagc agaggccccg gaaattgaca cttatgggca gcaacggaca 6661 tgagtttgtt ttccttctaa aaggccatga agatctgcgc caggatgagc gtgtgatgca 6721 gctcttcggc ctggttaaca cccttctggc caatgaccca acatctcttc ggaaaaacct 6781 cagcatccag agatacgctg tcatcccttt atcgaccaac tcgggcctca ttggctgggt 6841 tccccactgt gacacactgc acgccctcat ccgggactac agggagaaga agaagatcct 6901 tctcaacatc gagcatcgca tcatgttgcg gatggctccg gactatgacc acttgactct 6961 gatgcagaag gtggaggtgt ttgagcatgc cgtcaataat acagctgggg acgacctggc 7021 caagctgctg tggctgaaaa gccccagctc cgaggtgtgg tttgaccgaa gaaccaatta 7081 tacccgttct ttagcggtca tgtcaatggt tgggtatatt ttaggcctgg gagatagaca 7141 cccatccaac ctgatgctgg accgtctgag tgggaagatc ctgcacattg actttgggga 7201 ctgctttgag gttgctatga cccgagagaa gtttccagag aagattccat ttagactaac 7261 aagaatgttg accaatgcta tggaggttac aggcctggat ggcaactaca gaatcacatg 7321 ccacacagtg atggaggtgc tgcgagagca caaggacagt gtcatggccg tgctggaagc 7381 ctttgtctat gacccottgc tgaactggag gctgatggac acaaatacca aaggcaacaa 7441 gcgatcccga acgaggacgg attcctactc tgctggccag tcagtcgaaa ttttggacgg 7501 tgtggaactt ggagagccag cccataagaa aacggggacc acagtgccag aatctattca 7561 ttctttcatt ggagacggtt tggtgaaacc agaggcccta aataagaaag ctatccagat 7621 tattaacagg gttcgagata agctcactgg tcgggacttc tctcatgatg acactttgga 7681 tgttccaacg caagttgagc tgctcatcaa acaagcgaca tcccatgaaa acctctgcca 7741 gtgctatatt ggctggtgcc ctttctggta actggaggcc cagatgtgcc catcacgttt 7801 tttctgaggc ttttgtactt tagtaaatgc ttccactaaa ctgaaaccat ggtgagaaag 7861 tttgactttg ttaaatattt tgaaatgtaa atgaaaagaa ctactgtata ttaaaagttg 7921 gtttgaacca actttctagc tgctgttgaa gaatatattg tcagaaacac aaggcttgat 7981 ttggttccca ggacagtgaa acatagtaat accacgtaaa tcaagccatt cattttgggg 8041 aacagaagat ccataacttt agaaatacgg gttttgactt aactcacaag agaactcatc 8101 ataagtactt gctgatggaa gaatgaccta gttgctcctc tcaacatggg tacagcaaac 8161 tcagcacagc caagaagcct caggtcgtgg agaacatgga ttaggatcct agactgtaaa 8221 gacacagaag atgctgacct caccoctgcc acctatccca agacctcact ggtctgtgga 8281 cagcagcaga aatgtttgca agataggcca aaatgagtac aaaaggtctg tcttccatca 8341 gacccagtga tgctgcgact cacacgcttc aattcaagac ctgaccgcta gtagggaggt 8401 ttattcagat cgctggcagc ctcggctgag cagatgcaca gagggatca ctgtgcagtg 8461 ggaccaccct cactggcctt ctgcagcagg gttctgggat gttttcagtg gtcaaaatac 8521 tctgtttaga gcaagggctc agaaaacaga aatactgtca tggaggtgct gaacacaggg 8581 aaggtctggt acatattgga aattatgagc agaacaaata ctcaactaaa tgcacaaagt 8641 ataaagtgta gccatgtcta gacaccatgt tgtatcagaa taattttttgt gccaataaat 8701 gacatcagaa ttttaaacat atgtaaaaaa aaa
```

By "AZD-8055" [5-[2,4-Bis((3S)-3-methylmorpholin-4-yl)pyrido[2,3-d]pyrimidin-7-yl]-2-methoxyphenyl]methanol is meant a small molecule mTOR inhibitor having the following structure:

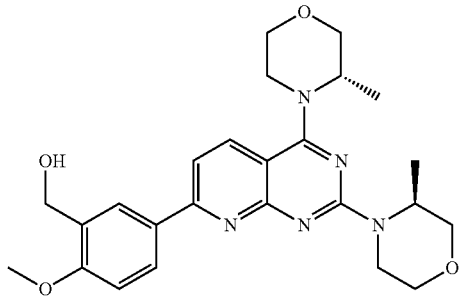 [SMILES: COc1ccc(-c2ccc3c(N4CCOC[C@@H]4C)nc(N4CCOC[C@@H]4C)nc3n2)cc1CO]

By "KU-0063794" [5-[2-(2,6-dimethylmorpholin-4-yl)-4-morpholin-4-ylpyrido[2,3-d]pyrimidin-7-yl]-2-methoxyphenyl]methanol is meant a small molecule mTOR inhibitor having the following structure:

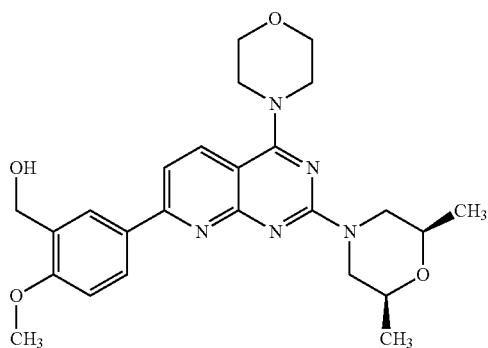 [SMILES: COc1ccc(-c2ccc3c(N4CCOCC4)nc(N4C[C@@H](C)O[C@@H](C)C4)nc3n2)cc1CO]

By "AZD-7762" 3-[(aminocarbonyl) amino]-5-(3-fluorophenyl)-N-(3S)-3-piperidinyl-2-thiophenecarboxamide is meant a small molecule CHK inhibitor having the following structure:

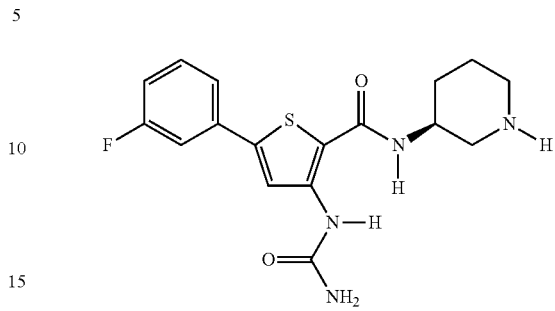

By "Checkpoint (CHK) Pathway Inhibitor" is meant any agent that inhibits the activity of the Checkpoint (CHK) signaling pathway.

By "Checkpoint (CHK) Inhibitor" is meant an agent that reduces or eliminates the biological function or activity of a Checkpoint 1 or 2 kinase (e.g., CHK, CHEK1 CHK1, CHEK2, CHK2) polypeptide. Exemplary biological activities or functions of a CHK polypeptide include serine/threonine protein kinase activity, coordination of DNA damage response (DDR) and cell cycle checkpoint response. Examples of a CHK inhibitor include, without limitation, AZD-7762, CHIR-124, LY2603618, MK-8776 (SCH 900776), and PF-477736.

By "Checkpoint kinase 1 polypeptide" is meant a polypeptide or a fragment thereof having at least about 85% amino acid identity to NCBI Accession No. O14757.2. Exemplary biological activities or functions of a Checkpoint kinase 1 polypeptide include serine/threonine protein kinase activity, coordination of DNA damage response (DDR) and cell cycle checkpoint response. The sequence of Checkpoint kinase 1 at NCBI Accession No. O14757.2 is shown below:

(SEQ ID NO.: 7)

```
  1 mavpfvedwd lvqtlgegay gevqlavnry teeavavkiv dmkravdcpe nikkeicink
 61 mlnhenvvkf yghrregniq ylfleycsgg elfdriepdi gmpepdaqrf fhqlmagvvy
121 lhgigithrd ikpenlllde rdnlkisdfg latvfrynnr erllnkmcgt lpyvapellk
181 rrefhaepvd vwscgivlta mlagelpwdq psdscqeysd wkekktylnp wkkidsapla
241 llhkilvenp saritipdik kdrwynkplk kgakrprvts ggvsespsgf skhiqsnldf
301 spvnsassee nvkysssqpe prtglslwdt spsyidklvq gisfsgptcp dhmllnsqll
361 gtpgssqnpw qrlvkrmtrf ftkldadksy qclketcekl gyqwkkscmn qvtisttdrr
421 nnklifkvnl lemddkilvd frlskgdgle fkrhflkikg klidivssqk iwlpat
```

By "Checkpoint kinase 1 polynucleotide" is meant a polynucleotide encoding any Checkpoint kinase 1 (e.g., CHK1 CHK) polypeptide. An exemplary Checkpoint kinase 1 polynucleotide sequence is provided at NCBI Accession No. AF016582.1. The sequence is provided below:

(SEQ ID NO.: 8)

```
  1 ggccggacag tccgccgagg tgctcggtgg agtcatggca gtgcctttg tggaagactg
 61 ggacttggtg caaaccctgg gagaaggtgc ctatggagaa gttcaacttg ctgtgaatag
121 agtaactgaa gaagcagtcg cagtgaagat tgtagatatg aagcgtgccg tagactgtcc
```

```
181 agaaaatatt aagaaagaga tctgtatcaa taaaatgcta aatcatgaaa atgtagtaaa 241 attctatggt cacaggagag aaggcaatat ccaatattta tttctggagt actgtagtgg 301 aggagagctt tttgacagaa tagagccaga cataggcatg cctgaaccag atgctcagag 361 attcttccat caactcatgg cagggtggt ttatctgcat ggtattggaa taactcacag 421 ggatattaaa ccagaaaatc ttctgttgga tgaaagggat aacctcaaaa tctcagactt 481 tggcttggca acagtatttc ggtataataa tcgtgagcgt ttgttgaaca agatgtgtgg 541 tactttacca tatgttgctc cagaacttct gaagagaaga gaatttcatg cagaaccagt 601 tgatgtttgg tcctgtgaa tagtacttac tgcaatgctc gctggagaat tgccatggga 661 ccaacccagt gacagctgtc aggagtattc tgactggaaa gaaaaaaaaa catacctcaa 721 cccttggaaa aaaatcgatt ctgctcctct agctctgctg cataaaatct tagttgagaa 781 tccatcagca agaattacca ttccagacat caaaaaagat agatggtaca acaaacccct 841 caagaaaggg gcaaaaaggc cccgagtcac ttcaggtggt gtgtcagagt ctcccagtgg 901 attttctaag cacattcaat ccaatttgga cttctctcca gtaaacagtg cttctagtga 961 agaaaatgtg aagtactcca gttctcagcc agaaccccgc acaggtcttt ccttatggga 1021 taccagcccc tcatacattg ataaattggt acaagggatc agcttttccc agcccacatg 1081 tcctgatcat atgcttttga atagtcagtt acttggcacc ccaggatcct cacagaaccc 1141 ctggcagcgg ttggtcaaaa gaatgacacg attcttacc aaattggatg cagacaaatc 1201 ttatcaatgc ctgaaagaga cttgtgagaa gttgggctat caatggaaga aagttgtat 1261 gaatcaggtt actatatcaa caactgatag gagaaacaat aaactcattt tcaaagtgaa 1321 tttgttagaa atggatgata aaatattggt tgacttccgg ctttctaagg gtgatggatt 1381 ggagttcaag agacacttcc tgaagattaa agggaagctg attgatattg tgagcagcca 1441 gaaggtttgg cttcctgcca catgatcgga ccatcggctc tggggaatcc tggtgaatat 1501 agtgctgcta tgttgacatt attcttccta gagaagatta tcctgtcctg caaactgcaa 1561 atagtagttc ctgaagtgtt cacttccctg tttatccaaa catcttccaa tttatttgt 1621 ttgttcggca tacaaataat acctatatct taattgtaag caaaactttg gggaaaggat 1681 gaatagaatt catttgatta tttcttcatg tgtgtttagt atctgaattt gaaactcatc 1741 tggtggaaac caagtttcag gggacatgag ttttccagct tttatacaca cgtatctcat 1801 ttttatcaaa acattttgtt t
```

By "Checkpoint kinase 2 polypeptide" is meant a polypeptide or a fragment thereof having at least about 85% amino acid identity to NCBI Accession No. O96017.1. Exemplary biological activities or functions of a Checkpoint kinase 1 polypeptide include serine/threonine-specific protein kinase activity, coordination of DNA damage response (DDR) and cell cycle checkpoint response. The sequence of Checkpoint kinase 2 at NCBI Accession No. O96017.1 is shown below:

(SEQ ID NO.: 9)
```
  1 msresdveaq qshgssacsq phgsvtqsqg sssgsggiss sststmpnss gsshsssgtl 61 ssletvstqe lysipedqep edqepeeptp apwarlwalq dgfanlecvn dnywfgrdks 121 ceycfdepll krtdkyrtys kkhfrifrev gpknsyiayi edhsgngtfv ntelvgkgkr 181 rpinnnseia lslsrnkvfv ffdltvddqs vypkalrdey imsktlgsga cgevklafer 241 ktckkvaiki iskrkfaigs areadpalnv eteieilkkl nhpciikikn ffdaedyyiv 301 lelmeggelf dkvvgnkrlk eatcklyfyq mllavqylhe ngiihrdlkp envllssqee 361 dclikitdfg hskilgetsl mrticgtpty lapevlvsvg tagynravdc wslgvilfic
```

```
-continued
421 lsgyppfseh rtqvslkdqi tsgkynfipe vwaevsekal dlvkkllvvd pkarftteea 481 lrhpwlqded mkrkfqdlls eenestalpq vlaqpstsrk rpregeaega ettkrpavca 541 avl
```

By "Checkpoint kinase 2 polynucleotide" is meant a polynucleotide encoding any Checkpoint kinase 2 polypeptide. An exemplary Checkpoint kinase 2 polynucleotide sequence is provided at NCBI Accession No. AB040105.1. The sequence is provided below:

```
                                                      (SEQ ID NO.: 10)
   1 atgtctcggg agtcggatgt tgaggctcag cagtctcatg gcagcagtgc ctgttcacag 61 ccccatggca gcgttaccca gtcccaaggc tcctcctcac agtcccaggg catatccagc 121 tcctctacca gcacgatgcc aaactccagc cagtcctctc actccagctc tgggacactg 181 agctccttag agacagtgtc cactcaggaa ctctattcta ttcctgagga ccaagaacct 241 gaggaccaag aacctgagga gcctacccct gcccctggg ctcgattatg ggcccttcag 301 gatggatttg ccaatcttga atgtgtgaat gacaactact ggtttgggag ggacaaaagc 361 tgtgaatatt gctttgatga accactgctg aaaagaacag ataaataccg aacatacagc 421 aagaaacact ttcggatttt cagggaagtg ggtcctaaaa actcttacat tgcatacata 481 gaagatcaca gtggcaatgg aacctttgta aatacagagc ttgtagggaa aggaaaacgc 541 cgtcctttga ataacaattc tgaaattgca ctgtcactaa gcagaaataa agtttttgtc 601 tttttgatc tgactgtaga tgatcagtca gtttatccta aggcattaag agatgaatac 661 atcatgtcaa aaactcttgg aagtggtgcc tgtggagagg taaagctggc tttcgagagg 721 aaaacatgta agaaagtagc cataaagatc atcagcaaaa ggaagtttgc tattggttca 781 gcaagagagg cagacccagc tctcaatgtt gaaacagaaa tagaaatttt gaaaaagcta 841 aatcatcctt gcatcatcaa gattaaaaac ttttttgatg cagaagatta ttatattgtt 901 ttggaattga tggaaggggg agagctgttt gacaaagtgg tggggaataa acgcctgaaa 961 gaagctacct gcaagctcta tttttaccag atgctcttgg ctgtgcagat tactgatttt 1021 gggcactcca agatttggg agagacctct ctcatgagaa ccttatgtgg aaccccacc 1081 tacttggcgc ctgaagttct tgtttctgtt gggactgctg ggtataaccg tgctgtggac 1141 tgctggagtt taggagttat tctttttatc tgccttagtg ggtatccacc tttctctgag 1201 cataggactc aagtgtcact gaaggatcag atcaccagtg gaaaatacaa cttcattcct 1261 gaagtctggg cagaagtctc agagaaagct ctggaccttg tcaagaagtt gttggtagtg 1321 gatccaaagg cacgttttac gacagaagaa gccttaagac acccgtggct tcaggatgaa 1381 gacatgaaga gaaagtttca agatcttctg tctgaggaaa atgaatccac agctctaccc 1441 caggttctag cccagccttc tactagtcga aagcggcccc gtgaagggga agccgagggt 1501 gccgagacca caaagcgccc agctgtgtgt gctgctgtgt tg
```

By "agent" is meant a small compound, polynucleotide, or polypeptide.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression or activity levels, preferably a 25% change, more preferably a 40% change, and most preferably a 50% or greater change in expression or activity levels. In one embodiment, compositions or methods of the invention increase the expression or activity of SLC16A11 by at least about 5%, 10%, 25%, 30%, 50%, 75% or 100%.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. In one embodiment, a disease is type 2 diabetes, a metabolic syndrome, and/or insulin resistance.

By "effective amount" is meant the amount of an agent of the invention required to ameliorate the symptoms of a disease relative to an untreated patient. In one embodiment, an effective amount of a recombinant SLC16A11 polypeptide or polynucleotide is the amount required to prevent or treat type 2 diabetes in a subject. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "naturally occurs" is meant is endogenously expressed in a cell of an organism.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

By "polypeptide" is meant any chain of amino acids, regardless of length or post-translational modification.

By "positioned for expression" is meant that the polynucleotide of the invention (e.g., a DNA molecule) is positioned adjacent to a DNA sequence that directs transcription and translation of the sequence (i.e., facilitates the production of, for example, a recombinant polypeptide of the invention, or an RNA molecule).

By "promoter" is meant a polynucleotide sufficient to direct transcription. Exemplary promoters include nucleic acid sequences of lengths 100, 250, 300, 400, 500, 750, 900, 1000, 1250, and 1500 nucleotides that are upstream (e.g., immediately upstream) of the translation start site. Virtually any mammalian promoter may be used to direct expression of a SLC16A11 protein. In one embodiment, SLC16A11 expression is driven by a tissue specific promoter that directs expression in a specific tissue or cell type, such as liver and hepatocytes. In another embodiment, the albumin promoter is used to direct SLC16A11 expression. In another embodiment, SLC16A11 is ubiquitously and/or constitutively expressed. In another embodiment SLC16A11 expression is driven by a CMV or E1a promoter.

By "increases" is meant a positive alteration of at least 10%, 25%, 50%, 75%, or 100%.

By "reference" is meant a standard or controlled condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those of ordinary skill in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those of ordinary skill in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those of ordinary skill in the art. Hybridization techniques are well known to those of ordinary skill in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 1A and 1B present schematics related to credible sets according to the invention. FIG. 1A provides a schematic depicting the steps of the analysis undertaken to generate the credible set. FIG. 1B provides a schematic depicting the fine mapping of type 2 diabetes (T2D) association at 17p13 within the credible set.

FIGS. 2A-2E provide data showing that the T2D risk haplotype contains a cis expression quantitative trait loci (eQTL) for SLC16A11 in liver. FIG. 2A (top panel) provides a box plot. For the liver biopsies, 21 samples were homozygous for the reference allele at rs1334692 (REF), 16 were heterozygous (HET), and 10 samples were homozygous for the risk allele (RISK). Gene expression values for BCL6B, SLC16A11, SLC16A13, and CLEC10A were measured with digital PCR (dPCR) and normalized to the housekeeping gene TBP, log 2 of relative values were then plotted. FIG. 2A (bottom panel) provides a box plot showing liver expression quantitative trait loci (eQTL) detected using a second droplet digital (dd) PCR gene expression assay. FIG. 2B (top panel) provides a graph showing eQTL analyses in liver using HPRT1 for normalization. FIG. 2B (bottom panel) provides a graph showing SLC16A11 transcript expression. For the 16 heterozygous samples, allele specific ddPCR probes were used to measure the percent of SLC16A11 transcript originating from the chromosome carrying the reference haplotype with respect to the chromosome carrying the T2D risk haplotype. rs1334692 was used to tag the T2D risk haplotype.

FIG. 2C (top panel) provides a box plot depicting visceral adipose expression quantitative trait loci (eQTL) detection. FIG. 2C (bottom panel) and FIG. 2D provide graphs showing that primary human hepatocytes from donors who were heterozygous for the T2D risk haplotype had a similar skew in SLC16A11 expression as observed in liver biopsies.

FIG. 2E (top panel) provides a series of graphs and ChIP-sequencing tracks. ChIP-sequencing was carried out to identify histone modifications in primary human hepatocytes from three individuals heterozygous for the T2D risk haplotype. ChIP-sequencing identified H3K27ac, H3K4me1, and H3K4me3 histone modifications in primary human hepatocytes from three individuals heterozygous for the T2D risk haplotype. Tracks overlapping variants in the T2D risk credible set are shown. Bar plots depict allelic proportions±SEM at rs13342692 and rs2292351. Asterisks indicate significance after Bonferroni correction for multiple hypotheses testing: *P<0.05, P<1×10$^{-3}$, *P<1×10$^{-5}$. FIG. 2E (bottom panel) shows ChIP-sequencing tracks in current study compared to previously published studies.

FIG. 2F and FIG. 2G provide graphs showing SLC16A11 transcript expression in heterozygous T2D risk carriers and in African haplotype carriers.

FIG. 2H shows ChIP-sequencing for H3K27ac, H3K4me1, and H3K4me3 histone modifications in primary human hepatocytes from three individuals heterozygous for the T2D risk haplotype (lots ACB, DSX, and QSK). ChIP-sequencing peaks overlapping variants in the T2D risk credible set are shown. FIG. 2H provides graphs that depict allelic proportions±SEM at indicated credible set SNPs. Asterisk indicates significance after Bonferroni correction for multiple hypothesis testing: ***P<1×10$^{-5}$.

FIG. 2J (top panel) provides a series of box plots showing quantitative traits associated with donors for liver eQTL analysis. Box plots depict quantitative trait associated with donors for liver (top panel) and visceral adipose (bottome panel) eQTL analyses. No significant changes in quantitative traits between genotype groups after correcting for multiple hypotheses testing. FIG. 2J (bottom panel) provides a series of box plots that depict quantitative traits associated with donors for liver RNA-sequencing. No significant changes in quantitative traits between genotype groups after correcting for multiple hypotheses testing.

FIGS. 3A-3N show data indicating that SLC16A11 is a proton (H$^+$)-coupled monocarboxylate transporter. FIG. 3A (top panel) provides a bioinformatic analysis showing amino acid sequences indicating that SLC16A11 is a Category I family member. In FIG. 3A, (top panel), the SEQ ID NOs: of the SLC16A family members containig a "TMD 1" region as shown in the figure are as follows: SLC16A11: (SEQ ID NO.: 11); SLC16A1: (SEQ ID NO.: 12); SLC16A3: (SEQ ID NO.: 13); SLC16A7: (SEQ ID NO.: 14); SLC16A8: (SEQ ID NO.: 15); SLC16A2: (SEQ ID NO.: 16); SLC16A10: (SEQ ID NO.: 17); SLC16A13: (SEQ ID NO.: 18); SLC16A6: (SEQ ID NO.: 19); SLC16A12: (SEQ ID NO.: 20); SLC16A4: (SEQ ID NO.: 21); SLC16A5: (SEQ ID NO.: 22); SLC16A9: (SEQ ID NO.: 23); and SLC16A14 (SEQ ID NO.: 24). In FIG. 3A, (top panel), the SEQ ID NOs: of the "TMD-8" regions of the SLC16A family members as shown in the figure are as follows: SLC16A11: (SEQ ID NO.: 95); SLC16A1: (SEQ ID NO.: 96); SLC16A3: (SEQ ID NO.: 97); SLC16A7: (SEQ ID NO.: 98); SLC16A8: (SEQ ID NO.: 99); SLC16A2: (SEQ ID NO.: 100); SLC16A10: (SEQ ID NO.: 101); SLC16A13: (SEQ ID NO.: 102); SLC16A6: (SEQ ID NO.: 103); SLC16A12: (SEQ ID NO.: 104); SLC16A4: (SEQ ID NO.: 105); SLC16A5: (SEQ ID NO.: 106); SLC16A9: (SEQ ID NO.: 107); and SLC16A14 (SEQ ID NO.: 108). FIG. 3A (bottom panel) shows coverage of the SLC16A11T2D protein (SEQ ID NO.: 25) by mass spectrometry. The experimental steps are depicted at the top. The protein sequence of SLC16A11$^{T2D}$ is shown. Residues that were covered by mass spectrometry and assessed for phosphorylation are shown in gray. The T2D risk coding variants are shown in larger font. No phosphorylated residues were detected. FIG. 3I provides data corresponding to Luciferase reporter assays with a fragment containing the SLC16A11 promoter and 5' UTR. FIG. 3I, top panel shows UCSC genome browser view of −425+342RISK. Note that rs77086571, rs74577409, and rs2292351 are shown by the lower peaks within the black brackets. FIG. 3I, middle panel, provides a series of graphs showing the results of the luciferase reporter assay in a panel of human cell lines; the x-axis denotes relative luminescence. Firefly luminescence is normalized by renilla luminescence. Data are from a single experiment and error bars are standard deviations. FIG. 3I, bottom panel, provides a graph showing the results of the luciferase reporter assay in HEK293T cells. Data are from four experiments (n=4) and error bars are standard deviations. Asterisks indicate significance after Bonferroni correction for multiple hypothesis testing: *P<0.05, P<1×10$^{-3}$, *P<1×10$^{-5}$. FIG. 3J provides a schematic the location of SNPs. FIG. 3K provides a plot showing the results of a metabolomics analysis of HuH7 cells expressing SLC16A11$^{REF}$. Volcano plot of SLC16A11$^{REF}$ versus CNTRL with metabolites having p-values<10$^{-5}$ highlighted in the upper left and upper right quandrants (triangle data points). FIG. 3L provides three graphs showing phenotype microarray analysis of HepG2 cells expressing SLC16A11$^{REF}$. Utilization rates of pyruvate (left panel), lactate (middle panel), and acetate (right panel) in HepG2 cells are depicted. Data are from one experiment and error bars are standard deviations. *P<0.05. FIG. 3N shows a graph illustrating that a difference in pyruvate transport between SLC16A11-expressing cells and control cells was only observed at neutral pH, likely due to activation of other endogenous SLC16 family members at acidic pH.

FIGS. 4A-4G show that T2D risk-associated coding variants abrogate SLC16A11 activity. FIG. 4A provides a graph showing the results of a FRET assay, which indicates that T2D risk SLC16A11 has a reduced rate of pyruvate transport (FRET assay). FIG. 4B provides a graph that shows a quantification of reduced rate of pyruvate transport. FIG. 4C provides a graph that provides pH traces for control, T2D risk and wild-type (WT). FIG. 4D (top panel) provides a graph showing a quantification of reduced rate of both acidification and alkalization. FIG. 4D (bottom panel) provides an image of a Western blot showing that SLC16A11 runs as a doublet under reducing SDS-PAGE conditions. Western blot images are of SLC16A11$^{REF}$-V5 and SLC16A11$^{T2D}$-V5 expressed in HuH7 (A) and HEK293T (B) cells. Note that SLC16A11 runs as a doublet and the top band of the doublet is more pronounced for SLC16A11$^{T2D}$ than SLC16A11$^{REF}$. Glycerol resolves the SLC16A11 doublet. Increasing the percentage of glycerol is sufficient to resolve the SLC16A11 doublet. This suggests that an alternative structural conformation likely underlies the doublet rather than a post-translational modification. Some membrane proteins do not fully denature under reducing SDS-PAGE conditions. FIG. 4E provides a box plot showing that cellular pyruvate levels in HuH7 hepatocarcinoma cells are altered by SLC16A11. FIG. 4F provides a box plot showing that cellular lactate levels in HuH7 hepatocarcinoma cells are altered by SLC16A11. FIG. 4G provides a schematic diagram and a chart showing SLC16A11 haplotypes and the frequency at which they occur in certain populations.

FIGS. 5A-5G provide data showing that T2D risk coding variants reduce plasma membrane localization by disrupting an interaction between SLC16A11 and BSG. FIG. 5A (top panel) provides a homology model of SLC16A11 with T2D risk-associated coding variants indicated.

FIG. 5A (bottom panel) provides an autoradiograph showing that SLC16A11 protein expression is low compared to expression of SLC16A1 and SLC16A13 in HuH7 a human hepatocellular carcinoma cell line. FIG. 5B (top panel, left) provides a Western blot showing that the presence of a proline to aspartic acid substitution (P2D) increases SLC16A11 protein levels.

FIG. 5B (top panel, right) provides a plot depicting proteins that were identified by quantitative mass spectrometry to be enriched in a proline to aspartic acid substitution (P2D) WT SLC16A11 immunoprecipitation (IP) versus control IP. Enriched proteins are shown in the upper right hand quadrant. SLC16A11 is shown in gray (labeled SLC16A11). Basigin (BSG) and Embigin (EMB), ancillary proteins for SLC16 type I category members, are shown along with other strongly enriched proteins in dark gray (labeled BSG and EMB). Biological replicates from two independent experiments are plotted. FIG. 5B (bottom panel) provides a Western blot showing that SLC16A11 is part of a larger molecular complex. Co-immunoprecip-itation of SLC16A11-HA and SLC16A11-V5 indicates that SLC16A11 might be part of a larger molecular complex that consists of at least two SLC16A11 molecules.

FIG. 5C (top panel) provides a plot showing that SLC16A11 protein levels are comparable in the P2D T2D risk SLC16A11 IP versus P2D WT SLC16A11 IP. BSG is significantly depleted in the P2D T2D risk SLC16A11 IP with respect to the P2D WT SLC16A11 IP indicating that the T2D risk coding variants disrupt the interaction between SLC16A11 and BSG. FIG. 5C (bottom panel) provides a schematic diagram illustrating GeNETs network analysis of WT/control interactome zoomed in on components of the proteosome.

FIG. 5D (top panel) provides two Western blots showing that SLC16A11 is degraded by the proteasome and has a short half-life relative to other SLC16 family members. FIG. 5D-A shows that SLC16A11 protein is rapidly degraded. HEK293T cells expressing V5-tagged SLC16A11$^{REF}$, SLC16A13, or SLC16A1 were treated with cycloheximide (10 µg/mL) for the indicated times. Note that the SLC16A11, SLC16A13, and SLC16A1 images are from different exposure times. FIG. 5D-B shows that SLC16A11 protein levels are increased by proteasome inhibition. HuH7 cells stably expressing SLC16A11$^{REF}$-V5 were treated with MG132 (5 µM) or cyclohexamide for 3 hrs. FIG. 5D (bottom panel) provides Western blot showing SLC16A11 and BSG co-immunoprecipitations. (5D-A-5D-C): Co-immunoprecipitation of SLC16A11 and BSG confirms the reduced interaction between SLC16A11$^{T2D}$ and BSG in HEK293T cells. BSG is glycosylated and runs as multiple bands by reducing SDS-PAGE. Molecular weight markers (kDa) are indicated. (5D-A): Interaction of BSG-V5 with immunoprecipitated SLC16A11-HA. (5D B): Interaction of SLC16A11-HA with immunoprecipitated BSG-V5. (C) Interaction of endogenous BSG with immunoprecipitated SLC16A11-HA.

FIG. 5E (top panel) provides a Western blot co-immunprecipitation with SLC16A11-HA and endogenous BSG to confirm reduced SLC16A11 and BSG interaction conferred by the T2D risk coding variants. FIG. 5E (bottom panel) provides a Western blot showing the effects of MG132 on SLC16A11 protein levels, with vinculin shown as a loading control. In the presence of MG132, total SLC16A11 levels are increased, indicating that over-expressed SLC16A11 is degraded by the proteosome. Also shown in the bottom panel of FIG. 5E are cycloheximide time-course experiments. These experiments indicate that no substantial difference exists between SLC16A11$^{REF}$ and SLC16A11$^{T2D}$ half-lives.

FIG. 5F (top panel) provides a Western blot showing that WT SLC16A11-V5 plasma membrane localization is reduced in BSG knock-out (KO) HEK293-T cells. Two different BSG knock-out cell lines were generated using CRISPR/Cas9 and a plasma membrane fraction were biochemically separated from intracellular membranes. FIG. 5F (bottom panel) provides a diagram and a Western blot relating to input for SLC16A11 proteomic studies. Experimental setup is depicted at the top. Input for immunoprecipitations was run by SDS-PAGE and shows comparable protein levels of SLC16A11$^{REF}$ and SLC16A11$^{T2D}$.

FIG. 5G (top panel) provides a Western blot showing WT SLC16A11-V5 and T2D risk SLC16A11-V5 expressed in HEK293-T cells. Markers show that a clean separation was achieved between intracellular membranes and plasma membrane. Intracellular membrane WT and T2D risk SLC16A11 levels are comparable while T2D risk SLC16A11 levels at the plasma membrane are reduced with respect to WT SLC16A11. FIG. 5G (bottom panel) provides a bar plot showing the relative fraction of SLC16A11 at the plasma membrane±SD (n=15, P=4×10$^{-8}$). ***P<1×10$^{-5}$. The PathHunter® assay was performed in U2OS cells transfected with SLC16A11 variants. Bar plots depict the relative amount of SLC16A11 at the plasma membrane±SD (n=5). *P<0.05, **P<1×10$^{-3}$.

FIG. 5I-A presents a Western blot analysis of BSG levels in wild-type and BSG-knockout U2OS MEM-EA cells. Two different BSG knockout lines were generated using two different sgRNAs and CRISPR/Cas9. Approximate locations of molecular weight markers (kDa) are indicated. FIG. 5I-B shows the results of a split β-galactosidase reporter assay in WT and BSG-knockout U2OS MEM-EA cells (DiscoveRx) and demonstrates that SLC16A11$^{REF}$ plasma membrane localization is reduced in BSG-knockout cells. Bar plots depict the relative amount of SLC16A11$^{REF}$ at plasma membrane±SD (n=4 for WT; n=8 for BSG knockout (4 each per BSG-knockout U2OS MEM-EA cell line); P=4×10$^{-5}$). FIG. 5I-C shows the results of a split β-galactosidase reporter assay in U2OS MEM-EA cells demonstrates a reduction in SLC16A11$^{T2D}$ at the cell surface relative to SLC16A11$^{REF}$. Bar plots depict the relative amount of SLC16A11 at the cell surface±SD (n=5; P=1×10$^{-5}$).**P<1×10$^{-3}$.

FIG. 6A provides a plot showing the comparison of gene expression in liver of T2D risk carrier/non-carriers demonstrating that SLC16A11 is the most significantly altered gene within 100 Kb of top SNP. FIG. 6B provides a plot showing the comparison of gene expression in liver of T2D risk carrier/non-carriers demonstrating that SLC16A11 is only SLC16 family member altered by the variant haplotype. FIGS. 6C and 6C-1 provide a series of box plots showing the effects of T2D risk or the reference allele (REF) (top panel) or type 2 diabetes (T2D) versus control on a variety of clinical parameters.

FIG. 8A provides western blot data. SLC16A1 is used as a positive control. FIG. 8A also provides a graph showing the uptake of radiolabelled pyruvate in oocytes expressing SLC16A11 versus controls. (x axis: $^{14}$C-pyruvate (mM); y-axis: picomol pyruvate/oocyte per minute).

FIG. 8B provides a schematic including a graph and table showing an analysis of SLC16A11 affinity for pyruvate transport parameters, in comparison to SLC16A1. Note, SLC16A11 has higher affinity and greater transport efficiency.

FIG. 9B (top panel) provides a series of graphs showing SLC16A11, SLC16A13, and SLC16A1 gene expression in primary human hepatocytes treated with siRNAs targeting SLC16A11. Bar plots depict relative gene expression±SD using TBP for normalization.

FIG. 9B (top and bottom panels) provide bar graphs showing transcript levels of relevant genes and fold-changes of glycolysis metabolites in cells treated with SLC16A11 siRNAs compared to cells treated with negative control siRNAs. FIG. 9B (bottom panel) indicates metabolites with fold-changes less than 0.9 or greater than 1.1.

FIG. 9C shows germline transmission in Slc16a11 and Slc16a13 CRISPR-Cas9 mouse models. The mosaic mice born from the microinjection of genome editing reagents were mated with wild-type C57BL/6 mice and resulted in the pups described. Genotypes were assessed by sequencing and are with respect to the wild-type sequence. For example, a deletion of 2 bp Slc16a11 KO model means that 2 bp were deleted in the wild-type Slc16a11 open reading frame resulting in a premature stop codon. Mutations that were not of interest are shown in gray. Mutations for which colonies were expanded are indicated with arrows. Ultimately, the deletion of 19 bp Slc16a11 KO mouse model was selected as a starting model for in-depth investigation of the role of Slc16a11 in organismal physiology.

FIG. 9D (top panel) provides a schematic diagram showing the endogenous Slc16a11 locus in both the Slc16a11* and Slc16a11-$^{Neo}$ knockout mouse models.

FIG. 9D (middle panel) provides a series of graphs showing gene expression data in Slc16a11* and Slc16a11-Neo knock out mice demonstrating altered Slc16a13 levels in Slc16a11* mice. Bar plots depict relative gene expression±SD using Tbp for normalization. Data are from 22 mice. FIG. 9D (bottom panel) provides a schematic diagram of the endogenous Slc16a11 and Slc16a13 loci in the CRISPR mouse models.

FIG. 9E (top and bottom panels) provides plots showing knock-out (SLC16AA11del19 CRISPIR) vs. wild-type gene expression changes. FIG. 9E (top panel) shows SLC16A11 and genes at locus. FIG. 9E (bottom panel) shows SLC16A11 family.

FIG. 9G provides two plots showing that malondialdehyde levels are increased in liver (Left panel) and plasma (Right panel) of SLC16A11 knock-out (KO) mice.

FIG. 9H provides two box plots showing that lipids are altered in liver (Left panel) and plasma (Right panel) of SLC16A11 knock-out (KO) mice.

FIG. 9I shows a gene set enrichment analysis of down-regulated genes in human carriers of the T2D risk haplotype in Slc16a11 knockout mice.

FIG. 9K-1 presents bar plots illustrating the expression of SLC16A11, SLC16A13, SLC16A1, SLC16A3, SLC16A7, SLC16A8, and BSG in primary human hepatocytes treated with siRNAs targeting SLC16A11 or negative control siRNAs. The bar plots depict relative gene expression±SD using TBP for normalization. (*$P\approx4.8\times10^{-3}$).

FIGS. 9K-2 and 9K-3 illustrate pathway enrichment analyses of intracellular (FIG. 9K-2) and extracellular (FIG. 9K-3) metabolic pathway changes following SLC16A11 knockdown compared to control primary human hepatocytes. Normalized enrichment scores quantify the concordance of individual metabolite fold-changes within a given metabolic pathway or class, with a positive score indicating enrichment and a negative score corresponding to depletion. Each dot represents a different metabolic pathway or metabolite class. P values are indicated by dot size. Significantly altered pathways (false discovery rate [FDR]<0.05) are labeled, with non-significant pathways (FDR>0.05) shown in gray. LPCs, lysophosphatidylcholines; PCs, phosphatidylcholines; PE, phosphatidylethanolamine; DAGs, diacylglycerols; TAGs, triacylglycerols.

FIG. 9K-4 provides a schematic depiction which summarizes the effects of T2D-associated variants at 17p13 on T2D risk. The T2D disease association at 17p13 is driven by variants that disrupt SLC16A11 function, which leads to changes in fatty acid and lipid metabolism that are associated with increased risk of T2D. The causality of the associations between increased acylcarnitines, diacylglycerols and triacylglycerols and disease is uncertain.

FIGS. 9L, 9M, 9N, and 9O illustrate foldchange in metabolites SLC16A11siRNA/control. FIG. 9M shows an enlargement of the right side of FIG. 9L.

FIG. 13A provides a series of graphs showing that mTOR inhibitors increase SLC16A11 expression. SNU761 (Left panel) and NCIH716 (Right panel) cells were treated with KU-0063794, AZD-8055, and methotrexate at the indicated concentrations and times. SLC16A11 expression was then assessed using droplet digital PCR (ddPCR). Bar plots depict relative fold-changes with respect to DMSO and error bars are standard deviations.

FIG. 13B shows the chemical structure of AZD-8055 (left panel) and KU 0063794 (right panel).

FIG. 15A provides a graph showing the distribution of the average connectivity scores across all 2837 compound signatures queried from the LINCS dataset. The top compounds, those generating signatures most resembling the query signature, are in the black box. The middle compounds that did not resemble the query signature are shown in the gray box. FIG. 15B provides a graph showing the distribution of fold-changes induced in SLC16A11 expression by compound treatments. DMSO is shown in black and is tightly centered on 1 (SLC16A11) with a density of approximately 2.5. FIG. 15C provides a heat map showing hierarchical clustering of the SLC16 expression profiles generated by the compound treatments. The color light gray corresponds to fold-changes greater than 1 and dark gray to black corresponds to fold-changes less than 1. The labels corresponding to the SLC16 expression profiles are as follows: A1 for SLC16A1; A13 for SLC16A13; $A11_1$, $A11_2$, and $A11_3$ correspond to SLC16A11 expression normalized by TBP from three biological replicates and $A11_{avg}$ is their average; A11* corresponds to SLC16A11 expression normalized by HPRT1.

FIG. 16 (top panel) provides a graph showing a dose response curve for the mTOR inhibitor AZD-8055 in SNU761 cells. AZD-8055 treatment results in the increase of SLC16A11 (A11) transcript levels. FIG. 16 (bottom panel) provides a graph indicating AZD-8055 increases SLC16A11 transcript levels in primary human hepatocytes. SLC16A11 (denoted by A11 when normalized by TBP and A11* for HPRT1), SLC16A13 (A13), and SLC16A1 (A1) in comparison with DMSO treated cells.

FIG. 22 provides bar graphs showing the effects of low and high concentrations of metabolic effectors (oleic acid (OA), insulin and glucagon) on expression levels of SLC16A11 and SLC16A13 transcripts in SNU761 cells cultured for 24 hours in the presence of low/high concentrations of OA (0.3 mM/1.5 mM); insulin (100 nM/500 nM); or glucagon (100 nM/500 nM). Relative transcript levels of SLC16A11 and SLC16A13 are shown, with 2-FBS (2% Fetal Bovine Serum) used as control.

FIG. 24 provides a listing of SLC16A11 T2D risk haplotype sequences.

DETAILED DESCRIPTION OF THE INVENTION

Figure 1B:
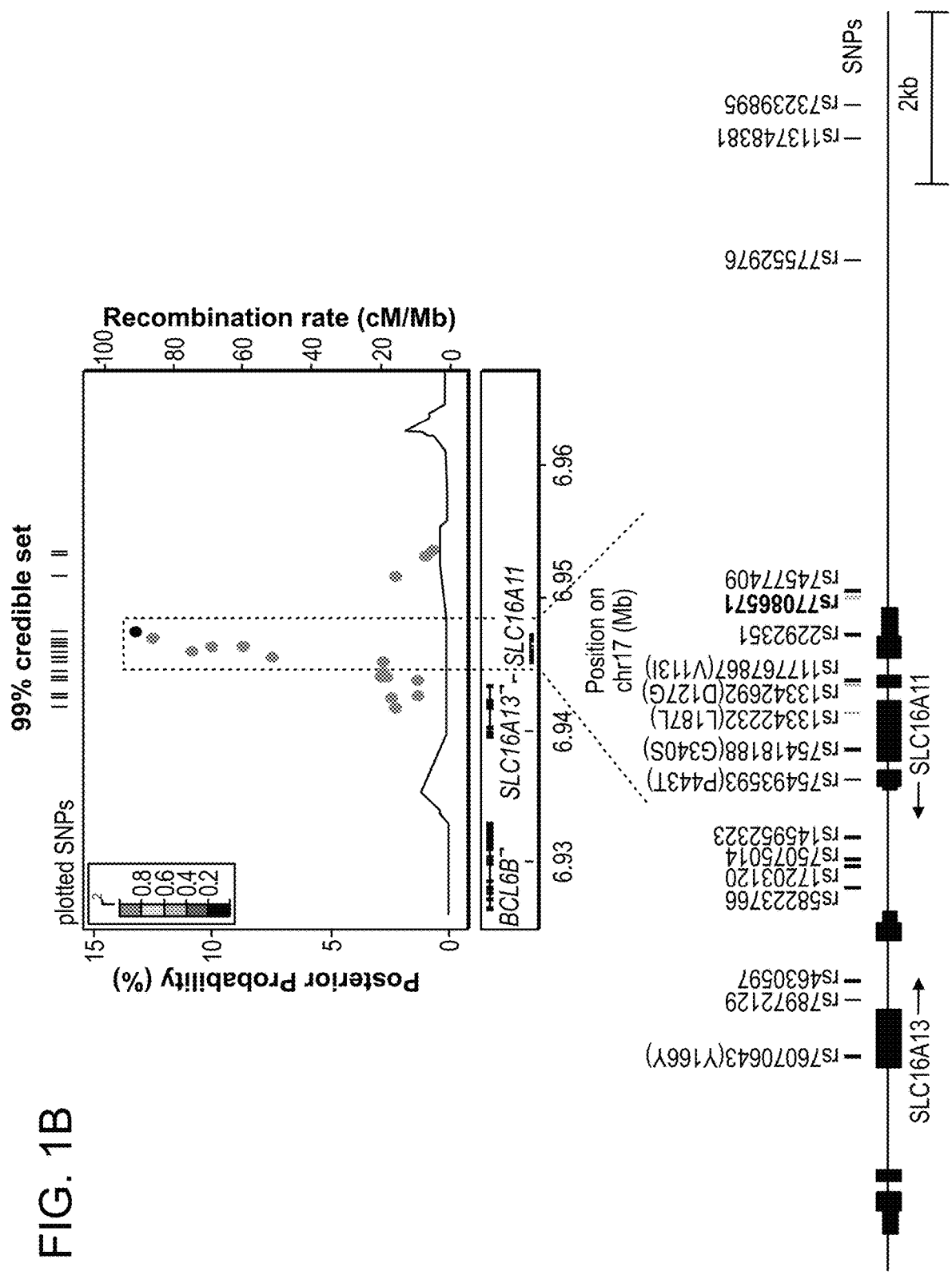

The invention features compositions and methods that are useful for increasing the level or activity of SLC16A11 in subjects having or at risk of developing type 2 diabetes (T2D). In one embodiment, the invention features compositions and methods useful for increasing the level or activity of SLC16A11 in carriers of the SLC16A11 risk haplotype, there by treating or preventing type 2 diabetes in those carriers.

The invention is based, at least in part, on the discovery of a variant haplotype in SLC16A11 that explains ~20% of the increased T2D prevalence in Mexico. Type 2 Diabetes affects Latinos at twice the rate seen in populations of European descent. Genetic fine-mapping defined a reduced set of tightly linked common variants likely to contain the causal allele. As described herein, a cis-eQTL was identified for SLC16A11 in human liver, associated with decreased SLC16A11 expression in risk allele carriers. Furthermore, T2D-associated coding variants in SLC16A11 were shown to attenuate activity by disrupting a key interaction with Basigin (BSG), thereby reducing plasma membrane localization. Both independent mechanisms indicate that SLC16A11 is the causal gene, and reduced SLC16A11 function is the T2D-relevant direction-of-effect. SLC16A11 was also shown to function as a $H^+$-coupled monocarboxylate transporter. Lower SLC16A11 expression in human carriers was accompanied by altered hepatic metabolism. Additionally, Slc16a11 knockout mouse models exhibit metabolic changes associated with insulin resistance and type 2 diabetes. Based on these findings, it is likely that increasing SLC16A11 function could be therapeutically beneficial for T2D.

The invention is also based, at least in part, on the discovery that agents that inhibit mTOR (e.g., tipifarnib-P2, calpeptin, KU-0063794, MEK1-2-inhibitor, Fostamatinib, AZD-8055, NVP-BEZ235, PP-30, PD-0325901, PIK-90, BMS-536924, PI-828 PI-103, KIN001-244, serdemetan, PP-2, WYE-354, methotrexate, U0126, U-0126, NU-7026, OSI-027, Selumetinib, deforolimus, PAC-1 and other such mTOR inhibitors) beneficially increase the expression of SLC16A11.

Accordingly, the invention provides compositions and methods for increasing SLC16A11 function and/or expression, as well as methods of using such compositions for the treatment of type 2 diabetes.

SLC16A11

Type 2 Diabetes (T2D) afflicts more than 415 million people and is a leading cause of morbidity and mortality worldwide. While T2D is influenced by environmental factors, it is also a highly heritable disorder, with genetic variation contributing to a disparity in T2D prevalence across populations. An example of this disparity is observed within American populations, where the prevalence of diabetes in individuals of Mexican or Latin American descent is approximately twice that of US non-Hispanic whites. Understanding the genetic influences on disease biology can help identify at-risk individuals, guide more effective personalized treatment approaches, and illuminate new targets and pathways for therapeutic development and intervention. To date, large-scale genetic studies in diverse populations have identified >100 genetic loci containing common variants associated with altered risk of T2D. However, few of these genetic findings have been translated into knowledge of the causal variant(s) or gene(s). Furthermore, most of the implicated genes are of unknown function and the molecular mechanisms by which the causal variant(s) alter gene regulation or protein function and ultimately contribute to disease biology remain elusive.

One T2D signal for which mechanistic insight has potential for meaningful impact is the risk association at 17p13. This factor was first identified through a genome-wide association study (GWAS) investigating genetic influences on diabetes risk in Mexico (SIGMA Nature. 2014 Feb. 6; 506(7486):97-101). The T2D risk haplotype at this locus is common among individuals of Mexican or Latin American descent (with an allele frequency of ~30%) yet rare among individuals of European (<2%) and African (0%) descent. Notably, this genetic association results in a 25% increase in T2D risk per copy of the risk haplotype carried and explains up to 20% of the increased T2D prevalence in Mexico (SIGMA Nature. 2014 Feb. 6; 506(7486):97-101). Variants contained in the T2D risk haplotype at 17p13 span two protein coding genes, SLC16A11 and SLC16A13. Interestingly, while most disease-associated common variants are in non-coding regions (Maurano et al., 2012, Science 337, 1190-1195), the T2D risk haplotype at 17p13 contains five coding variants in SLC16A11, including four missense mutations and one synonymous change. Of note, another haplotype carrying two of the five coding variants in SLC16A11 is found at high frequency (~38%) in Africa, but is rare in other populations (SIGMA Nature. 2014 Feb. 6; 506(7486):97-101), allowing for trans-ethnic fine-mapping to delineate the causal variant(s) underlying risk in the Latino population.

Both SLC16A11 and SLC16A13 are members of the SLC16 (or monocarboxylate transporter, MCT) family, a group of 14 solute carriers that are defined by two highly conserved sequences, and are all predicted to have 12 transmembrane domains with both N- and C-termini facing the cytoplasm. Despite these structural similarities, different members of this family have been shown to mediate transport of distinct substrates, utilizing two different mechanisms. SLC16A1, SLC16A3, SLC16A7, and SLC16A8 are known as Category I members of the SLC16 family and transport simple monocarboxylic acids, such as lactate, pyruvate and ketone bodies, via a proton ($H^+$)-coupled mechanism (Halestrap et al., Pflugers Arch. 2004 February; 447(5):619-28). Of these, SLC16A1 is the most extensively studied and has been shown to transport a wide range of monocarboxylic acids. In addition, these family members have been shown to interact with basigin (BSG) and embigin (EMB), two chaperone proteins important for plasma membrane localization of the transporters. In contrast, a second class of SLC16 transporters, known as Category II transporters, include SLC16A2 and SLC16A10 as members. SLC16A2 and SLC16A10 do not transport monocarboxylic acids, nor do they use a $H^+$-coupled mechanism; instead, these proteins transport larger hydrophobic molecules, such as triiodothyronine ($T_3$) and thyroxine ($T_4$) and aromatic amino acids, through facilitated diffusion (Halestrap, A. P. et al., 2004, Pflugers Arch, 447, 619-628). Furthermore, SLC16A2 does not interact with BSG or EMB. Studies of two other family members, SLC16A6 and SLC16A9, show that SLC16A6 transports ketone bodies (Hugo, S. E. et al., 2012, Genes Dev., 26, 282-293), suggesting that it may belong to Category I, and SLC16A9 transports carnitine via a $H^+$-independent mechanism (Suhre, K. et al., 2011, Nature, 477, 54-60), suggesting that it may belong to Category II. The members of the SLC16 family have distinct but overlapping expression patterns (Halestrap, A. et al., 2013, Mol. Aspects Med, 34:337-349). SLC16A11 is expressed in relatively few tissues, with the highest levels detected in thyroid, liver, and salivary gland, while SLC16A13 is more broadly expressed, with the highest levels in liver (SIGMA T2D Consortium et al., 2014, Nature, 506:97-101). To date, the roles of SLC16A11 and SLC16A13 in these tissues have not been characterized.

The results described herein support the genetic association at the 17p13 locus, using genetic fine-mapping and functional studies to delineate mechanisms underlying T2D risk at this locus. This provides evidence for two independent mechanisms by which variants on the T2D risk haplotype impact SLC16A11 action. Genetic variants at this locus have two distinct actions on SLC16A11, a category I SLC16 transporter. Variants, such as non-coding regulatory, on the T2D-risk haplotype lead to decreased gene expression of SLC16A11 in liver, while coding variants affect the interaction of the SLC16A11 protein with BSG, which leads to reduced levels of the transporter at the cell surface. In addition, disruption of SLC16A11 in primary human hepatocytes leads to T2D-relevant changes in fatty acid and lipid metabolism. Together, these studies implicate reduced SLC16A11 function in liver as a causal factor for T2D, and indicate that agents and methods that increase SLC16A11 would be therapeutically beneficial.

Type 2 Diabetes Therapy

The present invention provides methods of treating or preventing type 2 diabetes in subjects having or at risk of developing type 2 diabetes. In one embodiment, the subject is identified as having an alteration in the sequence of a SLC16A11 polypeptide or polynucleotide (e.g., any one or more of V113I, D127G, L187L, G340S, P443T). In one embodiment, a subject has a coding variant or a non-coding variant. Because the variants are tightly linked, a subject may carry none of the alterations, two alteration (e.g., L187L, D127G), or all 5 of these variants. The haplotype with all 5 coding variants and the non-coding variants have been definitively associated with T2D risk. In another embodiment, a subject carrying L187L and D127G also carries V113I, G340S, and/or P443T. In one embodiment, this sequence alteration affects the level or activity of a SLC16A11 polypeptide. In particular, the invention provides compositions and methods for increasing the level and/or activity of SLC16A11 in a subject.

As described herein, agents that inhibit mTOR have been identified as useful for increasing SLC16A11 expression for the treatment of diabetes. The mechanistic target of rapamycin (mTOR), (formerly mammalian target of rapamycin) is a member of the phosphatidylinositol 3-kinase-related kinase family of protein kinases. mTOR is present in two protein complexes, mTOR complex 1 (mTORC1) and mTOR complex 2 (mTORC2). mTOR functions as a serine/threonine protein kinase that regulates cell growth, cell proliferation, and other cellular activities, and also functions as a tyrosine kinase when present in mTORC2.

In one embodiment, a subject having type 2 diabetes is treated with one or more agents that inhibit mTOR. In one embodiment, the agent is tipifarnib-P2, calpeptin, KU-0063794, MEK1-2-inhibitor, Fostamatinib, AZD-8055, NVP-BEZ235, PP-30, PD-0325901, PIK-90, BMS-536924, PI-828, PI-103, KIN001-244, serdemetan, PP-2, WYE-354, methotrexate, U0126, U-0126, NU-7026, OSI-027, selumetinib, deforolimus, or PAC-1. In one embodiment, the agent is KU-0063794 or AZD-8055.

AZD-8055 is an ATP-competitive inhibitor of mTOR kinase activity, with an IC50 of 0.8 nmol/L (Chresta et al., Cancer Res. 2010 Jan. 1; 70(1):288-98). In studies by Chresta et al., AZD8055 showed selectivity (approximately 1,000-fold) against all class I phosphatidylinositol 3-kinase (PI3K) isoforms and other members of the PI3K-like kinase family. Furthermore, there was no significant activity against a panel of 260 kinases at concentrations up to 10 µmol/L. Interestingly, AZD-8055 can be orally administered.

Checkpoint kinase (e.g., Checkpoint kinase 1 and 2) is a Serine/threonine protein kinase. Checkpoint kinase (Chk) coordinates the DNA damage response (DDR) and cell cycle checkpoint response. Activation of Chk1 results in the initiation of cell cycle checkpoints, cell cycle arrest, DNA repair and cell death to prevent damaged cells from progressing through the cell cycle. Chk1 is also known to facilitate diverse cellular processes including gene transcription, embryo development, cellular responses to HIV infection and somatic cell viability. In embodiments of the present invention CHK is inhibited to prevent or treat type 2 diabetes.

In particular embodiments, the present invention features compositions comprising one or more agents that inhibit Checkpoint 1 kinase (CHK) or the mechanistic target of rapamycin (mTOR) signaling pathways. Such agents include small molecules described herein.

Small molecules capable of inhibiting mTOR include are known in the art, and include, for example, AZD-8055, KU-0063794, Apitolisib (GDC-0980, RG7422), BEZ235 (e.g., NVP-BEZ235, Dactolisib), BGT226 (NVP-BGT226), CC-223, Chrysophanic acid, CH5132799, CZ415, Deforolimus (AP23573, MK-8669, Ridaforolimus), Everolimus (RAD001), ETP-46464, GDC-0349, Gedatolisib (PF-05212384, PKI-587), GSK1059615, INK 128 (MLN0128), Omipalisib (GSK2126458, GSK458), OSI-027, Palomid 529 (P529), PF-04691502, PI-103, PP121, Sirolimus, Tacrolimus (FK506), Temsirolimus (CCI-779, NSC 683864), Torin 1, Torin 2, Torkinib (PP242), Vistusertib (AZD-2014), Voxtalisib (XL765, SAR245409), WAY-600, WYE-125132 (WYE-132), WYE-354, WYE-687, XL388, and Zotarolimus (ABT-578).

Small molecules capable of inhibiting CHK include AZD-7762, CHIR-124, LY2603618, MK-8776 (SCH 900776), and PF-477736.

In one embodiment, a subject having a reduction in SLC16A11 activity or level is treated by replacing the subject's endogenous SLC16A11 polynucleotide with a wild-type form of SLC16A11. In another approach, the subject is treated by expressing a heterologous polynucleotide encoding SLC16A11 in one or more tissues of the subject. In particular embodiments, the heterologous polynucleotide comprises a promoter upstream of SLC16A11, as well as the 5' untranslated region. Methods for the heterologous expression of polynucleotides are known in the art and described herein. Such methods are useful not only to those having a mutation in an SLC16A11 protein or nucleic acid sequence encoding the protein or regulating protein expression, but also to subjects suffering from type 2 diabetes who do not have such mutations.

In an embodiment, the expression level of the SLC16A11 protein in cells is stabilized and/or modulated by preventing proteasome-mediated degradation at the N-terminus of the protein as a therapeutic approach for treating T2D, both in the broader at-risk population and in risk variant carriers. The level of the SLC16A11 protein expressed in cells is stabilized and/or enhanced by inhibiting its proteasome-mediated degradation and blocking or preventing the ubiquitination of SLC16A11 at its N-terminus. In an embodiment, a stabilized SLC16A11 protein is provided wherein the protein comprises an N-terminus that is modified so as to block, hinder, interfere with, or inhibit N-terminal ubiquitination and subsequent proteosomal degradation of the protein.

Figure 5H:
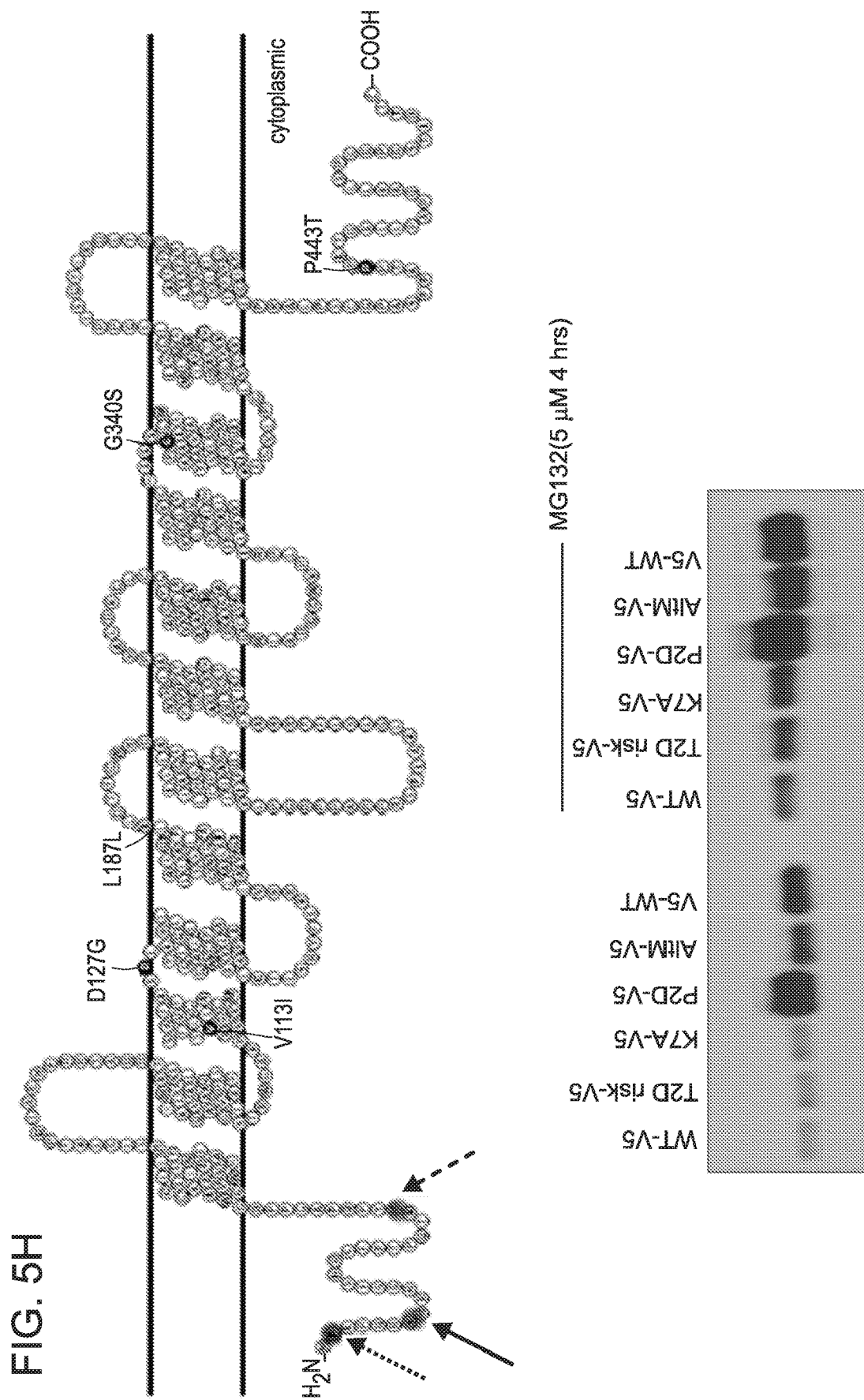
FIG. 5H provides a schematic diagram of SLC16A11 and a Western blot. The Western blot (blotted for the V5 epitope) analyzes the effect of various mutations on SLC16A11 protein levels in transiently transfected 293T cells and treatment with MG132 (5 µM for 4 hours), (right side of blot). WT-V5: SLC16A11 with V5 at the carboxy terminus; T2D risk-V5: type 2 diabetes risk-V5; K7A-V5 and P2D-V5: mutations at designated positions of SLC16A11; AltM-V5: removal of the N-terminal 24 amino acids of SLC16A11; V5-WT: SLC16A11 with V5 at the N-terminus; a SLC16A11 variant where the V5 epitope is moved from the C terminus to the N terminus. Note that the P2D variant increases SLC16A11 protein levels.

As described herein, the SLC16A11 protein was stabilized in cells by inhibition of proteasome degradation. The presence of a peptide at the N-terminus of SLC11A11 blocked N-terminal ubiquitination of the protein and prevented its proteosomal degradation, thereby providing increased and stabilized levels of SLC16A11 in the cell. More specifically, as described in Example 12 and shown in FIG. 5H, removing the N-terminal 24 amino acids of SLC16A11 and moving the V5 epitope tag from the C-terminus to the N-terminus of the protein increased. SLC16A11 protein levels. As also demonstrated infra, the P2D SLC16A11 variant having an aspartate amino acid residue at position 2 of the N-terminus of the protein, a potential site of regulation through an N-terminal ubiquitination pathway (Ciechanover, A., 2005, Methods Mol Biol, 301:255-270), to reduce N-terminal methionine excision (NME) while promoting N-terminal acetylation (N-Ac) of the initiator methionine, was able to compete with ubiquitination of this residue such that the variant exhibited increased SLC16A11 protein levels. The locations of the P2D, K7A, and AltM mutations in the SLC16A11 protein are shown in FIG. 5A (top panel).

In embodiments, methods, compounds, molecules, or agents that inhibit the proteasomal pathway and/or enzymes active in the ubiquitin pathway, may be used to block, interfere with, mask, or inhibit ubiquitination of SIX 16A11 at its N-terminus. Nonlimiting examples of agents (e.g., small molecules) that target various components of the ubiquitin pathway leading to protein degradation and that may be used according to the invention include, without limitation, proteasomal pathway inhibitors such as MG132, (see, e.g., Example 12 and FIG. 5E (bottom)), bortezomib (or the PS-341 active ingredient), epoxomicin, lactacystin, celastrol, aclacinomycin A, carfilzomib, MLN2238, MLN9708, oprozomib, or pharmaceutically acceptable derivatives, analogs, or forms thereof. In other embodiments, compounds that inhibit E3 ubiquitin ligase include, without limitation, SMER3 (a selective inhibitor of Skp1-Cullin-F-box ubiquitin ligase), thalidomide, TAME, NCS-66811, Nutlin-3, SL-01, SKPin C1, SMER3, PTC-209, or pharmaceutically acceptable derivatives, analogs, or forms thereof, may be useful. In other embodiments, compounds that inhibit the ubiquitin E1 enzyme include PYR-41 or a pharmaceutically acceptable derivative, analog, or form thereof, may be useful. Inhibitors of the chaperone-like protein p97, which guides protein substrates to the 26S proteasome for degradation may be useful and include DBeQ (inhibits the AAA-ATPase p97), MDBN (inhibits p97/valosin-containing protein and NMS-873 (an allosteric inhibitor of the ATPase activity of p97.

In accordance with the invention, the methods by which SLC16A11 is stabilized against proteasome-mediated degradation are not intended to be limiting. Any process that specifically blocks or interferes with the N-terminal region or residue(s) of the N-terminus of SLC16A11 that are involved in ubiquinating the protein may be used to prevent N-terminal ubiquitination and subsequent proteosomal degradation of SLC16A11. In a particular embodiment, an agent, e.g, a peptide, protein, or small molecule compound, that specifically binds to an N-terminal region or site involved in the ubiquitination of SLC16A11 and that specifically blocks, masks, hinders, or otherwise interferes with binding of one or more enzymes of the ubiquitin pathway at the N-terminus of SLC16A11, in particular, the amino acid residue at position 2 of the N-terminus of SLC16A11, may be suitable for use. In a particular embodiment, the agent blocks or masks the proline residue at amino acid position 2 of the N-terminus of the SLC16A11 protein. In an embodiment, the agent is an antibody or an antigen binding fragment thereof that binds to the N-terminus of SLC16A11. In a particular embodiment, such an antibody or an antigen binding fragment thereof blocks or masks the proline residue at amino acid position 2 of the the N-terminus of SLC16A11. In embodiments, such a peptide, protein (e.g., anti-SLC1611 antibody or an antigen binding fragment thereof), agent or small molecule compound may sterically or conformationally block one or more enzymes/proteins of the ubiquitination pathway to inhibit or thwart ubiquitination of the SLC16A11 protein. In an embodiment, the ubiquitination-blocking agent may be reversibly bound to the N-terminus of the SLC16A11 protein. In accordance with the methods described herein, the blocking/unblocking of the N-terminus of the SLC16A11 protein provides a useful approach to modulating the longevity of SLC16A11 in vivo.

In an embodiment, a small molecule that is specifically designed to target, and block or mask, the region or amino acid residue sites in the N-terminus of SLC16A11 that are bound by one or more proteins/enzymes of the ubiquitination system, may be provided, e.g., to a cell of a subject, thereby preventing proteasome degradation of SLC16A11 and stabilizing, enhancing, or increasing its expression level in the cell. In an embodiment, the N-terminus of the SLC16A11 protein can be blocked or unblocked to modulate (e.g., increase or decrease, respectively) the longevity of the SLC16A11 protein in a cell. In an embodiment, the small molecule blocks or masks the proline residue at amino acid position 2 of the N-terminus of the SLC16A11 protein. In an embodiment, the small molecule compound may be identified through one or more conventional screening assays that assess and determine whether the small molecule increases or stabilizes SLC16A11 expression level or activity in a cell that expresses SLC16A11, e.g., without limitation, an adipocyte, hepatocyte, myocyte, pancreatic cell, thyroid cell, salivary gland cell, and progenitor cells thereof.

In a particular embodiment, an SLC16A11 protein having a proline to aspartic acid substitution (P2D) at amino acid position 2 of the N-terminus may be used to increase SLC16A11 protein levels in a cell, such as, for example, a liver cell or a pancreatic cell.

Uses of CHK and mTOR Inhibitors

In particular embodiments, the invention features methods for increasing the expression or activity of SLC16A11 by contacting a cell with a Checkpoint (CHK) inhibitor or mechanistic target of rapamycin (mTOR) inhibitor to treat or prevent type 2 diabetes. In general, the method includes a step of contacting a diabetic or metabolically deficient cell with an effective amount of a compound of the invention. The present method can be performed on cells in culture, e.g., in vitro or ex vivo, or can be performed on cells present in an animal subject, e.g., as part of an in vivo therapeutic protocol. The therapeutic regimen can be carried out on a human or other subject.

The compounds of the invention or otherwise described herein can be tested initially in vitro for their effects on the metabolic function and expression of SLC16A11 on cells suitable for the study of type 2 diabetes. Examples of cell lines that can be used are any of the cell lines described herein (e.g., HuH7 human hepatocellular carcinoma cells) or any other suitable cell line known in the art. Alternatively, the activity of compounds of the invention can be tested in vivo using various animal models known in the art. Agents that increase the expression of SLC16A11 (A11) are identified as useful in the methods of the invention.

The methods discussed herein can be used to increase the expression of SLC16A11 in virtually any cell. The invention provides methods for treating or preventing type 2 diabetes by administering to the subject an effective amount of an agent that inhibits CHK or mTOR signaling as described herein. In certain embodiments, the subject is a mammal, in particular, a human. Agents that are determined to be effective for the prevention or treatment of type 2 diabetes in animals, e.g., dogs, rodents, may also be useful in the treatment of type 2 diabetes in humans.

Pharmaceutical Compositions

In particular embodiments, the invention provides pharmaceutical compositions for the prevention or treatment of type 2 diabetes, comprising an effective amount of an agent that inhibits Checkpoint kinase (CHK) or the mechanistic target of rapamycin (mTOR) and a pharmaceutically acceptable carrier. In particular embodiments, the effective amount is effective to increase the expression of SLC16A11 in a cell or to otherwise treat or prevent type 2 diabetes in a subject, as described herein.

In an embodiment, the agent is administered to the subject using a pharmaceutically-acceptable formulation. In certain embodiments, these pharmaceutical compositions are suitable for oral or parenteral administration to a subject. In still other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound. In certain embodiments, the subject is a mammal, e.g., a primate, e.g., a human.

The methods of the invention further include administering to a subject a therapeutically effective amount of a compound in combination with a pharmaceutically acceptable excipient. The phrase "pharmaceutically acceptable" refers to those compounds of the invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable excipient" includes pharmaceutically-acceptable material, composition or vehicle, such as a liquid or solid filler, diluent, carrier, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these compositions include the step of bringing into association a agent(s) with the carrier and, optionally, one or more accessory ingredients. In general, the formulations are prepared by uniformly and intimately bringing into association a compound with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent. The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants, such as wetting agents, emulsifying and suspending agents, sweetening, flavoring, coloring, perfuming and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound(s) include powders, sprays, ointments, pastes, creams, lotions, gels, solutions, patches and inhalants. The active compound(s) may be mixed under sterile conditions with a pharmaceutically-acceptable carrier, and with any preservatives, buffers, or propellants which may be required.

The ointments, pastes, creams and gels may contain, in addition to compound(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound(s), excipients, such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids, such as glycine, buffers, salts, sugars or sugar alcohols. Aerosols generally are prepared from isotonic solutions.

Transdermal patches have the added advantage of providing controlled delivery of a compound(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compound(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound(s) in biodegradable polymers, such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compound(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier. In one embodiment, AZD8055 is administered orally at a dose of 10 mg/kg twice daily or 20 mg/kg daily. In another embodiment, AZD8055 is administered orally at a dose of 1, 5, 10, 20, 25, 30, 40, or 50 mg/kg daily.

Regardless of the route of administration selected, the compound(s), which may be used in a suitable hydrated form, and/or the pharmaceutical compositions of the present invention, are formulated into pharmaceutically-acceptable dosage forms by conventional methods known to those of ordinary skill in the art.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic to the patient. An exemplary dose range is from about 0.1 µg to 20 milligram per kilogram of body weight per day (mg/kg/day) (e.g., 0.1 µm/kg to 10 mg/kg, 0.1-10 µm/kg, 0.1-1 mg/kg). In other embodiments, the amount varies from about 0.1 mg/kg/day to about 100 mg/kg/day. In still other embodiments, the amount varies from about 0.001 µg to about 100 µg/kg (e.g., of body weight). Ranges intermediate to the above-recited values are also intended to be part of the invention.

Agents of the invention can be used alone, or in combination with conventional therapeutics useful for the treatment of diabetes, such agents include oral agents that are generally used to promote insulin secretion (sulfonylureas and repaglinide), to improve insulin action in the liver (metformin), to improve insulin action in muscle and fat (troglitazone), or to delay the absorption of carbohydrates from the meal, allowing the delayed secretion of insulin to catch up with rapid carbohydrate absorption (acarbose or miglitol).

Genome Editing to Introduce SLC16A11

Therapeutic gene editing is a major focus of biomedical research, embracing the interface between basic and clinical science. A large number of different recessive hereditary human disease syndromes are caused by inheritance of biallelic inactivating point mutations of disease genes. The development of novel "gene editing" tools provides the ability to manipulate the DNA sequence of a cell at a specific chromosomal locus, without introducing mutations at other sites of the genome. This technology effectively enables the researcher to manipulate the genome of a subject's cells in vitro or in vivo, to effect a reversion of a deleterious genotype.

In one embodiment, gene editing involves targeting an endonuclease (an enzyme that causes DNA breaks internally within a DNA molecule) to a specific site of the genome and thereby triggering formation of a chromosomal double strand break (DSB) at the chosen site. If, concomitant with the introduction of the chromosome breaks, a donor DNA molecule is introduced (for example, by plasmid or oligonucleotide introduction), interactions between the broken chromosome and the introduced DNA can occur, especially if the two sequences share homology. In this instance, a process termed "gene targeting" can occur, in which the DNA ends of the chromosome invade homologous sequences of the donor DNA by homologous recombination (HR). By using the donor plasmid sequence as a template for HR, a seamless repair of the chromosomal DSB can be accomplished. Importantly, if the donor DNA molecule differs slightly in sequence from the chromosomal sequence, HR-mediated DSB repair will introduce the donor sequence into the chromosome, resulting in gene conversion/gene correction of the chromosomal locus. In the context of therapeutic gene targeting, the altered sequence chosen would be an active or functional fragment (e.g., wild type, normal) of the disease gene of interest. By targeting the nuclease to a genomic site that contains the disease-causing point mutation, the concept is to use DSB formation to stimulate HR and to thereby replace the mutant disease sequence with wild-type sequence (gene correction). The advantage of the HR pathway is that it has the potential to generate seamlessly a wild type copy of the gene in place of the previous mutant allele.

Current genome editing tools use the induction of double strand breaks (DSBs) to enhance gene manipulation of cells. Such methods include zinc finger nucleases (ZFNs; described for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, and U.S. Pat. Publ. Nos. 20030232410 and US2009020314, which are incorporated herein by reference), Transcription Activator-Like Effector Nucleases (TALENs; described for example in U.S. Pat. Nos. 8,440,431, 8,440,432, 8,450,471, 8,586,363, and 8,697,853, and U.S. Pat. Publ. Nos. 20110145940, 20120178131, 20120178169, 20120214228, 20130122581, 20140335592, and 20140335618, which are incorporated herein by reference), and the CRISPR (Clustered Regularly Interspaced Short Palindromic Repeats)/Cas9 system (described for example in U.S. Pat. Nos. 8,697,359, 8,771,945, 8,795,965, 8,871,445, 8,889,356, 8,906,616, 8,932,814, 8,945,839, 8,993,233, and 8,999,641, and U.S. Pat. Publ. Nos. 20140170753, 20140227787, 20140179006, 20140189896, 20140273231, 20140242664, 20140273232, 20150184139, 20150203872, 20150031134, 20150079681, 20150232882, and 20150247150, which are incorporated herein by reference). For example, ZFN DNA sequence recognition capabilities and specificity can be unpredictable. Similarly, TALENs and CRISPR/Cas9 cleave not only at the desired site, but often at other "off-target" sites, as well. These methods have significant issues connected with off-target double-stranded break induction and the potential for deleterious mutations, including indels, genomic rearrangements, and chromosomal rearrangements, associated with these off-target effects. ZFNs and TALENs entail use of modular sequence-specific DNA binding proteins to generate specificity for ~18 bp sequences in the genome.

RNA-guided nucleases-mediated genome editing, based on Type 2 CRISPR (Clustered Regularly Interspaced Short Palindromic Repeat)/Cas (CRISPR Associated) systems, offers a valuable approach to alter the genome. In brief, Cas9, a nuclease guided by single-guide RNA (sgRNA), binds to a targeted genomic locus next to the protospacer adjacent motif (PAM) and generates a double-strand break (DSB). The DSB is then repaired either by non-homologous end joining (NHEJ), which leads to insertion/deletion (indel) mutations, or by homology-directed repair (HDR), which requires an exogenous template and can generate a precise modification at a target locus (Mali et al., Science. 2013 Feb. 15; 339(6121):823-6). Unlike other gene therapy methods, which add a functional or partially functional copy of a gene to a patient's cells, but retain the original dysfunctional copy of the gene, this system can remove the defect. Genetic correction using engineered nucleases has been demonstrated in tissue culture cells and rodent models of rare diseases.

CRISPR has been used in a wide range of organisms including bakers yeast (S. cerevisiae), zebra fish, nematodes (C. elegans), plants, mice, and several other organisms. Additionally CRISPR has been modified to make programmable transcription factors that allow scientists to target and activate or silence specific genes. Libraries of tens of thousands of guide RNAs are now available.

Since 2012, the CRISPR/Cas system has been used for gene editing (silencing, enhancing or changing specific genes) that even works in eukaryotes like mice and primates. By inserting a plasmid containing cas genes and specifically designed CRISPRs, an organism's genome can be cut at any desired location.

CRISPR repeats range in size from 24 to 48 base pairs. They usually show some dyad symmetry, implying the formation of a secondary structure such as a hairpin, but are not truly palindromic. Repeats are separated by spacers of similar length. Some CRISPR spacer sequences exactly match sequences from plasmids and phages, although some spacers match the prokaryote's genome (self-targeting spacers). New spacers can be added rapidly in response to phage infection.

CRISPR-associated (cas) genes are often associated with CRISPR repeat-spacer arrays. As of 2013, more than forty different Cas protein families had been described. Of these protein families, Cas1 appears to be ubiquitous among different CRISPR/Cas systems. Particular combinations of cas genes and repeat structures have been used to define 8 CRISPR subtypes (E. coli, Y. pest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

Exogenous DNA is apparently processed by proteins encoded by Cas genes into small elements (about.30 base pairs in length), which are then somehow inserted into the CRISPR locus near the leader sequence. RNAs from the CRISPR loci are constitutively expressed and are processed by Cas proteins to small RNAs composed of individual, exogenously-derived sequence elements with a flanking repeat sequence. The RNAs guide other Cas proteins to silence exogenous genetic elements at the RNA or DNA level. Evidence suggests functional diversity among CRISPR subtypes. The Cse (Cas subtype E. coli) proteins (called CasA-E in E. coli) form a functional complex, Cascade, that processes CRISPR RNA transcripts into spacer-repeat units that Cascade retains. In other prokaryotes, Cas6 processes the CRISPR transcripts. Interestingly, CRISPR-based phage inactivation in E. coli requires Cascade and Cas3, but not Cas1 and Cas2. The Cmr (Cas RAMP module) proteins found in Pyrococcus furiosus and other prokaryotes form a functional complex with small CRISPR RNAs that recognizes and cleaves complementary target RNAs. RNA-guided CRISPR enzymes are classified as type V restriction enzymes. See also U.S. Patent Publication 2014/0068797, which is incorporated by reference in its entirety.

Cas9

Cas9 is a nuclease, an enzyme specialized for cutting DNA, with two active cutting sites, one for each strand of the double helix. The team demonstrated that they could disable one or both sites while preserving Cas9's ability to home located its target DNA. Jinek et al. (2012) combined tracrRNA and spacer RNA into a "single-guide RNA" molecule that, mixed with Cas9, could find and cut the correct DNA targets. It has been proposed that such synthetic guide RNAs might be able to be used for gene editing (Jinek et al., Science. 2012 Aug. 17; 337(6096):816-21).

Cas9 proteins are highly enriched in pathogenic and commensal bacteria. CRISPR/Cas-mediated gene regulation may contribute to the regulation of endogenous bacterial genes, particularly during bacterial interaction with eukaryotic hosts. For example, Cas protein Cas9 of Francisella novicida uses a unique, small, CRISPR/Cas-associated RNA (scaRNA) to repress an endogenous transcript encoding a bacterial lipoprotein that is critical for F. novicida to dampen host response and promote virulence. Coinjection of Cas9 mRNA and sgRNAs into the germline (zygotes) generated mice with mutations. Delivery of Cas9 DNA sequences also is contemplated.

gRNA

As an RNA guided protein, Cas9 requires a short RNA to direct the recognition of DNA targets. Though Cas9 preferentially interrogates DNA sequences containing a PAM sequence NGG it can bind here without a protospacer target. However, the Cas9-gRNA complex requires a close match to the gRNA to create a double strand break. CRISPR sequences in bacteria are expressed in multiple RNAs and then processed to create guide strands for RNA. Because Eukaryotic systems lack some of the proteins required to process CRISPR RNAs the synthetic construct gRNA was created to combine the essential pieces of RNA for Cas9 targeting into a single RNA expressed with the RNA polymerase type 2I promoter U6). Synthetic gRNAs are slightly over 100 bp at the minimum length and contain a portion which is targets the 20 protospacer nucleotides immediately preceding the PAM sequence NGG; gRNAs do not contain a PAM sequence.

In one approach, one or more cells of a subject are altered to express a wild-type form of SLC16A11 using a CRISPR-Cas system. Cas9 can be used to target a SLC16A11 comprising a mutation. Upon target recognition, Cas9 induces double strand breaks in the SLC16A11 target gene. Homology-directed repair (HDR) at the double-strand break site can allow insertion of a desired wild-type SLC16A11 sequence.

The following US patents and patent publications are incorporated herein by reference: U.S. Pat. No. 8,697,359, 20140170753, 20140179006, 20140179770, 20140186843, 20140186958, 20140189896, 20140227787, 20140242664, 20140248702, 20140256046, 20140273230, 20140273233, 20140273234, 20140295556, 20140295557, 20140310830, 20140356956, 20140356959, 20140357530, 20150020223, 20150031132, 20150031133, 20150031134, 20150044191, 20150044192, 20150045546, 20150050699, 20150056705, 20150071898, 20150071899, 20150071903, 20150079681, 20150159172, 20150165054, 20150166980, and 20150184139.

Cas9-Based Synthetic Transactivators

Figure 11:
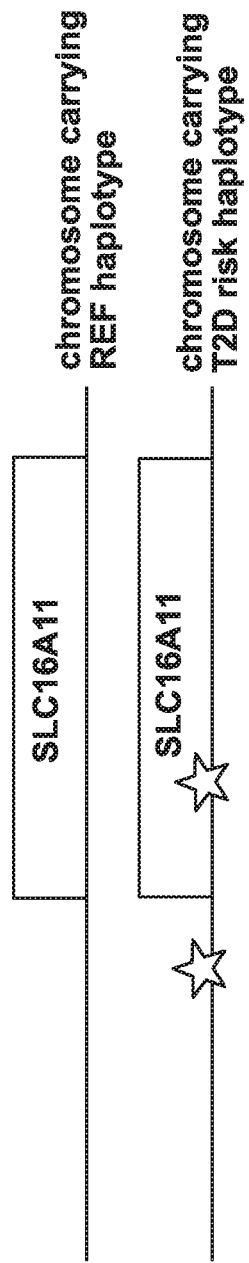
FIG. 11 provides a schematic depicting a strategy for increasing SLC16A11 activity from the reference allele (REF) in heterozygote carriers of the T2D risk haplotype. The rs77086571 nucleotide sequence (ACAACCCCCAGGCCCGGGGGAGG) presented in FIG. 11 is set forth in SEQ ID NO: 26. The rs74577409 nucleotide sequence (TCTCCCCTGCGCGCAGCAGGCGG) presented in FIG. 11 is set forth in SEQ ID NO: 27.
Figure 12:
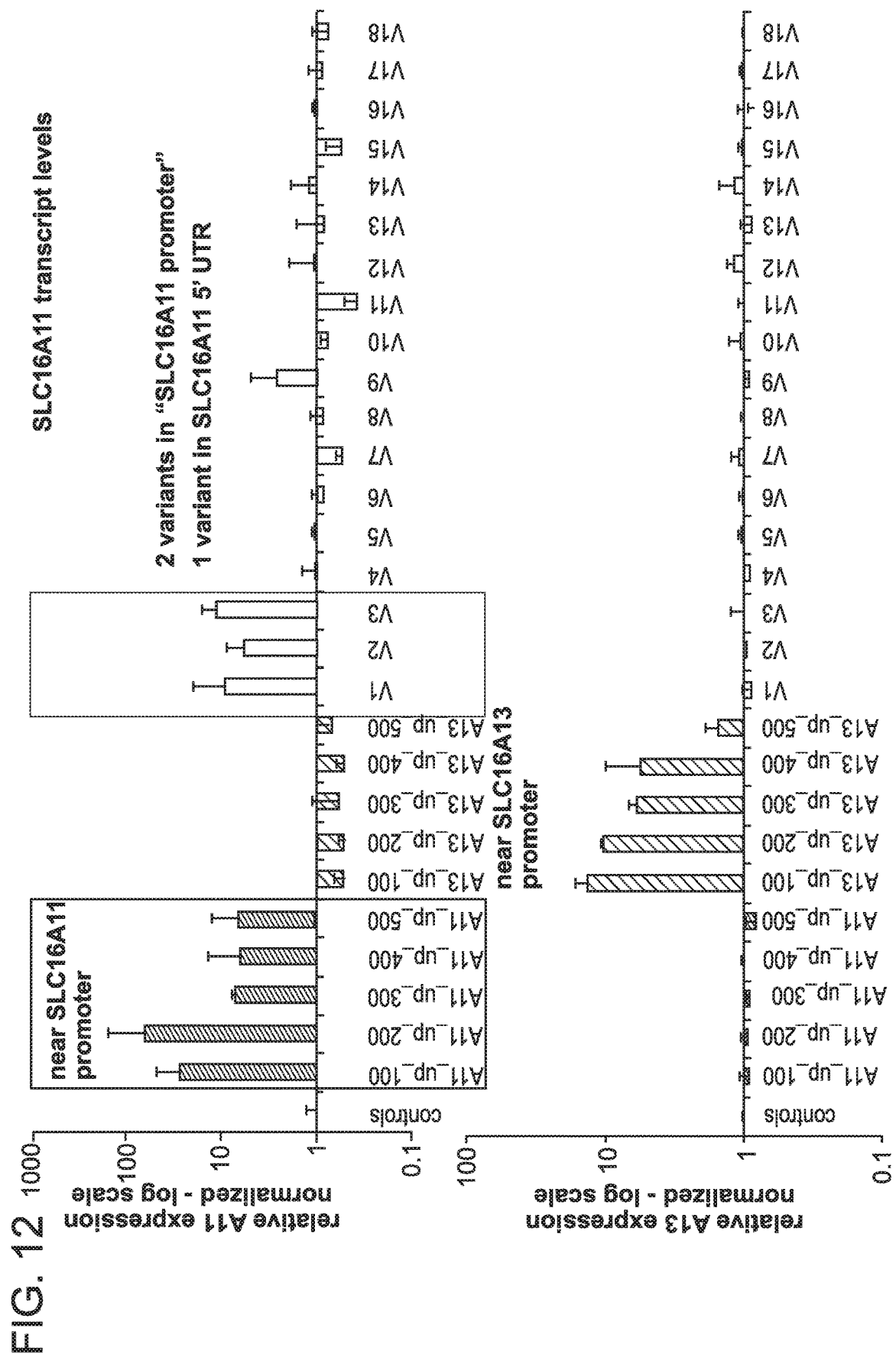
FIG. 12 provides a series of graphs showing the effects of transactivators on SLC16A11 transcript levels. Transactivators were targeted to genomic regions overlapping or immediately next to 18 non-coding variants (v1-v18) either in the credible set or in strong linkage disequilibrium with credible set variants. Gene expression assays were used in order to identify transactivators that increased SLC16A11 transcript levels. SLC16A13 expression was not affected by any transactivators targeted to variants in the credible set.

Given the presence of non-coding variants in the credible set proximal to the SLC16A11 transcription start site and the recent development of programmable transactivators, such transactivators could be used as a strategy for precisely increasing the levels of the reference SLC16A11 transcript. Heterozygous carriers of the T2D risk haplotype, as well as individuals in the general population at risk or with T2D, might benefit from such a strategy. For example, Cas9 based transactivators (SAM or synergistic activation mediators) as described in Konermann et al. (Nature 517: 583-588, 2015) could be targeted to sequences proximal to the SLC16A11 transcription start site such as rs77086571 or rs74577409 (FIG. 11). The effects of transactivators on SLC16A11 transcript levels are shown by FIG. 12. Since the T2D risk haplotype would carry the alternative allele at these variants which results in disrupted PAMs for guides targeting regions immediately proximal to these variants, the reference haplotype could be specifically targeted.

Polynucleotide Therapy

Polynucleotide therapy featuring a polynucleotide encoding a SLC16A11 protein, variant, or fragment thereof is another therapeutic approach for treating type 2 diabetes in a variety of subjects. Expression of such proteins in a cell of a subject is expected to ameliorate diabetes in the subject by increasing the level or activity of SLC16A11 in the subject. Such nucleic acid molecules can be delivered to cells of a subject expressing a wild-type or a variant form of SLC16A11. The nucleic acid molecules must be delivered to the cells of a subject in a form in which they can be taken up so that therapeutically effective levels of a SLC16A11 protein or fragment thereof can be produced.

Polynucleotide Delivery

Polynucleotides are introduced into cells using a variety of methods known in the art. Transducing viral (e.g., retroviral, adenoviral, and adeno-associated viral) vectors can be used to introduce a desired polynucleotide to the cell of a subject, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding a SLC16A11 protein, variant, or a fragment thereof, can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346). Most preferably, a viral vector is used to administer a SLC16A11 polynucleotide systemically.

Non-viral approaches can also be employed for the introduction of therapeutic to a cell of a patient. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by microinjection under surgical conditions (Wolff et al., Science 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Another therapeutic approach included in the invention involves administration of a recombinant therapeutic, such as a recombinant a SLC16A11 protein, variant, or fragment thereof, either directly to the site of a potential or actual disease-affected tissue or systemically (for example, by any conventional recombinant protein administration technique). The dosage of the administered protein depends on a number of factors, including the size and health of the individual patient. For any particular subject, the specific dosage regimes should be adjusted over time according to the individual need and the professional judgment of the person administering or supervising the administration of the compositions.

Diagnostics

Subjects having type 2 diabetes are likely to benefit by increasing SLC16A11 function. In particular embodiments, subjects are selected for treatment using a method of the invention by detecting the presence of the SLC16A11 risk haplotype. Methods for detecting this haplotype include, but are not limited to, detecting the presence of any one or more of V113I, D127G, L187L, G340S, or P443T or any other variant from the credible set (e.g., rs77086571, rs74577409, rs2292351, rs13342232, rs13342692, rs117767867, rs75418188, rs17203120, rs145952323, rs75493593, rs75075014, rs78972129, rs7607064 rs77552976, rs58223766, rs4630597, rs113748381, rs73239895) in a biological sample comprising genomic DNA from the subject. In one embodiment, the method includes detecting any or all of V113I, D127G, L187L, G340S, or P443T in a biological sample comprising genomic DNA from the subject. In another embodiment, the method involves detecting L187L in combination with any one or more of V113I, D127G, G340S, and P443T.

Allelic patterns, polymorphism patterns, or haplotype patterns can be identified by detecting any of the component alleles using any of a variety of available techniques, including: 1) performing a hybridization reaction between a nucleic acid sample and a probe that is capable of hybridizing to the allele; 2) sequencing at least a portion of the allele; or 3) determining the electrophoretic mobility of the allele or fragments thereof (e.g., fragments generated by endonuclease digestion). The allele can optionally be subjected to an amplification step prior to performance of the detection step. Preferred amplification methods are selected from the group consisting of: the polymerase chain reaction (PCR), the ligase chain reaction (LCR), strand displacement amplification (SDA), cloning, and variations of the above (e.g. RT-PCR and allele specific amplification). Oligonucleotides necessary for amplification may be selected, for example, from within the metabolic gene loci, either flanking the marker of interest (as required for PCR amplification) or directly overlapping the marker (as in allele specific oligonucleotide (ASO) hybridization). In a particularly preferred embodiment, the sample is hybridized with a set of primers, which hybridize 5' and 3' in a sense or antisense sequence to the associated allele, and is subjected to a PCR amplification.

An allele may also be detected indirectly, e.g. by analyzing the protein product encoded by the DNA. For example, where the marker in question results in the translation of a mutant protein, the protein can be detected by any of a variety of protein detection methods. Such methods include immunodetection and biochemical tests, such as size fractionation, where the protein has a change in apparent molecular weight either through truncation, elongation, altered folding or altered post-translational modifications.

Many methods are available for detecting specific alleles at human polymorphic loci. The preferred method for detecting a specific polymorphic allele will depend, in part, upon the molecular nature of the polymorphism. For example, the various allelic forms of the polymorphic locus may differ by a single base-pair of the DNA. Such single nucleotide polymorphisms (or SNPs) are major contributors to genetic variation, comprising some 80% of all known polymorphisms, and their density in the human genome is estimated to be on average 1 per 1,000 base pairs. SNPs are most frequently biallelic-occurring in only two different forms (although up to four different forms of an SNP, corresponding to the four different nucleotide bases occurring in DNA, are theoretically possible). Nevertheless, SNPs are mutationally more stable than other polymorphisms, making them suitable for association studies in which linkage disequilibrium between markers and an unknown variant is used to map disease-causing mutations. In addition, because SNPs typically have only two alleles, they can be genotyped by a simple plus/minus assay rather than a length measurement, making them more amenable to automation.

A variety of methods are available for detecting the presence of a particular single nucleotide polymorphic allele in a subject. Advancements in this field have provided accurate, easy, and inexpensive large-scale SNP genotyping.

Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

Several methods have been developed to facilitate analysis of single nucleotide polymorphisms. In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA® is described by Goelet, P. et al. (PCT Publication No. WO 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Publication No. WO91/02087), the method of Goelet, P. et al. is preferably a heterogeneous phase assay, in which the primer or the target molecule is immobilized to a solid phase.

Several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A)

88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)). These methods differ from GBA® in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46-59 (1993)).

For mutations that produce premature termination of protein translation, the protein truncation test (PTT) offers an efficient diagnostic approach (Roest, et. al., (1993) Hum. Mol. Genet. 2:1719-2 1; van der Luijt et. al., (1994) Genomics 20:1-4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

Any cell type or tissue may be utilized to obtain nucleic acid samples for use in the diagnostics described herein. In a preferred embodiment, the DNA sample is obtained from a bodily fluid, e.g., blood, obtained by known techniques (e.g. venipuncture) or saliva. Alternatively, nucleic acid tests can be performed on dry samples (e.g. hair or skin). When using RNA or protein, the cells or tissues that may be utilized must express a gene of interest (e.g., SLC16A11).

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, N.Y.).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

A preferred detection method is allele specific hybridization using probes overlapping a region of at least one allele of a SLC16A11 gene or haplotype and having about 5, 10, 20, 25, or 30 nucleotides around the mutation or polymorphic region. In an embodiment of the invention, several probes capable of hybridizing specifically to allelic variants of an SLC16A11 gene are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of ordinary skill in the art, and include, but are not limited to cloning, polymerase chain reaction (PCR), polymerase chain reaction of specific alleles (ASA), ligase chain reaction (LCR), nested polymerase chain reaction, self sustained sequence replication (Guatelli, J. C. et al., 1990, Proc. Natl. Acad. Sci. USA 87:1874-1878), transcriptional amplification system (Kwoh, D. Y. et al., 1989, Proc. Natl. Acad. Sci. USA 86:1173-1177), and Q-Beta Replicase (Lizardi, P. M. et al., 1988, Bio/Technology 6:1197).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

In one embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize 5' and 3' to at least one allele of a metabolic gene or haplotype under conditions such that hybridization and amplification of the allele occurs, and (iv) detecting the amplification product. These detection schemes are especially useful for the detection of nucleic acid molecules if such molecules are present in very low numbers.

In one embodiment of the subject assay, a haplotype is identified by alterations in restriction enzyme cleavage patterns. For example, sample and control DNA is isolated, amplified (optionally), digested with one or more restriction endonucleases, and fragment length sizes are determined by gel electrophoresis.

In yet another embodiment, any of a variety-of sequencing reactions known in the art can be used to directly sequence the allele. Exemplary sequencing reactions include those based on techniques developed by Maxim and Gilbert ((1977) Proc. Natl Acad Sci USA 74:560) or Sanger (Sanger et al (1977) Proc. Nat. Acad. Sci USA 74:5463). It is also contemplated that any of a variety of automated sequencing procedures may be utilized when performing the subject assays (see, for example Biotechniques (1995) 19:448), including sequencing by mass spectrometry (see, for example PCT publication WO 94/16101; Cohen et al. (1996) Adv Chromatogr 36:127-162; and Griffin et al. (1993) Appl Biochem Biotechnol 38:147-159). It will be evident to one of ordinary skill in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) Science 230:1242). In general, the art technique of "mismatch cleavage" starts by providing heteroduplexes formed by hybridizing (labeled) RNA or DNA containing the wild-type allele with the sample. The double-stranded duplexes are treated with an agent that cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/RNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) Proc. Natl Acad Sci USA 85:4397; and Saleeba et al (1992) Methods Enzymol. 217: 286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on an allele of a metabolic gene locus haplotype is hybridized to a CDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify a the SLC16A11 risk haplotype. For example, single strand conformation polymorphism (SSCP) may be used to detect differences in electrophoretic mobility between mutant and wild type nucleic acids (Orita et al. (1989) Proc Natl. Acad. Sci USA 86:2766, see also Cotton (1993) Mutat Res 285:125-144; and Hayashi (1992) Genet Anal Tech Appl 9:73-79). Single-stranded DNA fragments of sample and control SLC16A11 alleles are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of alleles in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting alleles include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) Nature 324:163); Saiki et al (1989) Proc. Natl Acad. Sci USA 86:6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren, U. et al. ((1988) Science 241:1077-1080). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. USA 87:8923-27). In this method, PCR is used to achieve the exponential amplification of target DNA, which is then detected using OLA.

Several techniques based on this OLA method have been developed and can be used to detect the SLC16A11 risk haplotype. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

Kits

The invention provides a kit or packaged pharmaceutical for treating type 2 diabetes in a subject. In one embodiment, the kit includes a therapeutic or prophylactic composition containing an effective amount of a compound of the invention, such as an mTOR inhibitor (e.g., KU-0063794, AZD-8055, NVP-BEZ235, PI-103, WYE-354, OSI-027, or deforolimus) in unit dosage form.

In another embodiment, the kit comprises a sterile container which contains a therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired a compound of the invention is provided together with instructions for administering the compound to a subject having or at risk of developing type 2 diabetes. The instructions will generally include information about the use of the composition for the treatment or prevention of type 2 diabetes. In other embodiments, the instructions include at least one of the following: description of the therapeutic agent; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

In another embodiment, the invention provides a SLC16A11 wild type polynucleotide, vectors comprising the polynucleotide and reagents suitable for overexpressing the SLC16A11 wild type polynucleotide in a cell of a subject or replacing the subject's variant SLC16A11 polynucleotide with a wild-type version. For use in genome editing, the kit comprises 2 guide RNA vectors in pCas-Guide to ensure an efficient cleavage, Donor vector with predesigned homologous arms, and/or synergistic activation mediators (SAM) (Cas9 based transactivators) as described by Konermann et al. (Nature 517: 583-588, 2015). These reagents would provide the means of targeting transcriptional activators to regions around the credible set variants.

If desired, the above-listed components are packaged in combination with probes/primer for hybridizing to or amplifying an SLC16A11 polynucleotide. Such primers and probes are useful for characterizing a SLC16A11 risk haplotype in a subject.

Kits or pharmaceutical systems according to this aspect of the invention comprise a carrier means, such as a box, carton, tube or the like, having in close confinement therein one or more container means, such as vials, tubes, ampoules, bottles and the like. The kits or pharmaceutical systems of the invention may also comprise associated instructions for using the agents of the invention.

The practice of the present invention employs, unless otherwise indicated, conventional techniques of molecular biology (including recombinant techniques), microbiology, cell biology, biochemistry and immunology, which are well within the purview of the artisan of ordinary skill. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Fine Mapping of the T2D Association at 17p13

Analyses were performed to identify variant(s) that are most likely causal for the T2D association at the 17p13 locus. The strength of association for all variants in the region was analyzed to construct a "99% credible set," namely, a set of variants that has a 99% probability of containing the causal variant(s). To define the T2D risk credible set at this locus, exome-chip, OMNI 2.5 genotyping array, and whole-exome sequencing data (http://www.ncbi.nlm.nih.gov/pubmed/24390345 http://www.ncbi.nlm.nih.gov/pubmed/24915262) from the Slim Initiative in Genomic Medicine for the Americas (SIGMA) Type 2 Diabetes Consortium were integrated and imputed with 1000 Genomes data (phase 3) (FIG. 1A). The posterior probability of causality for each variant was calculated with a minor allele frequency >0.1% and a $r^2 \geq 0.1$ with the top variant at the SLC16A11 locus. This analysis resulted in a 99% credible set and identified 18 variants (e.g., rs77086571, rs74577409, rs2292351, rs13342232, rs13342692, rs117767867, rs75418188, rs17203120, rs145952323, rs75493593, rs75075014, rs78972129, rs76070643, rs77552976, rs58223766, rs4630597, rs113748381, rs73239895 in the T2D credible set. Among these, three non-coding variant(s) proximal to the SLC16A11 transcription start site (rs77086571 and rs74577409 in the SLC16A11 proximal promoter region and rs2292351 in the 5' UTR) are suggested as the most likely causal variants (FIG. 1B and Tables 2A, 2B, 2C).

TABLE 2A*

99% credible sets for SLC16A11 associated region. Predicted effect and frequency in several ancestries according to 1000 Genomes project is also represented.

| RSID | MarkerName | High risk allele | Low risk allele | Odds Ratio | p-value | posterior probability | Consequence | IMPACT | SYMBOL | Amino Acids | SIFT | PolyPhen | GMAF | AFR_MAF | AMR_MAF | EAS_MAF | EUR_MAF | SAS_MAF | AA_MAF | EA_MAF |
|---|---|---|---|---|---|---|---|---|---|---|---|---|---|---|---|---|---|---|---|---|
| rs77086571 | chr17: 6947393 | c | g | 1.3 | 8.10E-13 | 0.13196989 | NA | NA | NA | NA | NA | NA | C: 0.0581 | C: 0.003 | C: 0.2421 | C: 0.0972 | C: 0.0169 | C: 0.0041 | — | — |
| rs74577409 | chr17: 6947453 | g | c | 1.3 | 8.22E-13 | 0.13196989 | NA | NA | NA | NA | NA | NA | G: 0.0581 | G: 0.003 | G: 0.2421 | G: 0.0972 | G: 0.0169 | G: 0.0041 | — | — |
| rs2292351 | chr17: 6946921 | g | c | 1.3 | 9.12E-13 | 0.12465609 | NA | NA | NA | NA | NA | NA | G: 0.0581 | G: 0.003 | G: 0.2421 | G: 0.0972 | G: 0.0169 | G: 0.0041 | G: 0.0036 | G: 0.0076 |
| rs13342232 | chr17: 6945940 | g | a | 1.29 | 1.01E-12 | 0.10841085 | synonymous_variant | LOW | SLC16A11 | L | — | — | G: 0.1631 | G: 0.3782 | G: 0.2752 | G: 0.0972 | G: 0.0229 | G: 0.0051 | G: 0.2556 | G: 0.0108 |
| rs13342692 | chr17: 6946287 | c | t | 1.29 | 1.14E-12 | 0.10032728 | missense_variant | MODERATE | SLC16A11 | D/G | tolerated(0.1) | benign(0) | C: 0.1635 | C: 0.3797 | C: 0.2752 | C: 0.0972 | C: 0.0229 | C: 0.0051 | C: 0.305 | C: 0.0126 |
| rs117767867 | chr17: 6946330 | t | c | 1.29 | 1.32E-12 | 0.08700712 | missense_variant | MODERATE | SLC16A11 | I/V | — | — | T: 0.0581 | T: 0.003 | T: 0.2421 | T: 0.0972 | T: 0.0169 | T: 0.0041 | T: 0.0041 | T: 0.0074 |
| rs75418188 | chr17: 6945483 | t | c | 1.29 | 1.55E-12 | 0.07484217 | missense_variant | MODERATE | SLC16A11 | S/G | — | — | T: 0.0579 | T: 0.003 | T: 0.2406 | T: 0.0972 | T: 0.0169 | T: 0.0041 | T: 0.0035 | T: 0.006 |
| rs17203120 | chr17: 6943989 | g | t | 1.29 | 4.16E-12 | 0.02896951 | NA | NA | NA | NA | NA | NA | G: 0.0587 | G: 0.003 | G: 0.2421 | G: 0.1002 | G: 0.0169 | G: 0.0041 | — | — |
| rs145952323 | chr17: 6944349 | c | g | 1.29 | 4.31E-12 | 0.02792187 | NA | NA | NA | NA | NA | NA | C: 0.0587 | C: 0.003 | C: 0.2421 | C: 0.1002 | C: 0.0169 | C: 0.0041 | — | — |
| rs75493593 | chr17: 6945087 | t | g | 1.29 | 4.24E-12 | 0.02792187 | missense_variant | MODERATE | SLC16A11 | T/P | — | — | T: 0.0587 | T: 0.003 | T: 0.2421 | T: 0.1002 | T: 0.0169 | T: 0.0041 | T: 0.0039 | T: 0.0075 |
| rs75075014 | chr17: 6944089 | a | g | 1.29 | 4.45E-12 | 0.02741264 | NA | NA | NA | NA | NA | NA | A: 0.0587 | A: 0.003 | A: 0.2421 | A: 0.1002 | A: 0.0169 | A: 0.0041 | — | — |
| rs78972129 | chr17: 6942330 | a | g | 1.29 | 4.94E-12 | 0.02455024 | NA | NA | NA | NA | NA | NA | A: 0.0599 | A: 0.0076 | A: 0.2421 | A: 0.1002 | A: 0.0169 | A: 0.0041 | — | — |
| rs76070643 | chr17: 6941625 | t | c | 1.29 | 5.10E-12 | 0.02323545 | synonymous_variant | LOW | SLC16A13 | Y | — | — | T: 0.0601 | T: 0.0076 | T: 0.2421 | T: 0.1002 | T: 0.0179 | T: 0.0041 | T: 0.0118 | T: 0.0079 |
| rs77552976 | chr17: 6951612 | t | c | 1.29 | 5.76E-12 | 0.02281335 | NA | NA | NA | NA | NA | NA | T: 0.0581 | T: 0.003 | T: 0.2421 | T: 0.0972 | T: 0.0169 | T: 0.0041 | — | — |
| rs58223766 | chr17: 6943729 | t | c | 1.28 | 8.97E-12 | 0.01391709 | NA | NA | NA | NA | NA | NA | T: 0.0817 | T: 0.0847 | T: 0.2522 | T: 0.1002 | T: 0.0169 | T: 0.0041 | — | — |
| rs4630597 | chr17: 6942546 | c | t | 1.28 | 9.02E-12 | 0.01388876 | NA | NA | NA | NA | NA | NA | C: 0.0915 | C: 0.1157 | C: 0.2522 | C: 0.1012 | C: 0.0229 | C: 0.0051 | — | — |
| rs113748381 | chr17: 6953155 | a | g | 1.28 | 1.28E-11 | 0.01041364 | NA | NA | NA | NA | NA | NA | A: 0.0847 | A: 0.0983 | A: 0.2522 | A: 0.0972 | A: 0.0169 | A: 0.0041 | — | — |
| rs73239895 | chr17: 6953558 | t | c | 1.28 | 1.72E-11 | 0.00753164 | NA | NA | NA | NA | NA | NA | T: 0.0861 | T: 0.1036 | T: 0.2522 | T: 0.0972 | T: 0.0169 | T: 0.0041 | — | — |

*Table 2A should be read from left to right across both the top and bottom panels.

TABLE 2B

T2D risk credible set at 17p13.

| rsID | Annotation | Odds Ratio | p-value | Posterior Probability |
|---|---|---|---|---|
| rs77086571 | SLC16A11 promoter | 1.30 | $8.10 \times 10^{-13}$ | 0.1320 |
| rs74577409 | SLC16A11 promoter | 1.30 | $8.22 \times 10^{-13}$ | 0.1320 |
| rs2292351 | SLC16A11 5' UTR | 1.30 | $9.12 \times 10^{-13}$ | 0.1247 |
| rs13342232 | SLC16A11 L187L | 1.29 | $1.01 \times 10^{-12}$ | 0.1084 |
| rs13342692 | SLC16A11 D127G | 1.29 | $1.14 \times 10^{-12}$ | 0.1003 |
| rs117767867 | SLC16A11 V113I | 1.29 | $1.32 \times 10^{-12}$ | 0.0870 |
| rs75418188 | SLC16A11 G340S | 1.29 | $1.55 \times 10^{-12}$ | 0.0748 |
| rs17203120 | intergenic | 1.29 | $4.16 \times 10^{-12}$ | 0.0290 |
| rs145952323 | intergenic | 1.29 | $4.31 \times 10^{-12}$ | 0.0279 |
| rs75493593 | SLC16A11 P443T | 1.29 | $4.24 \times 10^{-12}$ | 0.0279 |
| rs75075014 | intergenic | 1.29 | $4.45 \times 10^{-12}$ | 0.0274 |
| rs78972129 | SLC16A13 intron | 1.29 | $4.94 \times 10^{-12}$ | 0.0246 |
| rs76070643 | SLC16A13 Y166Y | 1.29 | $5.10 \times 10^{-12}$ | 0.0232 |
| rs77552976 | intergenic | 1.29 | $5.76 \times 10^{-12}$ | 0.0228 |
| rs58223766 | intergenic | 1.28 | $8.97 \times 10^{-12}$ | 0.0139 |
| rs4630597 | SLC16A13 intron | 1.28 | $9.02 \times 10^{-12}$ | 0.0139 |
| rs113748381 | intergenic | 1.28 | $1.28 \times 10^{-11}$ | 0.0104 |
| rs73239895 | intergenic | 1.28 | $1.72 \times 10^{-11}$ | 0.0075 |

Shown in Table 2B is the credible set of T2D-associated variants at the SLC16A11 locus, with annotation, odds ratio, p-value and posterior probability. The first three rsIDs (i.e., rs77086571, rs74577409 and rs2292351) are coding variants proximal to the SLC16A11 transcription start site. In the table, coding variants in SLC16A11 include rs13342232, rs13342692, rs117767867, rs75418188 and rs75493593.

TABLE 2C

T2D risk credible set highlights both non-coding and coding variants.

| variant | annotation | chromosomal position | posterior probability | cumulative probability | frequency | R2 |
|---|---|---|---|---|---|---|
| rs77086571 | A11 promoter | chr17: 6947393 | 0.13197 | 0.13197 | 0.369 | 1.00000 |
| rs74577409 | A11 promoter | chr17: 6947453 | 0.13197 | 0.26894 | 0.369 | 1.00000 |
| rs2292351 | A11 5' UTR | chr17: 6946921 | 0.12466 | 0.38860 | 0.369 | 0.99394 |
| rs13342232 | A11 L187L | chr17: 6945940 | 0.10841 | 0.49701 | 0.386 | 0.92966 |
| rs13342692 | A11 D127G | chr17: 6946287 | 0.10033 | 0.59733 | 0.386 | 0.92960 |
| rs117767867 | A11 V113I | chr17: 6946330 | 0.08701 | 0.68434 | 0.368 | 0.99670 |
| rs75418188 | A11 G340S | chr17: 6945483 | 0.07484 | 0.75918 | 0.369 | 0.99889 |
| rs17203120 | between A11 and A13 | chr17: 6943989 | 0.02697 | 0.78815 | 0.369 | 0.99174 |
| rs145952323 | between A11 and A13 | chr17: 6944349 | 0.02792 | 0.81607 | 0.369 | 0.99229 |
| rs75493593 | A11 P443T | chr17: 6945087 | 0.02792 | 0.84400 | 0.369 | 0.99174 |
| rs75075014 | between A11 and A13 | chr17: 6944089 | 0.02741 | 0.87141 | 0.369 | 0.99229 |
| rs78972129 | A13 intron | chr17: 6942330 | 0.02455 | 0.89596 | 0.369 | 0.99173 |
| rs76070643 | A13 Y166Y | chr17: 6941625 | 0.02824 | 0.91919 | 0.369 | 0.99119 |
| rs77552976 | A11 upstream | chr17: 6951612 | 0.02281 | 0.94201 | 0.368 | 0.99345 |
| rs58223766 | between A11 and A13 | chr17: 6943729 | 0.01392 | 0.96598 | 0.370 | 0.98637 |
| rs4630597 | A13 intron | chr17: 6942546 | 0.01389 | 0.96991 | 0.375 | 0.96899 |
| rs113748381 | A11 upstream | chr17: 6953155 | 0.01041 | 0.98023 | 0.369 | 0.97028 |
| rs73239895 | A11 upstream | chr17: 6953558 | 0.00753 | 0.98776 | 0.369 | 0.96813 |

| annotation | number of variants in credible set |
|---|---|
| within 500 bp of TSSs (A11) | 3 |
| exonic (T2O risk coding variants in A11) | 6 |
| intronic | 2 |
| far from TSSs | 7 |

TABLE 2D

T2D risk credible set at 17p13 and variant frequencies across populations

| rs ID | Chromosomal Position | Reference Allele | Risk Allele | GMAF |
|---|---|---|---|---|
| rs77086571 | chr17: 6947393 | G | C | C: 0.0581 |
| rs74577409 | chr17: 6947453 | C | G | G: 0.0581 |
| rs2292351 | chr17: 6946921 | C | G | G: 0.0581 |
| rs13342232 | chr17: 6945940 | A | G | G: 0.1631 |
| rs13342692 | chr17: 6946287 | T | C | C: 0.1635 |
| rs117767867 | chr17: 6946330 | C | T | T: 0.0581 |
| rs75418188 | chr17: 6945483 | C | T | T: 0.0579 |
| rs17203120 | chr17: 6943989 | T | G | G: 0.0587 |
| rs145952323 | chr17: 6944349 | G | C | C: 0.0587 |
| rs75493593 | chr17: 6945087 | G | T | T: 0.0587 |
| rs75075014 | chr17: 6944089 | G | A | A: 0.0587 |
| rs78972129 | chr17: 6942330 | G | A | A: 0.0599 |
| rs76070643 | chr17: 6941625 | C | T | T: 0.0601 |
| rs77552976 | chr17: 6951612 | C | T | T: 0.0581 |
| rs58223766 | chr17: 6943729 | C | T | T: 0.0817 |
| rs4630597 | chr17: 6942546 | T | C | C: 0.0915 |
| rs113748381 | chr17: 6953155 | G | A | A: 0.0847 |
| rs73239895 | chr17: 6953558 | C | T | T: 0.0861 |

| rs ID | AFR_MAF | AMR_MAF | EAS_MAF | EUR_MAF | SAS_MAF |
|---|---|---|---|---|---|
| rs77086571 | C: 0.003 | C: 0.2421 | C: 0.0972 | C: 0.0169 | C: 0.0041 |
| rs74577409 | G: 0.003 | G: 0.2421 | G: 0.0972 | G: 0.0169 | G: 0.0041 |
| rs2292351 | G: 0.003 | G: 0.2421 | G: 0.0972 | G: 0.0169 | G: 0.0041 |
| rs13342232 | G: 0.3782 | G: 0.2752 | G: 0.0972 | G: 0.0229 | G: 0.0051 |
| rs13342692 | C: 0.3797 | C: 0.2752 | C: 0.0972 | C: 0.0229 | C: 0.0051 |
| rs117767867 | T: 0.003 | T: 0.2421 | T: 0.0972 | T: 0.0169 | T: 0.0041 |
| rs75418188 | T: 0.003 | T: 0.2406 | T: 0.0972 | T: 0.0169 | T: 0.0041 |
| rs17203120 | G: 0.003 | G: 0.2421 | G: 0.1002 | G: 0.0169 | G: 0.0041 |
| rs145952323 | C: 0.003 | C: 0.2421 | C: 0.1002 | C: 0.0169 | C: 0.0041 |
| rs75493593 | T: 0.003 | T: 0.2421 | T: 0.1002 | T: 0.0169 | T: 0.0041 |
| rs75075014 | A: 0.003 | A: 0.2421 | A: 0.1002 | A: 0.0169 | A: 0.0041 |
| rs78972129 | A: 0.0076 | A: 0.2421 | A: 0.1002 | A: 0.0169 | A: 0.0041 |
| rs76070643 | T: 0.0076 | T: 0.2421 | T: 0.1002 | T: 0.0179 | T: 0.0041 |
| rs77552976 | T: 0.003 | T: 0.2421 | T: 0.0972 | T: 0.0169 | T: 0.0041 |
| rs58223766 | T: 0.0847 | T: 0.2522 | T: 0.1002 | T: 0.0169 | T: 0.0041 |
| rs4630597 | C: 0.1157 | C: 0.2522 | C: 0.1012 | C: 0.0229 | C: 0.0051 |

TABLE 2D-continued

T2D risk credible set at 17p13 and variant frequencies across populations

| rs113748381 | A: 0.0983 | A: 0.2522 | A: 0.0972 | A: 0.0169 | A: 0.0041 |
| rs73239895 | T: 0.1036 | T: 0.2522 | T: 0.0972 | T: 0.0169 | T: 0.0041 |

Table 2D provides the T2D risk credible set at 17p13 and variant frequencies across populations. Chromosomal position is hg19/GRC37. GMAF is the general minor allele frequency. The following were used as abbreviation for minor allele frequencies in human populations: AFR: African, AMR: Ad mixed American, EAS: East Asian, EUR: European, and SAS: South Asian.

Other potentially causal variants within the credible set include the previously reported coding variants in SLC16A11 (SIGMA Nature. 2014 Feb. 6, 506(7486):97-101). To improve fine-mapping of this region, the SIGMA results were integrated with the largest available African American genome-wide association meta-analysis data from the MEDIA consortium, Since most of the variants that are common in the SIGMA credible set are absent or rare in the MEDIA data, the updated credible set did not change the previous ranking of variants. However, the two variants that are common in the African American population (rs13342232 and rs13342692) are less strongly associated with T2D.

Example 2

Variants on the T2D Risk Haplotype at 17p13 Decrease SLC16A11 Expression in Liver The credible set analysis narrowed the search for a potential causal mechanism, and pointed to altered gene expression at the 17p13 locus as a plausible hypothesis. To investigate this further, the expression levels of genes spanned by variants comprising the T2D risk credible set (SLC16A11 and SLC16A13), and three additional genes in the vicinity of this region (BCL6B, CLEC10A, and RNASEK) was examined in T2D-relevant tissues, liver and visceral adipose from Mexican T2D risk haplotype carriers and non-carriers (i.e., individuals from Mexico who carried 0, 1, or 2 copies of the T2D risk haplotype). Gene expression in liver and visceral adipose biopsies was quantified using droplet digital PCR (ddPCR), an extremely sensitive assay that can detect transcripts from lowly-expressed genes such as SLC16A11 (SIGMA Nature. 2014 Feb. 6; 506(7486):97-101), and then analyzed for association with genotype by using variant rs13342692 to tag the T2D risk haplotype, controlling for T2D status, sex, age, and body mass index (BMI).

Figure 9A:
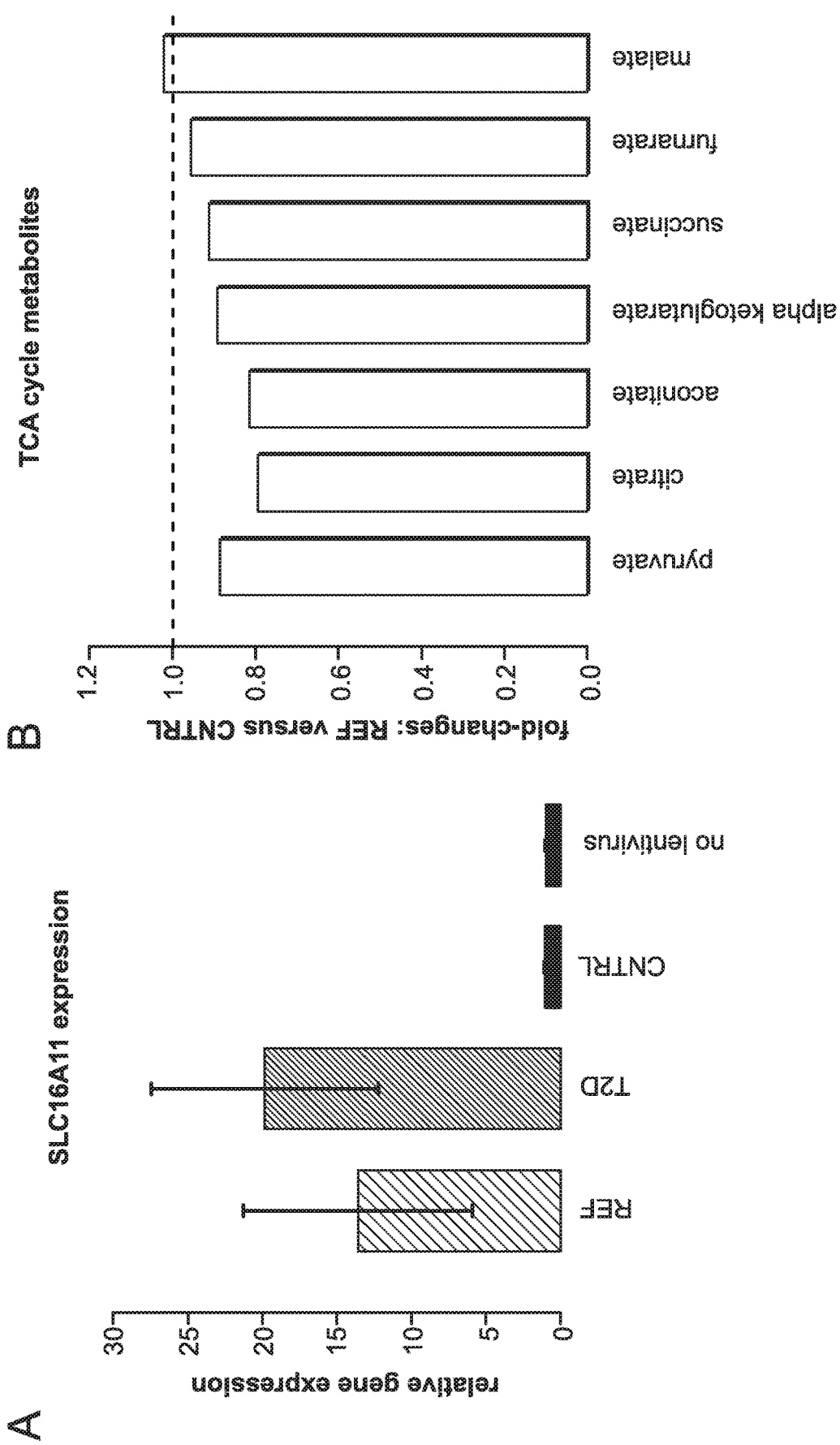
FIG. 9A provides data showing the overexpression of SLC16A11 in primary human hepatocytes transduced with SLC16A11 lentivirus or controls. Bar plots depict relative gene expression±SD using TATA binding protein (TBP) for normalization (FIG. 9A-A). Fold-changes of TCA cycle metabolites in cells expressing SLC16A11$^{REF}$ compared to cells expressing controls are presented in FIG. 9A-B.
Figure 9F:
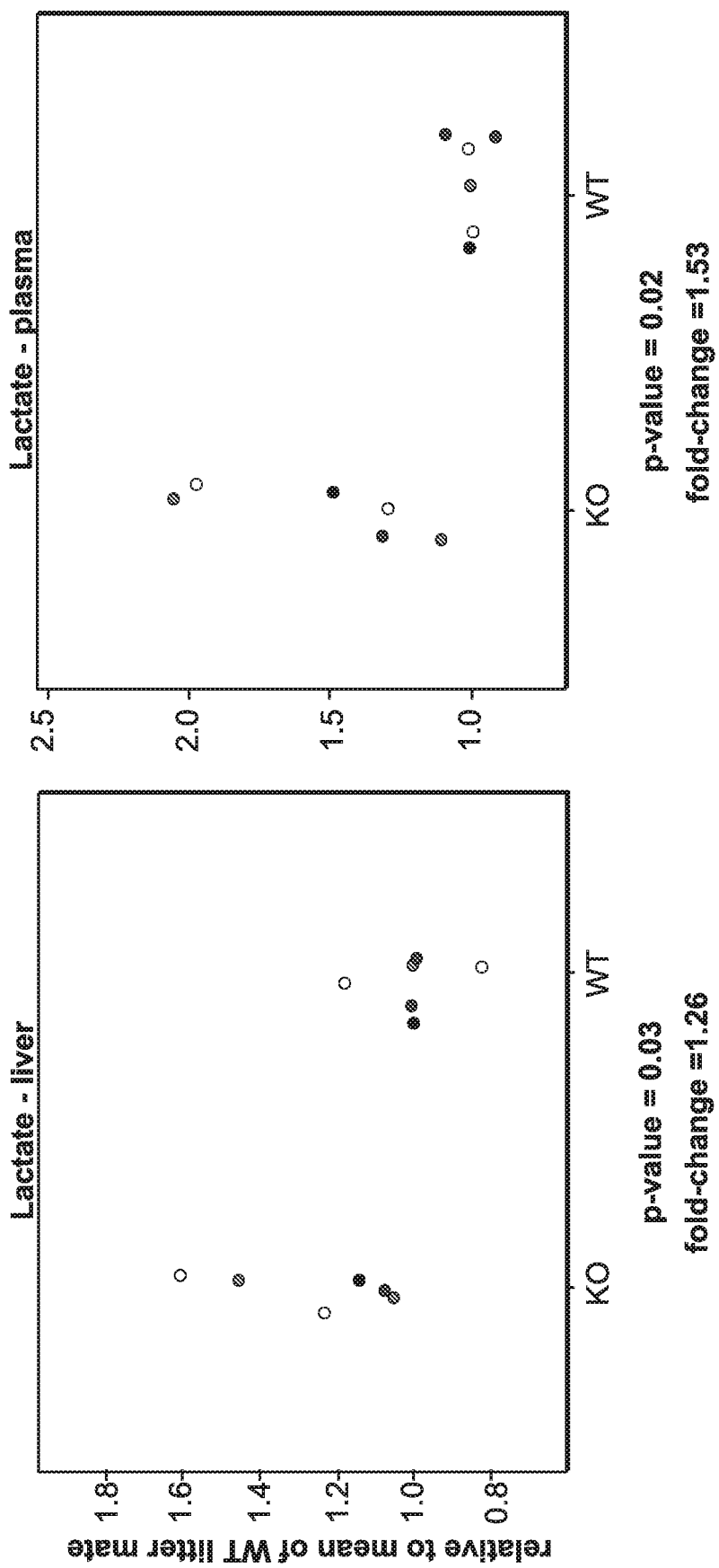
FIG. 9F provides two plots showing that lactate levels are increased in liver (Left panel) and plasma (Right panel) of SLC16A11 knock-out (KO) mice.
Figure 9I:
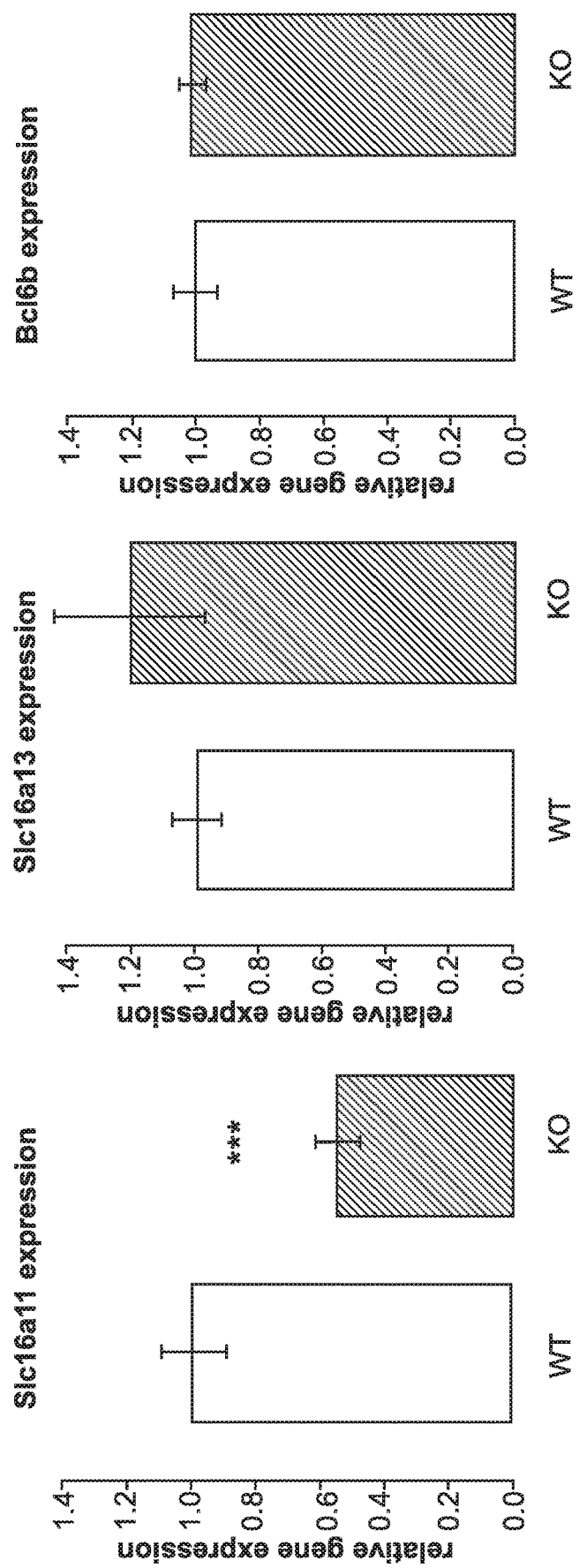
FIG. 9I provides three bar graphs showing Slc16a11, Slc16a13, and Bcl6b levels in Slc16a11 del19 mice. Digital droplet PCR (ddPCR) results in mouse liver samples that were used for RNA-sequencing. Error bars depict standard deviations. Asterisk indicates significance: ***$P<1\times10^{-5}$.
Figure 9J:
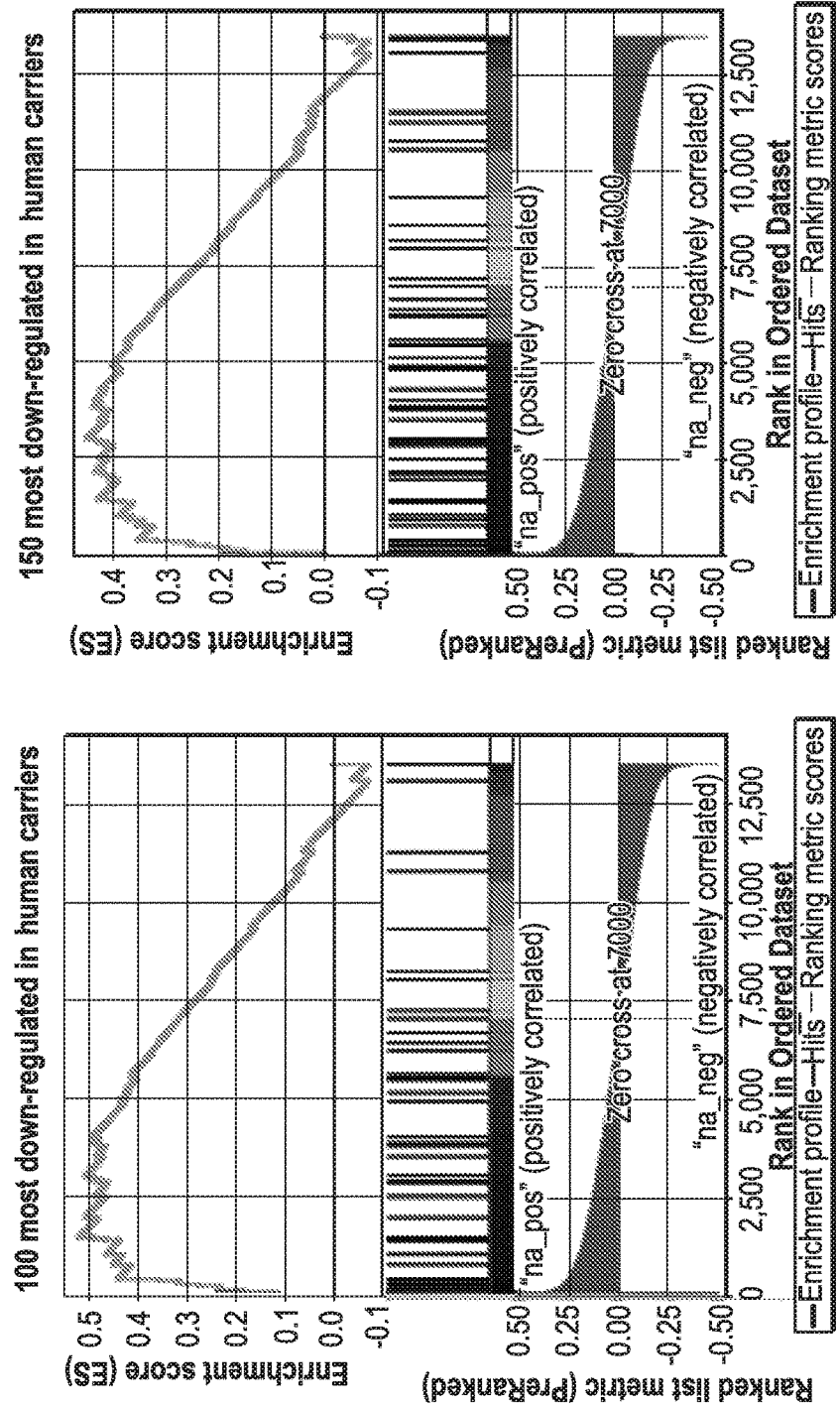
FIG. 9J illustrates genes down-regulated in human carriers.
Figures 1, 9K:
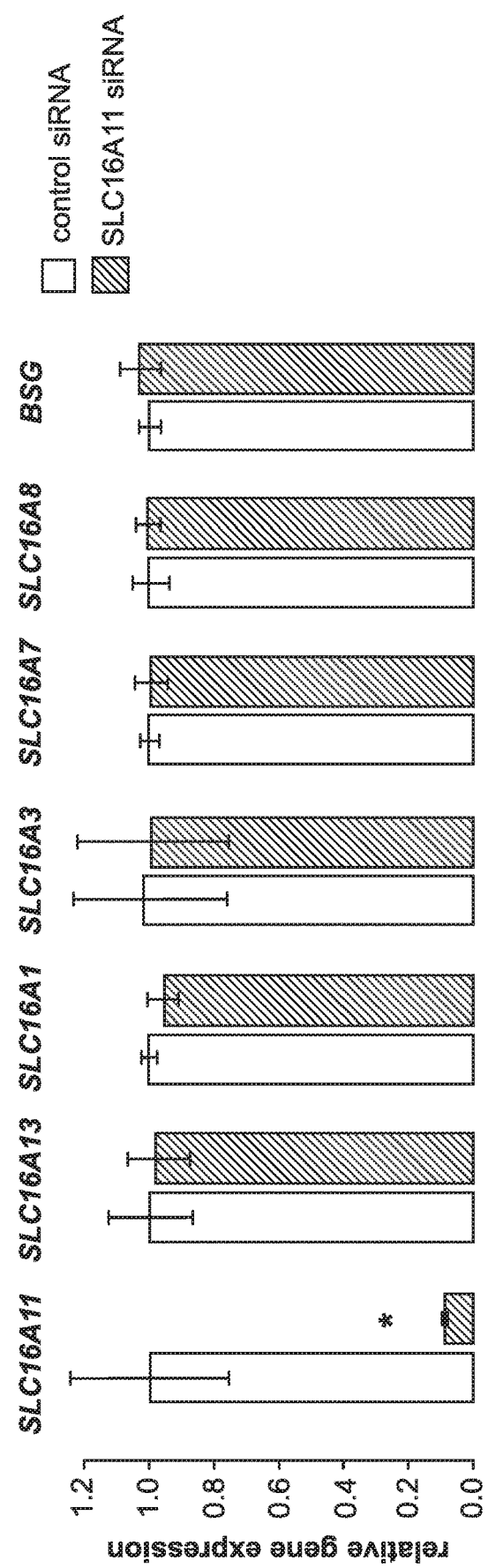
Figures 2B, 9K:
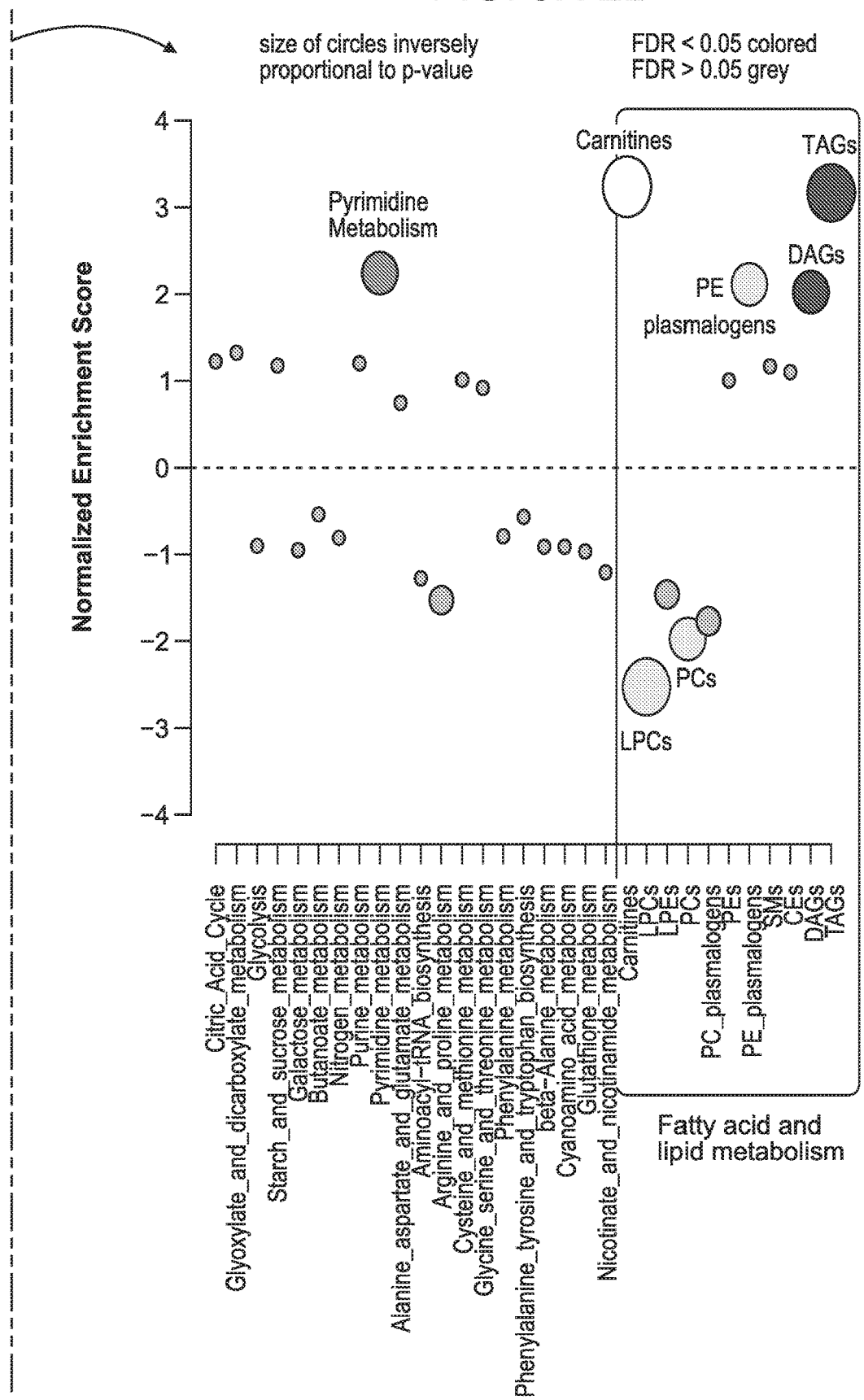
Figures 3, 9K:
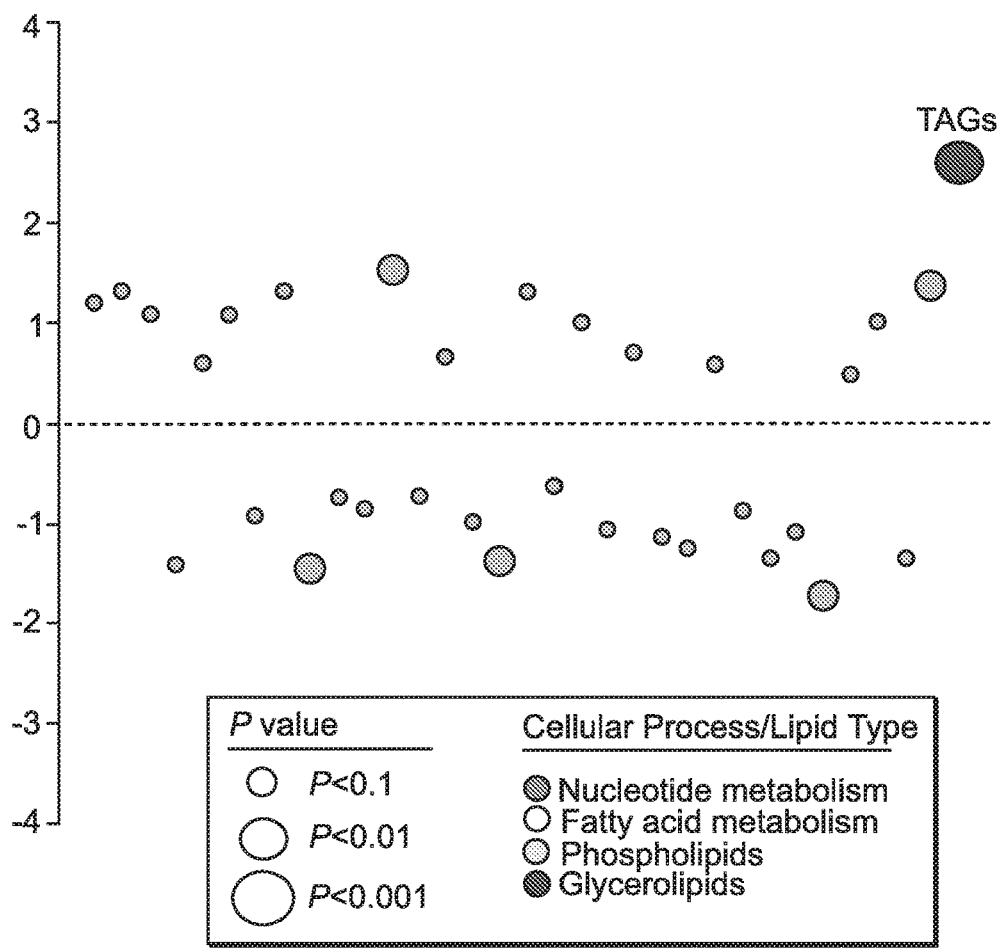
Figures 4, 9K:
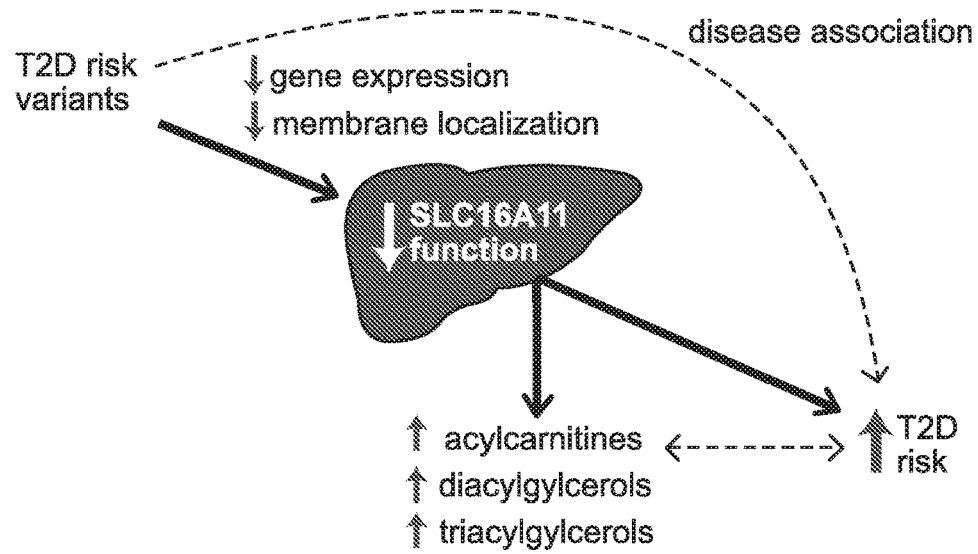
Figure 9M:
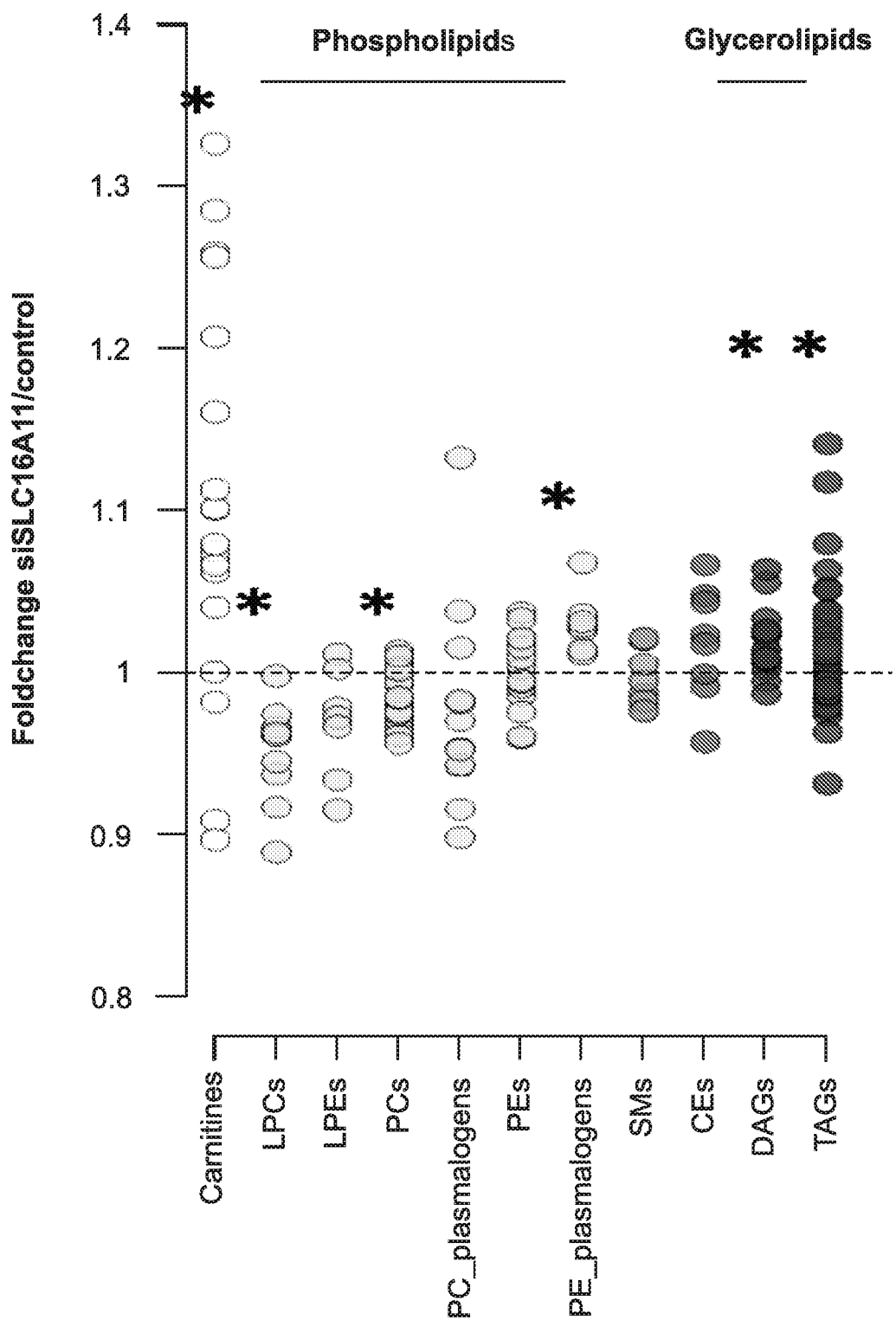
Figure 9N:
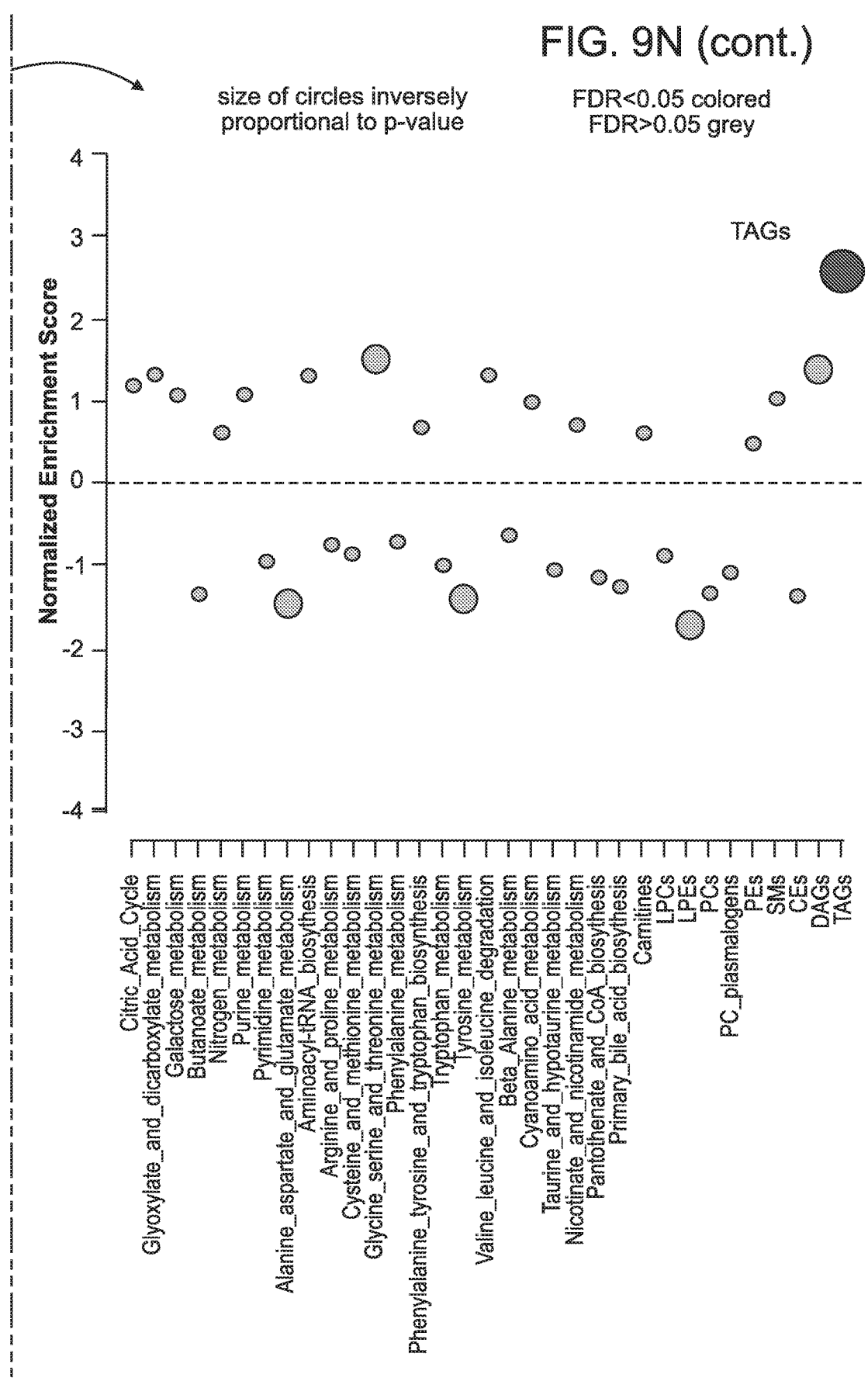
Figure 9O:
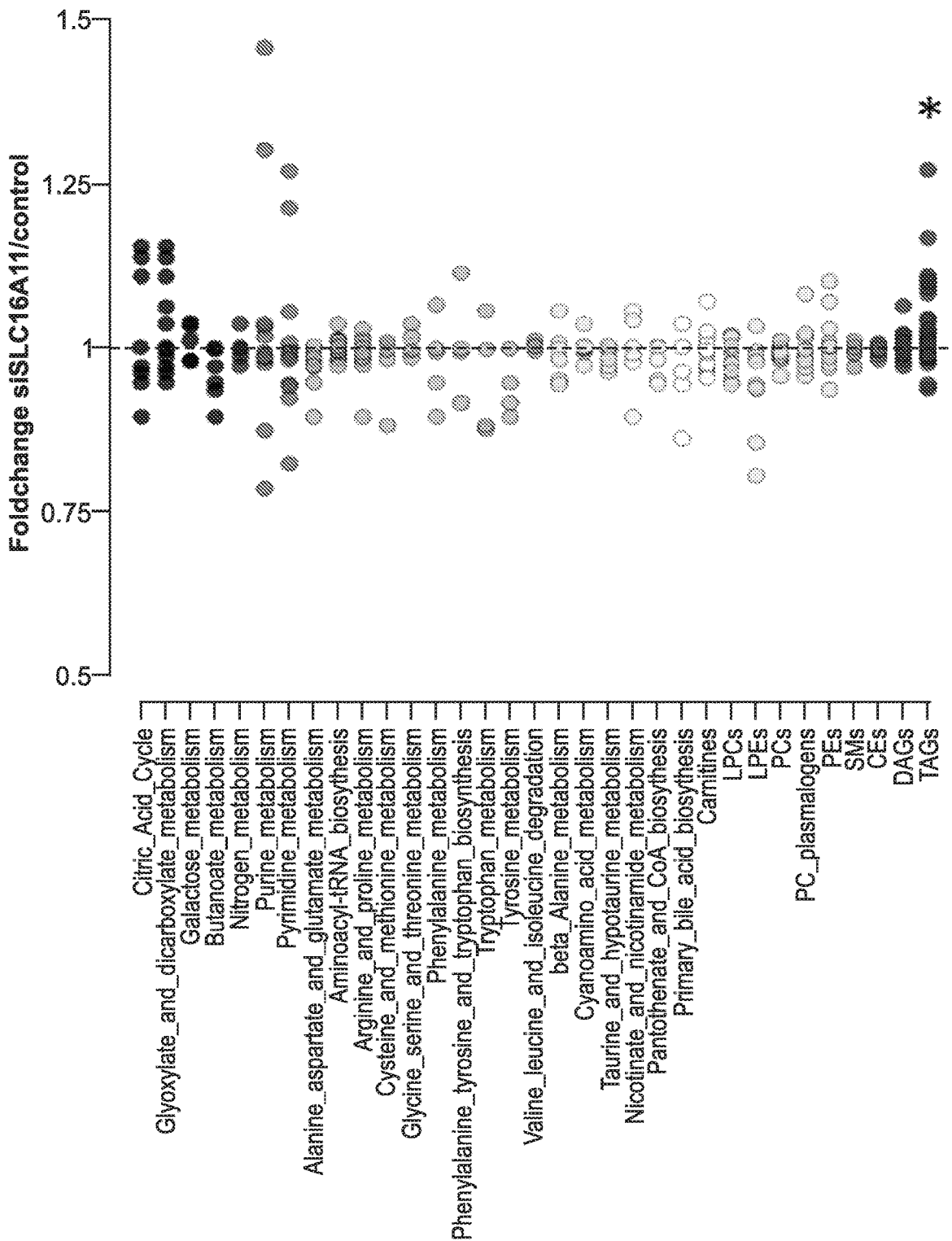

In liver, SLC16A11 expression was significantly reduced in a dose-dependent manner in carriers of the T2D risk haplotype, (P≈$1.4\times10^{-4}$), (FIG. 2A (top and bottom panels), FIG. 2B (top panel) and FIG. 2J). Heterozygous individuals had a 42% decrease in SLC16A11 expression with respect to individuals homozygous for the reference allele (n=16 heterozygous and 21 homozygous reference; P=$2\times10^{-3}$), whereas individuals homozygous for the T2D risk haplotype had a 66% decrease in SLC16A11 expression (n=10 homozygous risk; P=$2\times10^{-5}$). None of the other genes measured displayed robust genotype-dependent expression changes. A nominal increase in CLEC10A expression was detected in the homozygous reference and homozygous risk comparison (33% increase, P=0.04) for one of the probes, but this was not replicated with a second probe. None of the genes tested displayed altered expression in visceral adipose (FIG. 2C (top panel)). Information about the quantitative traits of liver and visceral adipose eQTL donors are provided at FIG. 2J (top panel) and for donors for liver RNA-sequencing analysis at FIG. 2J (bottom panel). The sensitive droplet digital PCR assay used was unable to detect any changes in RNASEK expression, for which the T2D risk haplotype was recently reported to have an eQTL effect in subcutaneous adipose, skeletal muscle, and whole blood cells (Traurig, M. et al., 2016, Diabetes, 65:510-519). These results provide evidence that the T2D risk haplotype contains an eQTL affecting SLC16A11TL expression in human liver, one of the tissues in which SLC16A11 is most highly expressed (SIGMA Nature. 2014 Feb. 6; 506(7486):97-101) and a tissue in which disruption of metabolic processes is implicated in T2D pathophysiology. (Muoio, D. M. and Newgard, C. B., 2008, Nat Rev Mol Cell Biol, 9:193-205; Perry, R. J. et al., 2014, Nature, 510: 84-91).

Example 3

SLC16A11 Expression and H3K27ac Marks are Skewed in Heterozygous Carriers of the T2D Risk Haplotype Altered SLC16A11 gene expression could result from a direct effect of T2D risk variants on transcript levels or an indirect result from other cellular processes altered by T2D risk haplotype variants. By way of example, the T2D-risk variants could reduce SLC16A11 gene expression by acting directly in cis (affecting expression of the SLC16A11 allele carried on the risk haplotype) or indirectly in trans (affecting other cellular processes that feedback on SLC16A11 expression on both haplotypes). To determine whether the observed reduction in SLC16A11 expression in carriers of the T2D risk haplotype resulted from a decrease in SLC16A11 transcript originating from the chromosome carrying the T2D risk haplotype, allele-specific ddPCR probes that distinguish the reference and risk allele at rs13342692 were used to measure allelic SLC16A11 expression in the 16 heterozygous liver samples. Consistent with the idea that variants on the T2D risk haplotype are directly responsible for the reduced expression in carriers, SLC16A11 transcript expression is skewed, with 73% of the transcript originating from the reference allele and 27% from the T2D risk allele (P=$1\times10^{-9}$, FIG. 2B (bottom) and FIG. 2C (bottom)). This allelic effect size is in line with the 66% reduction in total SLC16A11 transcript levels found in T2D risk allele homozygotes.

To confirm the findings from intact liver, allelic SLC16A11 expression ex vivo was examined using primary human hepatocytes from T2D risk haplotype heterozygous donors (Table 3; cells from Bioreclamation IVT).

TABLE 3

Allelic SLC16A11 expression ex vivo using primary
human hepatocytes from T2D risk haplotype.

| Donor number | Hepatocyte lot (Bioreclamation IVT) | Genotype (heterozygote for) |
|---|---|---|
| d1 | ACB | T2D risk haplotype |
| d2 | BEB | T2D risk haplotype |
| d3 | DSX | T2D risk haplotype |
| d4 | NQA | T2D risk haplotype |
| d5 | PAA | T2D risk haplotype |
| d6 | QSK | T2D risk haplotype |
| d7 | AIH | African haplotype |
| d8 | FRY | African haplotype |
| d9 | GEB | African haplotype |
| d10 | JLP | African haplotype |
| d11 | KDD | African haplotype |
| d12 | NRE | African haplotype |
| d13 | ZBG | African haplotype |
| d14 | ZXO | African haplotype |

Figure 2D:
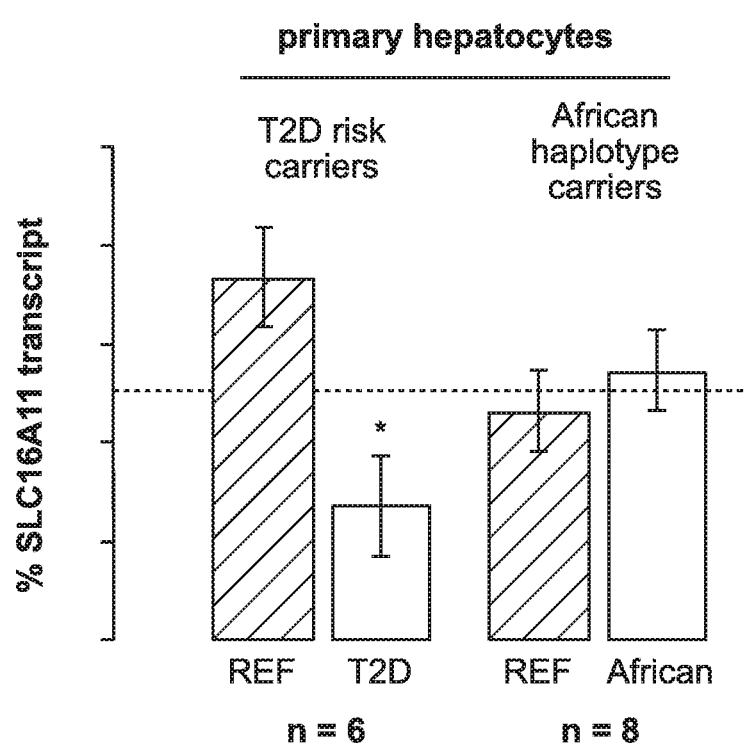

As was observed in vivo, SLC16A11 transcript expression is skewed in primary hepatocytes, with 73% of the transcript originating from the reference allele and 27% from the T2D risk allele (n=6; P=1×10$^{-3}$, FIG. 2D and FIG. 2F). Interestingly, allelic SLC16A11 expression is not skewed in human primary hepatocytes from individuals heterozygous for the African haplotype at this locus (FIG. 2D and FIG. 2G). Using the largest available African-American genome-wide association meta-analysis from the MEDIA consortium, involving 8,284 cases and 15,543 control individuals (Ng, M. C. et al., 2014, PLoS Genet 10, e1004517), no significant association with T2D risk was found: the two-coding-variant haplotype in African-Americans had an odds ratio of ~1.06 (P≈0.08), whereas the five-coding-variant haplotype in Mexico had an odds ratio of ~1.29 (P≈1.7×10$^{-11}$ to 8.1×10$^{-13}$) in the Mexican study. When comparing the effect sizes between the two studies, a statistically significant heterogeneity was seen ($P_{HET}$≈4.1×10$^{-5}$). As the African haplotype carries two coding variants (rs13342692 and rs13342232) (SIGMA Nature. 2014 Feb. 6; 506(7486):97-101) and essentially none of the other variants were in the T2D risk credible set, this suggests that the two coding variants present at high frequency in Africa, rs13342692 and rs13342232, are not sufficient to cause an association with T2D or confer skewed SLC16A11 gene expression and that the SLC16A11 cis-eQTL in human liver may not be present in individuals of African descent.

To further characterize the context of T2D risk haplotype-associated changes in SLC16A11 expression, the epigenetic state of this locus was examined. The allele-specific regulatory landscape in primary human hepatocytes from three heterozygous carriers of the T2D risk haplotype was ascertained by performing ChIP-sequencing on several histone modifications (FIG. 2E (top panel and bottom panel), Table 3 and Table 4), including H3K27ac (active enhancer and promoter mark), H3K4me3 (associated with promoters and transcription start sites), and H3K4me1 (associated with enhancers).

TABLE 4A

| chrom | pos | mark | d1_counts | d3_counts | d6_counts | d1_pvals | d3_pvals | d6_pvals | metap | signif |
|---|---|---|---|---|---|---|---|---|---|---|
| chr17 | 6941625 | H3K27ac | 88.101 | 61.59 | None | 0.38278459 | 0.92731502 | None | 0.72261185 | FALSE |
| chr17 | 6941625 | H3K4me1 | 15.14 | 10.10 | None | 1 | 1 | None | 1 | FALSE |
| chr17 | 6941625 | H3K4me3 | 83.95 | 83.75 | None | 0.40973607 | 0.57774284 | None | 0.57780747 | FALSE |
| chr17 | 6941625 | input | 3.5 | 1.2 | None | 0.7265625 | 1 | None | 0.95864892 | FALSE |
| chr17 | 6942330 | H3K27ac | 77.57 | 36.45 | None | 0.1003657 | 0.37417442 | None | 0.16080622 | FALSE |
| chr17 | 6942330 | H3K4me1 | 26.12 | 14.26 | None | 0.03355244 | 0.08069047 | None | 0.01871269 | FALSE |
| chr17 | 6942330 | H3K4me3 | 19.23 | 25.15 | None | 0.64396896 | 0.15385994 | None | 0.32813826 | FALSE |
| chr17 | 6942330 | input | 3.2 | 2.1 | None | 1 | 1 | None | 1 | FALSE |
| chr17 | 6942546 | H3K27ac | 42.16 | 17.32 | None | 0.00086178 | 0.04438416 | None | 0.0004273 | FALSE |
| chr17 | 6942546 | H3K4me1 | 5.22 | 5.8 | None | 0.00151372 | 0.58105469 | None | 0.00706818 | FALSE |
| chr17 | 6942546 | H3K4me3 | 5.12 | 7.9 | None | 0.14346313 | 0.80361938 | None | 0.36435099 | FALSE |
| chr17 | 6942546 | input | 4.4 | 5.7 | None | 1 | 0.77441406 | None | 0.97239192 | FALSE |
| chr17 | 6943989 | H3K27ac | 14.10 | 8.8 | 7.16 | 0.54125619 | 1 | 0.09313965 | 0.42599241 | FALSE |
| chr17 | 6943989 | H3K4me1 | 28.11 | 22.10 | 31.17 | 0.0094753 | 0.05010246 | 0.05946338 | 0.00187272 | TRUE |
| chr17 | 6943989 | input | 6.1 | 0.2 | 2.1 | 0.125 | 0.5 | 1 | 0.4760133 | FALSE |
| chr17 | 6944089 | H3K27ac | 6.6 | 3.12 | 14.7 | 1 | 0.03515625 | 0.18924713 | 0.12359025 | FALSE |
| chr17 | 6944089 | H3K4me1 | 17.23 | 19.16 | 31.22 | 0.42959051 | 0.7358788 | 0.27167917 | 0.55547285 | FALSE |
| chr17 | 6944089 | input | 4.1 | 1.1 | 3.3 | 0.375 | 1 | 1 | 0.92319085 | FALSE |
| chr17 | 6944349 | H3K4me1 | 13.16 | 12.17 | 22.19 | 0.7110711 | 0.45825832 | 0.75522866 | 0.83300457 | FALSE |
| chr17 | 6945087 | H3K4me1 | 9.9 | 5.5 | 15.12 | 1 | 1 | 0.70110804 | 0.99426858 | FALSE |
| chr17 | 6945087 | input | 3.3 | 3.0 | 0.1 | 1 | 0.25 | 1 | 0.8368001 | FALSE |
| chr17 | 6945483 | H3K4me1 | 6.6 | 10.0 | 12.14 | 1 | 0.00195313 | 0.84501898 | 0.04609604 | FALSE |
| chr17 | 6945483 | input | 0.1 | 3.2 | 4.1 | 1 | 1 | 0.375 | 0.92319085 | FALSE |
| chr17 | 6945940 | H3K27ac | 6.9 | 10.3 | 9.7 | 0.60723877 | 0.09228516 | 0.80361938 | 0.4010907 | FALSE |
| chr17 | 6945940 | H3K4me1 | 16.12 | 5.15 | 7.15 | 0.57158819 | 0.04138947 | 0.13380051 | 0.07381178 | FALSE |
| chr17 | 6945940 | H3K4me3 | 15.18 | 39.10 | 6.8 | 7.28E-01 | 3.85E-05 | 0.79052734 | 0.00153134 | FALSE |
| chr17 | 6945940 | input | 2.1 | 3.1 | 0.2 | 1 | 0.625 | 0.5 | 0.88737835 | FALSE |
| chr17 | 6946287 | H3K27ac | 16.10 | 14.15 | 13.7 | 0.32693958 | 1 | 0.26317596 | 0.55594745 | FALSE |
| chr17 | 6946287 | H3K4me1 | 19.11 | 13.14 | 11.30 | 0.20048842 | 1 | 0.004324 | 0.02852651 | FALSE |
| chr17 | 6946287 | H3K4me3 | 19.14 | 26.20 | 12.10 | 0.48685024 | 0.46139118 | 0.8318119 | 0.76316196 | FALSE |
| chr17 | 6946287 | input | 4.3 | 1.1 | 1.2 | 1 | 1 | 1 | 1 | FALSE |
| chr17 | 6946330 | H3K27ac | 20.6 | 9.16 | 11.8 | 0.00935531 | 0.22952294 | 0.6476059 | 0.04062336 | FALSE |
| chr17 | 6946330 | H3K4me1 | 23.9 | 17.7 | 13.32 | 0.02006161 | 0.06391466 | 0.00660882 | 0.00068531 | FALSE |
| chr17 | 6946330 | H3K4me3 | 21.10 | 26.17 | 9.9 | 0.07075555 | 0.22205282 | 1 | 0.21648176 | FALSE |
| chr17 | 6946330 | input | 3.2 | 2.0 | 1.3 | 1 | 0.5 | 0.625 | 0.88737835 | FALSE |
| chr17 | 6946921 | H3K27ac | 42.27 | 69.10 | 35.8 | 9.12E-02 | 5.54E-12 | 4.19E-05 | 1.64E-14 | TRUE |
| chr17 | 6946921 | H3K4me1 | 3.14 | 17.7 | 9.15 | 0.01272583 | 0.06391466 | 0.30745625 | 0.01092499 | FALSE |
| chr17 | 6946921 | H3K4me3 | 77.91 | 81.58 | 58.39 | 0.31587491 | 0.06164934 | 0.0670518 | 0.03877028 | FALSE |
| chr17 | 6946921 | input | 5.4 | 0.1 | 3.2 | 1 | 1 | 1 | 1 | FALSE |
| chr17 | 6947393 | H3K27ac | 6.17 | 23.7 | 8.3 | 0.03468966 | 0.00522288 | 0.2265625 | 0.00254967 | FALSE |
| chr17 | 6947393 | H3K4me1 | 14.13 | 11.7 | 12.13 | 1 | 0.48068237 | 1 | 0.96177923 | FALSE |

TABLE 4A-continued

| chrom | pos | mark | d1_counts | d3_counts | d6_counts | d1_pvals | d3_pvals | d6_pvals | metap | signif |
|---|---|---|---|---|---|---|---|---|---|---|
| chr17 | 6947393 | H3K4me3 | 23.36 | 26.27 | 23.14 | 0.11747735 | 1 | 0.18774156 | 0.26661106 | FALSE |
| chr17 | 6947393 | input | 4.0 | 0.5 | 2.6 | 0.125 | 0.0625 | 0.2890625 | 0.05793972 | FALSE |
| chr17 | 6947453 | H3K27ac | 9.15 | 22.7 | 6.3 | 0.30745625 | 0.00813006 | 0.5078125 | 0.03796454 | FALSE |
| chr17 | 6947453 | H3K4me1 | 25.15 | 14.9 | 13.13 | 0.15385994 | 0.40487289 | 1 | 0.4752195 | FALSE |
| chr17 | 6947453 | H3K4me3 | 22.24 | 21.20 | 9.14 | 0.88299591 | 1 | 0.40487289 | 0.91436024 | FALSE |
| chr17 | 6947453 | input | 5.2 | 0.2 | 0.4 | 0.453125 | 0.5 | 0.125 | 0.30914032 | FALSE |
| chr17 | 6951612 | input | 3.7 | 3.2 | 3.3 | 0.34375 | 1 | 1 | 0.90680646 | FALSE |
| chr17 | 6953155 | input | 5.0 | 2.0 | 1.5 | 0.0625 | 0.5 | 0.21875 | 0.12587336 | FALSE |
| chr17 | 6953558 | input | 0.1 | 3.4 | 2.1 | 1 | 1 | 1 | 1 | FALSE |

Figure 2H:
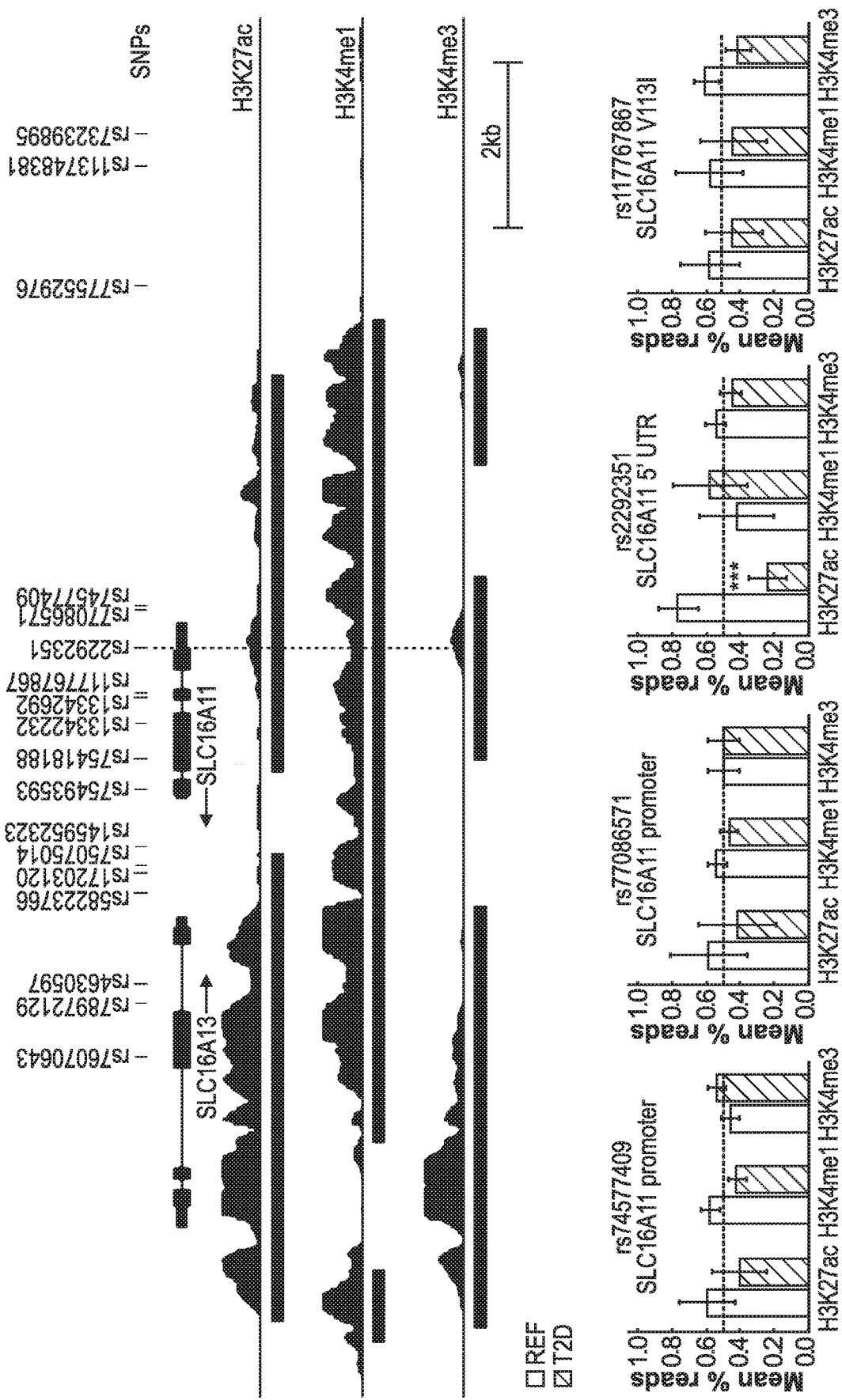
FIG. 2H provides a series of graphs and ChIP sequencing tracks.
Figures 1, 2H:
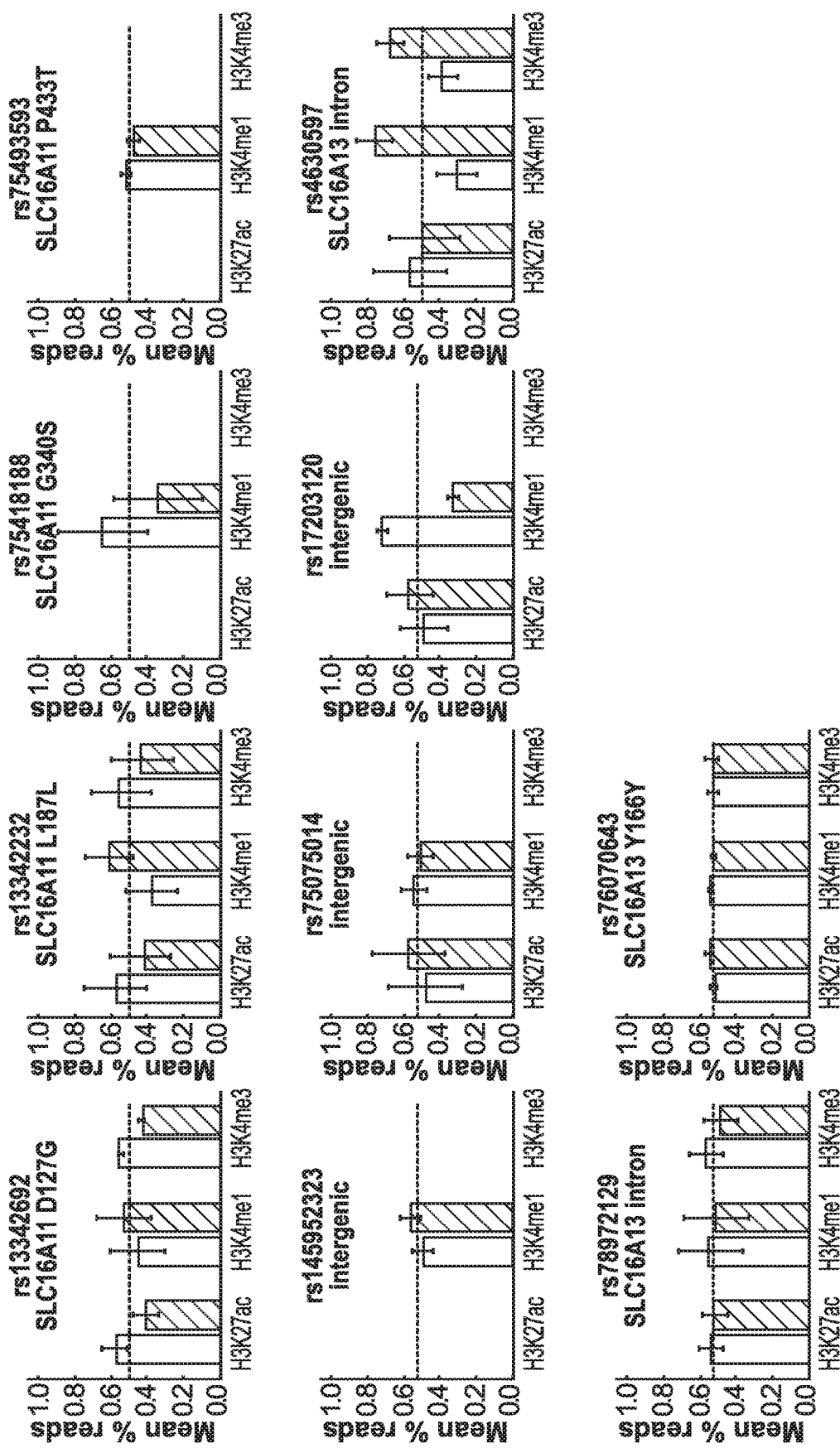
FIGS. 6A-6C-1 provide plots depicting results from RNA-sequencing of liver from carriers and non-carriers of T2D risk haplotype indicating that carriers of the T2D risk haplotype have altered liver metabolism.

Consistent with reduced SLC16A11 promoter activity from the T2D risk allele, H3K27ac marks near the variant located in the SLC16A11 5'UTR are significantly biased toward the reference allele at the expense of the T2D risk allele (r52292351; $P=2\times10^{-14}$). Aside from H3K4me1 marks near rs17203120 being skewed in favor of the reference allele ($P=2\times10^{-3}$ no additional significant allelic-skews in chromatin marks near other variants in the T2D risk credible set) were observed (FIG. 2H).

Together, these data demonstrate the presence of a SLC16A11 cis-eQTL in human liver on the T2D risk haplotype, providing support for SLC16A11 as a likely casual gene at this locus and indicating reduced SLC16A11 function as the disease-relevant direction of effect.

Example 4

SLC16A11 Expression is Skewed in Heterozygous Carriers of the T2D Risk Haplotype In principle, the T2D-risk variants could reduce SLC16A11 gene expression by acting directly in cis (affecting expression of the SLC16A11 allele carried on the risk haplotype) or indirectly in trans (affecting other cellular processes that feedback on SLC16A11 expression on both haplotypes). To distinguish between these possibilities, the expression levels from the T2D-risk and reference (non-risk) haplotypes were compared in liver samples from 16 heterozygous individuals. Expression from the two haplotypes was measured by ddPCR, with probes that distinguish between the reference and risk allele at rs13342692. The results provide strong support for a cis-effect: expression from the risk allele is 62% lower than from the non-risk haplotype ($P=2\times10^{-73}$, FIG. 2B bottom panel and FIG. 2C bottom panel) consistent with the 66% lower expression level seen in homozygotes for the risk haplotype than the non-risk haplotype.

A similar allelic skew was observed in primary hepatocytes, cultured ex vivo from 6 heterozygous individuals: expression from the risk haplotype is 66% lower than from the non-risk haplotype ($P=2\times10^{-63}$, FIG. 2F and FIG. 2G). Notably, no allelic skew was found in primary hepatocytes from individuals heterozygous for the African haplotype (FIGS. 2D and 2E (bottom panel)). These analyses indicate that the two coding variants present at high frequency in Africa, rs13342692 and rs13342232, are not alone sufficient to cause the association with T2D or confer skewed gene expression of SLC16A11, and that the SLC16A11 cis-eQTL in human liver is not present in these individuals of African descent.

Example 5

Allelic Imbalance of Histone Modifications in Carriers

Experiments were conducted to determine whether the lower expression of SLC16A11 from the T2D risk haplotype is associated with chromatin structure in cis, indicative of altered transcription at the gene. The chromatin landscape on each haplotype was examined, in hepatocytes, from 3 heterozygous individuals by performing ChIP-sequencing for several histone modifications, including H3K27ac (active enhancer and promoter mark), H3K4me1 (associated with enhancers), and H3K4me3 (associated with promoters and transcription start sites) (Encode Project Consortium, 2012, Nature, 489:57-74). It was noted that peaks obtained from the histone modification ChIP-sequencing dataset are consistent with data at 17p13 (FIG. 2E, bottom panel). Consistent with reduced SLC16A11 promoter activity from the T2D risk allele, the expected allelic skew (69% lower from the T2D risk allele) was observed for the activating mark H3K27ac at a variant located near the 5'-end of SLC16A11 (r52292351; $P=2\times10^{-14}$, FIG. 2E top panel). The result is significant after Bonferroni correction for multiple hypothesis testing, and no additional significant allelic-skews in chromatin marks near other variants in the T2D risk credible set (FIG. 2H).

Figure 2I:
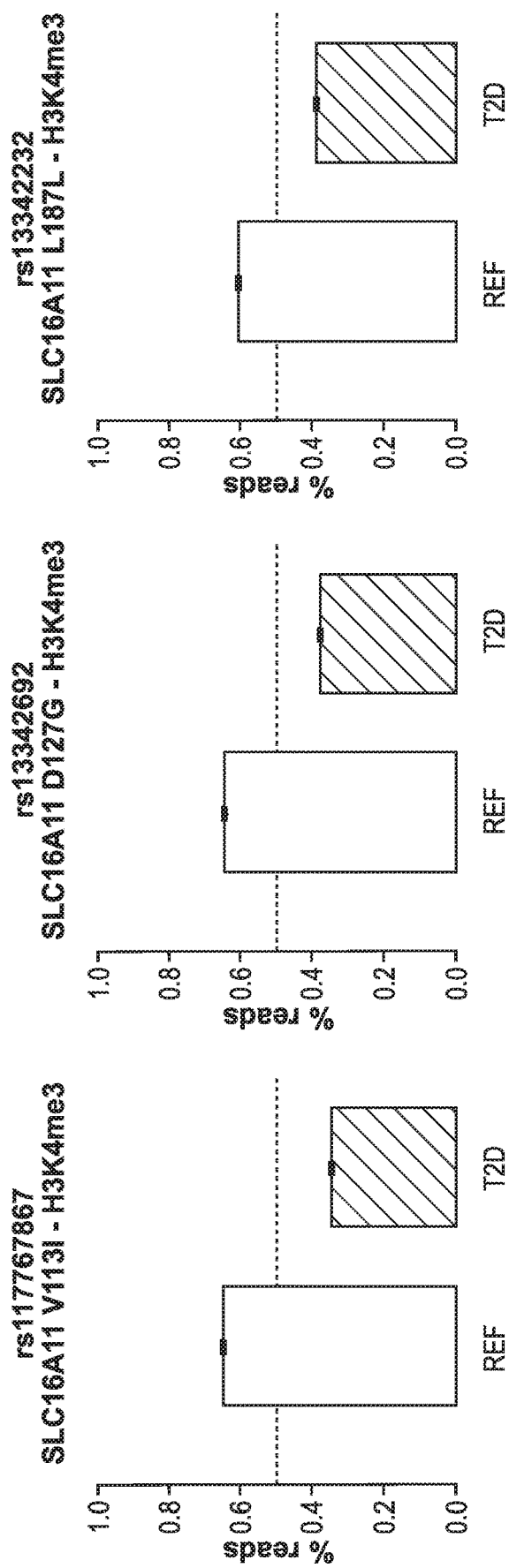
FIG. 2I provides graphs showing the allelic ratios by PCR amplification for H3K4me3 in primary human hepatocytes from three individuals heterozygous for the T2D risk haplotype. H3K4me3 is skewed in favor of the reference haplotype over the T2D risk haplotype at the variants encoding V113I, D127G, and L187L. Error bars depict standard deviations.

ChIP-sequencing generates genome-wide data, but for a single locus it might not provide enough read counts to enable allelic imbalance studies with sufficient power. Consequently, the data lead to analysis of the ChIP libraries and next targeted PCR amplification of regions spanning T2D risk credible set variants, followed by sequencing the resulting amplicons. Of particular interest, were variants in which the coding sequence of SLC16A11. Given that the data points to reduced SLC16A11 transcription from the T2D risk haplotype, it may be expected that H3K4me3, a mark associated with active promoters and transcript start sites, to be skewed in favor of the reference haplotype over the T2D risk haplotype. Reductions in H3K4me3 were observed from the T2D risk allele at rs117767867 (46% decrease; P=0), rs13342692 (42% decrease; P=0), and rs13342232 (36% decrease; P=0) (FIG. 2I). These variants correspond to the missense mutations V113I, D127G, and L187L respectively, and are the closest coding variants to the SLC16A11 transcription start site. These data further support decreased SLC16A11 transcription from the chromosome carrying the T2D risk haplotype.

Together, these data demonstrate the presence of a SLC16A11 cis-eQTL in liver carried on the risk haplotype, providing support for SLC16A11 as a causal gene at this locus and indicating decreased SLC16A11 function as the disease-relevant direction of effect.

Example 6 rs77086571 Reduces Luciferase Reporter Activity from a Fragment Containing the SLC16A11 Promoter and 5' UTR Next experiments investigated whether variants of the T2D risk haplotype alter expression of a luciferase reporter in-vitro. Given that decreased SLC16A11 expression is associated with the T2D risk haplotype, of particular interest would be whether a single variant reduces luciferase reporter activity. The experiments focused on the three non-coding variant(s) proximal to the SLC16A11 transcription start site (r577086571, rs74577409, and r52292351) for the following reasons: 1) these variants rank as the most likely causal variants in the T2D risk credible set (Table 2B) and 2) these variants are located in the proximal promoter and the 5' UTR of SLC16A11 making them likely candidates for altering SLC16A11 expression. Non-coding and coding variants are highlighted by the T2D risk credible set and are show in Table 2C.

Figure 3B:
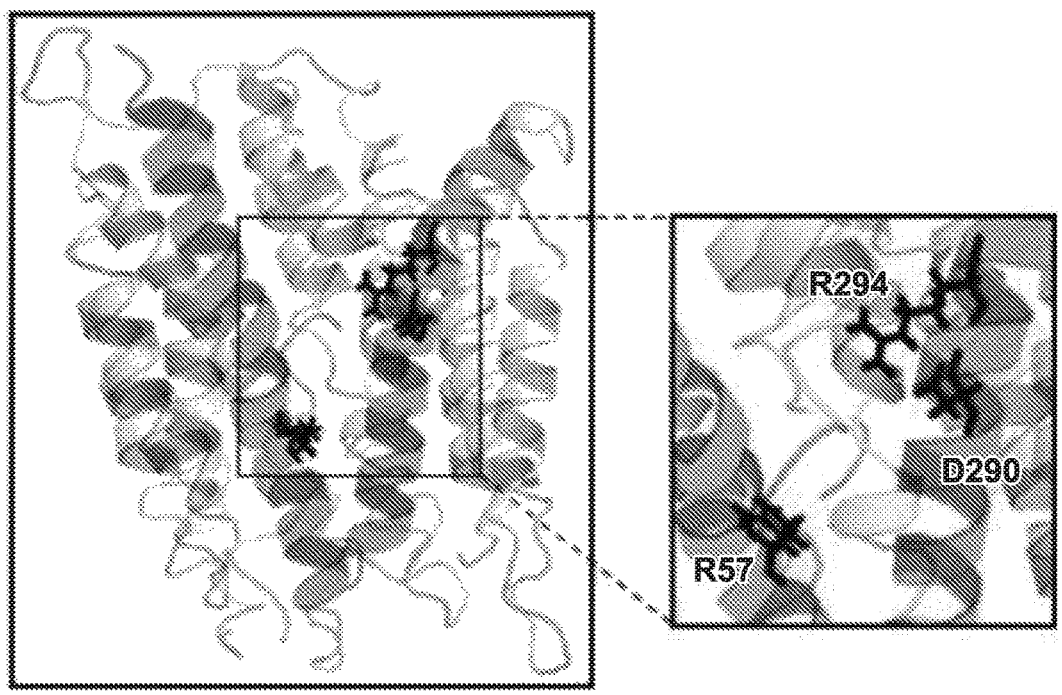
FIG. 3B provides a ribbon diagram of SLC16A11 showing the position of particular residues of interest (e.g., R57, R294, D290).
Figure 3C:
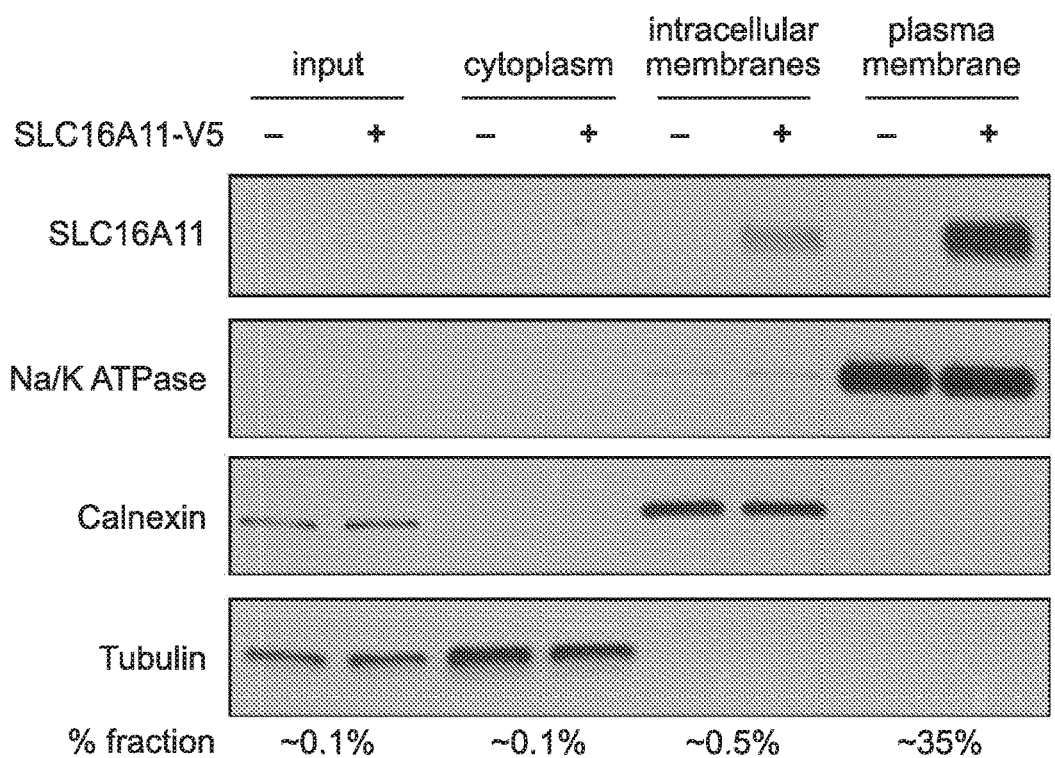
FIG. 3C provides a Western blot analysis showing that SLC16A11 localizes to the plasma membrane.
Figure 3D:
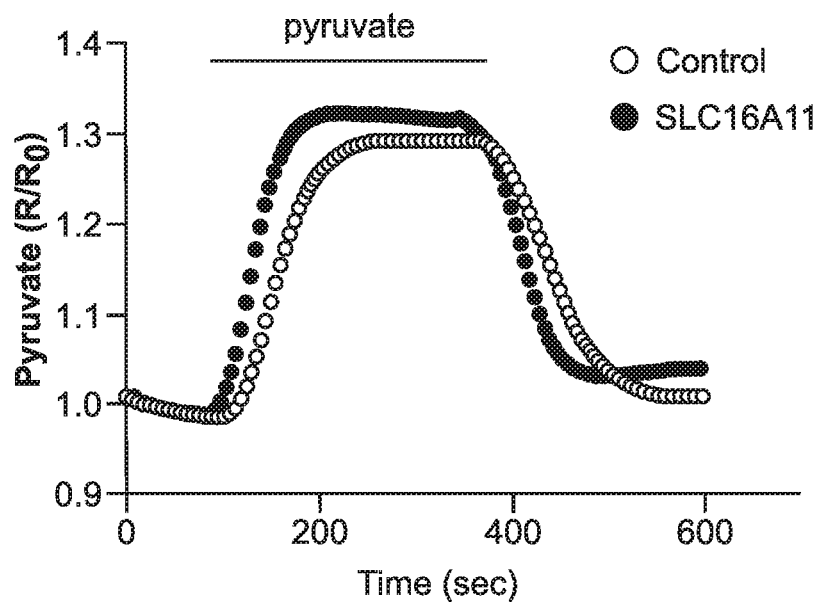
FIG. 3D provides a graph showing results of a pyronic Fluorescence Resonance Energy Transfer (FRET) assay, which indicates that SLC16A11 transports pyruvate.
Figure 3E:
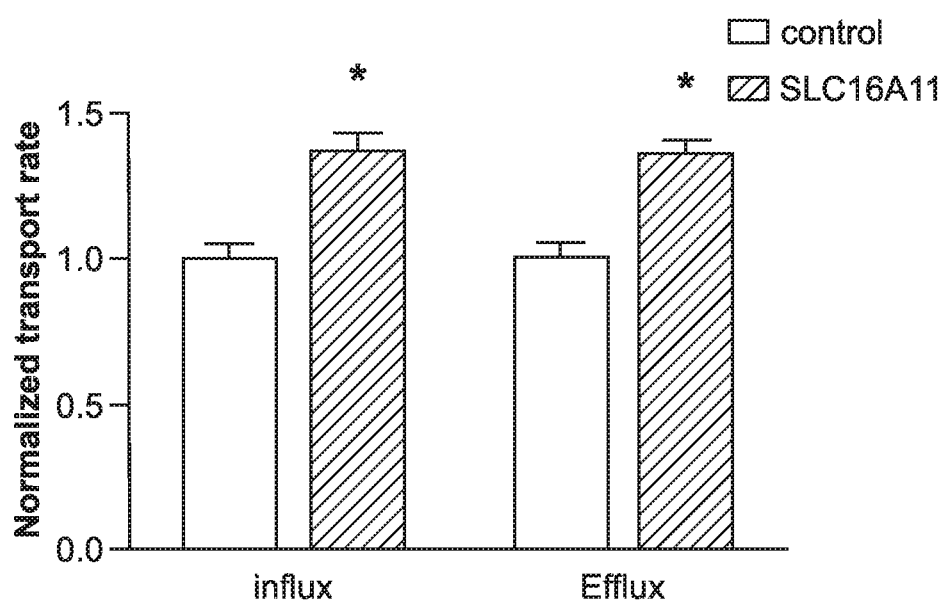
FIG. 3E provides a graph showing quantification of reduced rate of pyruvate transport.
Figure 3F:
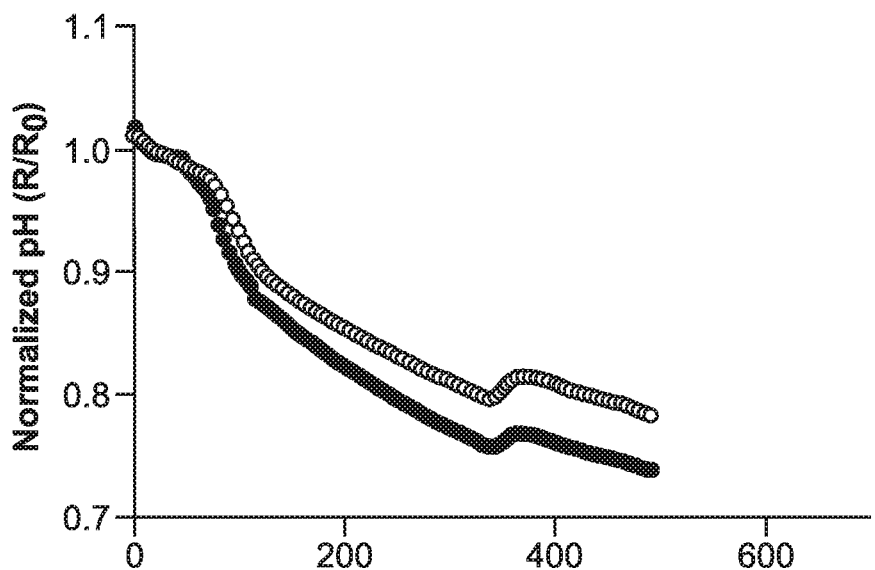
FIG. 3F provides a graph showing that SLC16A11 transport is proton-coupled (pH sensor).
Figure 3G:
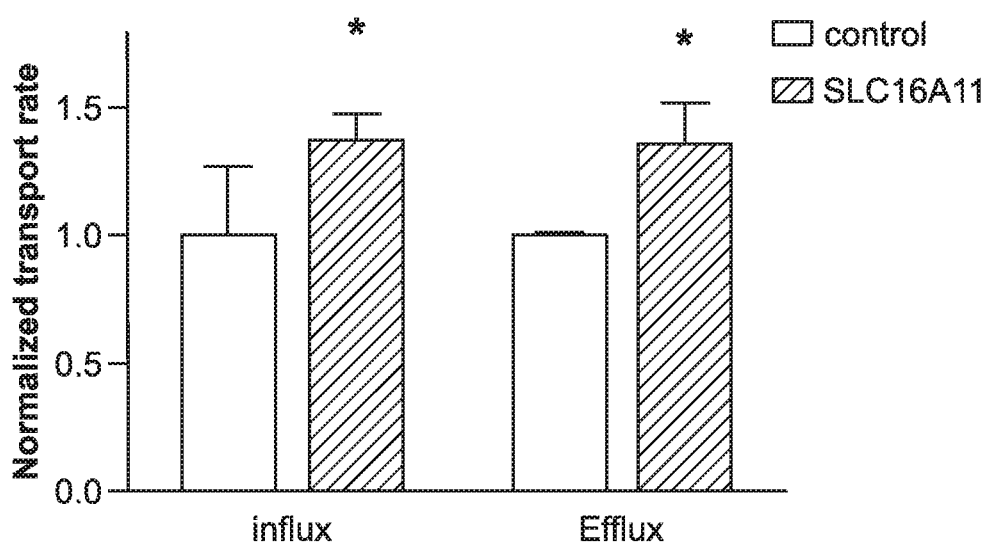
FIG. 3G provides a graph showing a quantification of rate of acidification.
Figure 3H:
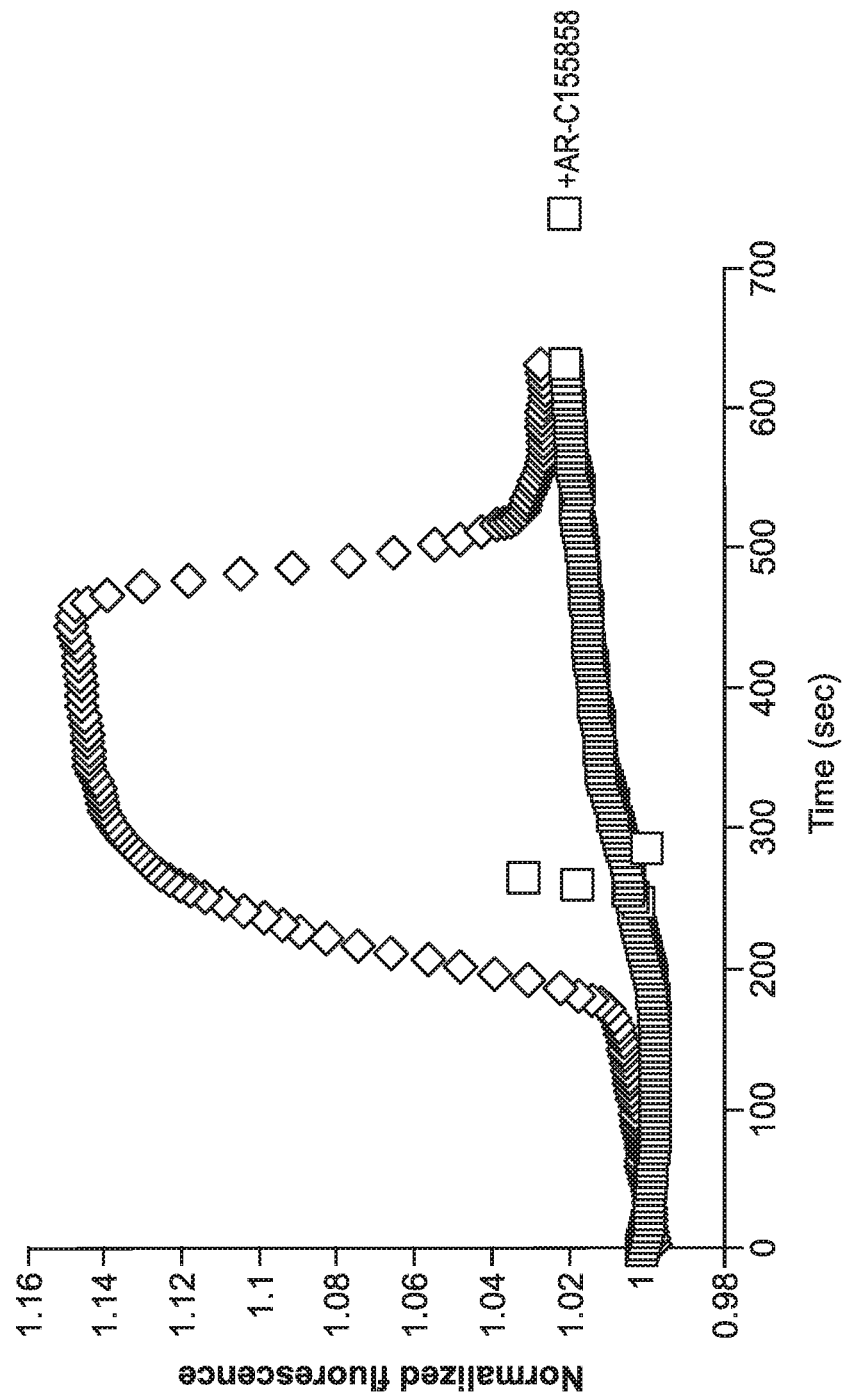
FIG. 3H provides a graph showing pyronic validation with an SLC16 family inhibitor.
Figures 1, 31:
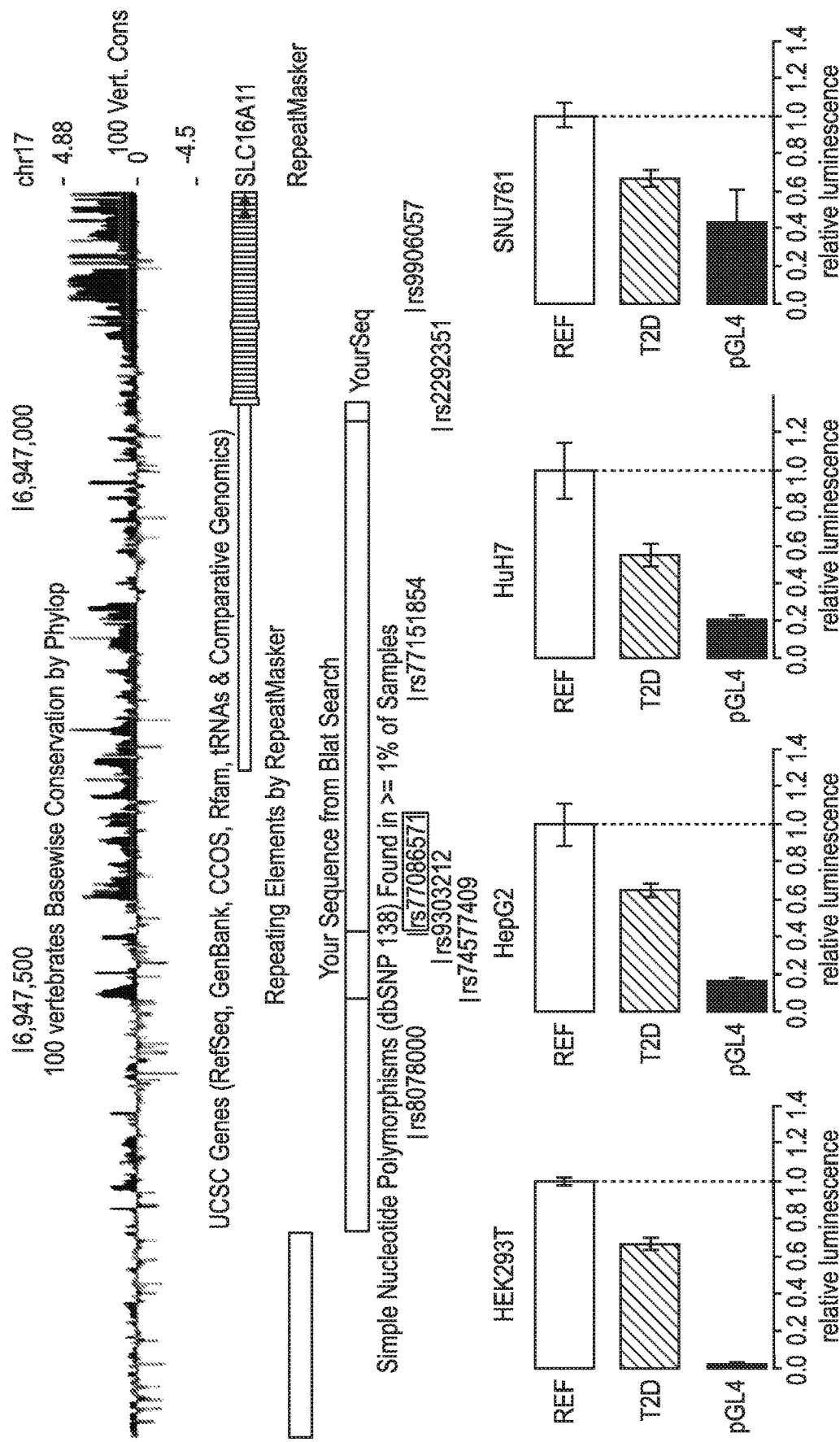
Figures 2, 3I:
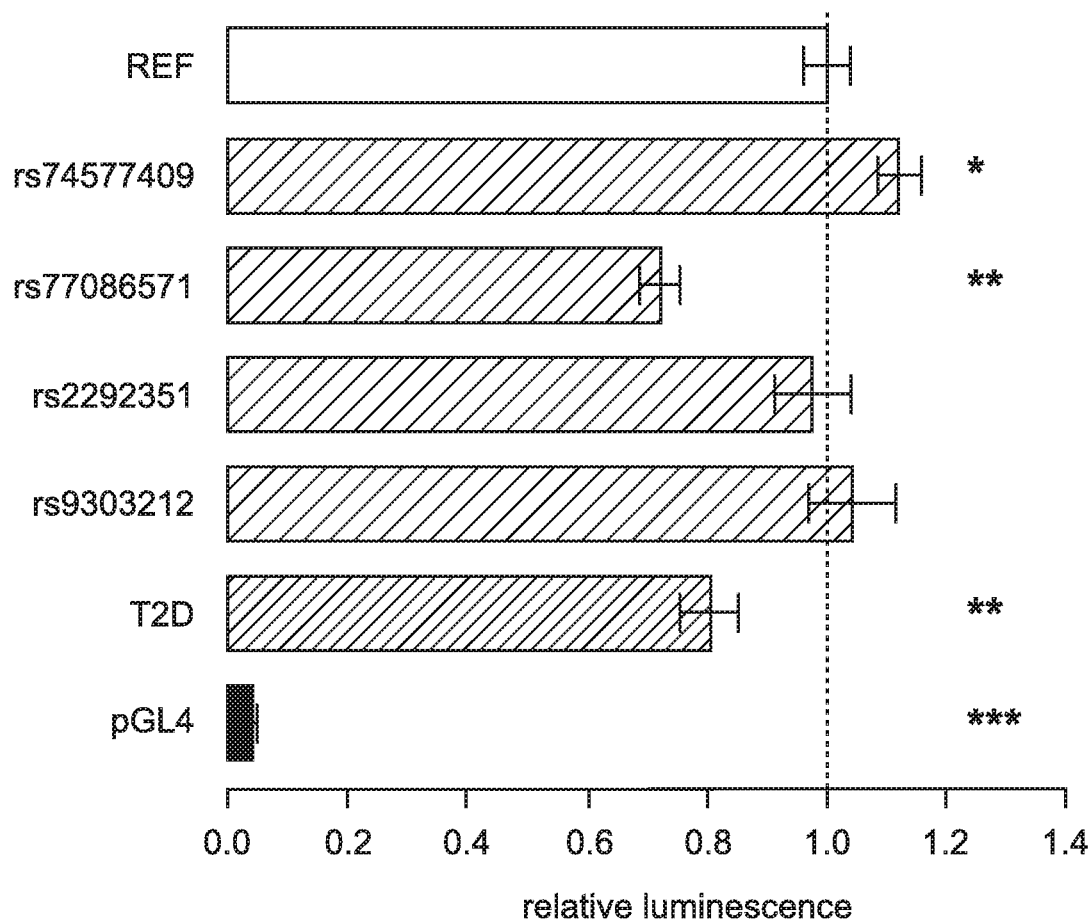

A 767 bp fragment was cloned into a luciferase reporter vector. This fragment spans 425 bp upstream of the SLC16A11 transcription start site (TSS) to the start of a repetitive region and 342 bp downstream of the SLC16A11 TSS to the initiator methionine of SLC16A11 (FIG. 3I, top panel). The construct containing the fragment with the reference alleles at rs77086571, rs74577409, and rs2292351 is denoted as REF and the construct with T2D risk alleles at all three of these variants as RISK. A panel of cell lines was transfected with REF and RISK: HEK293T, HepG2, HuH7, and SNU761 cells. Reduced luciferase reporter activity was noted in the presence of all three T2D risk alleles in all four of these cell lines (FIG. 3I, middle panel).

Figure 3J:
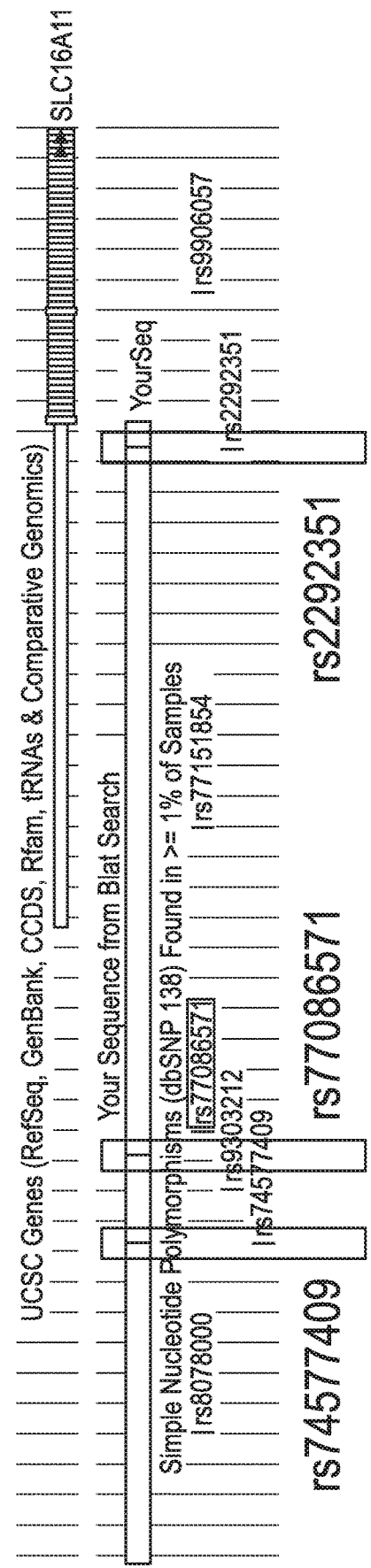
FIG. 3J provides a schematic showing the location of SNPs.

In order to dissect which individual variant is sufficient to reduce reporter activity, three additional luciferase reporter constructs were made with each variant individually (FIG. 3I (bottom panel)). HEK293T cells were transfected and with respect to REF: a 20% decrease was obtained with RISK ($P=9\times10^{-4}$), a 28% decrease with $-$rs77086571 ($P=5\times10^{-5}$), and a 12% increase with rs74577409 ($P=4\times10^{-3}$). rs2292351 and rs9303212 did not significantly alter luciferase reporter activity. The variant rs9303212, found in Mexico and Latin America, was included due to its genomic location between rs77086571 and rs74577409, but is not part of the T2D risk credible set. Together, these data indicate that a single variant rs77086571 is sufficient for reduced reporter activity. The location of SNPs for variants are shown by FIG. 3J (top panel). A motif analysis elucidated the sequences that result in altered transcription factor binding at variants in the SLC16A11 promoter (FIG. 3K).

Example 7

Metabolic Processes are Altered in Livers from T2D Risk Haplotype Carriers

In order to investigate which cellular pathways are altered in liver from individuals carrying the T2D risk haplotype, RNA-sequencing was performed in 8 homozygotes for the risk haplotype (RISK) and 8 homozygotes for the reference haplotype (REF). All individuals were female and there were no significant differences in age, BMI, fasting glucose, total cholesterol, triglycerides, HDL cholesterol, insulin, Hb1Ac, systolic BP, or diastolic BP. In addition within each genotype, there were 4 individuals with type 2 diabetes (T2D) and 4 non-diabetics (CNTRL).

The following Table 4B shows the down-regulated metabolic processes in liver from carriers of the T2D risk haplotype.

TABLE 4B

|  | size | NES | p-value | FDR |
| --- | --- | --- | --- | --- |
| COMPLEMENT & COAGULATION CASCADES | 69 | −2.40 | 0.000 | 0.000 |
| CITRATE CYCLE TCA CYCLE | 29 | −2.38 | 0.000 | 0.000 |
| DRUG METABOLISM OTHER ENZYMES | 51 | −2.22 | 0.000 | 0.000 |
| PPAR SIGNALING PATHWAY | 63 | −2.23 | 0.000 | 0.001 |
| PARKINSONS DISEASE | 104 | −2.11 | 0.000 | 0.001 |
| PORPHYRIN & CHLOROPHYLL METABOLISM | 40 | −2.13 | 0.000 | 0.001 |
| VALINE LEUCINE & ISOLEUCINE DEGRADATION | 43 | −2.09 | 0.000 | 0.001 |
| OXIDATIVE PHOSPHORYLATION | 107 | −2.08 | 0.000 | 0.001 |
| HUNTINGTONS DISEASE | 163 | −2.00 | 0.000 | 0.002 |
| PENTOSE PHOSPHATE PATHWAY | 23 | −2.00 | 0.000 | 0.002 |
| FATTY ACID METABOLISM | 42 | −2.01 | 0.000 | 0.002 |
| LYSOSOME | 114 | −2.02 | 0.000 | 0.002 |
| FRUCTOSE & MANNOSE METABOLISM | 34 | −2.02 | 0.000 | 0.002 |
| PENTOSE & GLUCURONATE INTERCONVERSIONS | 26 | −2.03 | 0.000 | 0.002 |
| PROTEASOME | 43 | −1.94 | 0.000 | 0.004 |
| BUTANOATE METABOLISM | 31 | −1.93 | 0.000 | 0.004 |
| ADIPOCYTOKINE SIGNALING PATHWAY | 61 | −1.92 | 0.000 | 0.004 |
| SPLICEOSOME | 123 | −1.91 | 0.000 | 0.004 |
| PYRUVATE METABOLISM | 38 | −1.89 | 0.000 | 0.004 |
| ASCORBATE & ALDARATE METABOLISM | 24 | −1.89 | 0.000 | 0.004 |

Top 20 pathways with an FDR<0.05 are shown. Size refers to the gene set size, NES stands for normalized enrichment score, and FDR stands for false discovery rate.

In the RISK versus REF comparison, a single gene APOA4 was significantly altered after correcting for multiple hypothesis testing (50% decrease; $P=9\times10^{-7}$). As expected SLC16A11 was one of the most significantly altered genes ranking 55 out of over 20,000 genes tested for differential expression (38% decrease; $P=3\times10^{-4}$). It is noted that SLC16A11 is expressed in liver at low levels and hence precise quantification of a change in expression by RNA-sequencing is challenging. Despite this caveat, SLC16A11 was the most differentially expressed gene within 100 kb of rs77086571 and among all SLC16 family members in the RISK versus REF comparison.

Example 8

Metabolomics Analysis of Human Liver Cell Line Expressing SLC16A11$^{REF}$

Unbiased approaches, such as metabolomics and phenotype microarrays, were used to generate hypotheses about what substrates SLC16A11REF, the protein encoded by the non-risk haplotype, might transport. Next, target assays were used to test whether individual metabolites are transported by SLC16A11.

SLC16A11$^{REF}$ was expressed in HuH7, a human hepatoma cell line, and after 72 hours samples were collected to measure steady-state levels of over 150 metabolites by mass spectrometry. The 18 biological replicates of SLC16A11$^{REF}$ and 24 controls (denoted by CNTRL and consisting of BFP, GFP, HcRed, and Luciferase) were profiled across two different experiments. The data indicated that the levels of 10 intracellular metabolites in HuH7 cells were significantly altered ($P<10^{-5}$) by expression of SLC16A11$^{REF}$ (Table 5B). Since members of the SLC16 family transport monocarboxylates, experiments were conducted to identify which of these metabolites had a single carboxylate group and found: pantothenate, glutathione-oxidized, lactate, GABA, pyruvate, and asparagine. Of particular interest are pyruvate and lactate because SLC16 family members transport both (FIG. 3K).

Perturbing a transporter and observing significantly altered metabolites does not directly provide evidence that the altered metabolites are substrates for the transporter. Conversely, it is not necessarily expected that the steady state levels of a substrate will be altered by perturbing its transporter. This is due to redundancy in transporters and significant overlap among metabolic pathways. Results from these experiments were combined with other information to generate hypotheses about what substrates SLC16A11 might transport, which were then tested with targeted assays.

Example 9

SLC16A11 is an H$^+$-Coupled Monocarboxylate Transporter

To better understand the consequence of reduced SLC16A11 activity on T2D risk, the function of this previously uncharacterized protein was assessed. As noted supra, characterized members of the SLC16 family can be segregated into, at least, two distinct categories: chaperone-dependent, H$^+$-coupled monocarboxylate transporters (category I) or facilitators of hydrophobic monocarboxylate diffusion (category II), with SLC16A11 falling into a third category of as-yet-uncharacterized transporters (Table 5A).

TABLE 5A

SLC16A family of monocarboxylate transporters.

| Category | Family member | Primary substrates | Mechanism | Ancillary proteins |
| --- | --- | --- | --- | --- |
| I | SLC16A1 | Pyruvate, Lactate, Ketone bodies | H$^+$ coupled | Basigin (BSG) Embigin (EMB) |
| | SLC16A3 | | | |
| | SLC16A7 | | | |
| | SLC16A8 | Lactate | | |
| II | SLC16A2 | T3, T4 hormones | Facilitated diffusion | No interaction |
| | SLC16A10 | Aromatic amino acids | | — |
| Uncharacterized | SLC16A6 | β-hydroxybutyrate | — | — |
| | SLC16A9 | Carnitine | Not H$^+$ coupled | |
| | SLC16A4 | — | — | |
| | SLC16A5 | | | |
| | SLC16A11 | | | |
| | SLC16A12 | | | |
| | SLC16A13 | | | |
| | SLC16A14 | | | |

Table 5A: Categorization of SLC16 family members with transport substrates, mechanism, and ancillary proteins indicated. SLC16A11 (in bold) is an uncharacterized member of the family.

To gain insight into which category SLC16A11 might reside, the structures of category I and category II SLC16 family members was compared to identify structural motifs corresponding to the differences in function. Previously, transmembrane domains (TMDs) 1 and 8 have been highlighted as mediating the catalytic core in SLC16A1, with charged residue K38 on TMD 1 and residues D309 and R313 on TMD 8 singled out as mediating monocarboxylate transport. While R313 is present in all six members of the two categories, multiple sequence alignment revealed that residues K38 and D309 are only conserved in the four category I SLC16 proteins, but are replaced by non-charged residues in SLC16 proteins identified as category II (FIG. 3A). In SLC16A11, the charges at these positions are conserved and correspond to positions R57, D290, and R294. Three-dimensional homology modeling of SLC16A11 based on the bacterial glycerol-3-phosphate transporter (G1PT) supports this finding, placing these three residues in the inner pore of the protein in a similar fashion as modeled for SLC16A1 (FIG. 3B). These structural analyses suggest SLC16A11 is a category I SLC16 family member, and would thus transport monocarboxylates via a H$^+$-coupled mechanism. To study the transport properties of SLC16A11, the protein encoded by the non-risk haplotype, denoted SLC16A11 (or SLC16A11$^{REF}$), and the protein encoded by the risk haplotype—which contains all five coding variants found on the T2D risk allele (denoted SLC16A11$^{T2D}$) were studied.

To inform the development of an assay to monitor substrate transport, experiments were conducted to verify the subcellular localization of SLC16A11. Through immunofluorescent imaging, previously conducted experiments reported that V5-tagged SLC16A11 localizes to the endoplasmic reticulum (SIGMA Nature. 2014 Feb. 6; 506(7486): 97-101). Other SLC16 family members have been reported to localize to the plasma membrane as well as to intracellular membranes. To explore the possibility that SLC16A11 is also present at the cell surface, membrane extraction assays were performed with HEK293T ("293T") cells expressing SLC16A11. Consistent with previous findings, the majority of SLC16A11 remains associated with intracellular membranes (FIG. 3C). Nevertheless, a portion (5%) of SLC16A11 localized to the plasma membrane, indicating it might modulate metabolite transport across the plasma membrane.

Figure 3M:
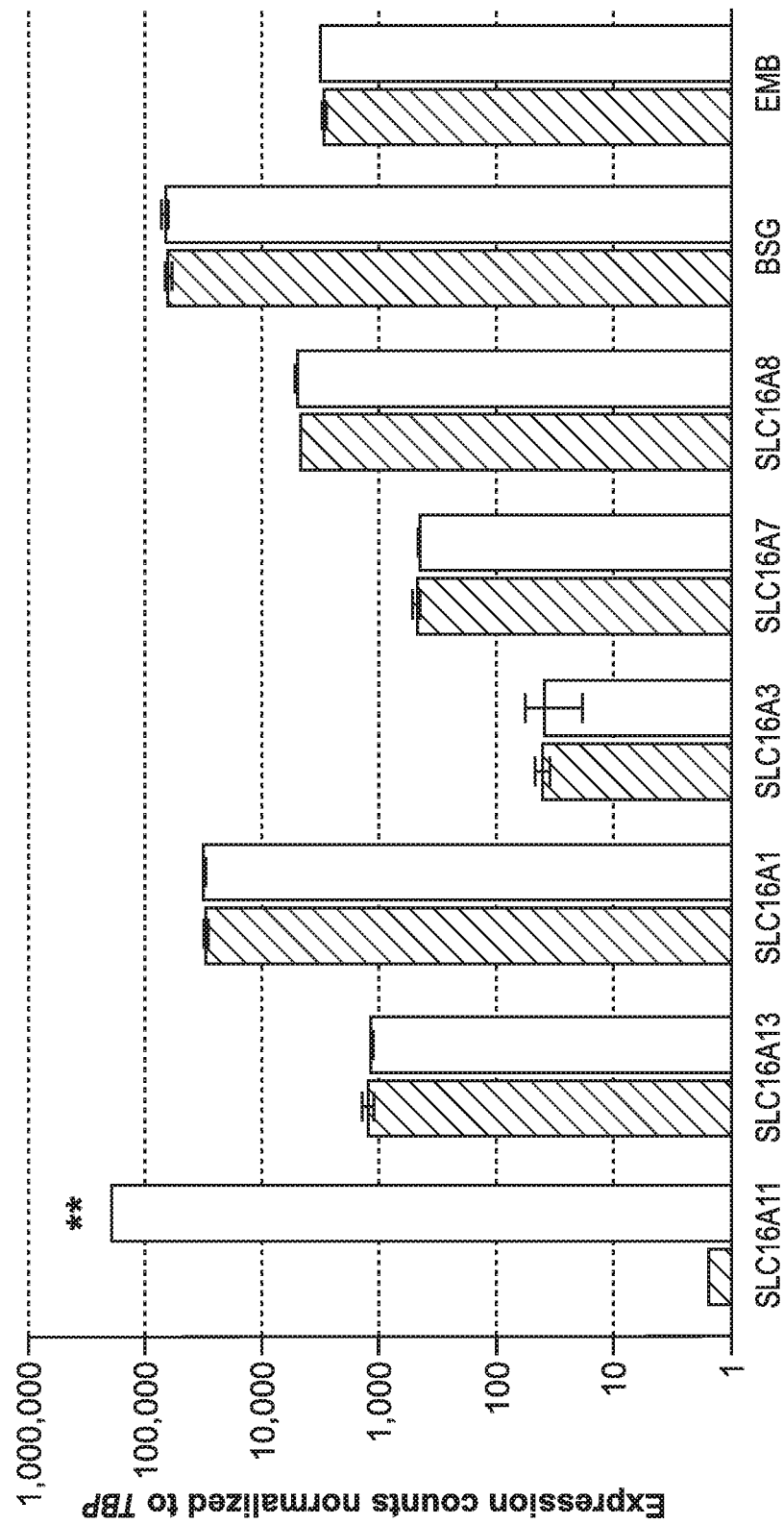
FIG. 3M shows a bar graph illustrating that in 293T cells co-transfected with pyronic and SLC16A11-V5, SLC16A11 levels are increased without affecting other category I family members.

To obtain "proof of concept" for monocarboxylate transport by SLC16A11, pyruvate was focused on as the metabolite transported by all four SLC16 category I proteins, whose real-time transport in mammalian cells can be readily studied by the pyruvate FRET sensor, pyronic. 293T cells were co-transfected with pyronic and either empty vector control or SLC16A11-V5, which increases SLC16A11 levels without affecting other category I family members (FIG. 3M). Cells were perfused in physiological pH 7.4 Ringer's solution and 0.4 mM pyruvate was added at the indicated time point (FIG. 3D), resulting in an increase of the fluorescence signal, indicative of pyruvate uptake. This signal is completely diminished upon pre-incubation of the cells with AR-C155858 (FIG. 3H), a chemical inhibitor of SLC16A1 and SLC16A7 transport. Thus, this is consistent with the increase in fluorescence resulting from SLC16-dependent pyruvate transport.

Figure 3N:
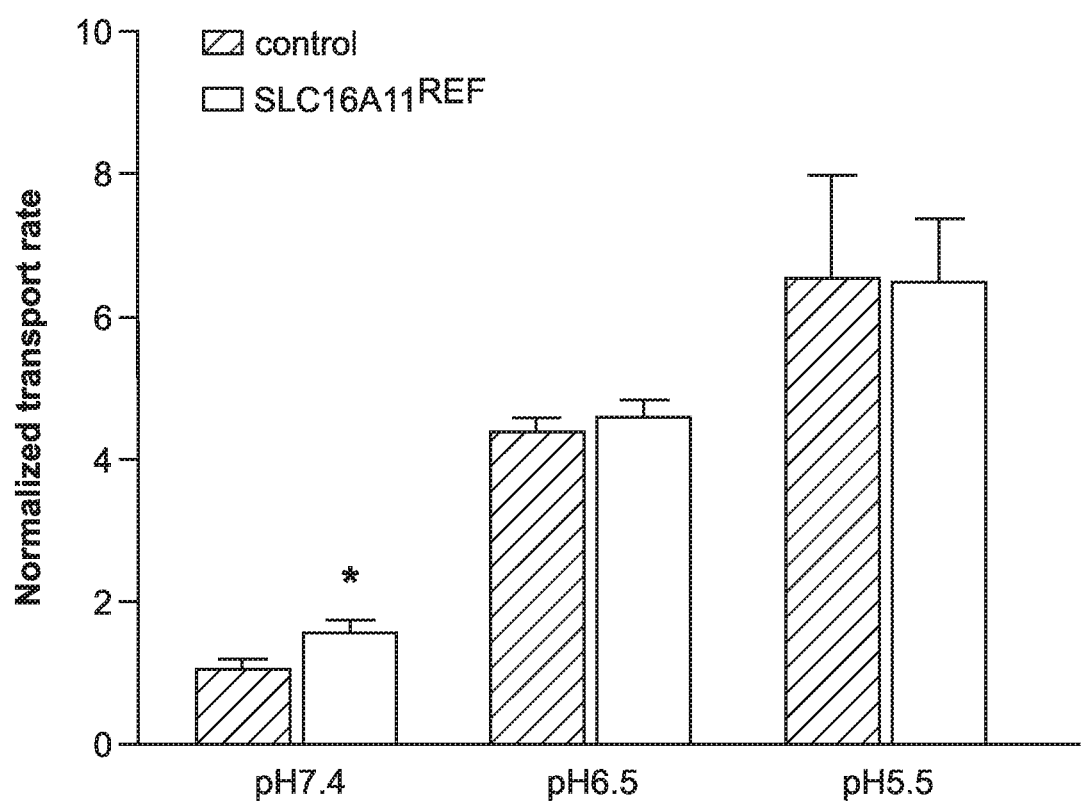

Influx (rising phase) and efflux (falling phase) rates of pyruvate transport were compared in SLC16A11-expressing and control cells. Pyruvate transport rates in both directions were found to be ~45% higher in cells expressing SLC16A11 (FIG. 3E), supporting the idea that SLC16A11 is a category I monocarboxylate transporter. Similar patterns of bi-directional transport have been previously reported for other members of the SLC16 family. A difference between SLC16A11-expressing cells and control cells was only observed at neutral pH, likely due to activation of other, endogenous SLC16 family members at acidic pH. (FIG. 3N).

To assess if SLC16A11 utilizes a $H^+$-coupled transport mechanism similar to other category I family members, pH changes were monitored in SLC16A11-expressing and control 293T cells using BCECF-AM, a pH-sensitive fluorescent probe. An ~40% increase in the rates of acidification and alkalization was observed, with both phases reciprocal to influx and efflux of pyruvate, supporting a $H^+$-coupled mechanism underlying SLC16A11 transport (FIG. 3F and FIG. 3G).

Figure 8A:
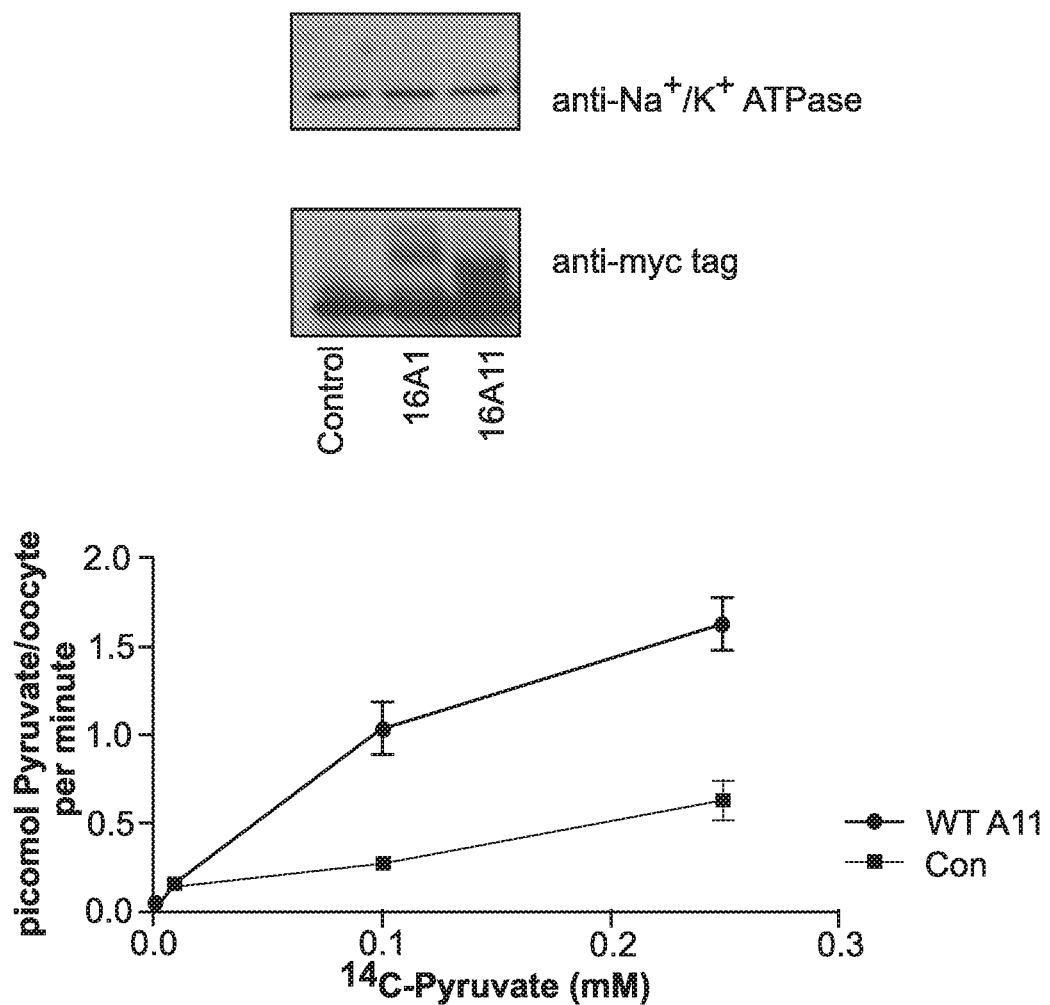
FIG. 8A provides data showing pyruvate uptake in *Xenopus Oocytes* overexpressing SLC16A11.

To further support this finding, SLC16A11 mRNA was injected into *Xenopus oocytes*, following which labeled pyruvate was added to the media. Oocytes were then lysed and labeled, and pyruvate uptake was monitored by a scintillation counter. Expression of SLC16A11 was sufficient to provide for pyruvate uptake (FIG. 8A), and SLC16A11 affinity to pyruvate was found to be higher than that of SLC16A1 (FIG. 8B).

Expression of SLC16A11 in oocytes was sufficient to provide for pyruvate uptake. SLC16A11 has higher affinity to pyruvate and greater translocation efficiency. To determine if SLC16A11 modulates steady state levels of cellular pyruvate, metabolic profiling was performed on a human liver cell line, HuH7, expressing WT SLC16A11 or control proteins. Expression of WT SLC16A11 resulted in a 22% increase in steady-state cellular pyruvate levels ($P=9\times10^{-7}$) (FIG. 4E). Similarly, intracellular levels of lactate, a derivative of pyruvate and a substrate for other SLC16 category I transporters, increased by 29% ($P=1\times10^{-7}$) (FIG. 4F). These results support the notion that SLC16A11 plays a role in monocarboxylate transport.

Thus, bioinformatic analyses combined with transport assays firmly place SLC16A11 into category I with other $H^+$-coupled, monocarboxylate transporters.

Example 10

T2D Risk Coding Variants Attenuate SLC16A11 Transport Activity

Figure 4A:
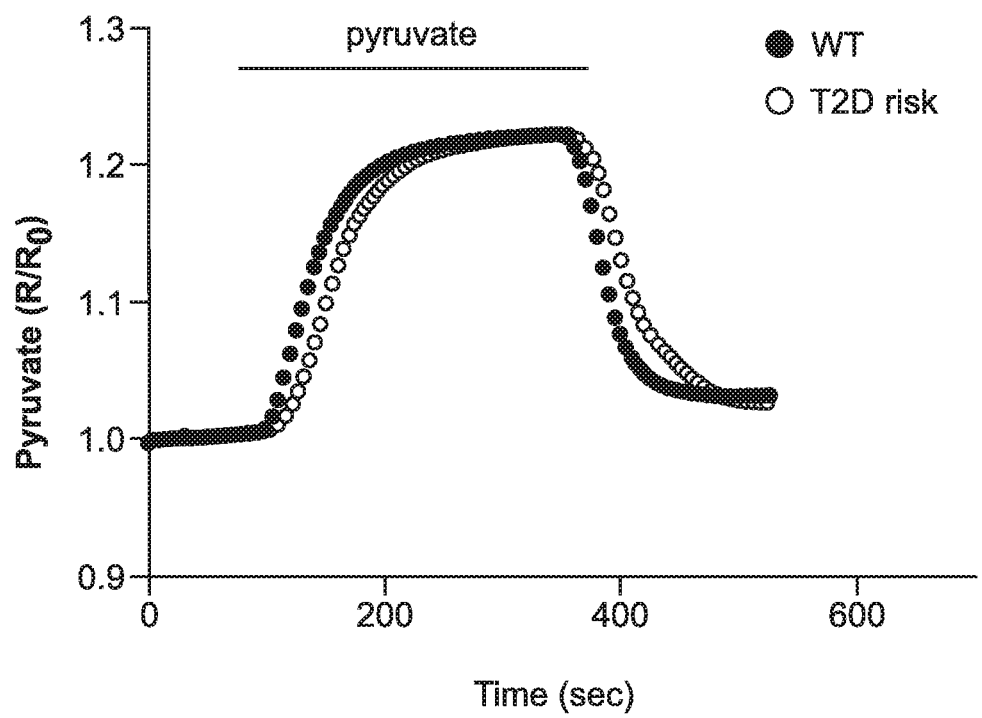
Figure 4B:
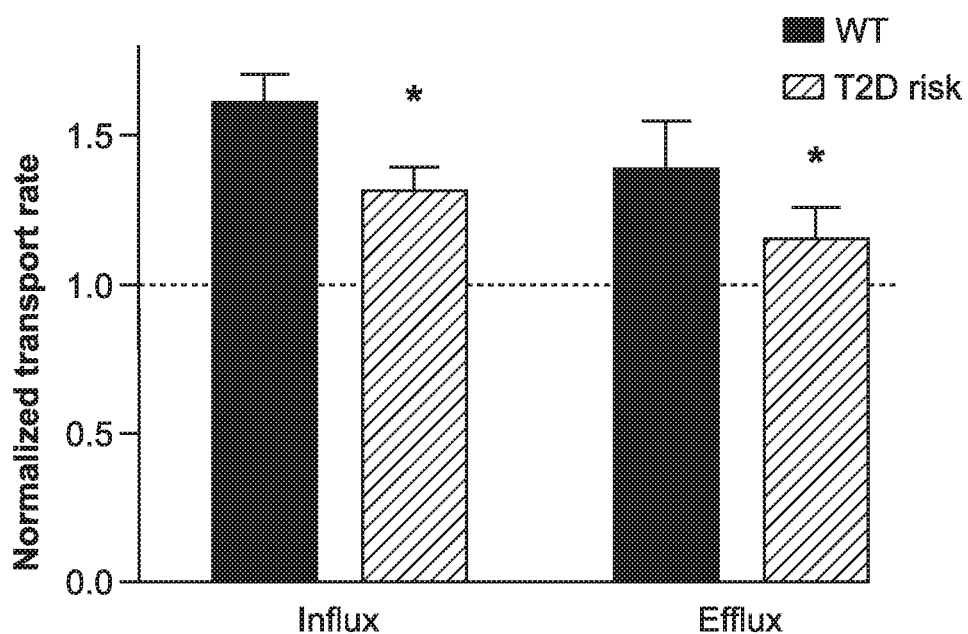
Figure 4G:
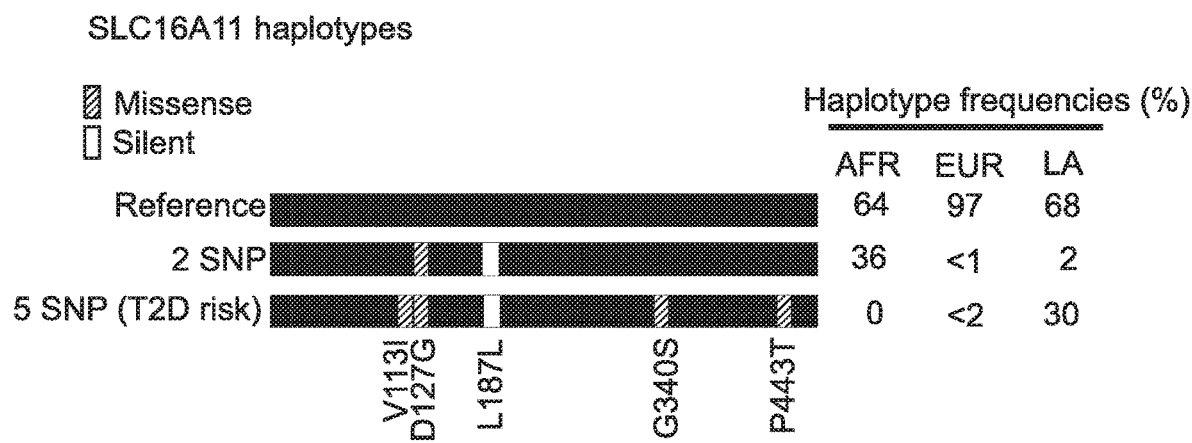

The T2D risk haplotype contains five variants in the coding sequence of SLC16A11: four of these are missense variants and result in amino acid altering mutations (V113I, D127G, G340S, and P443T), and one is a silent variant (L178L). These SLC16A11 haplotypes and the frequency at which they occur in certain populations are shown in FIG. 4G. The positions of single nucleotide polymorphism (SNP) locations for V113I, D127G, G340S, and L187L are depicted on a SLC16A11 ribbon diagram (FIG. 5A, top panel).

To determine if these coding changes altered SLC16A11 function, the transport activity of wild-type (WT, the human reference protein) and T2D risk SLC16A11 (the mutant protein resulting from the presence of all five T2D risk-associated coding variants) was compared. Using the pyronic based assay in 293T cells, pyruvate transport rates of WT and T2D risk SLC16A11 were compared (FIG. 4A). Pyruvate influx and efflux rates mediated by T2D risk SLC16A11 were found to be approximately half that of WT SLC16A11 (FIG. 4B). Similarly, proton transport rates were reduced in T2D risk SLC16A11 expressing cells, when compared to WT SLC16A11 (SLC16A11$^{REF}$) expressing cells (FIG. 4C and FIG. 4D, top panel). FIG. 4E and FIG. 4F show normalized abundance of pyruvate and lactate in wild-type and control cells. These data demonstrate that the T2D risk-associated coding variants resulted in reduced SLC16A11 transport activity, consistent with the disease-relevant direction of effect observed for the SLC16A1 cis-eQTL.

TABLE 5B

Significantly altered metabolites in HuH7 cells expressing SLC16A11$^{REF}$. Intracellular polar metabolites significantly altered in the SLC16A11$^{REF}$ versus CNTRL comparison (p-value < 10-5)

| Metabolite name | Percent change | p-value |
| --- | --- | --- |
| pantothenate | −32% | $6.79 \times 10^{-11}$ |
| glutathione-oxidized | −33% | $4.12 \times 10^{-8}$ |
| C5-carnitine | 10% | $1.01 \times 10^{-7}$ |
| lactate | 29% | $1.28 \times 10^{-7}$ |
| GABA | −37% | $1.29 \times 10^{-7}$ |
| 2-aminoadipate | 31% | $1.58 \times 10^{-7}$ |
| pyruvate | 22% | $9.27 \times 10^{-7}$ |
| asparagine | −17% | $1.36 \times 10^{-5}$ |
| inositol | 29% | $3.19 \times 10^{-6}$ |
| lactose | 16% | $7.17 \times 10^{-6}$ |
| guanosine | −30% | $8.38 \times 10^{-6}$ |

In addition to steady-state measurement of metabolite levels, flux was measured through metabolic pathways.

SLC16A11$^{REF}$ or an empty vector control was expressed in HepG2, a human hepatocellular carcinoma cell line, and used phenotype microarrays to determine rates of metabolite utilization. A phenotype microarray is a 96-well plate where each well contains a unique metabolite that serves as an energy source. Cells are grown in minimal media in order to consume their internal energy stores. After this, they consume the metabolite found in the well. Energy status of the cells is by measuring the NADH reduction of a tetrazolium dye.

Data were collected for 4 biological replicates of SLC16A11$^{REF}$ and empty vector control in one experiment, enabling the simultaneous analysis of the utilization rates of more than 90 metabolites. A phenotype microarray was profiled that consisted of carbon and other energy sources, and found that utilizations of the following three metabolites were significantly altered (P<0.05) upon the expression of SLC16A11$^{REF}$: pyruvate, lactate, and acetate (FIG. 3L). Together with the metabolomics analysis in HuH7 cells, these data indicate that SLC16A11 likely alters pyruvate and lactate levels, perhaps by mediating transport of these metabolites.

Figure 19:
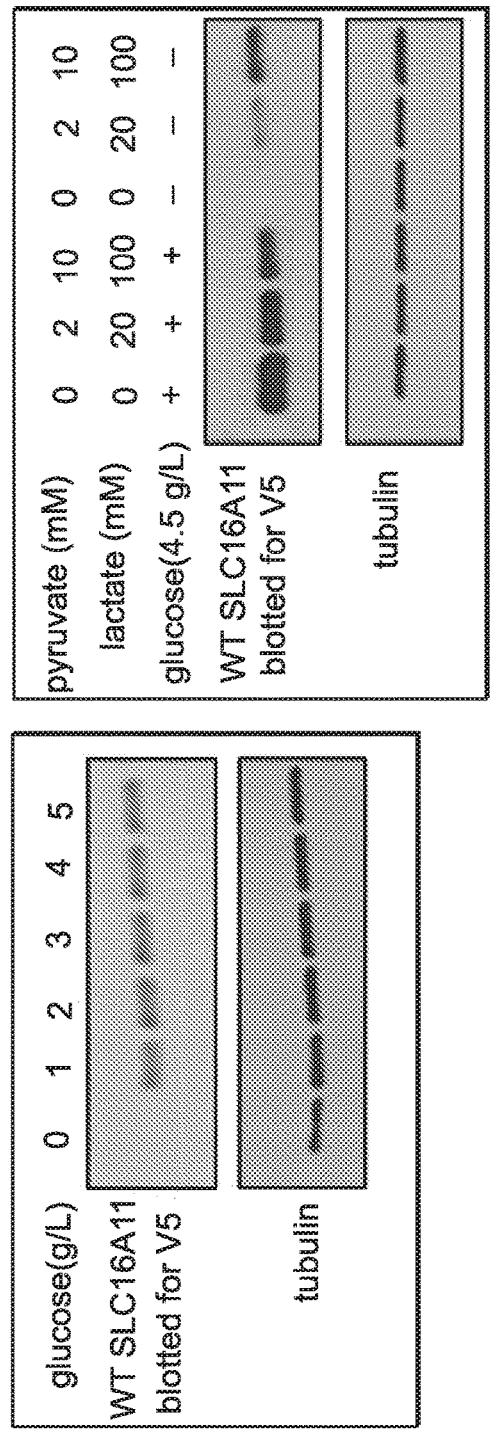
FIG. 19 provides Western blots and experimental protocol steps involved in the analysis of SLC16A11 protein levels after culture of HuH7 cells stably expressing SLC16A11 in the presence or absence of various metabolites, namely, pyruvate, lactate and glucose. Cell lysates were used in the analysis. The left blot shows SLC16A11 blotted for V5 following culture of cells with or without glucose at different concentrations for 24 hr. The right blot shows SLC16A11 blotted for V5 following culture of cells with or without pyruvate and lactate and with or without glucose at different concentrations for 24 hr. Tubulin is shown as a reference. As shown, glucose, pyruvate and lactose are metabolites that affect SLC16A11 protein levels.
Figure 20:
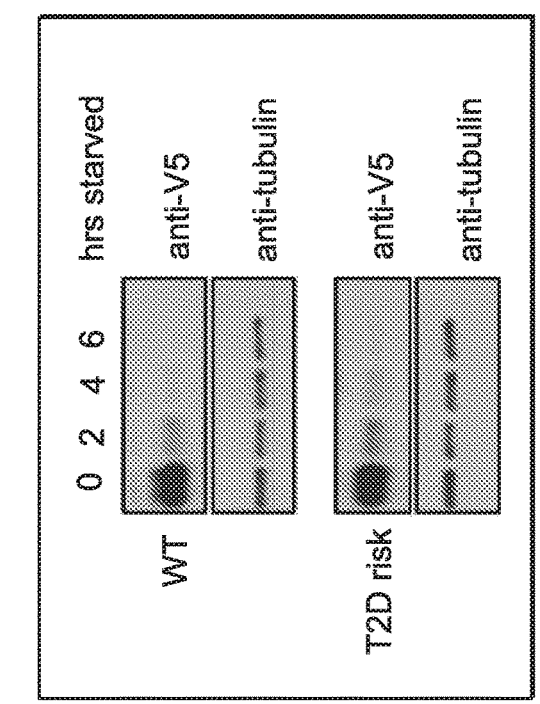
FIG. 20 provides Western blots of V5-tagged SLC16A11 (WT) and the V5-tagged SLC16A11 variant, T2D risk, stably expressed in HuH7 cells that had been glucose-starved for the times indicated. Cell lysates were used in the analysis. As observed, glucose deprivation resulted in a rapid decrease (starting at 2 hrs) in SLC16A11 protein levels in the SLC16A11-expressing cells. A similar finding is observed in the left blot of FIG. 19, above, in which no SLC16A11 protein was detected in cell lysates cultured for 24 hrs without glucose compared with detectable levels of SLC16A11 protein found in lysates from cultures containing 1-5 g/L of glucose.
Figure 21:
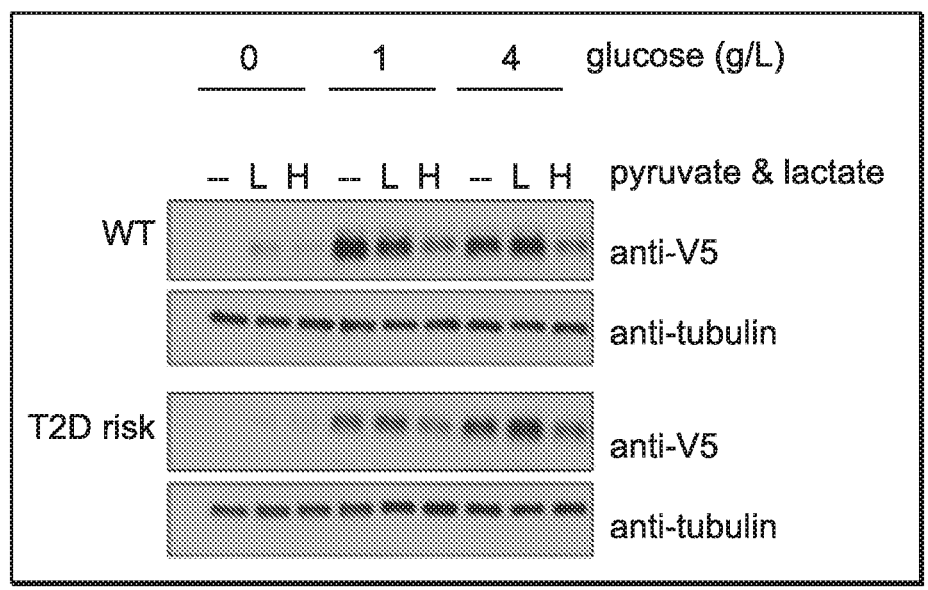
FIG. 21 provides Western blots of V5-tagged SLC16A11 (WT) and the V5-tagged SLC16A11 variant, T2D risk, stably expressed in HuH7 cells that been cultured for 24 hours with or without glucose and with either low (L) or high (H) concentrations of pyruvate and lactate as indicated. Cell lysates were used in the analysis. As observed in FIG. 21, both low and high concentrations of pyruvate and lactate altered the levels of the SLC16A11 (WT) and the T2D risk variant proteins.

In other analyses, the metabolites pyruvate, lactate and glucose were found to alter SLC16A11 protein levels in HuH7 cells stably expressing SLC16A11 and cultured with these metabolites (FIG. 19). FIG. 20 provides results of experiments showing that glucose deprivation of HuH7 cells stably expressing SLC16A11 resulted in a rapid decrease of SLC16A11 protein levels. FIG. 21 provides results of experiments showing that pyruvate and lactate alter protein levels of SLC16A11 in HuH7 cells stably expressing SLC16A11 and cultured in the presence of these metabolites at high and low concentrations.

Example 11

SLC16A11 Runs as a Doublet Under Reducing SDS-PAGE Conditions

The data indicated that the SLC16A11 protein generates a doublet under reducing SDS-PAGE conditions. Remarkably the ratio of the lower to upper band of the doublet is consistently reduced for SLC16A11$^{T2D}$ compared to SLC16A11$^{REF}$ (FIG. 4D (bottom panel)). It was hypothesized that a post-translational modification of SLC16A11 might be resulting in the doublet.

Mass spectrometry was used to search for phosphorylated residues on SLC16A11. Detecting membrane proteins by mass spectrometry is challenging, but eventually this technique was able to achieve 78% coverage of SLC16A11$^{T2D}$. Despite good coverage, phosphorylated residues were not detected.

The data indicated that the SLC16A11 doublet is sensitive to the amount of glycerol present when running the SLC16A11 protein on a reducing SDS-PAGE gel. Phosphatase treatment was able to resolve the SLC16A11 doublet but this was attributed to the glycerol that was used to stabilize the phosphatase. In addition, data indicated that the SLC16A11 doublet was sensitive to the reducing agent used to prepare samples before they were run on a SDS-PAGE gel. Beta-mercaptoethanol, but not dithiothreitol, was able to resolve the doublet.

Together this data indicated that the SLC16A11 doublet is most likely a result of incomplete denaturation of the protein under reducing SDS-PAGE conditions. This can occur for some membrane proteins. When combined with the altered ratio of the doublet for SLC16A11$^{T2D}$, this might indicate that SLC16A11$^{T2D}$ adopts a slightly different conformation from SLC16A11$^{REF}$. This could affect how SLC16A11$^{T2D}$ sits in the membrane and consequently might affect transport or protein-protein interactions.

Example 12

SLC16A11 Interacts with SLC16 Category I Ancillary Proteins

There are a number of mechanisms by which the T2D risk-associated coding variants could reduce SLC16A11 activity. Based on the SLC16A11 homology model, the T2D risk coding variants are distant from the putative catalytic site formed between TMDs 1 and 8 (FIG. 5A (top panel)). This data indicates that the T2D risk coding variants are unlikely to directly interfere with transport.

Alternatively, these variants may result in reduced transport because they disrupt protein-protein interactions responsible for correct SLC16A11 function. To explore this possibility, SLC16A11 was immunoprecipitated from HEK293T cells expressing either REF or T2D risk SLC16A11-V5 or empty vector control and quantitative mass spectrometry was used to define the SLC16A11 interactome. Comparable levels of SLC16A11$^{REF}$ and SLC16A11$^{T2D}$ protein expression was achieved (FIG. 5F, bottom panel).

Another mechanism through which the variants could affect activity is through disruption of protein-protein interactions. To explore this possibility, quantitative mass spectrometry-based protein-protein interaction studies were performed to define the SLC16A11 interactome and evaluate if the T2D risk coding variants alter any interactions. FIG. 5B, top right panel shows SLC16A11$^{REF}$ protein-protein interactions with a plot showing the enrichment of protein immunoprecipitated from HECK293T cells expressing P2D SLC16A11$^{REF}$-V5 compared to cells expressing empty vector control. Putative proteins that interact with SLC16A11 are shown in Table 5C.

TABLE 5C

| Putative SLC16A11 Interactors (top 20/53). | | | | |
|---|---|---|---|---|
| geneSymbol | proteinName | B.A. logFC | B.A. P.Value | B.A. adj.P.Val |
| SEC61A1 | Protein transport protein Sec61 subunit | 1.84 | 1.42E−05 | 3.26E−03 |
| DHCR7 | 7-dehydrocholesterol reductase | 1.69 | 4.15E−05 | 3.26E−03 |
| EMC3 | ER membrene protein complex subunit | 1.65 | 7.04E−05 | 3.26E−03 |
| SLC25A3 | Phosphate carrier protein, mitochondria | 1.65 | 1.11E−05 | 3.26E−03 |
| DDOST | Dolichyl-diphosphooligossceharide | 1.65 | 4.87E−05 | 3.26E−03 |
| SEC61A2 | Protein transport protein Sec61 subunit | 1.59 | 4.82E−05 | 3.26E−03 |

TABLE 5C-continued

Putative SLC16A11 Interactors (top 20/53).

| geneSymbol | proteinName | B.A. logFC | B.A. P.Value | B.A. adj.P.Val |
|---|---|---|---|---|
| EMB | Embigin | 1.55 | 1.43E−05 | 3.26E−03 |
| BSG | Basigin | 1.43 | 2.08E−05 | 3.26E−03 |
| RNF5 | E3 ubiquitin-protein ligase RNF5 | 1.42 | 1.04E−05 | 3.26E−03 |
| CANX | Caloexin | 1.38 | 5.14E−05 | 3.26E−03 |
| SLC16A11 | Monocarboxylate transporter 11 | 1.34 | 2.94E−05 | 3.26E−03 |
| SURF4 | Surfelt locus protein 4 | 1.33 | 6.67E−05 | 3.26E−03 |
| PSMD14 | 26S proteasome non-ATPase regular | 1.31 | 7.60E−05 | 3.26E−03 |
| HSDI7B12 | Estrediol 17-beta-dehydrogenase 1 | 1.26 | 7.07E−05 | 3.26E−03 |
| SACM1L | Phosphutidylinositide phosphatase | 1.26 | 3.68E−05 | 3.26E−03 |
| BAG2 | BAG family molecular chsperone | 1.26 | 6.68E−05 | 3.26E−03 |
| TMEM33 | Transmembrane protein 33 | 1.25 | 3.77E−05 | 3.26E−03 |
| FAP2 | FAS-associated factor 2 | 1.23 | 4.86E−05 | 3.26E−03 |
| TIMM23B | Putative mitochondrial import inner | 1.22 | 7.22E−05 | 3.26E−03 |
| UBAC2 | Ubiquitin-associated domain-contain | 1.21 | 8.68E−05 | 3.26E−03 |
| PSMA1 | Proteasome subunit alpha type-1 | 1.20 | 5.64E−05 | 3.26E−03 |

TABLE 5D shows putative SLC16A11$^{REF}$ interaction partners.

| gene symbol | accession number | BA log fold change | BA p-value | BA adjusted p-value |
|---|---|---|---|---|
| SEC61A1 | B4DR61 | 1.84 | 1.42E−05 | 3.26E−03 |
| DHCR7 | Q9UBM7 | 1.69 | 4.15E−05 | 3.26E−03 |
| EMC3 | Q9P0I2 | 1.65 | 7.04E−05 | 3.26E−03 |
| SLC25A3 | Q00325-2 | 1.65 | 1.11E−05 | 3.26E−03 |
| DDOST | P39656 | 1.65 | 4.87E−05 | 3.26E−03 |
| SEC61A2 | Q9H9S3 | 1.59 | 4.82E−05 | 3.26E−03 |
| *EMB* | *Q6PCB8* | *1.55* | *1.43E−05* | *3.26E−03* |
| *BSG* | *P35613* | *1.43* | *2.08E−05* | *3.26E−03* |
| RNF5 | Q99942 | 1.42 | 1.04E−04 | 3.26E−03 |
| CANX | P27824-2 | 1.38 | 5.14E−05 | 3.26E−03 |
| SLC16A11 | Q8NCK7 | 1.34 | 2.94E−05 | 3.26E−03 |
| SURF4 | O15260 | 1.33 | 6.67E−05 | 3.26E−03 |
| PSMD14 | O00487 | 1.31 | 7.60E−05 | 3.26E−03 |
| HSD17B12 | Q53GQ0 | 1.26 | 7.07E−05 | 3.26E−03 |
| SACM1L | Q9NTJ5 | 1.26 | 3.68E−05 | 3.26E−03 |
| BAG2 | O95816 | 1.26 | 6.68E−05 | 3.26E−03 |
| TMEM33 | P57088 | 1.25 | 3.77E−05 | 3.26E−03 |
| FAF2 | Q96CS3 | 1.23 | 4.86E−05 | 3.26E−03 |
| TIMM23B | Q5SRD1 | 1.22 | 7.22E−05 | 3.26E−03 |
| UBAC2 | Q8NBM4 | 1.21 | 8.68E−05 | 3.26E−03 |
| PSMA1 | P25786-2 | 1.20 | 5.64E−05 | 3.26E−03 |
| SLC25A22 | Q9H936 | 1.20 | 9.47E−05 | 3.26E−03 |
| PPP6R3 | Q5H9R7-5 | 1.18 | 6.98E−05 | 3.26E−03 |
| PSMD12 | O00232 | 1.18 | 9.84E−05 | 3.26E−03 |
| ATP1B3 | P54709 | 1.18 | 5.64E−05 | 3.26E−03 |
| PSMC3 | P17980 | 1.16 | 5.09E−05 | 3.26E−03 |
| LPCAT1 | Q8NF37 | 1.16 | 5.48E−05 | 3.26E−03 |
| AGPAT6 | Q86UL3 | 1.16 | 9.94E−05 | 3.26E−03 |
| XPO5 | Q9HAV4 | 1.14 | 7.76E−05 | 3.26E−03 |
| VDAC2 | P45880-1 | 1.14 | 5.53E−05 | 3.26E−03 |
| PHGDH | O43175 | 1.11 | 7.84E−05 | 3.26E−03 |
| ADCK4 | Q96D53 | 1.11 | 1.03E−04 | 3.26E−03 |
| TECR | Q9NZ01 | 1.10 | 6.44E−05 | 3.26E−03 |
| AUP1 | Q9Y679 | 1.10 | 6.41E−05 | 3.26E−03 |
| ATP1A1 | P05023-4 | 1.10 | 6.50E−05 | 3.26E−03 |
| MAGED1 | Q9Y5V3-2 | 1.09 | 1.02E−04 | 3.26E−03 |
| PSMA3 | P25788 | 1.09 | 9.50E−05 | 3.26E−03 |
| SCFD1 | Q8WVM8 | 1.08 | 6.87E−05 | 3.26E−03 |
| BAG6 | P46379-3 | 1.08 | 7.04E−05 | 3.26E−03 |
| DNAJB4 | Q9UDY4 | 1.08 | 9.21E−05 | 3.26E−03 |
| QIL1 | Q5XKP0 | 1.08 | 7.28E−05 | 3.26E−03 |
| DNAJC7 | Q99615 | 1.05 | 7.96E−05 | 3.26E−03 |
| TUBA1B | P68363 | 1.05 | 1.04E−04 | 3.26E−03 |
| TUBA1C | F5H5D3 | 1.04 | 8.74E−05 | 3.26E−03 |
| BRAT1 | Q6PJG6 | 1.04 | 9.57E−05 | 3.26E−03 |
| HEATR2 | Q86Y56 | 1.03 | 9.04E−05 | 3.26E−03 |
| PSMD11 | O00231-2 | 1.02 | 8.89E−05 | 3.26E−03 |
| TUBA4A | P68366 | 1.02 | 9.90E−05 | 3.26E−03 |
| GCN1L1 | Q92616 | 1.01 | 9.27E−05 | 3.26E−03 |
| PSMD2 | Q13200 | 0.98 | 1.05E−04 | 3.26E−03 |
| KIAA0368 | J3KN16 | 1.16 | 1.08E−04 | 3.27E−03 |
| STT3A | P46977 | 1.27 | 1.16E−04 | 3.36E−03 |
| DNAJC3 | Q13217 | 1.22 | 1.23E−04 | 3.36E−03 |

SLC16A11 is in bold while BSG and EMB are shown in italics. The 53 proteins in the table are the top 10% with a Blandt-Altman-adjusted P<0.05. BA is used for Blandt-Altman.

SLC16A11 protein levels were low, even after transient overexpression (FIG. 5A (bottom panel)). To provide robust levels for the protein-interaction studies, SLC16A11 proteins containing a proline to aspartic acid substitution (P2D) that was found to increase SLC16A11 protein levels were utilized (FIG. 5B (top panel)).

Examination of proteins enriched following immunoprecipitation of WT SLC16A11 when compared to the empty vector control immunoprecipitation revealed strong enrichment of SLC16A11 (FIG. 5B (bottom)). Notably, BSG and EMB, the ancillary proteins previously shown to interact with SLC16 category I family members, were also among the most enriched proteins. As interactions with BSG and EMB are an additional parameter segregating SLC16 category I and category II family members (Table 2); this provides additional support for SLC16A11 belonging to category I.

SLC16A1 is part of a larger molecular complex (FIG. 5B (bottom panel)) composed of stoichiometry 2 SLC16A1 molecules and 2 BSG molecules. Given this, experiments tested whether SLC16A11 might also be part of a larger molecular complex containing more than one SLC16A11 molecule. Co-immunoprecipitation assays were used to demonstrate that SLC16A11$^{REF}$ interacts with SLC16A11$^{REF}$ and SLC16A11$^{T2D}$ interacts with SLC16A11$^{T2D}$. Further work is needed to determine the stoichiometry.

GeNets (http://apps.broadinstitute.org/genets#), a pathway-based analysis tool, were used to identify and visualize protein networks enriched for interaction with WT SLC16A11 (FIG. 5C (bottom)). This analysis revealed that SLC16A11 interacts with a cluster of proteasome components, which is consistent with the results demonstrating that transiently expressed SLC16A11 protein is rapidly degraded and undergoes proteasome-mediated degradation (FIG. 5D (top panel) and FIG. 5E (top and bottom panels)). These data indicate that SLC16A11 protein levels may be tightly regulated.

Figure 18:
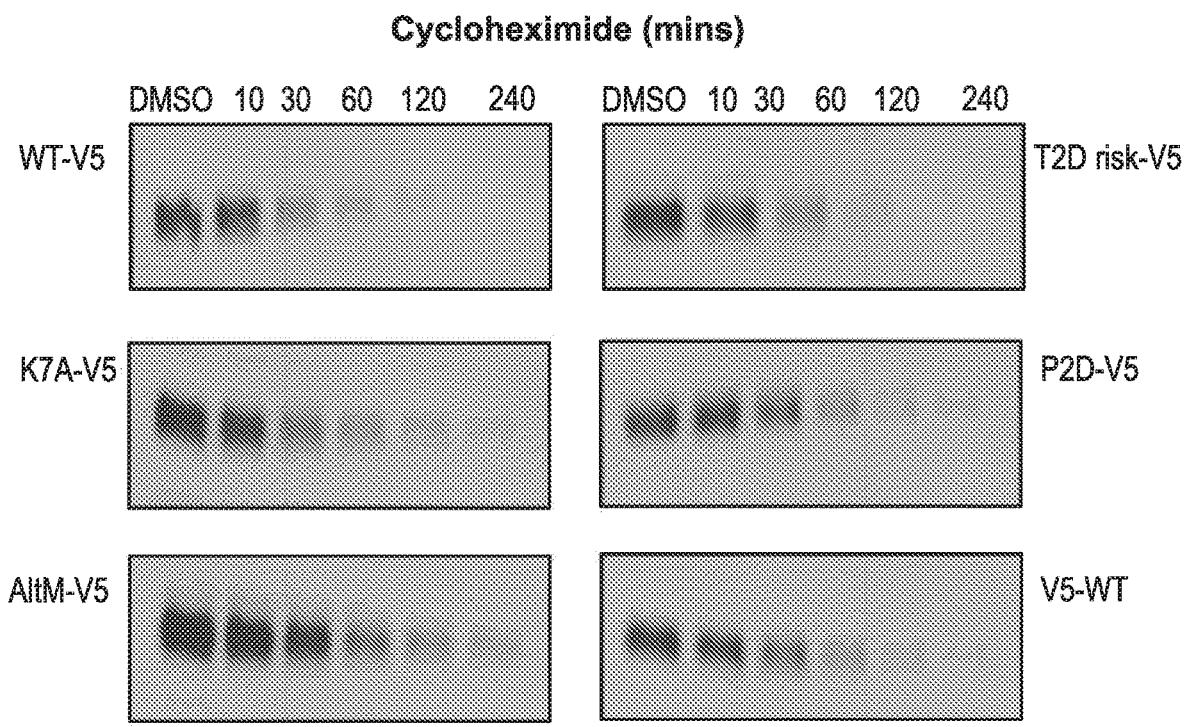
FIG. 18 provides Western blots of V5-tagged SLC16A11 and SLC16A11 variants, transiently expressed in HEK293T cells and blotted for V5. HEK293T cells expressing V5-tagged SLC16A11 with V5 at the C-terminus (WT-V5), or the K7A, AltM, T2Drisk, PD2 and SLC16A11 with V5 at the N-terminus (V5-WT) variants were treated with cycloheximide for the indicated times. Cell lysates were used in the analysis. Note that the images are from different exposure times. As observed, the half-lives of the variant (mutant) forms of the SLC16A11 protein were not significantly altered.

Translation was inhibited with cycloheximide and the results indicated that SLC16A11 has a short half-life on the order of 45 minutes (FIG. 5D (top panel)). The other SLC16 family members tested, SLC16A1 and SLC16A13, do not undergo the same rapid degradation as was observed for SLC16A11. Other SLC16A11 variants did not have significantly altered half-lives compared to reference SLC16A11 (FIG. 18). Experiments were also conducted to determine whether the T2D risk variants altered SLC16A11 protein half-life and did not detect any appreciable differences between SLC16A11$^{T2D}$ and SLC16A11$^{REF}$. Observations that SLC16A11 protein undergoes proteasome-mediated degradation were confirmed by inhibiting the proteasome with MG132 and observing increased SLC16A11 protein levels (FIG. 5E (bottom panel)). Together, these data suggest that exogenous SLC16A11 is rapidly degraded by the proteasome.

In order to identify variants that might enable proteomic studies and potentially illuminate pathways underlying SLC16A11 degradation, a panel of SLC16A11 variants were generated, it was hypothesized the variants might alter protein levels. Given that targeting to the proteasome canonically occurs through ubiquitination on lysine residues, first the sole lysine in SLC16A11 (K7) was mutated (K7A). The data indicated that this had no effect on protein levels (FIG. 5H). Interestingly, removal of the N-terminal 24 amino acids of SLC16A11 (AltM) and moving the V5 epitope from the C terminus to the N terminus both increased protein levels (FIG. 5H). These findings led us to hypothesize that N-terminal ubiquitination of SLC16A11 might be occurring (Ciechanover, A., 2005, Methods Mol Biol, 301:255-270).

After translation, proteins undergo N-terminal post-translational modifications (NPMs). Residues at position two are particularly important for determining whether NPMs such as N-terminal methionine excision (NME) or N-terminal acetylation (N-Ac) occur. An acidic residue at the second position decreases NME while increasing N-Ac. SLC16A11 is predicted to undergo NME. This would result in an unacetylated proline residue being exposed, which could then serve as a site for N-terminal ubiquitination. Because it was observed that the SLC16A11 protein was rapidly degraded following inhibition of protein synthesis and was stabilized by proteasome inhibition (FIGS. 5D-A and 5D-B), experiments were conducted to stabilize SLC16A11 against proteasome-mediated degradation. A P2D SLC16A11 variant (having a proline to aspartic acid substitution (P2D) at a potential site of regulation through a N-terminal ubiquitination pathway) was generated with the logic that aspartate at position 2 would reduce NME while promoting N-Ac of the initiator methionine. This would then compete with ubiquitination of this residue. While mutation of the sole lysine residue in SLC16A11 had no effect, it was found that the P2D SLC16A11 variant increased SLC16A11 protein levels (FIG. 5B (top panel, left). Therefore, SLC16A11 proteins containing the P2D mutation were used in proteomic studies, resulting in successful enrichment of tagged SLC16A11 and associated proteins in immunoprecipitations. (FIG. 5H). The locations of P2D, K7A, and AltM variants are shown in FIG. 5A top panel.

Mass spectrometry was used to identify proteins that interact with SLC16A11$^{REF}$. Among the ~50 most highly enriched proteins (top 10% of interactors with a Blandt-Altman adjusted P<0.05; FIG. 5B (top panel, right)), the BSG and EMB proteins stood out. BSG and EMB act as chaperones that promote cell-surface localization of SLC16 proteins in category I, and co-localize with these SLC16 family members at the cell surface. The interactions between SLC16A11 and BSG and EMB provide further support that SLC16A11 is a member of category I.

In addition, proteins in the SLC16A11$^{REF}$ interactome were analyzed using the pathway-based analysis tool GeNets (http://apps.broadinstitute.org/genets#) (FIG. 5C (bottom panel)). This analysis revealed that SLC16A11 interacts with a cluster of proteasome components, which explains the low levels of SLC16A11 found in transient expression experiments, namely, that the protein undergoes proteasome-mediated degradation (FIGS. 5D-A and 5D-B (top panel)).

Collectively these data indicate that SLC16A11 protein levels may be tightly regulated. It is noted that all of the stability studies were performed on exogenous SLC16A11.

Example 13

T2D Risk Coding Variants Reduce SLC16A11 Localization to the Plasma Membrane by Disrupting an Interaction with BSG How the T2D risk coding variants alter the SLC16A11 interactome was examined. By comparing the enrichment of proteins bound to T2D risk SLC16A11 versus WT SLC16A11, a single protein interaction that was disrupted by the T2D risk coding variants was identified: the interaction with BSG (FIG. 5C (top panel)). Using co-immunoprecipitation assays, both the interaction between WT SLC16A11 and BSG was confirmed, as well as the finding that T2D risk-associated coding variants in SLC16A11 disrupt this interaction (FIG. 5D (bottom) and FIG. 5E (top panel)).

Figure 5I:
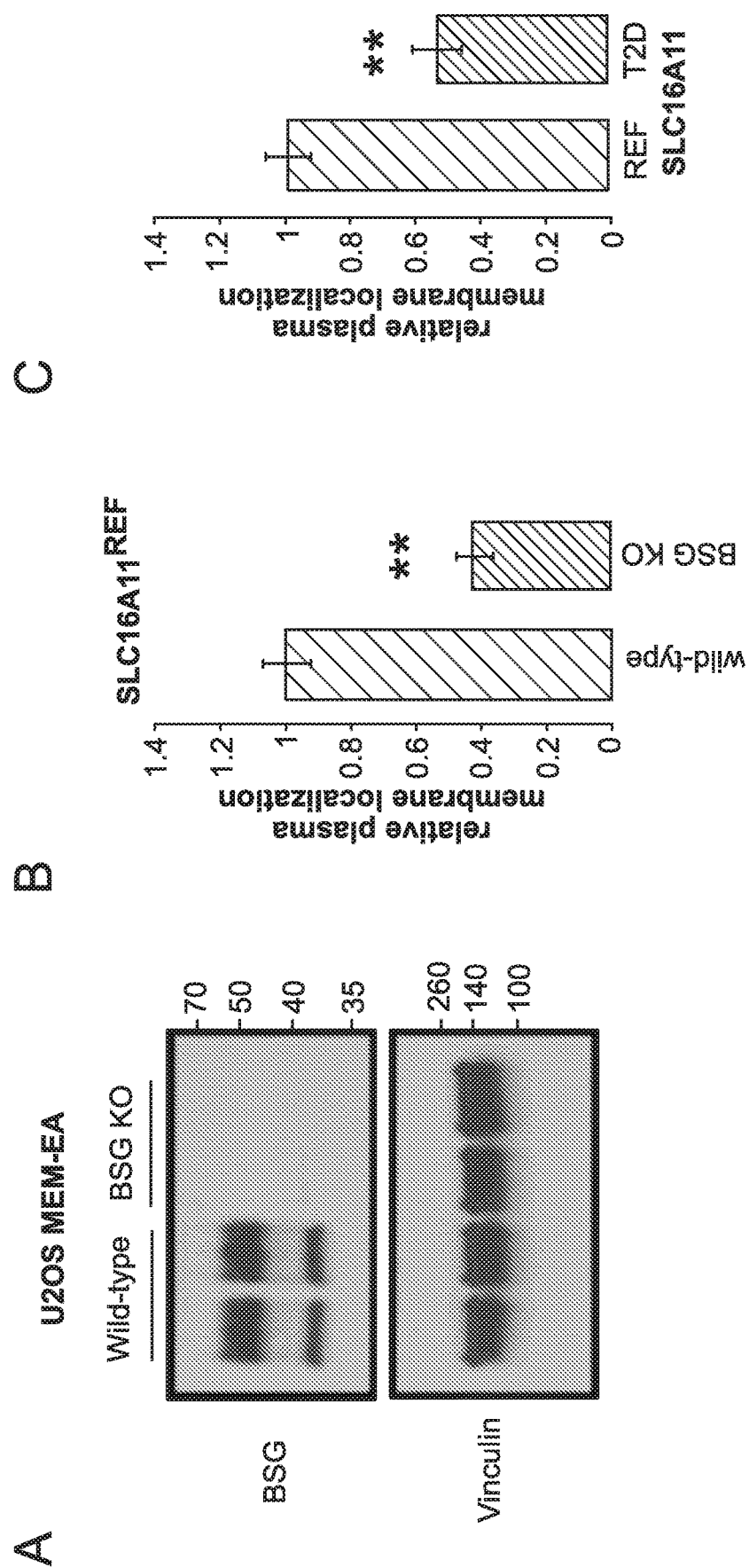
FIG. 5I (FIGS. 5I-A, 5I-B and 5I-C) show a Western blot and graphs illustrating that SLC16A11 cell surface localization is BSG-dependent and reduced by the T2D risk coding variants.

BSG plays a key role in plasma membrane localization of other SLC16 category I family members. To determine whether BSG performs a similar function for SLC16A11, CRISPR/Cas9 was used with two different sgRNAs to generate BSG-knockout 293T cells and then examined SLC16A11 localization by plasma membrane extraction. Indeed, plasma membrane localization of SLC16A11 was significantly reduced (by ~80%) in the absence of BSG (FIG. 5F top and bottom panels). In contrast, intracellular membrane localization of SLC16A11 is unaltered by BSG. These results were confirmed using an orthogonal plasma-membrane localization assay based on a split β-galactosidase reporter, in which enzyme complementation and activity was restored only when SLC16A11 localized to the cell surface (FIGS. 5I-A and 5I-B). As expected by the BSG-dependence of SLC16A11 plasma membrane localization and the finding that the T2D risk-associated coding variants disrupt the interaction between SLC16A11 and BSG, the T2D risk coding variants reduce SLC16A11 plasma membrane localization (FIG. 5G, top and bottom panels). These data demonstrate that the T2D risk coding variants reduce SLC16A11 activity through a molecular mechanism involving disruption of its interaction with the ancillary protein BSG, preventing proper plasma membrane localization. This was confirmed, as an approximately 60% reduction in plasma membrane localization of SLC16A11$^{T2D}$ with respect to SLC16A11$^{REF}$ was observed (FIG. 5G (top and bottom panels) and FIGS. 5I-C).

Together, these experiments establish that the T2D-risk variants reduce SLC16A11 activity in two distinct ways: (i) the variants decrease SLC16A11 gene expression and (ii) the coding variants alter the protein in a manner that disrupts its interaction with BSG, decreasing the amount of SLC16A11 protein at the plasma membrane. Without wishing to be bound by a particular theory, under a model whereby T2D risk variants reduce both SLC16A11 gene expression and plasma membrane localization each by ~60% per copy of the T2D risk allele, it is estimated that homozygous carriers may have up to ~85% less SLC16A11 at the cell surface. Importantly, these findings indicate that diminished levels of SLC16A11 at the plasma membrane is the causal mechanism of increased T2D risk associated with variants at this locus.

Example 14

T2D Risk Haplotype Induced Disruption of SLC16A11 is Associated with Changes in Liver Metabolism As noted supra, these data indicate that one or more variants on the T2D risk haplotype contribute to decreased SLC16A11 function through two independent mechanisms involving: 1) lower SLC16A11 expression resulting from gene regulation effects, and 2) attenuated SLC16A11 activity resulting from reduced plasma membrane localization due to the disruption of its interaction with BSG. Together, these findings indicate that diminished SLC16A11 function is likely a causal factor for the increased T2D risk associated with this locus.

To gain insight into the cellular impact of T2D risk-associated variants and the consequences of reduced SLC16A11 activity in human liver, which might lead to increased risk of T2D, cellular metabolic pathway changes associated with the T2D risk haplotype were examined by RNA-sequencing. Gene expression profiles from liver biopsies of Mexican individuals homozygous for either the T2D risk or reference haplotype at 17p13 were generated. When stratified based on either SLC16A11 genotype or T2D status, these individuals did not display differences in glycemic traits, including body mass index (BMI), Fasting Glucose, HbA1c, and plasma insulin levels (FIG. 6C).

Figure 6A:
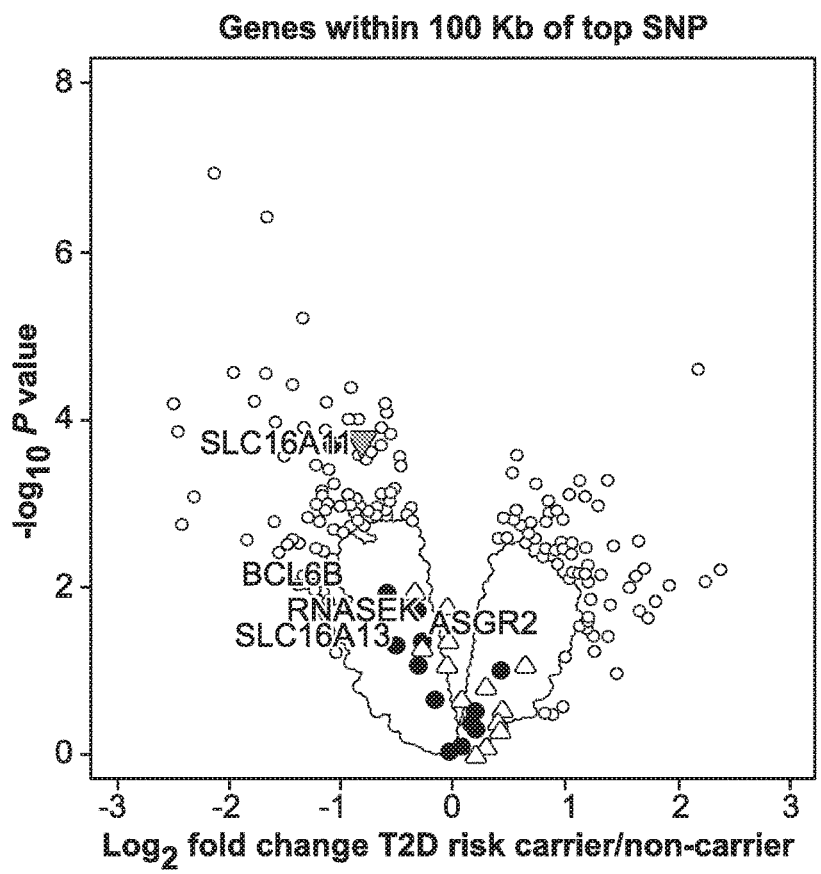

In line with the SLC16A11 liver cis-eQTL, transcriptome profiling identified SLC16A11 as one of the most differentially expressed genes between carriers and non-carriers of the T2D risk haplotype (FIG. 6A, Table 6A and Table 6B provide a summary).

TABLE 6A

Summary human liver RNAseq genes

| | Gene_Symbol | BaseMean | log2FoldChange | pvalue | padj |
|---|---|---|---|---|---|
| 1 | APOA4 | 93.133 | −0.994 | 8.99E−07 | 0.025 |
| 2 | RP11-5A19.5 | 26.524 | −0.730 | 3.48E−06 | 0.049 |
| 3 | SEMA6D | 2063.586 | 0.678 | 9.07E−06 | 0.086 |
| 4 | FITM1 | 27.097 | −0.699 | 1.49E−05 | 0.105 |
| 5 | CTD-2050N2.1 | 37.860 | 0.740 | 2.58E−05 | 0.130 |
| 6 | SENP7 | 2699.001 | 0.221 | 2.83E−05 | 0.130 |
| 7 | SSU72 | 559.820 | −0.267 | 3.79E−05 | 0.130 |
| 8 | P3H1 | 207.411 | −0.324 | 3.88E−05 | 0.130 |

TABLE 6A-continued

Summary human liver RNAseq genes

| | Gene_Symbol | BaseMean | log2FoldChange | pvalue | padj |
|---|---|---|---|---|---|
| 9 | ACTR1A | 344.893 | −0.288 | 4.90E−05 | 0.130 |
| 10 | ATP6V0D1 | 437.463 | −0.338 | 6.14E−05 | 0.130 |
| 11 | ACO2 | 1178.974 | −0.314 | 6.52E−05 | 0.130 |
| 12 | ECE2 | 47.805 | −0.590 | 7.08E−05 | 0.130 |
| 13 | RAB43 | 872.435 | −0.608 | 8.30E−05 | 0.130 |
| 14 | MIR22HG | 140.991 | −0.715 | 8.37E−05 | 0.130 |
| 15 | AVPR1A | 1086.571 | −0.788 | 8.43E−05 | 0.130 |
| 16 | RP11-98F14.11 | 21.561 | −0.775 | 9.03E−05 | 0.130 |
| 17 | CIC | 392.476 | −0.377 | 9.09E−05 | 0.130 |
| 18 | SCAPER | 5464.252 | 0.284 | 9.39E−05 | 0.130 |
| 19 | PEF1 | 352.702 | −0.329 | 9.90E−05 | 0.130 |
| 20 | SLC16A11 | 13.956 | −0.700 | 3.32E−04 | 0.171 |

TABLE 6B

Summary of top 20 differently expressed genes in RISK and REF.

| | gene symbol | baseMean | log2Fold-Change | pvalue | padj |
|---|---|---|---|---|---|
| 1 | APOA4 | 93.13 | −0.99 | 8.99E−07 | 0.03 |
| 2 | RP11-5A19.5 | 26.52 | −0.73 | 3.48E−06 | 0.05 |
| 3 | SEMA6D | 2063.59 | 0.68 | 9.07E−06 | 0.09 |
| 4 | FITM1 | 27.10 | −0.70 | 1.49E−05 | 0.11 |
| 5 | SSU72 | 559.82 | −0.27 | 3.79E−05 | 0.13 |
| 6 | PEF1 | 352.70 | −0.33 | 9.90E−05 | 0.13 |
| 7 | P3H1 | 207.41 | −0.32 | 3.88E−05 | 0.13 |
| 8 | RP11-529E15.1 | 21.56 | −0.78 | 1.22E−04 | 0.13 |
| 9 | CSRNP1 | 212.82 | −0.79 | 1.24E−04 | 0.13 |
| 10 | SENP7 | 2699.00 | 0.22 | 2.83E−05 | 0.13 |
| 11 | RAB43 | 872.44 | −0.61 | 8.30E−05 | 0.13 |
| 12 | ISY1-RAB43 | 1059.66 | −0.54 | 1.04E−04 | 0.13 |
| 13 | ECE2 | 47.80 | −0.59 | 7.08E−05 | 0.13 |
| 14 | TCTEX1D2 | 43.19 | 0.57 | 1.40E−04 | 0.13 |
| 15 | FST | 619.96 | −0.77 | 1.34E−04 | 0.13 |
| 16 | SNRNP48 | 526.08 | 0.30 | 1.42E−04 | 0.13 |
| 17 | RHBDD2 | 206.59 | −0.35 | 1.20E−04 | 0.13 |
| 18 | ACTR1A | 344.89 | −0.29 | 4.90E−05 | 0.13 |
| 19 | KBTBD3 | 281.27 | 0.31 | 1.15E−04 | 0.13 |
| 20 | AVPR1A | 1086.57 | −0.79 | 8.43E−05 | 0.13 |
| ... | | | | | |
| → 55 | SLC16A11 | 13.96 | −0.70 | 3.32E−04 | 0.17 |

Pathway-based analysis revealed that transcripts encoding proteins involved in a number of metabolic pathways are significantly altered in carriers of the T2D risk haplotype (false-discovery rate (FDR)<0.20) (Table 7A).

TABLE 7A

| NAME | SIZE | ES | NES | NOM p-val | FDR q-val |
|---|---|---|---|---|---|
| KEGG_COMPLEMENT_AND_COAGULATION_CASCADES | 69 | −0.58 | −2.43 | 0.00E+00 | 0.00E+00 |
| KEGG_CITRATE_CYCLE_TCA_CYCLE | 29 | −0.69 | −2.41 | 0.00E+00 | 0.00E+00 |
| KEGG_PPAR_SIGNALING_PATHWAY | 63 | −0.55 | −2.23 | 0.00E+00 | 0.00E+00 |
| KEGG_DRUG_METABOLISM_OTHER_ENZYMES | 51 | −0.57 | −2.2 | 0.00E+00 | 0.00E+00 |
| KEGG_PORPHYRIN_AND_CHLOROPHYLL_METABOLISM | 40 | −0.57 | −2.09 | 0.00E+00 | 0.00E+00 |
| KEGG_PARKINSONS_DISEASE | 104 | −0.47 | −2.08 | 0.00E+00 | 0.00E+00 |
| KEGG_VALINE_LEUCINE_AND_ISOLEUCINE_DEGRADATION | 43 | −0.56 | −2.08 | 0.00E+00 | 0.00E+00 |
| KEGG_LYSOSOME | 114 | −0.45 | −2.04 | 0.00E+00 | 9.52E−04 |
| KEGG_OXIDATIVE_PHOSPHORYLATION | 107 | −0.46 | −2.04 | 0.00E+00 | 1.07E−03 |
| KEGG_PENTOSE_AND_GLUCURONATE_INTERCONVERSIONS | 26 | −0.61 | −2.03 | 0.00E+00 | 1.13E−03 |
| KEGG_HUNTINGTONS_DISEASE | 163 | −0.42 | −1.99 | 0.00E+00 | 1.36E−03 |
| KEGG_FATTY_ACID_METABOLISM | 42 | −0.53 | −2 | 0.00E+00 | 1.45E−03 |
| KEGG_PENTOSE_PHOSPHATE_PATHWAY | 23 | −0.62 | −1.99 | 2.08E−03 | 1.46E−03 |
| KEGG_FRUCTOSE_AND_MANNOSE_METABOLISM | 34 | −0.57 | −2 | 0.00E+00 | 1.59E−03 |
| KEGG_RNA_POLYMERASE | 29 | −0.57 | −1.92 | 0.00E+00 | 2.80E−03 |
| KEGG_SPLICEOSOME | 123 | −0.42 | −1.91 | 0.00E+00 | 2.94E−03 |
| KEGG_ASCORBATE_AND_ALDARATE_METABOLISM | 24 | −0.59 | −1.91 | 0.00E+00 | 3.11E−03 |
| KEGG_BUTANOATE_METABOLISM | 31 | −0.55 | −1.91 | 0.00E+00 | 3.30E−03 |
| KEGG_PYRUVATE_METABOLISM | 38 | −0.52 | −1.9 | 2.15E−03 | 3.38E−03 |
| KEGG_ADIPOCYTOKINE_SIGNALING_PATHWAY | 61 | −0.47 | −1.87 | 0.00E+00 | 4.39E−03 |

Figure 6B:
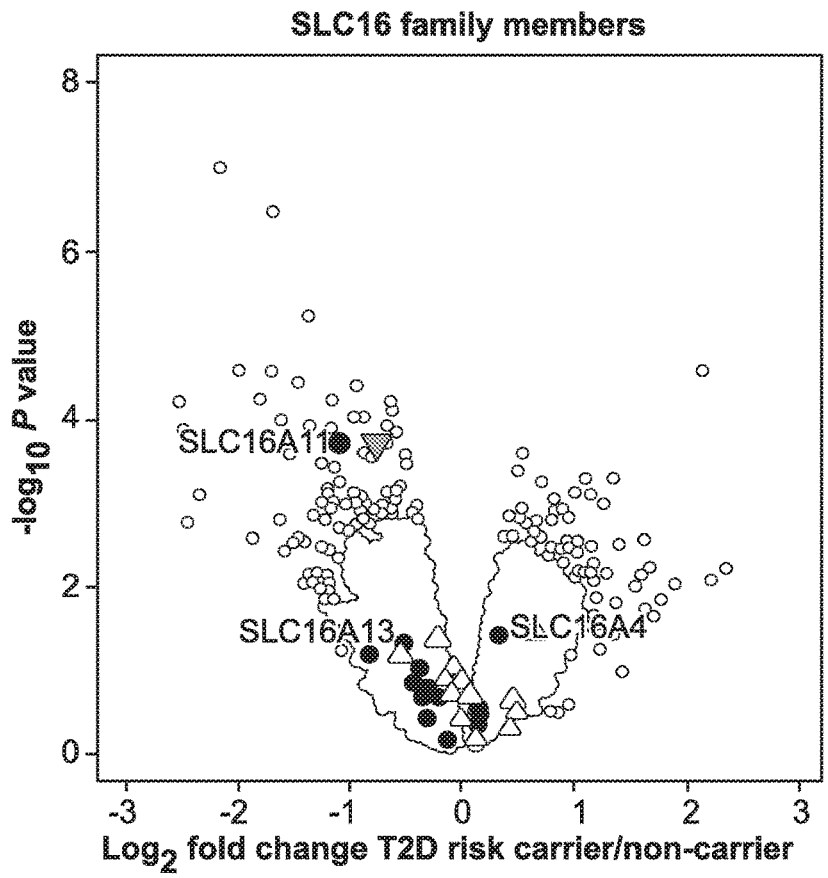
Figure 6C:
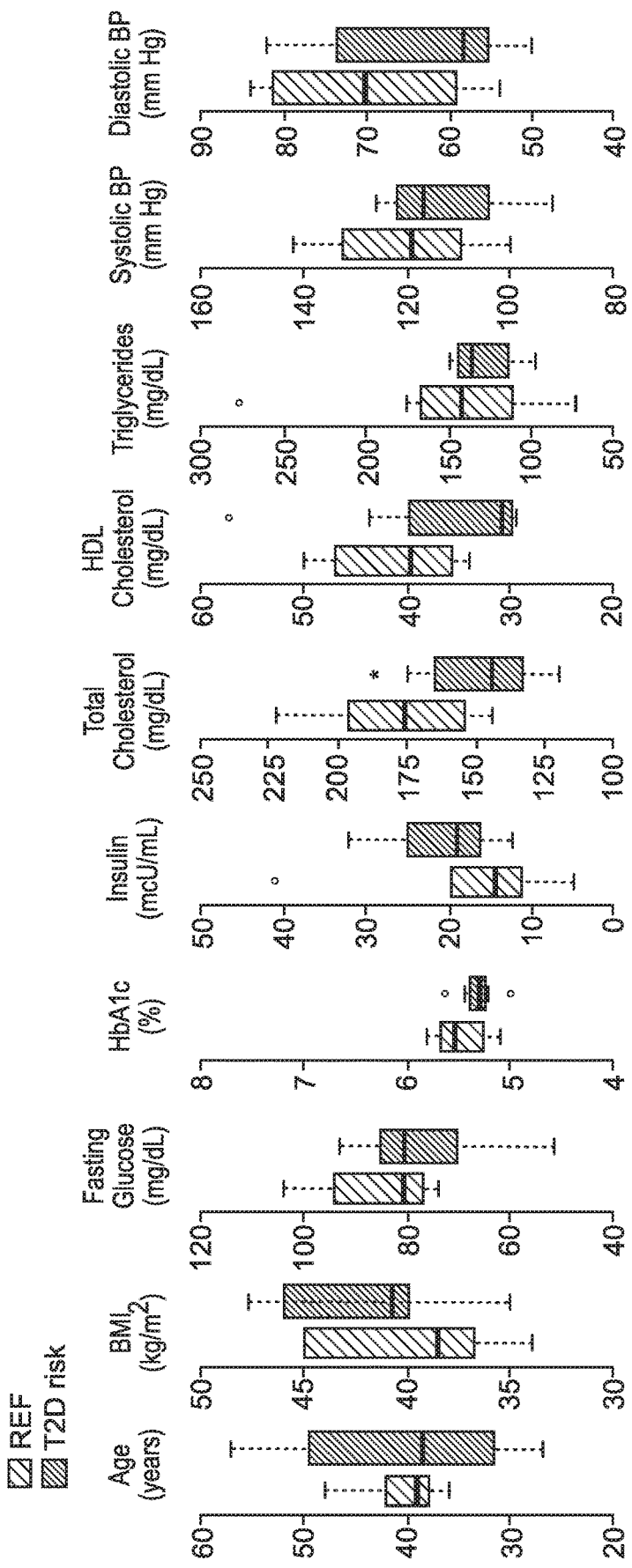
Figures 1, 6C:
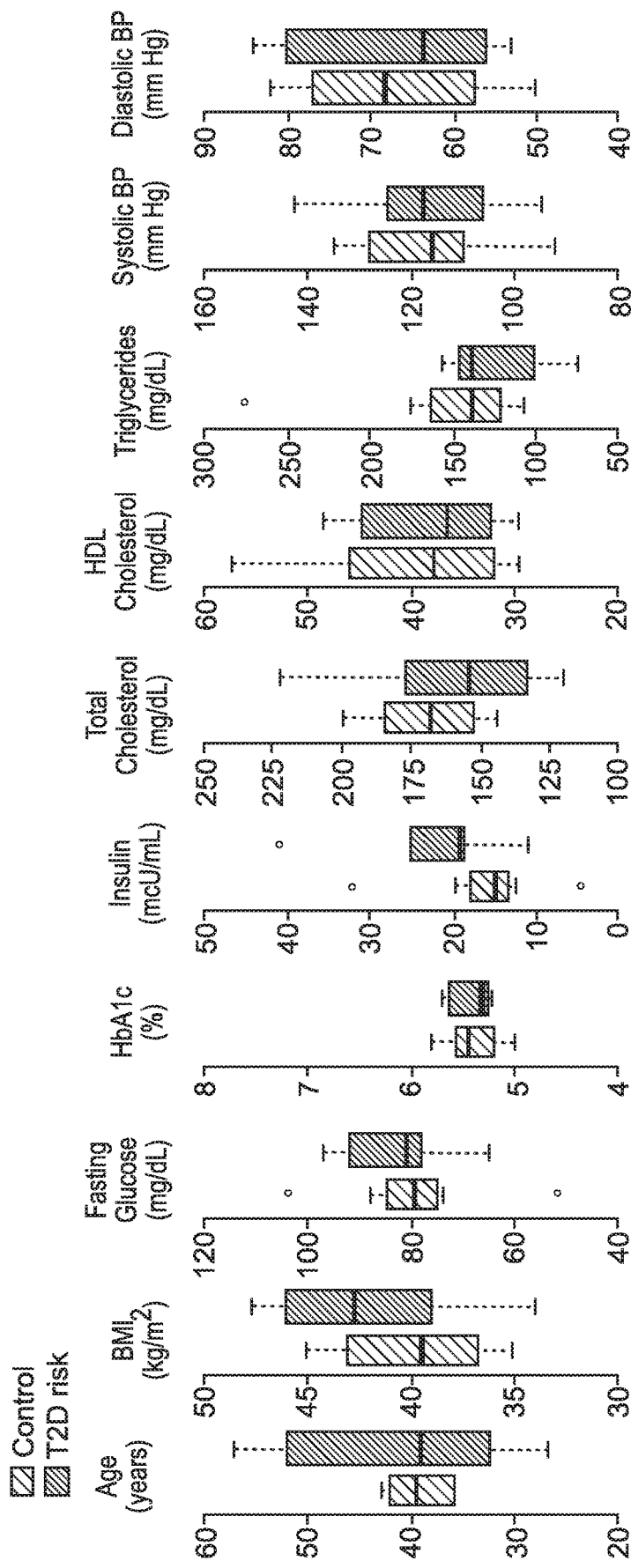

These include pathways in which pyruvate plays a central role—the TCA cycle, amino acid, fatty acid, and lipid metabolism—and which are implicated in insulin resistance and T2D pathogenesis. As SLC16A11 is the only significantly altered gene within 100 Kb of the T2D risk haplotype (FIG. 6A) and no other SLC16 family members are significantly altered (FIG. 6B), these data point to disruption of SLC16A11 as a driver of altered hepatic metabolic function in individuals carrying the T2D risk haplotype.

Example 15

Expressing SLC16A11$^{REF}$ and SLC16A11$^{T2D}$ in Primary Human Hepatocytes

In order to investigate which metabolic pathways SLC16A11 plays a role in and how the T2D risk coding variants alter these roles, SLC16A11$^{REF}$ and SLC16A11$^{T2D}$ were over-expressed in primary human hepatocytes and steady-state levels of 60 intracellular polar metabolites were measured. Eight biological replicates of SLC16A11$^{REF}$, SLC16A11$^{T2D}$, and empty vector control (denoted by CNTRL) were profiled across two different experiments. Primary human hepatocytes were transduced with lentivirus expressing the relevant vectors and samples for metabolite profiling were collected 96 hours after transduction. An increase of ~17 fold was achieved in SLC16A11 transcript levels in hepatocytes transduced with SLC16A11 lentivirus, with comparable SLC16A11 levels in cells transduced with SLC16A11$^{REF}$ or SLC16A11$^{T2D}$ (FIG. 9A).

In hepatocytes transduced with SLC16A11$^{REF}$ (REF) versus control (CNTRL), the levels of 2 intracellular metabolites were significantly altered after correcting for multiple hypothesis testing (Table 7B). These metabolites were phosphocreatine, citrate, hexose monophosphate (denoting glucose 6-phosphate or fructose 6-phosphate which could not be distinguish in the dataset), and fructose 1-phosphate. Citrate is an intermediate in the TCA cycle and it can be used to transport acetyl-CoA from mitochondria to the cytoplasm to be used in fatty acid synthesis. Glucose 6-phosphate and fructose 6-phosphate are intermediates in glycolysis. No significant changes in pyruvate levels were observed. As noted above, steady state levels of SLC16A11 substrates were not necessarily expected to be altered.

For the REF versus CNTRL comparison, two significantly altered metabolic pathways were found (FDR<0.05): glyoxylate and dicarboxylate metabolism and TCA cycle (Table 7C). FDR (false discovery rate) and NES (normalized enrichment score). There is some debate on whether vertebrates use the glyoxylate/dicarboxylate pathway (Davis and Goodman, 1992). This pathway shares similarities to the TCA cycle and many overlapping metabolites. Over-expression of SLC16A11$^{REF}$ resulted in decreased TCA cycle metabolites suggesting that SLC16A11 might play a role in mediating flux through this pathway. It was noted that the most altered metabolites in the TCA cycle (citrate and aconitate) are immediately downstream of where acetyl-CoA (a major source of which is pyruvate) enters the pathway. Decreasing flux through a central pathway such as the TCA cycle could result in the remodeling of cellular metabolism. Sufficient metabolites in glycolysis were not measured so as to analyze overall changes in this pathway.

TABLE 7B

Altered metabolites in primary human hepatocytes expressing SLC16A11$^{REF}$.

| Metabolite name | Percent change | p-value |
|---|---|---|
| phosphocreatine | −16% | 2.84 × 10$^{−6}$ |
| citrate | −20% | 2.81 × 10$^{−5}$ |
| hexose monophosphate | +13% | 2.74 × 10$^{−4}$ |
| fructose 1-phosphate | +12% | 2.74 × 10$^{−4}$ |
| aconitate | −18% | 6.56 × 10$^{−4}$ |
| fructose 1,6-bisphosphate | +46% | 1.83 × 10$^{−3}$ |
| alpha-glycerophosphate | +24% | 5.62 × 10$^{−3}$ |
| alpha/beta-hydroxybutyrate | −6% | 6.81 × 10$^{−3}$ |
| hippurate | +27% | 1.06 × 10$^{−2}$ |
| DHAP/glyceraldehyde-3-phosphate | +12% | 1.29 × 10$^{−2}$ |

TABLE 7C

Altered metabolic pathways in primary human hepatocytes expressing SLC16A11$^{REF}$.

| Name | size | members | p-value | FDR | NES | Information |
|---|---|---|---|---|---|---|
| Citrate cycle (TCA cycle) | 9 | 8 | 0.001 | 0.00 | −2.21 | Depleted |
| Glyoxylate/ dicarboxylate metabolism | 12 | 7 | 0.001 | 0.00 | −2.08 | Depleted |

Significantly altered metabolic pathways as assessed by metabolite set enrichment analysis (FDR<0.05). FDR is the false discovery rate and NES is the normalized enrichment score.

In the RISK versus REF comparison, no individual metabolites were significantly altered after correcting for multiple hypotheses testing. However, in this comparison, 2 significantly altered metabolic pathways (FDR<0.05) were found: a decrease in purine metabolism metabolites and an increase in glyoxylate/dicarboxylate metabolism metabolites. Given that over-expression of SLC16A11$^{REF}$ resulted in a decrease in glyoxylate/dicarboxylate metabolism metabolites, and under the assumption that the T2D risk coding variants confer reduced activity, one might expect an increase in glyoxylate/dicarboxylate metabolism metabolites in the RISK versus REF comparison.

In the REF versus CNTRL comparison, a 46% increase in fructose-1,6-bisphosphate levels in hepatocytes expressing SLC16A11$^{REF}$ (P=2×10$^{-3}$) was observed. Compared to other metabolite fold-changes observed in these studies, this is a large fold-change. This metabolite was nominally significant in the RISK versus REF comparison, with a 19% decrease in fructose-1,6-bisphosphate levels in cells expressing SLC16A11$^{T2D}$ compared to cells expressing SLC16A11$^{REF}$ (P=0.03). Fructose-1,6-bisphosphate is generated by the one of the critical step in glycolysis whereby phosphofructokinase converts fructose-6-phosphate to fructose-1,6-bisphosphate.

Interestingly, SLC16A11 expression was highly correlated with PFKL expression (which encodes the major phosphofructokinase isoform in liver). This follows from an analysis of 119 human liver samples from the Genotype-Tissue Expression project (GTEx) where PFKL expression across these samples ranked 19 out of over 45,000 transcripts tested in terms of correlation to SLC16A11 expression (Spearman correlation coefficient=0.64; P=0). Analysis of this dataset will be described further in the Examples that follow. Without wishing to be bound by theory, this data suggest that increasing SLC16A11 activity results in shifting from reliance on the TCA cycle to reliance on glycolysis for energy production.

Example 16

Knocking-Down SLC16A11 in Primary Human Hepatocytes

The data presented herein strongly support the notion that the T2D risk haplotype disrupts SLC16A11 activity in liver. Consequently, a key question is how disrupted SLC16A11 activity increases T2D risk.

As a first step, how decreased SLC16A11 levels impact metabolism in primary human hepatocytes was studied. SLC16A11 was knocked-down in primary human hepatocytes and 48 hours after adding siRNAs to cells, samples were collected for metabolite profiling. Steady-state levels of ~350 polar and lipid intracellular metabolites and 339 polar and lipid metabolites in the media (extracellular) were measured. The samples consisted of 8 or 12 biological replicates of hepatocytes treated either with pooled siRNAs targeting SLC16A11 or pooled negative controls across 2 or 3 replicate experiments. A ~90% knock-down of SLC16A11 transcript levels was achieved with no effect on SLC16A13, other category I SLC6 family members (SLC16A1, SLC16A3, SLC16A7, SLC16A8), or BSG transcript levels (FIG. 9B, top panel).

In the SLC16A11 siRNA versus negative control siRNA comparison, no metabolites were significantly altered between the two groups (FIG. 9B, bottom panel). In the same comparison in media, 4 individual metabolites were significantly altered: C58:8 TAG (27% increase, P=7.40× 10$^{-7}$), C56:8 TAG (10% increase, P=5.92×10$^{-6}$), 1-methylguanosine (9% decrease, P=4.96×10$^{-5}$), and C56:5 TAG (10% increase, P=1.03×10$^{-4}$). Interestingly, 3 of these species are triacylglycerols (TAGs).

In this comparison, 6 significantly altered metabolic pathways (FDR<0.05) were found (FIG. 9B and Table 7F). Acylcarnitines were increased in the SLC16A11 knockdown cells. Without wishing to be bound by theory, this might suggest a decrease in fatty acid degradation and possibly an increase in fatty acid synthesis. Acylcarnitines levels are increased in the plasma of patients with mutations in fatty acid oxidation compared to controls and these levels have been found to correlate with acylcarnitine levels in the liver. Acylcarnintines levels in plasma are increased in type 2 diabetics. Acylcarnitines transfer fatty acids into the mitochondria for degradation and this process is inhibited by malonyl-CoA, which is formed in the committed step of fatty acid synthesis.

Among the lipids measured, levels of triacylglycerols (TAGs) and diacylglycerols (DAGs) were increased while lysophosphatidylcholines (LPCs) and phosphatidylcholines (PCs) were decreased. It is interesting to note that TAGs and PCs compete for the same pool of fatty acids through intermediate DAGs. Without wishing to be bound by theory, these results suggest that reduced SLC16A11 activity results in a shift of fatty acid usage in preference of triacylglycerols over other lipid species such as phosphatidylcholines. The increases in triacylglycerols and diacylglycerols are particularly intriguing given that increases in both are associated with diabetic insulin resistance. Although neither was significant, TCA cycle intermediates were increased and glycolytic intermediates were decreased in SLC16A11 knockdown cells.

Table 7D shows the top 10 metabolites with the smallest p-values are ranked by increasing p-value. Table 7E shows significantly altered metabolic pathways as assessed by metabolite set enrichment analysis (FDR<0.05). FDR is the false discovery rate and NES is the normalized enrichment score.

TABLE 7D

Altered metabolites resulting from knockdown of SLC16A11 in primary human hepatocytes.

| Metabolite name | Percent change | p-value |
| --- | --- | --- |
| cAMP | -32% | 0.01 |
| DHAP/G3P | -19% | 0.03 |
| adenine | 109% | 0.05 |
| 3-methyladipate/pimelate | -32% | 0.05 |
| hippurate | 55% | 0.07 |
| UDP-galactose/UDP-glucose | 11% | 0.07 |
| alpha-hydroxybutyrate | -14% | 0.08 |
| adipate | -18% | 0.10 |
| quinolinate | -15% | 0.11 |
| UMP | 14% | 0.12 |

TABLE 7E

Altered metabolic pathways resulting from knockdown of SLC16A11 in primary human hepatocytes.

| Name | size | members | p-value | FDR | NES | Information |
|---|---|---|---|---|---|---|
| TAGs | 58 | 48 | 0.001 | 0.000 | 3.27 | Enriched |
| Carnitines | 20 | 12 | 0.001 | 0.000 | 2.97 | Enriched |
| LPCs | 11 | 10 | 0.001 | 0.000 | −2.36 | Depleted |
| Pyrimidine metabolism | 21 | 11 | 0.002 | 0.004 | 2.17 | Enriched |
| PCs | 25 | 21 | 0.002 | 0.021 | −2.08 | Depleted |
| DAGs | 10 | 9 | 0.011 | 0.029 | 1.73 | Enriched |

In the SLC16A11 siRNA versus negative control siRNA comparison in media, we found 2 significantly altered metabolic pathways (FDR<0.05) (FIG. 9B and Table 7F). Of particular interest is the increase in triacylglycerols in media. Hepatocytes secrete excess triacylglycerols and other lipids in the form of very low-density lipoproteins (VLDL). Triacylglycerols are increased in plasma of type 2 diabetics.

TABLE 7F

Altered metabolic pathways resulting from knockdown of SLC16A11 in media from primary human hepatocytes.

| Name | size | members | p-value | FDR | NES | Information |
|---|---|---|---|---|---|---|
| LPEs | 8 | 6 | 0.001 | 0.000 | −2.23 | Depleted |
| TAGs | 58 | 38 | 0.001 | 0.003 | 2.23 | Enriched |

Significantly altered metabolic pathways as assessed by metabolite set enrichment analysis (FDR<0.05). FDR is the false discovery rate and NES is the normalized enrichment score.

Thus, SLC16A11 is likely involved in mediating flux through central metabolite pathways, possibly by acting on the key intermediate metabolite, pyruvate. This resulted in increased intracellular levels of diacylglycerols and triacylglycerols—lipids implicated in insulin resistance and T2D.

FIGS. 9K-9O illustrate several key observations on the impact of SLC16A11 disruption on cellular metabolism from the metabolite profiling dataset. Intracellular increases in acylcarnitines, DAGs, and TAGs were observed, as well as extracellular increases in TAGs, which are secreted by hepatocytes in the form of VLDLs. (FIG. 9K (top panel)). Acylcarnitine levels increased in plasma of patients with mutations in fatty acid degradation and T2D; importantly plasma levels correlated with liver levels. In addition, intracellular DAGs were associated with diabetic insulin resistance, while intracellular TAGs, which are a hallmark of hepatic steatosis and associated with inflammation, liver damage, diabetic insulin resistance, and T2D showed increased levels in the plasma of type 2 diabetics. Together, the results demonstrate that disruption of SLC16A11 in primary human hepatocytes leads to T2D-relevant changes in fatty acid and lipid metabolism. More specifically, these changes demonstrate that SLC16A11 affects cellular fatty acid and lipid metabolism, with the increase in acylcarnitines indicating an effect on fatty acid β-oxidation by the mitochondria and the increases in DAGs and TAGs indicating a shift toward energy storage in the form of glycerolipids. These results implicate reduced SLC16A11 functions in liver as a causal factor for T2D.

The metabolic changes found in these experiments match those seen in the pathophysiology of insulin resistance and T2D: (1) acylcarnitines are elevated in the plasma of people with type 2 diabetes; (2) DAGs are associated with hepatic and skeletal muscle insulin resistance; and (3) TAG accumulation in liver and plasma is associated with diabetic insulin resistance and T2D.

Thus, variants on the T2D risk haplotype disrupt SLC16A11 function through two distinct molecular mechanisms and result in changes in cellular metabolism consistent with those seen in insulin resistance and T2D in human patients. (FIG. 9K (bottom panel)).

Example 17

Generating CRISPR-Cas9 Slc16a11 and Slc16a13 Mouse Models

A Slc16a11 global knockout mouse model was generated by replacing endogenous Slc16a11 with a LacZ Neo cassette (denote as Slc16a11* in FIG. 9C, top panel). This mouse was generated using traditional methods. Homozygous knockout mice die by 4 weeks of age. These mice are smaller in size and have lower fasting glucose levels than their wild-type littermates. In this mouse model, the data showed that both Slc16a11 and Slc16a13, and possibly Bcl6b to a lesser extent, were perturbed in liver (FIG. 9C, middle panel). Similar results were obtained in kidney. In mice, Slc16a11 and Slc16a13 are separated by only ~400 bp. This data indicated that this mouse model was likely a double knockout for Slc16a11 and Slc16a13. Upon the removal of the Neo cassette, Slc16a13 and Bcl6b levels were no longer altered (denote as Slc16a11$^{-Neo}$ in FIG. 9C, top and middle panel). In parallel, additional Slc16a11 knockout mouse models were generated.

A Slc16a11 global knockout mouse model with CRISPR-Cas9 (FIG. 9D, bottom panel) was generated. In addition, a Slc16a13 global knockout mouse model was generated. Data presented herein supports SLC16A11 as the effector gene through which variation on the T2D risk haplotype acts. The Slc16a13 models were generated with the intention of also studying the other gene at this locus that likely has many overlapping roles with SLC16A11. Of particular interest would be any unique functions that SLC16A11 has, but not SLC16A13.

sgRNAs targeting Slc16a11 or Slc16a13 were prepared. Together with Cas9 mRNA these were microinjected into mouse zygotes by the Genome Modification Facility at Harvard University. A total of 32 pups were born from Slc16a11 injections (99% mutant at the targeted locus) and 46 pups from Slc16a13 injections (96% mutant). Subsets of these pups were then crossed with wild-type C57BL/6J mice in order to achieve germline transmission. A 92% germline transmission was achieved for the Slc16a11 models and 94% for the Slc16a13 models. Colonies of Slc16a11 CRISPR-Cas9 KO mice with multiple independent mutant alleles were established. The experiments focused on one line in particular, Slc16a11 del19 (a deletion of 19 bp resulting in an out-of-frame mutation in the Slc16a11 reading frame and a truncated Slc16a11 protein), and began phenotyping this model. Expression levels of Slc16a11, Slc16a13, and Bcl6b are shown in FIG. 9I. A gene set enrichment analysis of down-regulated genes in human carriers of the T2D risk haplotype in Slc16a11 knockout mice is shown at FIG. 9J. At the top are shown the Gene Set Enrichment Analysis (GSEA) results. Query gene sets were made from the 50, 100, and 150 most down-regulated (by fold-change) genes or 50, 100, and 150 most up-regulated genes in human liver from homozygotes for the T2D risk haplotype (RISK) versus homozygotes for the reference haplotype (REF).

These gene sets were queried against a ranked list (also ordered by fold-change) generated from Slc16a11 knockout versus wild-type mouse liver. FDR stands for false discovery rate and gene sets with FDR<0.05 are indicated with arrows. Enrichment plots for the genes down-regulated in liver from human carriers of the T2D risk haplotype but up-regulated in Slc16a11 knockout mouse liver are shown below.

Example 18

Targeted Knockout of SLC16A11 in Mice Leads to Changes in Liver Metabolism that are Associated with Insulin Resistance and T2D To evaluate the physiological consequences of Slc16a11 and Slc16a13 perturbation in mice, multiple Slc16a11 and Slc16a13 knockout mouse models were generated using CRISPR/Cas9 technology. Following co-injection of zygotes with Cas9 mRNA and either Slc16a11- or Slc16a13-targeting guide RNAs, high percentage mosaic founders carrying a variety of inactivating mutations in the Slc16a11 and Slc16a13 genes were obtained. These animals were bred to achieve germline transmission and multiple, independent lines carrying distinct inactivating (frameshift) mutations were established.

To examine the short-term metabolic changes associated with Slc16a11 loss-of-function, four-week old Slc16a11 wild-type and knockout animals were placed on a high fat diet for one week, and then liver and plasma samples were collected for metabolite profiling and RNA-sequencing (FIG. 9D). Analyses of transcriptional changes revealed an increase in pathways related to glucose metabolism, inflammation, and mitochondrial function (Table 8 and Table 9), indicating the Slc16a11 knockout animals have an increased metabolic burden following this short-term nutritional challenge.

TABLE 8

Mouse KO RNAseq GSEA Pathway Results

| NAME | SIZE | ES | NES | NOM p-val | FDR q-val |
|---|---|---|---|---|---|
| KEGG_RIBOSOME | 67 | 0.72 | 2.97 | 0.00E+00 | 0.00E+00 |
| KEGG_SYSTEMIC_LUPUS_ERYTHEMATOSUS | 56 | 0.57 | 2.23 | 0.00E+00 | 0.00E+00 |
| KEGG_PROTEASOME | 39 | 0.58 | 2.12 | 0.00E+00 | 4.27E−04 |
| KEGG_LEISHMANIA_INFECTION | 47 | 0.52 | 1.98 | 0.00E+00 | 7.61E−03 |
| KEGG_OXIDATIVE_PHOSPHORYLATION | 90 | 0.42 | 1.85 | 1.47E−03 | 2.56E−02 |
| KEGG_FRUCTOSE_AND_MANNOSE_METABOLISM | 32 | 0.51 | 1.8 | 4.90E−03 | 2.76E−02 |
| KEGG_ANTIGEN_PROCESSING_AND_PRESENTATION | 36 | 0.5 | 1.8 | 6.45E−03 | 2.83E−02 |
| KEGG_PARKINSONS_DISEASE | 88 | 0.41 | 1.77 | 1.42E−03 | 3.07E−02 |
| KEGG_HEMATOPOIETIC_CELL_LINEAGE | 64 | 0.44 | 1.81 | 1.54E−03 | 3.20E−02 |
| KEGG_PRION_DISEASES | 33 | 0.51 | 1.81 | 3.17E−03 | 3.62E−02 |
| KEGG_GLYCOLYSIS_GLUCONEOGENESIS | 48 | 0.45 | 1.74 | 4.68E−03 | 3.73E−02 |
| KEGG_PATHOGENIC_ESCHERICHIA_COLI_INFECTION | 47 | 0.44 | 1.69 | 6.19E−03 | 4.79E−02 |
| KEGG_LYSOSOME | 109 | 0.38 | 1.69 | 4.22E−03 | 4.90E−02 |

TABLE 9A

Top 20 Differentially expressed genes in KO compared to WT

| | gene_symbol | human_gene_symbol | baseMean | log2FoldChange | pvalue | padj |
|---|---|---|---|---|---|---|
| 1 | Serpina3e-ps | | 621.52 | 0.57 | 2.62E−10 | 5.38E−06 |
| 2 | Gpaa1 | GPAA1 | 419.30 | 0.30 | 6.26E−06 | 4.29E−02 |
| 3 | 2510039O18Rik | KIAA2013 | 566.57 | 0.34 | 1.40E−05 | 5.13E−02 |
| 4 | Slc38a10 | SLC38A10 | 2339.35 | 0.28 | 1.50E−05 | 5.13E−02 |
| 5 | Sugct | SUGCT | 10540.20 | −0.36 | 1.46E−05 | 5.13E−02 |
| 6 | Pgp | PGP | 133.23 | 0.47 | 2.11E−05 | 5.48E−02 |
| 7 | Nfe2l2 | NFE2L2 | 2977.29 | −0.27 | 5.29E−05 | 8.39E−02 |
| 8 | Gm43980 | | 186.70 | −0.35 | 5.02E−05 | 8.39E−02 |
| 9 | Prkcsh | PRKCSH | 1744.14 | 0.34 | 4.60E−05 | 8.39E−02 |
| 10 | Tysnd1 | TYSND1 | 1021.91 | 0.32 | 5.71E−05 | 8.39E−02 |
| 11 | Nme1 | NME1 | 628.68 | 0.38 | 5.46E−05 | 8.39E−02 |
| 12 | Frmpd4 | FRMPD4 | 42.84 | −0.50 | 4.62E−05 | 8.39E−02 |
| 13 | Gpc1 | GPC1 | 121.91 | 0.42 | 1.04E−04 | 9.23E−02 |
| 14 | Rmdn3 | RMDN3 | 1060.79 | 0.20 | 1.35E−04 | 9.23E−02 |
| 15 | Rcc2 | RCC2 | 686.17 | 0.31 | 1.00E−04 | 9.23E−02 |
| 16 | Urad | URAD | 885.92 | 0.26 | 1.47E−04 | 9.23E−02 |
| 17 | Irgq | IRGQ | 535.61 | 0.29 | 1.64E−04 | 9.23E−02 |
| 18 | Mir5121 | | 44.34 | 0.49 | 9.05E−05 | 9.23E−02 |
| 19 | RP23-474J16.2 | | 153.01 | −0.40 | 1.42E−04 | 9.23E−02 |
| 20 | RP24-178G20.2 | | 99.39 | 0.44 | 7.30E−05 | 9.23E−02 |
| ... | | | | | | |
| 45 | Slc16a11 | SLC16A11 | 106.45 | −0.43 | 2.34E−04 | 9.42E−02 |

Figure 10:
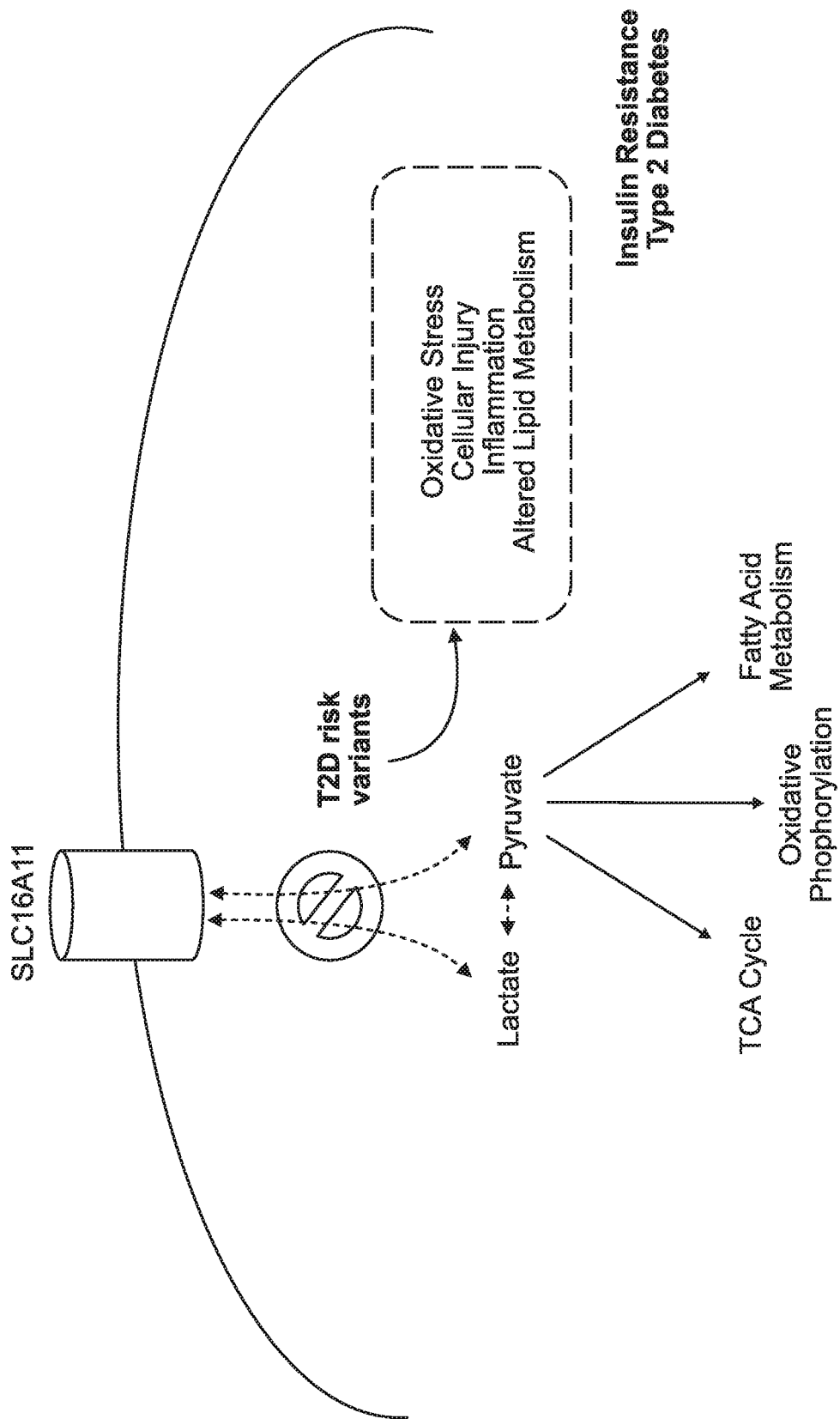
FIG. 10 provides a schematic diagram showing the impact of a reduction in SLC16A11 function.

As with the transcriptional changes in human carriers of the T2D risk haplotype, Slc16a11 is the only significantly altered gene at this locus (FIG. 9E, top) and expression of no other SLC16 family members is significantly altered (FIG. 9E, bottom), pointing toward the targeted disruption of Slc16a11 as the driver these changes. Examination of metabolite levels revealed the Slc16a11 knockout has increased levels of liver and plasma metabolites that are associated with insulin resistance and T2D pathogenesis, including lactate, diacylglycerols (DAGs), triacylglycerols (TAGs), and malondialdehyde (MDA), a marker of lipid oxidation and oxidative stress (FIG. 9F, FIG. 9G, FIG. 9H). Increases in these biomarkers of insulin resistance and T2D support the idea that reduced SLC16A11 has physiological consequences related to T2D (FIG. 10).

TABLE 9B

Significantly altered metabolite pathways in livers of Slc16a11 del19 knockout mice versus wild-type littermates.

| Name | p-value | FDR | NES | Information |
|---|---|---|---|---|
| Aminoacyl-tRNA biosynthesis | 0.001 | 0.000 | -2.63 | Depleted |
| CEs | 0.001 | 0.000 | -2.76 | Depleted |
| *TAGs* | 0.001 | 0.002 | 2.32 | Enriched |
| *DAGs* | 0.001 | 0.002 | 2.26 | Enriched |
| LPCs | 0.001 | 0.003 | 2.35 | Enriched |
| Cyanoamino acid metabolism | 0.001 | 0.005 | -2.31 | Depleted |
| PEs | 0.008 | 0.020 | 1.81 | Enriched |
| Propanoate metabolism | 0.008 | 0.020 | 1.76 | Enriched |
| LPEs | 0.009 | 0.022 | 1.83 | Enriched |
| Primary bile acid biosynthesis | 0.005 | 0.024 | -1.88 | Depleted |
| Glycine serine and threonine metabolism | 0.006 | 0.026 | -1.90 | Depleted |
| Carnitines | 0.002 | 0.026 | -1.98 | Depleted |
| Glutathione metabolism | 0.004 | 0.029 | -1.92 | Depleted |
| Biosynthesis of unsaturated fatty acids | 0.003 | 0.033 | -1.79 | Depleted |
| Histidine metabolism | 0.007 | 0.035 | -1.77 | Depleted |
| PCs | 0.020 | 0.037 | -1.71 | Depleted |
| Nitrogen metabolism | 0.015 | 0.039 | -1.72 | Depleted |
| Arginine and proline metabolism | 0.021 | 0.039 | -1.67 | Depleted |

Triacylglycerols and diacylglycerols are shown in bold italics.
FDR stands for false discovery rates. Only pathways with an FDR <0.05 are shown.

TABLE 9C

Significantly altered metabolite pathways in plasma of Slc16a11 del19 knockout mice versus wild-type littermates.

| Name | p-value | FDR | NES | Information |
|---|---|---|---|---|
| *TAGs* | 0.001 | 0.000 | 4.39 | Enriched |
| CEs | 0.001 | 0.000 | -2.87 | Depleted |
| *DAGs* | 0.001 | 0.000 | 2.90 | Enriched |
| PCs | 0.001 | 0.001 | -2.69 | Depleted |
| Biosynthesis of unsaturated fatty acids | 0.001 | 0.002 | -2.27 | Depleted |

TABLE 9C-continued

Significantly altered metabolite pathways in plasma of Slc16a11 del19 knockout mice versus wild-type littermates.

| Name | p-value | FDR | NES | Information |
|---|---|---|---|---|
| SMs | 0.001 | 0.003 | -2.27 | Depleted |
| LPCs | 0.001 | 0.003 | -2.30 | Depleted |
| Purine metabolism | 0.001 | 0.009 | 2.13 | Enriched |

Triacylglycerols and diacylglycerols are shown in bold italics.
FDR stands for false discovery rates. Only pathways with an FDR <0.05 are shown.

Example 19

SLC16A11 is Regulated at the mRNA Level

Figure 7A:
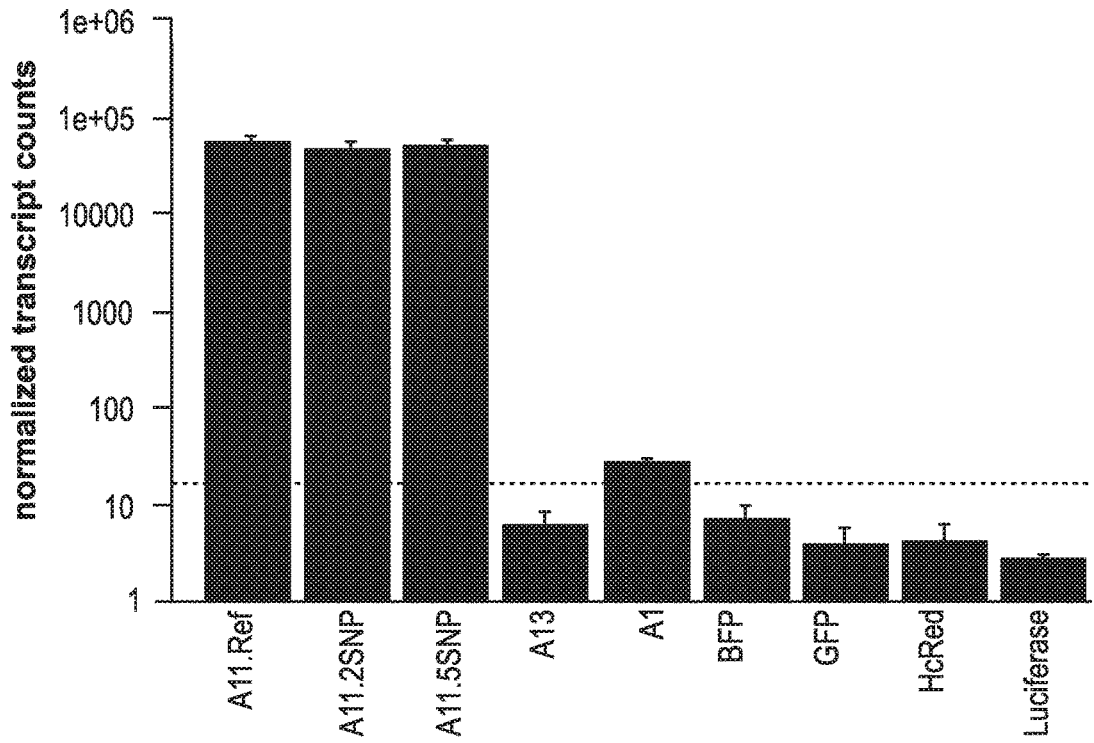
FIGS. 7A-7C provide graphs depicting gene expression results upon transcript expression of SLC16A11, SLC16A1 and SLC16A13 transiently expressed in HeLa cells following overexpression from a CMV-driven promoter. Despite being expressed from the same plasmid with the same promoter, SLC16A11 levels are an order of magnitude lower than SLC16A13 and SLC16A1, indicating SLC16A11 is being regulated at the mRNA level by a mechanism involving sequencings within the SLC16A11 open reading frame.
Figure 7B:
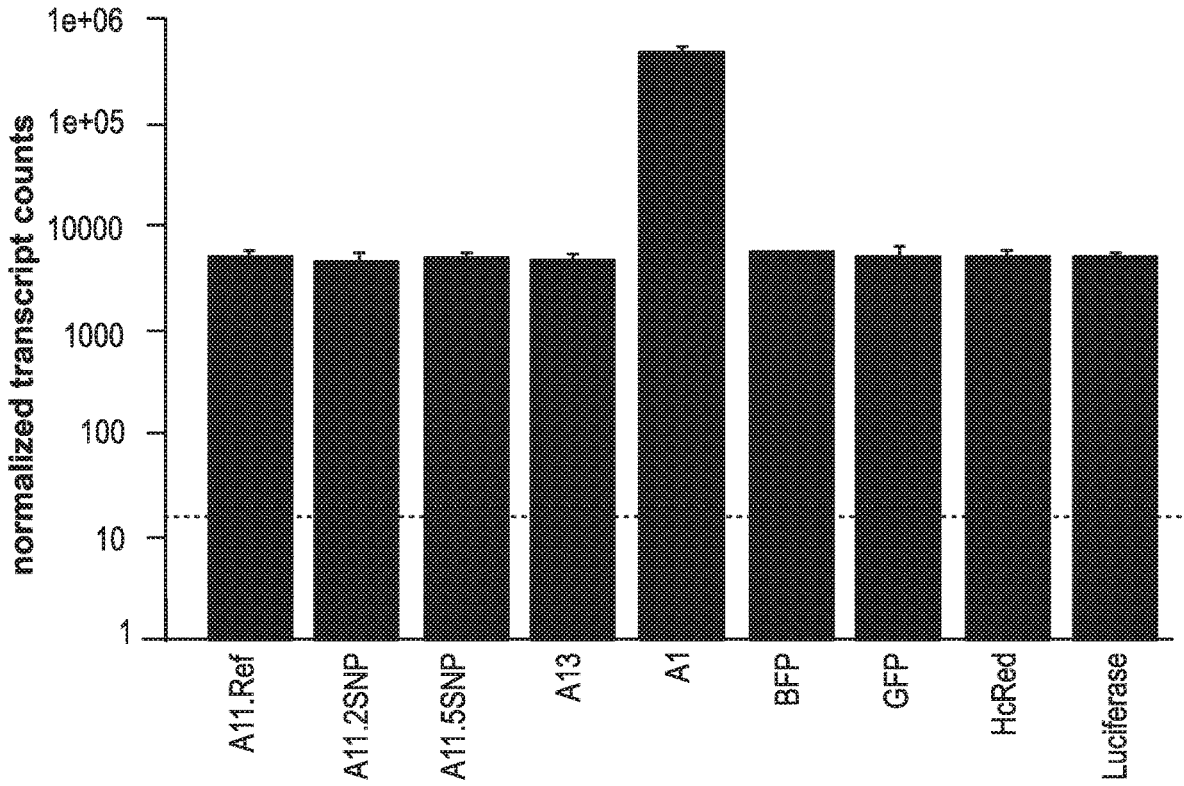
Figure 7C:
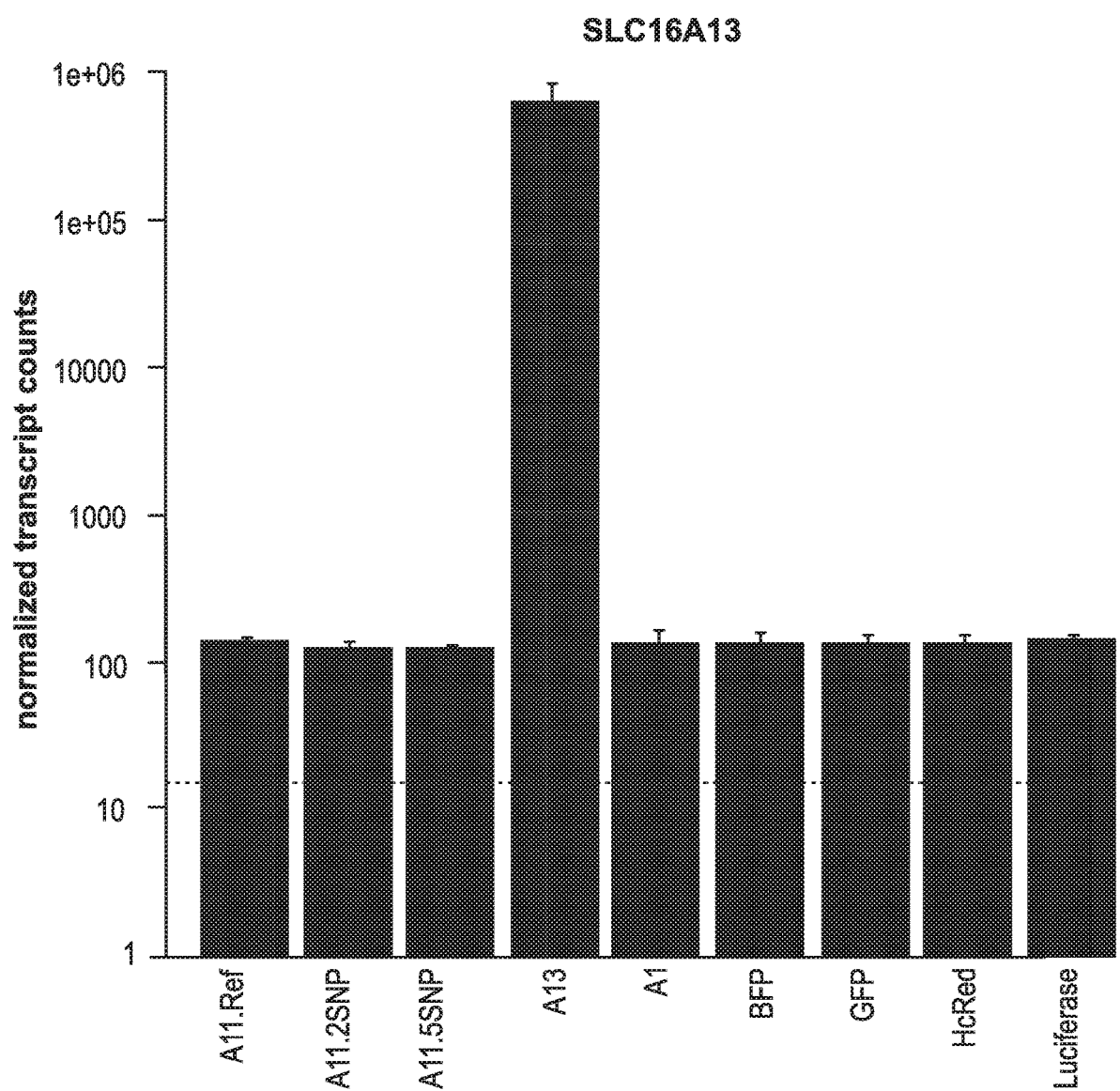

SLC16A11, SLC16A1 and SLC16A13 were transiently expressed in HeLa cells using a CMV-driven promoter. Despite being expressed from the same plasmid with the same promoter, SLC16A11 levels are an order of magnitude lower than SLC16A13 and SLC16A1, indicating SLC16A11 is being regulated at the mRNA level by a mechanism involving sequencings within the SLC16A11 open reading frame (FIGS. 7A, 7B and 7C).

Example 20

SLC16A11 is Regulated at the mRNA Level

SLC16A11, SLC16A1 and SLC16A13 were transiently expressed in HeLa cells using a CMV-driven promoter, and gene expression was measured using Nanostring nCounter (SIGMA T2D Consortium, 2014 Nature, 506:97-101). Despite being expressed from the same plasmid with the same promoter, SLC16A11 levels are an order of magnitude lower than SLC16A13 and SLC16A1, indicating SLC16A11 is being regulated at the mRNA level by a mechanism involving sequences within the SLC16A11 open reading frame (FIGS. 7A, 7B and 7C). Determining the mechanism underlying SLC16A11 mRNA instability may lead to future therapeutic strategies.

Example 21

SpCas9-Based Transactivation of SLC16A11 Expression

These experiments are based upon Cas9 based transactivators (SAM or synergistic activation mediators) as described in Konermann et al (Nature 517: 583-588, 2015). Similar experiments based on other types of transactivators that are more finely tuned to distal activation such as those described in Hilton et al. (Nature 33:510-518, 2015) could also be envisioned. Cas9 was used to target transactivators to sites near individual variants in the credible set. Their ability to activate SLC16A11 gene expression was assessed (Table 10).

TABLE 10

| rs id | target sequence 1 | target sequence 2 | Increases SLC16A11 transcript levels in trans-activator assay | Variant disrupts PAM targeting |
|---|---|---|---|---|
| rs77086571 | AACCCCCAGGCCCGGGGAG | TCGCCGCTCCCCCCTCCCCC | TRUE | YES |
| rs74577409 | ACCTGCCGCCTGCTGCGCGC | CCCTGCGCGCAGCAGGCGGC | TRUE | YES |

TABLE 10-continued

| rs id | target sequence 1 | target sequence 2 | Increases SLC16A11 transcript levels in trans-activator assay | Variant disrupts PAM targeting |
|---|---|---|---|---|
| rs2292351 | AGCCTCTGGCTGCTCGCCCG | CACCCCGGGCGAGCAGCCAG | TRUE | NO |
| rs17203120 | CTTATTTGATTTTATCTCAA | TTATTTGATTTTATCTCAAA | FALSE | N/A |
| rs145952323 | CAAAAATTAGCCGGGTGTGT | CAGGCACACGCCAACACACC | FALSE | N/A |
| rs75075014 | GGAAGTGGAGGAGAGTGTCC | GGAGTCATGCCTGGAAGTGG | FALSE | N/A |
| rs78972129 | GATGCTATGGTTGGCCACGC | AGTACAGTACACAGCCTGCG | FALSE | N/A |
| rs77552976 | GAAAGGGCTGCCGTGCTGTT | CCTGGCTGGACCTAACAGCA | FALSE | N/A |
| rs58223766 | TCAGGAGTTCGAGACCATCC | GATCCACCCCCCCCCCCCT | FALSE | N/A |
| rs4630597 | GGTGCCTCAGATACCTGGTT | AACCAGGTATCTGAGGCACC | FALSE | N/A |
| rs113748381 | GCCTCGGCCTCCCAAAGTGC | GCACTTTGGGAGGCCGAGGC | FALSE | N/A |
| rs73239895 | ACTCCTGCCGGAGGTTCTCG | AGGCCCCGAGAACCTCCGGC | FALSE | N/A |
| rs186568031 | GATTTTCACTCTTGTTGCCC | TTCACTCTTGTTGCCCAGGC | FALSE | N/A |
| rs312457 | TGATGAAACCTGGCCGGGCA | GTGAGCCACCGTGCCCGGCC | FALSE | N/A |
| rs17203148 | TCTGCCAATCTTGGCTCTGT | GAAACCTACAGAGCCAAGAT | FALSE | N/A |
| rs1698227 | TGGTGCTAAGGGGCACACAC | TGCTCATTTTCCTCTGCACT | FALSE | N/A |
| rs191133 | TGAAAGTAAGTCAATCATGG | ATGATTGACTTACTTTCATC | FALSE | N/A |
| rs193399 | TAGAACCAGCTTCTAGGTTC | TCCTTCCTGAACCTAGAAGC | FALSE | N/A |
| NA | TCACGCGCGGCTTGCCGGAT | TGGGACGCGGGGTGTACGGA | TRUE | N/A |
| NA | GTACATAATTCAATCCCCGT | GCGGCGAGAAATGAATGCAG | TRUE | N/A |
| NA | CTATTTCCACGCGTTGGCGG | ACCTGCCGCCTGCTGCGCGC | TRUE | N/A |
| NA | TGTTCTCAGGAACGTTGCCG | ATTGATATCCGAGATTTACC | TRUE | N/A |
| NA | TTACAGGCTTGCACCGCGCC | TGGGTGAATCACCTGACGTC | TRUE | N/A |
| NA | ACGGAAACTGGCGCGCTCCA | TATCACTGGGGTGTCCGGGC | TRUE | N/A |
| NA | GCGGGATTTAGGCATTGTTG | CGGGAGCCCCGCGTCCTCAT | TRUE | N/A |
| NA | TGGCAGTCCCCGCGTCACGT | CATGCGTAAGGAGGGGCGTT | TRUE | N/A |
| NA | TGGCTCTGGGTGCTGAAACG | GACTCTCTTGCTTTAATGAG | TRUE | N/A |
| NA | GGCTGCGTGTTAGTGGCTTC | GGAATTGCAAGGCCCTGTTG | TRUE | N/A |

In Table 10, the polynucleotide sequences for target sequence 1 are denoted as follows: rs7708657: aaccccaggcccgggggag (SEQ ID NO: 28); rs74577409: acctgccgcctgctgcgcgc (SEQ ID NO: 29); rs2292351: agcctctggctgctcgcccg (SEQ ID NO: 30); rs17203120: cttatttgattttatctcaa (SEQ ID NO: 31); rs145952323: caaaaattagccgggtgtgt (SEQ ID NO: 32); rs75075014: ggaagtggaggagagtgtcc (SEQ ID NO: 33); rs78972129: gatgctatggttggccacgc (SEQ ID NO: 34); rs77552976: gaaagggctgccgtgctgtt (SEQ ID NO: 35); rs58223766: tcaggagttcgagaccatcc (SEQ ID NO: 36); rs4630597: ggtgcctcagatacctggtt (SEQ ID NO: 37); rs113748381: gcctcggcctcccaaagtgc (SEQ ID NO: 38); rs73239895: actcctgccggaggttctcg (SEQ ID NO: 39); rs186568031: gattttcactcttgttgccc (SEQ ID NO: 40); rs312457: tgat- gaaacctggccgggca (SEQ ID NO: 41); rs17203148: tctgc- caatcttggctctgt (SEQ ID NO: 42); rs1698227: tggtgctaaggggcacacac (SEQ ID NO: 43); rs191133: tgaaagtaagtcaatcatgg (SEQ ID NO: 44); rs193399: tagaaccagcttctaggttc (SEQ ID NO: 45); NA: tcacgcgcggcttgccggat (SEQ ID NO: 46); NA: gtacataatt- caatccccgt (SEQ ID NO: 47); NA: ctatttccacgcgttggcgg (SEQ ID NO: 48); NA: tgttctcaggaacgttgccg (SEQ ID NO: 49); NA: ttacaggcttgcaccgcgcc (SEQ ID NO: 50); NA: acggaaactggcgcgctcca (SEQ ID NO: 51); NA: gcgggatttagg- cattgttg (SEQ ID NO: 52); NA: tggcagtccccgcgtcacgt (SEQ ID NO: 53); NA: tggctctgggtgctgaaacg (SEQ ID NO: 54); and NA: ggctgcgtgttagtggcttc (SEQ ID NO: 55).

In Table 10, the polynucleotide sequences for target sequence 2 are denoted as follows: rs77086571:

tcgccgctccccctccccc (SEQ ID NO: 56); rs74577409: ccctgcgcgcagcaggcggc (SEQ ID NO: 57); rs2292351: caccccgggcgagcagccag (SEQ ID NO: 58); rs17203120: ttatttgattttatctcaaa (SEQ ID NO: 59); rs145952323: caggcacacgccaacacacc (SEQ ID NO: 60); rs75075014: ggagtcatgcctggaagtgg (SEQ ID NO: 61); rs78972129: agtacagtacacagcctgcg (SEQ ID NO: 62); rs77552976: cctggctggacctaacagca (SEQ ID NO: 63); rs58223766: gatccacccccccccccct (SEQ ID NO: 64); rs4630597: aaccaggtatctgaggcacc (SEQ ID NO: 65); rs113748381: gcactttgggaggccgaggc (SEQ ID NO: 66); rs73239895: aggccccgagaacctccggc (SEQ ID NO: 67); rs186568031: ttcactcttgttgcccaggc (SEQ ID NO: 68); rs312457: gtgagccaccgtgcccggcc (SEQ ID NO: 69); rs17203148: gaaacctacagagccaagat (SEQ ID NO: 70); rs1698227: tgctcattttcctctgcact (SEQ ID NO: 71); rs191133: atgattgacttactttcatc (SEQ ID NO: 72); rs193399: tccttcctgaacctagaagc (SEQ ID NO: 73); NA: tgggacgcggggtgtacgga (SEQ ID NO: 74); NA: gcggcgagaaatgaatgcag (SEQ ID NO: 75); NA: acctgccgcctgctgcgcgc (SEQ ID NO: 29); NA: attgatatccgagatttacc (SEQ ID NO: 76); NA: tgggtgaatcacctgacgtc (SEQ ID NO: 77); NA: tatcactggggtgtccggc (SEQ ID NO: 78); NA: cgggagccccgcgtcctcat (SEQ ID NO: 79); NA: catgcgtaaggaggggcgtt (SEQ ID NO: 80); NA: gactctcttgctttaatgag (SEQ ID NO: 81); and NA: ggaattgcaaggccctgttg (SEQ ID NO: 82).

Significantly, transactivators targeted to regions proximal to a gene promoter increased that gene's transcript levels. In 293T cells, only transactivators targeted to the three variants proximal to the SLC16A11 transcriptional start site increased expression of this gene. In this context, transactivators targeted to the other 15 non-coding variants did not alter the expression of SLC16A11. Moreover, SLC16A13 expression was not altered by any of the variant-directed transactivators. This demonstrated the specificity of this approach. Due to the sequence specificity required for transactivator targeting, gRNAs that overlap a variant would be expected to specifically induce expression of the non-variant allele.

Example 22

Mining Library of Integrated Cellular Signatures (LINCS) Dataset for Connections to SLC16A11 Gene Expression Signatures Given that gene expression is tightly correlated, measuring a small number of genes is sufficient to impute most of the gene expression content of the transcriptome. For the Library of Integrated Cellular Signatures (LINCS) dataset, 978 genes are directly measured and an inference model, trained on publically available Affymetrix microarray data, is then used to impute gene expression for 20,000 additional probes. Given that SLC16A11 gene expression was not directly measured nor was it inferred, query signature was generated first.

Gene expression data in 119 human liver samples was obtained from the Genotype-Tissue Expression project (GTEx) and ranked genes by how well correlated their expression was to SLC16A11 expression. Samples were selected from 50, 100, and 150 of the most positively and negatively correlated genes respectively and used them to generate 3 SLC16A11 gene expression signatures. These signatures served as surrogates for SLC16A11 transcript levels. These query signatures were used to search the entire space of compounds profiled in the LINCS dataset. The goal was to identify compound signatures that were most similar to the query signature. It was predicted that these signatures were generated by compound treatments that might also increase SLC16A11 expression.

A connectivity score ranging from 100 for a positive connection to −100 for a negative connection was used to quantify the similarity between signatures as previously described. A positive connection between two signature means that both signatures result from similar changes in gene expression. Conversely for a negative connection, the changes in gene expression are opposite meaning that the set of genes most up-regulated in one signature tend to be down-regulated in the other and vice versa. The results from the three query signatures were averaged to nominate compound treatments that consistently made positive connections with the SLC16A11 gene expression signature as shown in Table 11. Connectivity scores for the top 25 positive connections to the SLC16A11 gene expression signature are shown in Table 11A. The signature size corresponds to the number of positively and negatively correlated genes used in the query signature. Compounds that were annotated as inhibiting the mechanistic target of rapamycin (mTOR) are shown in bold.

TABLE 11A

Mining LINCS dataset for connections to SLC16A11 gene expression signatures.

| Compound Name | SLC16A11 signature size 50 | SLC16A11 signature size 100 | SLC16A11 signature size 150 | Average |
|---|---|---|---|---|
| tipifarnib-P2 | 99.51 | 98.95 | 98.56 | 99.01 |
| calpeptin | 98.94 | 99.15 | 98.87 | 98.99 |
| KU-0063794 | 98.66 | 98.98 | 98.98 | 98.87 |
| MEK1-2-inhibitor | 98.66 | 98.77 | 98.98 | 98.80 |
| fostamatinib | 98.31 | 99.33 | 98.73 | 98.79 |
| AZD-8055 | 98.48 | 98.80 | 98.73 | 98.67 |
| NVP-BEZ235 | 98.48 | 98.80 | 98.70 | 98.66 |
| PP-30 | 99.05 | 98.45 | 98.20 | 98.57 |
| PD-0325901 | 98.06 | 98.17 | 96.81 | 97.68 |
| PIK-90 | 96.93 | 97.92 | 97.95 | 97.60 |
| BMS-536924 | 97.31 | 95.91 | 98.20 | 97.14 |
| PI-828 | 96.34 | 97.89 | 97.00 | 97.08 |
| PI-103 | 97.11 | 96.93 | 96.48 | 96.84 |
| KIN001-244 | 94.96 | 96.52 | 97.43 | 96.30 |
| serdemetan | 96.36 | 95.53 | 96.97 | 96.29 |
| PP-2 | 96.67 | 95.95 | 96.05 | 96.22 |
| WYE-354 | 97.28 | 96.34 | 94.74 | 96.12 |
| methotrexate | 94.72 | 95.56 | 98.02 | 96.10 |
| U0126 | 91.55 | 97.78 | 98.94 | 96.09 |
| U-0126 | 89.44 | 98.73 | 98.13 | 95.43 |
| NU-7026 | 97.96 | 96.01 | 92.29 | 95.42 |
| OSI-027 | 97.46 | 94.66 | 93.87 | 95.33 |
| selumetinib | 93.12 | 97.43 | 95.24 | 95.26 |
| deforolimus | 95.95 | 96.13 | 93.56 | 95.21 |
| PAC-1 | 96.36 | 95.08 | 91.90 | 94.45 |

Among the top 25 positive connections to the SLC16A11 gene expression signature, compounds that had been annotated with mTOR inhibition as a mechanism of action had generated 7 signatures. There were a 2837 signatures queried in total and 22 of these were annotated as mTOR inhibitors. This represented a highly significant enrichment of mTOR inhibitors among the most 25 positive connections ($P=1\times10^{-10}$ by the hypergeometric test) and indicates in favor of the hypothesis that mTOR inhibition might increase SLC16A11 expression.

Table 11B shows the top 25 compounds and gene targets from the 2837 signatures.

TABLE 11B

Top 25 connections from dataset for connections to SLC16A11 gene expression signatures

| cell_id | gene_target | id | moa | pert_id | pert_iname | pert_type | A11_SCORR_UP_50 | A11_SCORR_UP_100 | A11_SCORR_UP_150 | AVG |
|---|---|---|---|---|---|---|---|---|---|---|
| SUMMLY | FNTA\|FNTB | BRD-K62965 | farnesyltransferase inhibitor | BRD-K62965 | tipifarnib-P2 | trt_cp | 99.51 | 98.95 | 98.56 | 99.01 |
| SUMMLY | -666 | BRD-A84045 | calpain inhibitor | BRD-A84045 | calpeptin | trt_cp | 98.94 | 99.15 | 98.87 | 98.99 |
| SUMMLY | MTOR | BRD-K67566 | mTOR inhibitor | BRD-K67566 | KU-0063794 | trt_cp | 98.66 | 98.98 | 98.98 | 98.87 |
| SUMMLY | MAP2K1\|MA | BRD-K12244 | MEK inhibitor | BRD-K12244 | MEK1-2-inhibitor | trt_cp | 98.66 | 98.77 | 98.98 | 98.80 |
| SUMMLY | SYK\|FLT3\|R8 | BRD-K20285 | SYK inhibitor | BRD-K20285 | fostamatinib | trt_cp | 98.31 | 99.33 | 98.73 | 98.79 |
| SUMMLY | MTOR | BRD-K69932 | mTOR inhibitor | BRD-K69932 | AZD-8055 | trt_cp | 98.48 | 98.8 | 98.73 | 98.67 |
| SUMMLY | MTOR\|PIK3O | BRD-K12184 | mTOR inhibitor | BRD-K12184 | NVP-BEZ235 | trt_cp | 98.48 | 98.8 | 98.7 | 98.66 |
| SUMMLY | RAF1 | BRD-K30677 | RAF inhibitor | BRD-K30677 | PP-30 | trt_cp | 99.05 | 98.45 | 98.2 | 98.57 |
| SUMMLY | MAP2K1\|MA | BRD-K49865 | MEK inhibitor | BRD-K49865 | PD-0325901 | trt_cp | 98.06 | 98.17 | 96.81 | 97.68 |
| SUMMLY | -666 | BRD-K99818 | PI3K inhibitor | BRD-K99818 | PIK-90 | trt_cp | 96.93 | 97.92 | 97.95 | 97.60 |
| SUMMLY | IGF1R\|AKT1 | BRD-K34581 | IGF-1 inhibitor | BRD-K34581 | BM5-536924 | trt_cp | 97.31 | 95.91 | 98.2 | 97.14 |
| SUMMLY | -666 | BRD-K97365 | PI3K inhibitor | BRD-K97365 | PI-828 | trt_cp | 96.34 | 97.89 | 97 | 97.08 |
| SUMMLY | PIK3CA\|PIK3 | BRD-K67868 | mTOR inhibitor | BRD-K67868 | PI-103 | trt_cp | 97.11 | 96.83 | 96.48 | 96.84 |
| SUMMLY | PDPK1 | BRD-K09186 | dihydrofolate | BRD-K09186 | KIN001-244 | trt_cp | 94.96 | 96.52 | 97.43 | 96.30 |
| SUMMLY | MDM2 | BRD-K60219 | MDM inhibitor | BRD-K60219 | serdemetan | trt_cp | 96.36 | 95.53 | 96.97 | 96.29 |
| SUMMLY | SRC\|LCK\|AB | BRD-K95785 | src inhibitor | BRD-K95785 | PP-2 | trt_cp | 96.67 | 95.95 | 96.05 | 96.22 |
| SUMMLY | MTOR | BRD-K77008 | mTOR inhibitor | BRD-K77008 | WYE-354 | trt_cp | 97.28 | 96.34 | 94.74 | 96.12 |
| SUMMLY | DHFR\|AOX1 | BRD-K59456 | phosphoinositide | BRD-K59456 | methotrexate | trt_cp | 94.72 | 95.56 | 98.02 | 96.10 |
| SUMMLY | JAK2\|MAP2K | BRD-K46419 | MEK inhibitor | BRD-K46419 | U0126 | trt_cp | 91.55 | 97.78 | 98.94 | 96.09 |
| SUMMLY | AKT1\|CHEK1 | BRD-K18787 | MEK inhibitor | BRD-K18787 | U-0126 | trt_cp | 89.44 | 98.73 | 98.13 | 95.43 |
| SUMMLY | PRKDC | BRD-K09537 | DNA dependent | BRD-K09537 | NU-7026 | trt_cp | 97.96 | 96.01 | 92.29 | 95.42 |
| SUMMLY | MTOR | BRD-K94294 | mTOR inhibitor | BRD-K94294 | OSI-027 | trt_cp | 97.46 | 94.66 | 93.87 | 95.33 |
| SUMMLY | MAP2K1\|MA | BRD-K57080 | MEK inhibitor | BRD-K57080 | selumetinib | trt_cp | 93.12 | 97.43 | 95.24 | 95.26 |
| SUMMLY | MTOR | BRD-K29733 | mTOR inhibitor | BRD-K29733 | deforolimus | trt_cp | 95.95 | 96.13 | 93.56 | 95.21 |
| SUMMLY | CASP3 | BRD-K92991 | caspase active | BRD-K92991 | PAC-1 | trt_cp | 96.36 | 95.08 | 91.9 | 94.45 |

Example 23 mTOR Inhibitors as Modulators of SLC16A11 Gene Expression

Figure 14A:
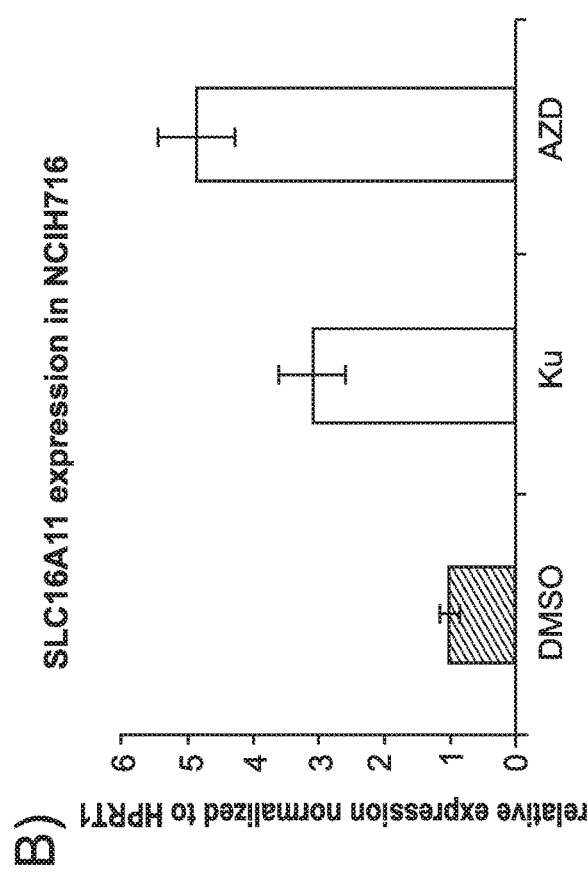
FIGS. 14A-14D provide graphs showing that mTOR inhibitors increase SLC16A11, but not SLC16A1 transcript levels. SNU761 cells (FIGS. 14A and 14C) and NCIH716 cells (FIGS. 14B and 14D) were treated with KU-0063794 (denoted as Ku) or AZD-8055 (denoted as AZD) at 10 μM for 24 hours. SLC16A11 (FIGS. 14A and 14B) and SLC16A1 (FIGS. 14C and 14D) expression was then assessed using droplet digital PCR (ddPCR). Bar plots depict relative fold-changes with respect to DMSO and error bars and standard deviations. Expression is normalized to housekeeping genes TBP or HPRT1.
Figure 14B:
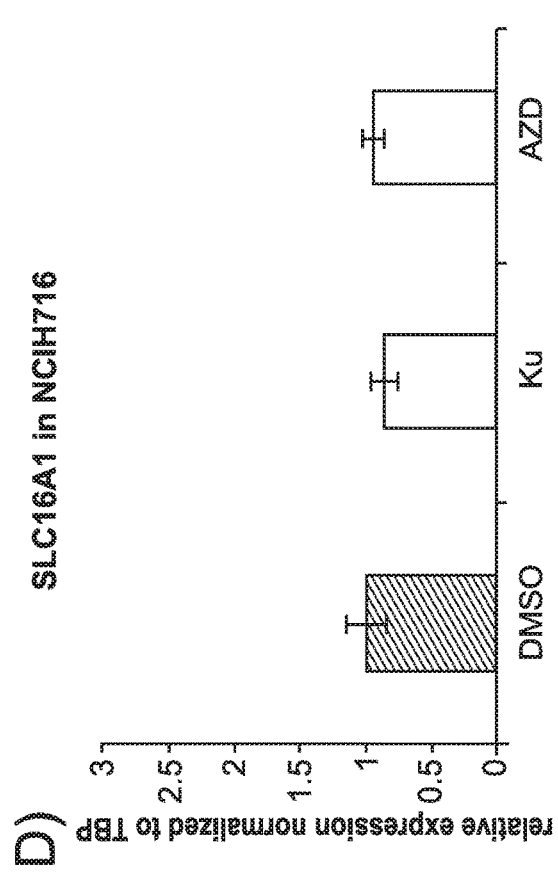
Figure 14C:
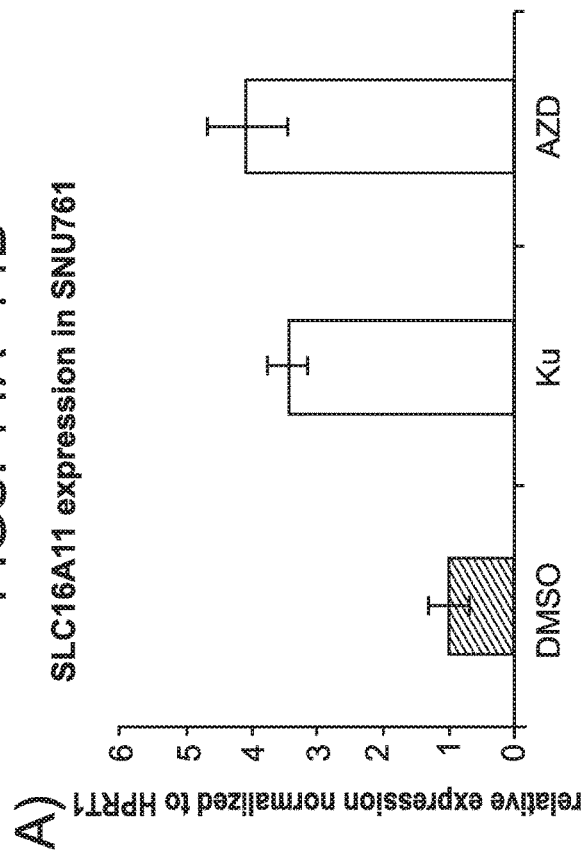
Figure 14D:
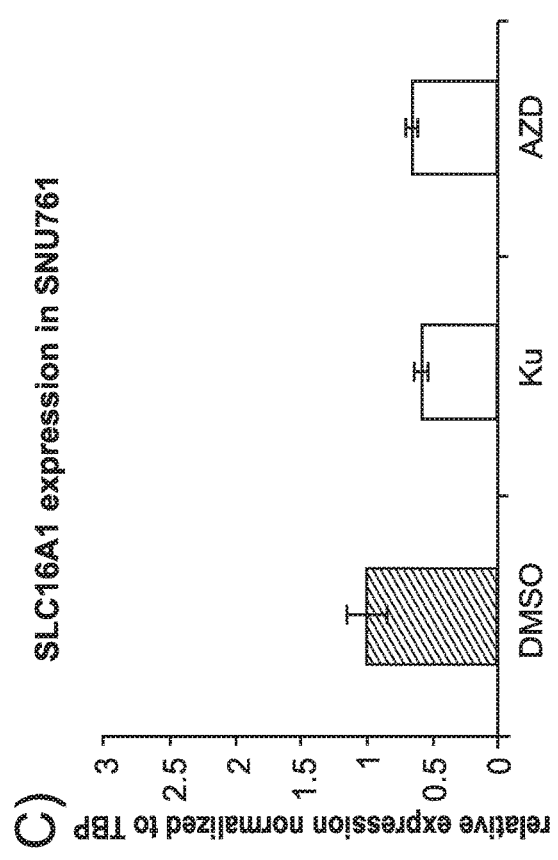

A small number of the compounds that made the strongest positive connections to the SLC16A11 gene expression signature were selected and tested. The inhibitor KU-0063794 and AZD-8055 were selected because they are both mTOR inhibitors. Methotrexate was also included, which had been annotated as a dihydrofolate reductase inhibitor. SNU761 cells (derived from a human hepatocellular carcinoma) and NCIH716 cells (derived from a human cecum adenocarcinoma), which both express SLC16A11, were treated with the compounds. The same compound concentrations and treatment times were used as in the LINCS dataset experiments. The results indicated the mTOR inhibitors, KU-0063794 and AZD-8055, increased SLC16A11 transcript levels about 3-fold in compound treated cells compared to DMSO treated cells (FIG. 13A, left and right panels). The chemical structures of the mTOR inhibitors AZD-8055 and KU-00637947 are shown in FIG. 13B. In contrast, methotrexate did not alter SLC16A11 transcript levels and thus represented a false positive result obtained through mining of the Library of Integrated Cellular Signatures (LINCS) dataset. For normalization, a different housekeeper gene, HPRT1, was used and obtained similar results with the mTOR inhibitors (FIGS. 14A and 14B). The expression of SLC16A1 was also measured and the data indicated that these mTOR inhibitors did not increase expression of this gene, but rather resulted in a slight decrease (FIGS. 14C and 14D). The graphs presented in FIGS. 14A-D thus show that mTOR inhibitors increase SLC16A11 but not SLC16A1 transcript levels.

Next an unbiased approach was used to investigating the compounds that made the strongest positive connections to the SLC16A11 gene expression signature (Table 11C).

TABLE 11C

| moa | pert_iname | avg_fc | pvalue_fc |
|---|---|---|---|
| CHK inhibitor | AZD-7762 | 4.92401276 | 0.02949981 |
| mTOR inhibitor | AZD-8055 | 4.2531982 | 0.06697925 |
| mTOR inhibitor | KU-0063794 | 4.00923817 | 0.02591343 |
| mTOR inhibitor | WYE-354 | 3.51686403 | 0.00252449 |
| mTOR inhibitor | OSI-027 | 3.38355907 | 0.00401379 |
| mTOR inhibitor | WYE-125132 | 3.33600456 | 0.02742533 |
|  |  | 3.33141845 | 0.00994261 |
|  |  | 3.27703893 | 0.01331774 |
| SYK inhibitor | fostamatinib | 3.27387727 | 0.04164977 |
| Aurora kinase inhibitor | reversine | 3.23490477 | 0.00732965 |
| mTOR inhibitor | torin-2 | 2.84341284 | 0.03756893 |
| mTOR inhibitor | torin-1 | 2.83974255 | 0.03157075 |
| mTOR inhibitor|PI3K inhibitor | NVP-BEZ235 | 2.77949368 | 0.06359898 |
| mTOR inhibitor|PI3K inhibitor | PI-103 | 2.45335902 | 0.08424547 |
| MEK inhibitor | PD-0325901 | 2.18064833 | 0.01367536 |
| PI3K inhibitor | AZD-6482 | 2.17592976 | 0.02429224 |
| PI3K inhibitor | GDC-0941 | 2.07949266 | 0.00714229 |
| MEK inhibitor | selumetinib | 1.96392721 | 0.02357516 |
| mTOR inhibitor | deforolimus | 1.90342737 | 0.00016188 |
| MEK inhibitor | U0126 | 1.88524262 | 0.10090469 |
|  |  | 1.78730201 | 0.06046331 |
| RAF inhibitor | HG-6-64-01 | 1.72832221 | 2.80E−05 |
| MEK inhibitor | AS-703026 | 1.68014838 | 0.25778722 |
| mTOR inhibitor | sirolimus | 1.66202644 | 0.05653636 |
| VEGFR inhibitor | tivozanib | 1.64672418 | 0.1283144 |
| PI3K inhibitor | PIK-90 | 1.48685288 | 0.03401197 |
| MEK inhibitor | PD-184352 | 1.44468429 | 0.22689753 |
| MEK inhibitor | MEK1-2-inhibitor | 1.41413951 | 0.11185062 |
| ATPase inhibitor | digitoxin | 1.37498564 | 0.29793571 |
| mTOR inhibitor | temsirolimus | 1.3723327 | 0.22240465 |
| EGFR inhibitor|receptor tyrosine protein kinase inhibitor | CP-724714 | 1.36950068 | 0.04682589 |
| RAF inhibitor | vemurafenib | 1.36812997 | 0.20857533 |
| JNK inhibitor | CG-930 | 1.33675685 | 0.19881349 |
| PI3K inhibitor | PI-828 | 1.33568521 | 0.46648565 |
|  |  | 1.32817918 | 0.00953097 |
| gamma secretase inhibitor | DAPT-GSI-IX | 1.28555707 | 0.04853151 |
| PI3K inhibitor | GSK-1059615 | 1.25007248 | 0.54883079 |
| protein synthesis inhibitor | cycloheximide | 1.24299068 | 0.32796445 |
| src inhibitor | PP-2 | 1.18969809 | 0.45381445 |
| opioid receptor antagonist | naltrexone | 1.18344455 | 0.33874774 |
| lanosterol demethylase inhibitor|sterol demethylase inhibitor | econazole | 1.17782824 | 0.04437152 |
| MEK inhibitor | nobiletin | 1.1292611 | 0.11222204 |
| PARP inhibitor | DR-2313 | 1.12695386 | 0.42639695 |
| DNA dependent protein kinase inhibitor|mTOR inhibitor|PI3K inhibitor | NU-7026 | 1.11955507 | 0.07115831 |
| PI3K inhibitor | TG100-115 | 1.08577313 | 0.51539111 |
| phosphoinositide dependent kinase inhibitor | KIN001-244 | 1.08422339 | 0.39899681 |
| farnesyltransferase inhibitor | tipifarnib-P2 | 1.07986686 | 0.59434491 |
|  |  | 1.07891653 | 0.54130639 |
| cyclooxygenase inhibitor | valdecoxib | 1.06912194 | 0.72926832 |
| hepatocyte growth factor receptor inhibitor|tyrosine kinase inhibitor | SU-11274 | 1.0592887 | 0.77051943 |
| calpain inhibitor | calpeptin | 1.03354484 | 0.7689418 |
| dopamine receptor antagonist|serotonin receptor antagonist | quetiapine | 1.01854187 | 0.91762955 |
| nucleoside reverse transcriptase inhibitor | zalcitabine | 1.01005088 | 0.81043915 |
| PI3K inhibitor | AS-604850 | 1.00926516 | 0.94312224 |
|  |  | 0.99207472 | 0.95545578 |
| serotonin receptor partial agonist | RS-56812 | 0.9914154 | 0.79583413 |
| src inhibitor | PP-1 | 0.98793731 | 0.96979528 |
|  |  | 0.98600855 | 0.85805542 |
| ephrin inhibitor | ALW-II-38-3 | 0.97344232 | 0.86528021 |
| acetylcholinesterase inhibitor | herniarin | 0.9563387 | 0.69522575 |
| dopamine receptor |  |  |  |

TABLE 11C-continued

| moa | pert_iname | avg_fc | pvalue_fc |
|---|---|---|---|
| antagonist\|serotonin receptor antagonist | clozapine | 0.9466189 | 0.54015202 |
| | | 0.94300019 | 0.54918996 |
| cyclooxygenase inhibitor | meloxicam | 0.94140559 | 0.73523383 |
| potassium channel blocker | E-4031 | 0.94109648 | 0.5025332 |
| dehydropeptidase inhibitor | cilastatin | 0.93712719 | 0.50908085 |
| MAP kinase inhibitor | FR-180204 | 0.91499016 | 0.66896245 |
| antihypertensive agent | aliskiren | 0.88528492 | 0.13659314 |
| p38 MAPK inhibitor | VX-702 | 0.8683097 | 0.45056948 |
| potassium channel blocker | linopirdine | 0.86287534 | 0.07291565 |
| adrenergic receptor antagonist\|serotonin receptor antagonist | carpindolol | 0.85483751 | 0.07955479 |
| calcium channel blocker | bepridil | 0.85445892 | 0.50041792 |
| phosphodiesterase inhibitor | T-0156 | 0.83784524 | 0.43354974 |
| serotonin receptor agonist | MK-212 | 0.80218908 | 0.45970382 |
| MEK inhibitor | PD-98059 | 0.79292953 | 0.34910221 |
| sodium/potassium/chloride transporter inhibitor | bendroflumethiazide | 0.79167177 | 0.29891918 |
| PI3K inhibitor | AS-605240 | 0.79075412 | 0.17814334 |
| sodium channel blocker | ranolazine | 0.76544356 | 0.15748844 |
| protein tyrosine kinase inhibitor | tyrphostin-AG-112 | 0.75944216 | 0.09151528 |
| acetylcholine receptor agonist | pilocarpine | 0.73789297 | 0.08551291 |
| AKT inhibitor | MK-2206 | 0.69718673 | 0.16777507 |
| serotonin receptor agonist | GR-46611 | 0.66093209 | 0.01348733 |
| coloring agent | erythrosine | 0.64902572 | 0.01655812 |
| MDM inhibitor | serdemetan | 0.63835589 | 0.09413608 |
| adenosine inhibitor | cladribine | 0.59937722 | 0.01922744 |
| HDAC inhibitor | JNJ-26854165 | 0.53282722 | 0.00040551 |
| CDK inhibitor\|PKC inhibitor | bisindolylmaleimide | 0.42648463 | 0.01118945 |

Figure 15A:
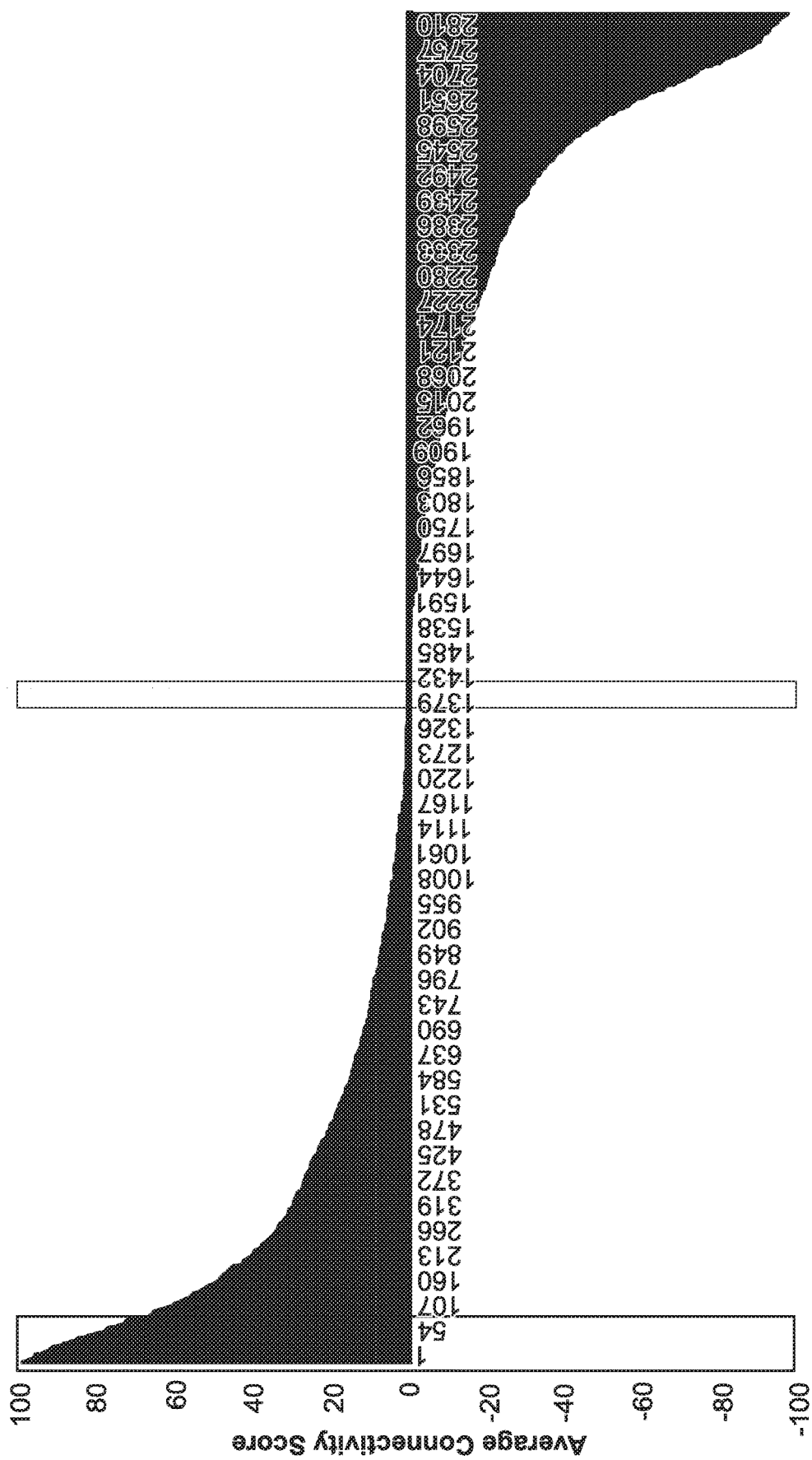
FIGS. 15A-15C provide a series of graphs and a heat map showing the effect of compound treatments on SLC16A11 expression.
Figure 15B:
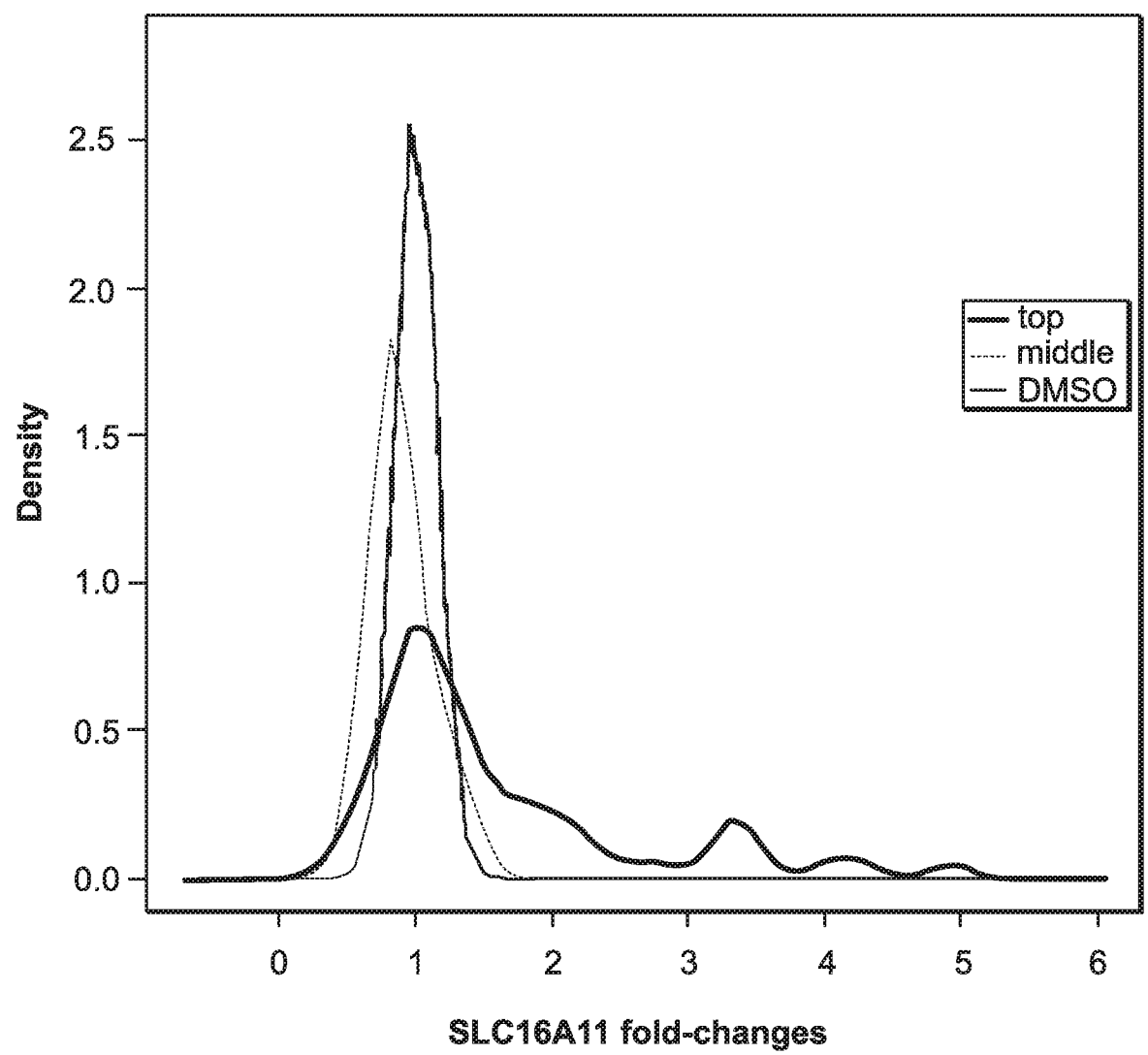
Figures 1, 15C:
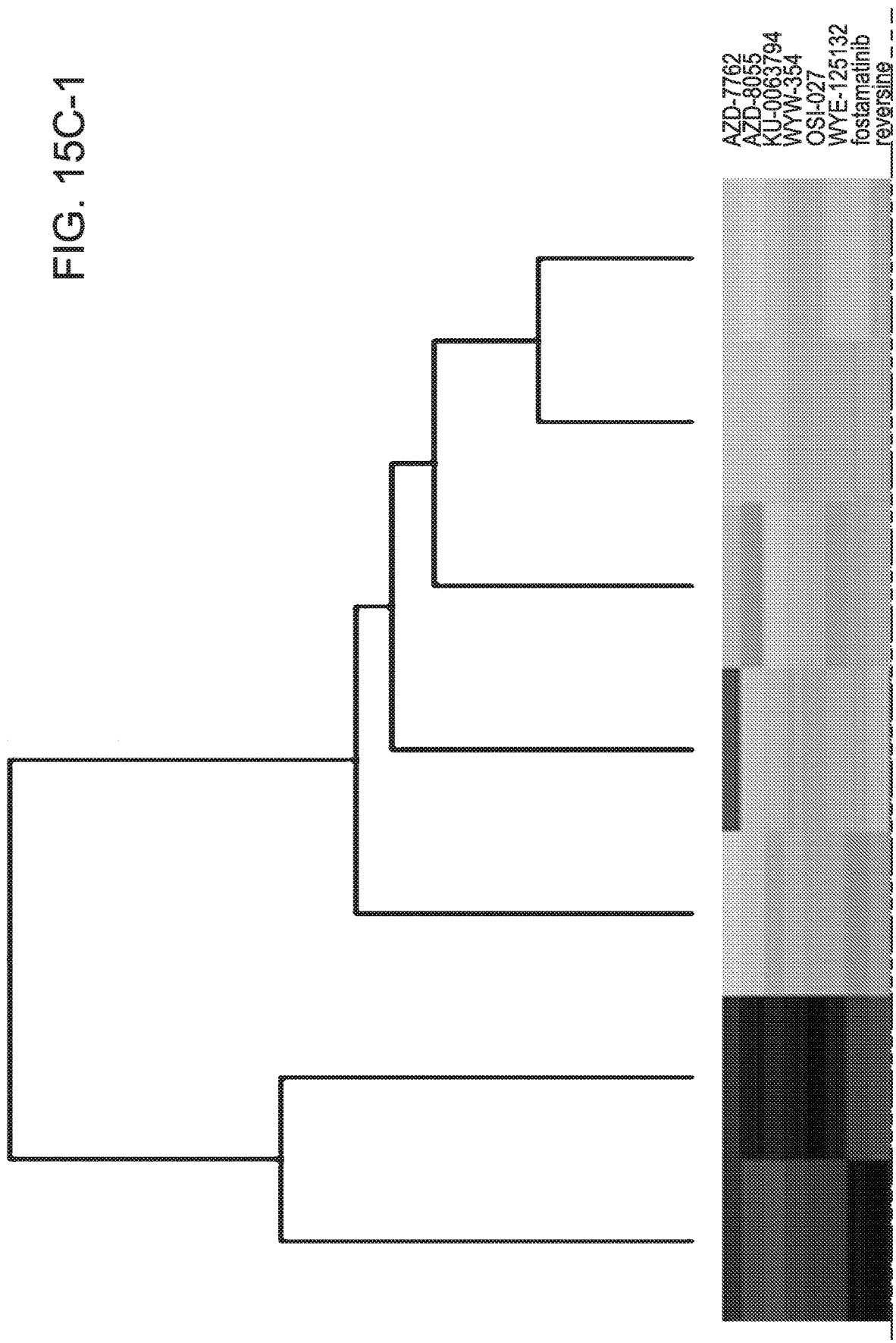
Figures 2, 15C:
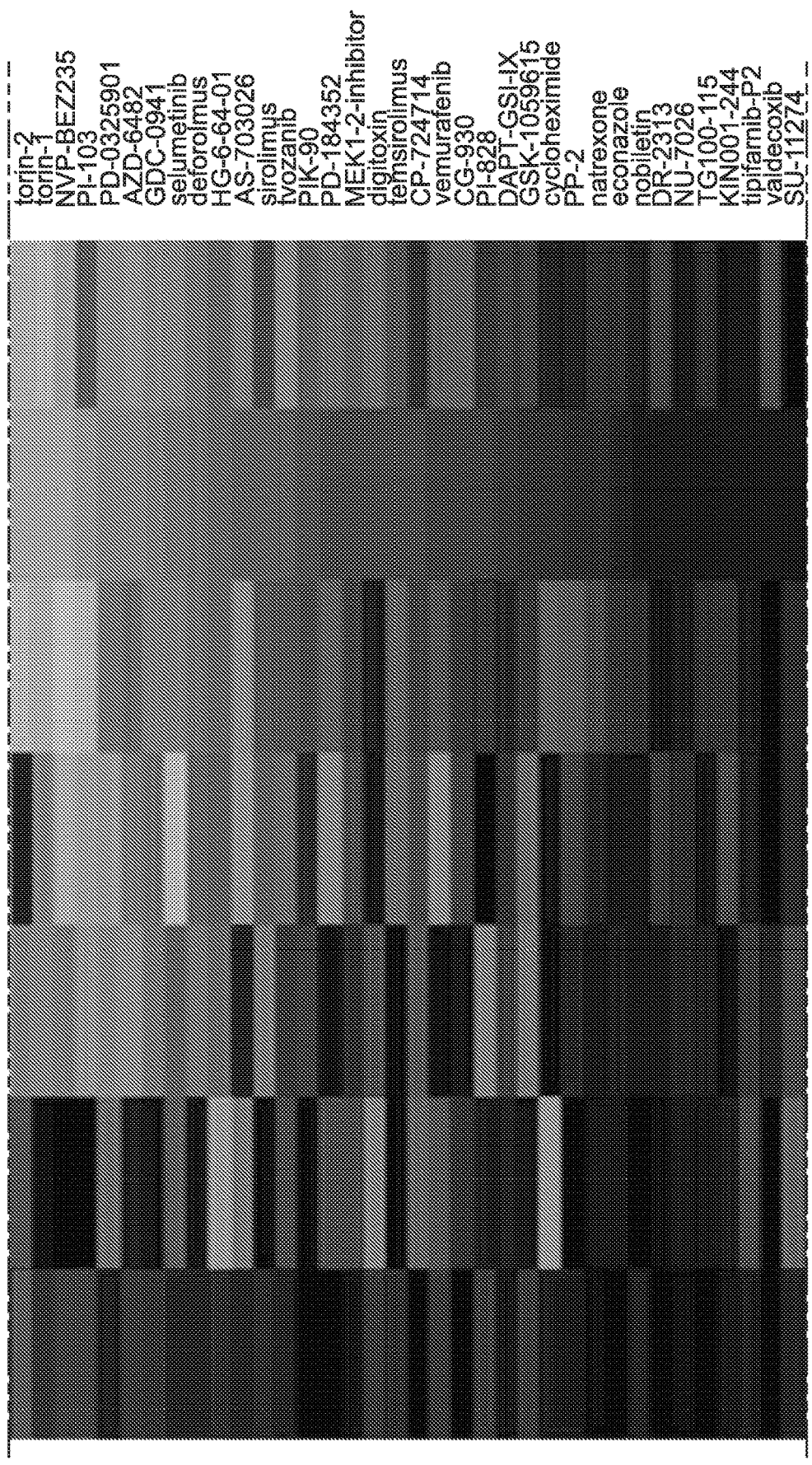
Figures 3, 15C:
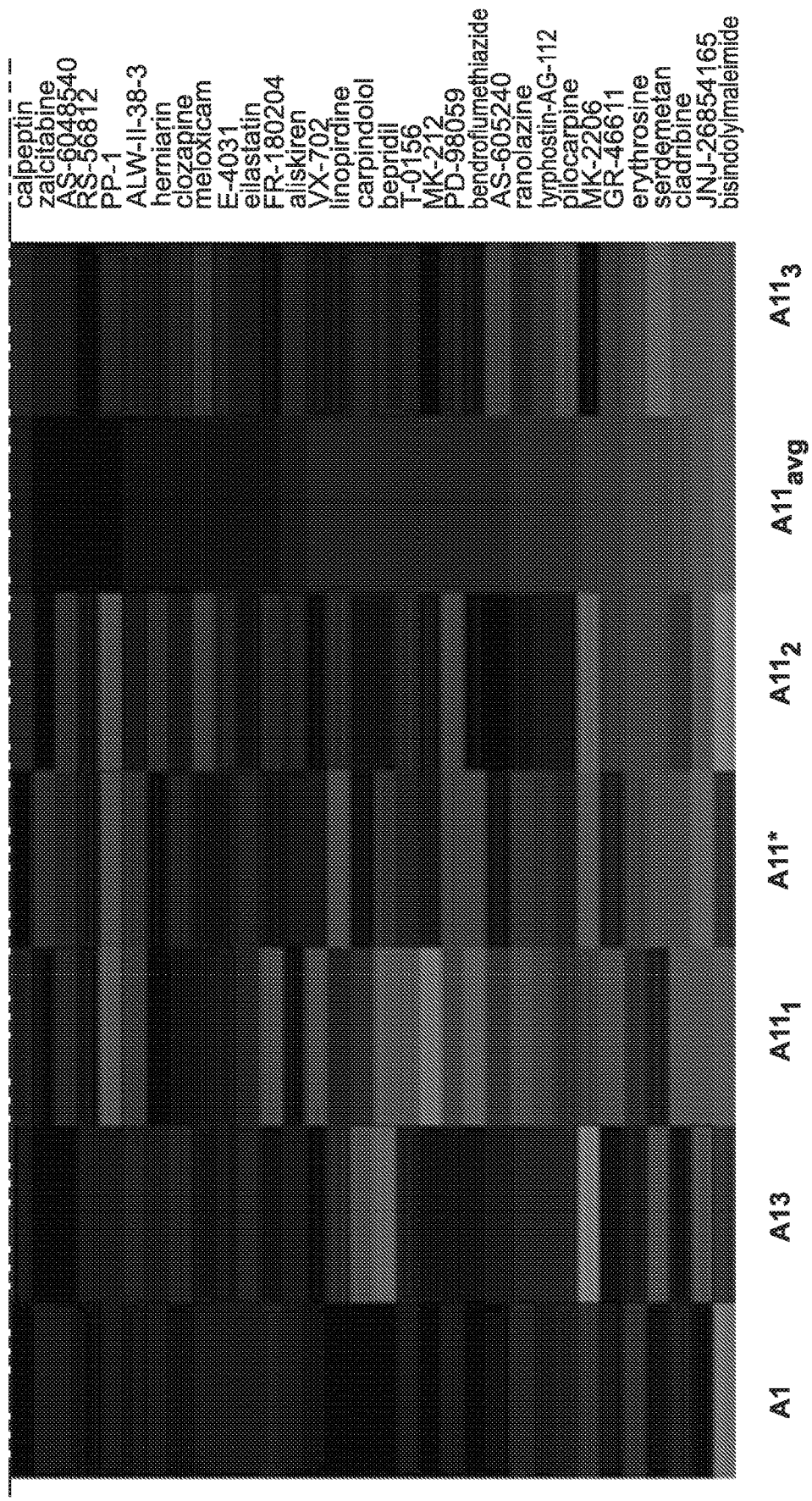

From the total list of compounds, 59 readily available compounds were selected from the 79 compounds with the largest connectivity scores to the query signature and 20 middle compounds with connectivity scores centered on 0 (FIG. 15A) and then treated SNU761 cells at the same doses and treatment times as were used in the LINCS dataset. It was expected that the top compounds would be enriched for compounds that increased SLC16A11 expression. It was expected that the middle compounds would not alter SLC16A11 expression, as their signatures did not resemble the query signature. The results were aligned with the expectations (FIG. 15B). Hierarchical clustering of the SLC16 expression profiles generated by the compound treatments are shown by the heat map in FIG. 15C.

The compounds AZD-8055 and KU-0063794 ranked second and third in their ability to increase SLC16A11 expression, each with about a 4-fold increase. AZD-7762, annotated as a Checkpoint Kinase (CHK) inhibitor, was ranked first and increased SLC16A11 expression by about 5-fold. In total, 13 compounds annotated as mTOR inhibitors were tested, and 9 of these resulted in at least 2-fold increases in SLC16A11 expression in compound treated cells compared to DMSO treated cells (Table 11C). Interestingly, compounds that increased SLC16A11 expression in SNU761 for the most part did not affect SLC16A13 expression while most decreased SLC16A1 expression. The most promising compound, AZD-8055, was selected to confirm that it was able to increase SLC16A11 expression in human hepatocytes (FIG. 16). In human hepatocytes, this compound resulted in decreased SLC16A13 and SLC16A1 expression.

The data presented herein indicates that treating cells, including cell lines, such as SNU761 and NCIH716, as well as primary human hepatocytes, with AZD-8055 results in increased SLC16A11 expression. mTOR exists as 2 protein complexes: mTORC1 and mTORC2. AZD-8055 is an ATP-competitive inhibitor of mTOR and inhibits both mTORC1 and mTORC2. At concentrations of 10 µM, the concentration used in the experiments described herein, AZD-8055 is reported to not show significant activity against a panel of 260 other kinases. Inhibiting mTORC1 with rapamycin has been shown to rapidly shift metabolism from TCA cycle and oxidative phosphorylation to reliance on glycolysis in human leukemia cells. This is reminiscent of experiments showing that over-expression of SLC16A11 was found to result in decreased TCA cycle metabolites. This data again indicates that SLC16A11 might be involved in mediating flux through central metabolite pathways such as glycolysis and TCA cycle.

SLC16A11 is expressed at low levels in a small number of human tissues indicating that SLC16A11 expression may be under tight regulation. One might speculate that some signal induces SLC16A11 expression. Mining the LINCS dataset for connections to an SLC16A11 gene expression signature is an unbiased approach to identify cellular conditions that result in increased SLC16A11 expression. Alternatively, more targeted experiments testing metabolically relevant metabolites and hormones such as pyruvate, lactate, oleic acid, insulin, and glucagon could be performed.

The data presented herein indicates that the T2D risk variants result in reduced SLC16A11 activity in liver. One might wonder how disruption of SLC16A11 leads to T2D risk when other family members, and in particular SLC16A13, which might share overlapping functions, are also expressed in liver. Without wishing to be bound to theory, one possibility is that these genes are regulated differently and SLC16A11 is particularly relevant under some yet to be determined physiological conditions. The data in presented herein indicates that at least some differences in gene regulation for SLC16A11, SLC16A13, and SLC16A1 exist, with mTOR inhibition increasing SLC16A11 expression but decreasing SLC16A13 and SLC16A1 expression in primary human hepatocytes.

Example 24

Development of Droplet Digital PCR (ddPCR) Based Screening for Modulators of SLC16A11 Expression Expression of SLC16A11 is low and does not reach the threshold of detection for standard PCR techniques. Therefore, the utilization of highly sensitive droplet digital PCR (ddPCR) is a more suitable strategy to detect SLC16A11 expression. However, manual assays that take advantage of the sensitivity of ddPCR are low-throughput, and can only test the effect of a low number of small molecules on SLC16A11 expression at a time. Although the entire process cannot be automated, automating RNA extraction improves efficiency. The improved assay will allow for a higher throughput screening process that can test the effects of thousands of small molecules on SLC16A11 expression.

As detailed herein above, SLC16A11 (A11) belongs to a family of monocarboxylate transporters. Expression of A11 was studied in SNU 761 cell lines. These liver cancer cells are ideal for studying SLC16A11 expression because A11 is expressed in higher quantity in liver cells, although expression of the gene in all tissues is extremely low. The 5 SNP risk haplotype causes lowered expression and interferes with protein-protein interactions between A11 and a cofactor protein, indicating loss of function. Therefore, increasing A11 expression in individuals with the risk haplotype is likely beneficial.

Figure 17A:
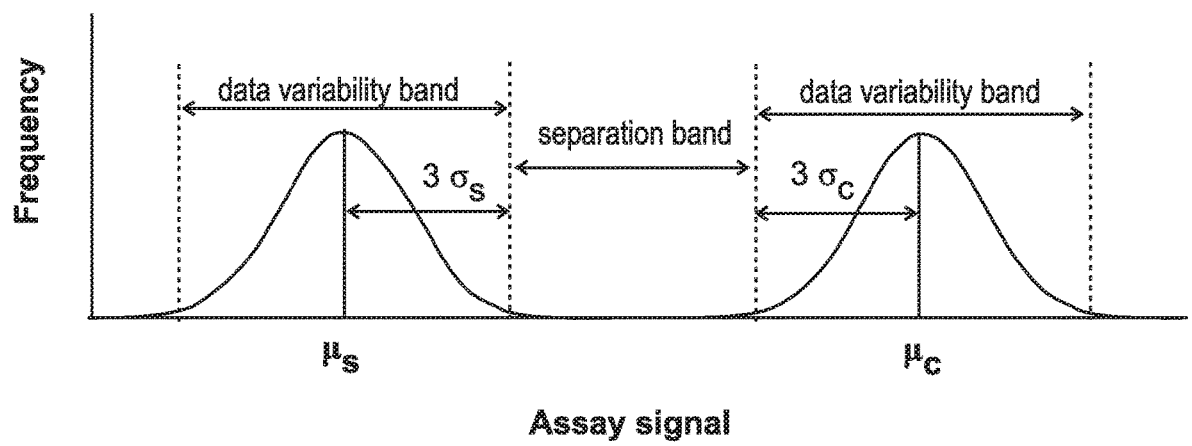
FIG. 17A provides a schematic showing a separation band, and data variability bands, with assay signal plotted along the x axis and frequency along the y axis.

In order find small molecules that can increase SLC16A11 (A11) expression a strong assay to screen for small molecules of interest is required. Strong assays have a high signal to background ratio, low variability, and are highly sensitive. A schematic graph showing the output of an assay is shown in FIG. 17A, including a separation band, data variability bands, with frequency (y axis) and assay signal (x axis). Strong assays have a large separation band, meaning they can differentiate between positive and negative controls.

The quality of an assay can be quantified by Z', a measure of how well the assay can differentiate between the positive and negative controls. Using the formula:

$$Z' = 1 - \frac{(3\sigma_{C+} + 3\sigma_{C-})}{|\mu_{C+} - \mu_{C-}|}$$

a cell based assay was developed, where the formula output can be categorized using the following ranges: Excellent: $0.5<Z'<1$; Good: $0.3<Z'<0.5$; Poor: $0<Z'<0.3$; and Unusable: $Z'<0$. Statistical parameters for use in evaluation and validation of high throughput screening assays are described by Zhang et al. (1999, J Biomol Screen., 4(2):67-73).

Methods and Assay Optimization

First the cells were treated with inhibitor compounds, their RNA was extracted, and that RNA was used as a template to create DNA. Then, the DNA was quantified using droplet digital PCR (ddPCR), analyzed and quantified using QuantaSoft™ (BioRad).

The compounds AZD 8055 and KU-0063794 were tested for their effect on SLC16A11 (A11) expression. The compounds are chemically similar and inhibit mTOR, a metabolic regulator (FIG. 13B).

Automation of this assay was developed after validating manual protocol for RNA extraction. A protocol for a Bravo liquid handling machine was created and implemented to make the RNA extraction faster and more efficient due to decreased human intervention.

Next the RT reaction was optimized. The One-step RT-ddPCR Advanced kit was highly efficient because it performed the RT reaction and included all the reagents needed for ddPCR in a single step. This saved time and decreased variability by eliminating pipetting steps.

Figure 17B:
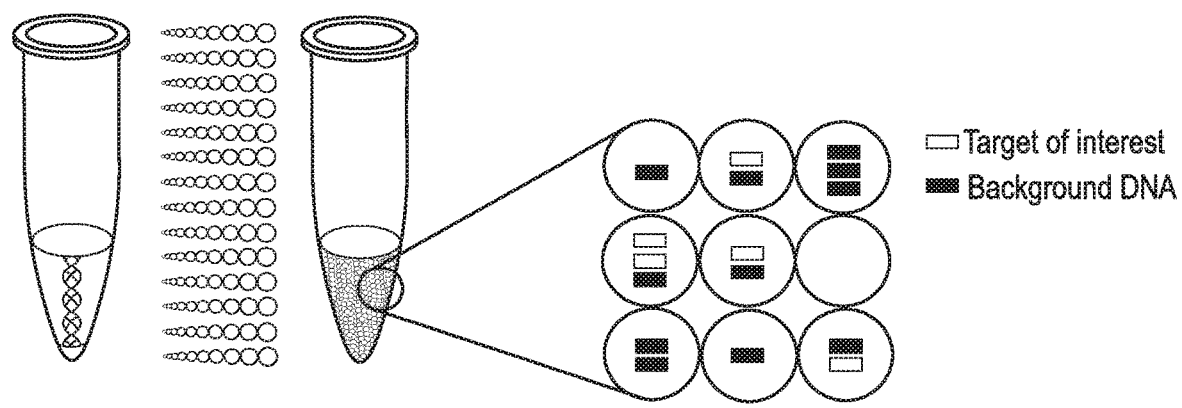
FIG. 17B provides a simplified schematic showing the partitioning of a PCR sample for droplet digital PCR (ddPCR).

Assay development for A11 is especially difficult because A11 is expressed at levels below the detection threshold for standard PCR techniques. Therefore, highly sensitive droplet digital PCR (ddPCR) was utilized, which uses microfluidics to create thousands of droplets from a single sample. FIG. 17B shows a schematic of partitioning of a PCR sample into thousands of samples in ddPCR. Each droplet has its own PCR reaction, and is scored positive if it has the gene of interest, or negative if it does not. This scoring gives an exact copy number of the gene of interest instead of a relative abundance.

Assay Results

Figure 17C:
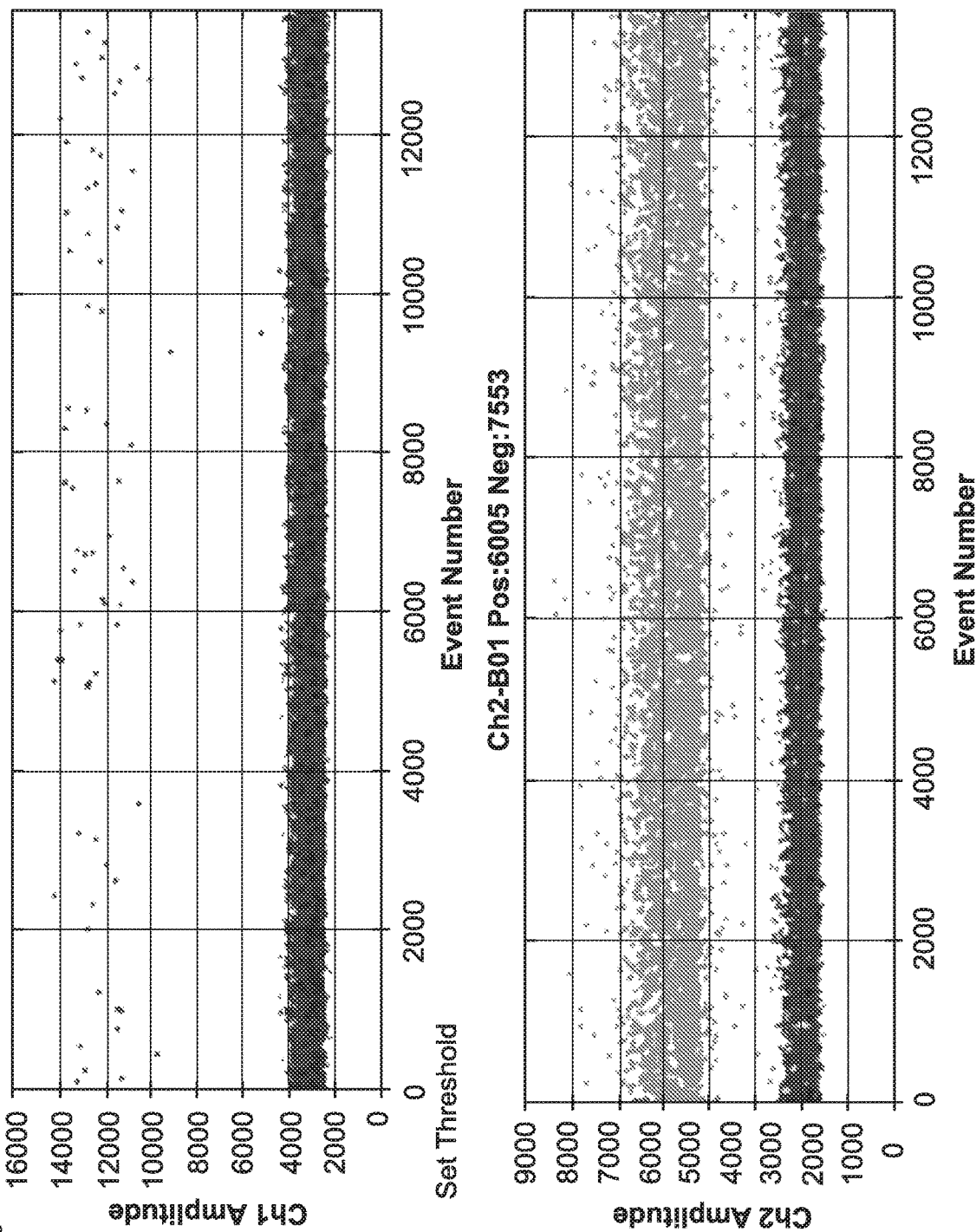
FIG. 17C provides a series of graphs showing QuantaSoft ddPCR analysis. Each point represents a single droplet. Points in light gray had the gene of interest and were scored as positive. SLC16A11 (A11) was scored in the top graph.
Figure 17D:
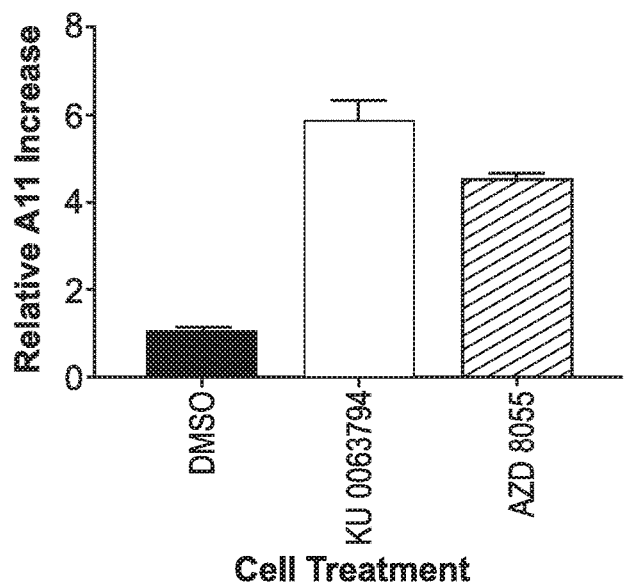
FIG. 17D provides a graph quantifying the relative increase in SLC16A11 (A11) gene expression in response to inhibitor treatment.

From the QuantaSoft scoring of each droplet, the means and standard deviations of SLC16A11 expression levels was determined in response to compound treatment. Using QuantaSoft ddPCR analysis, each point represents a single droplet. Points in light gray had the gene of interest and were scored as positive (FIG. 17C). SLC16A11 was scored in the graph. Since AZD 8055 and KU-0063794 increased A11 expression, they could be used to as positive controls and calculate Z's for the manual assay (FIG. 17D). The Z' for AZD was 0.65 and the Z' for KU was 0.69. Since both Z's were above 0.6, a strong assay could be developed for screening small molecules that increase A11. It is probable that the Z' score will improve once the assay is fully automated.

Example 25

Assessment of Metabolic Effectors on SLC16A11 and SLC16A13 Transcript Levels

To assess whether metabolic effectors regulated SLC16A11 and SLC16A13 transcript levels, endogenous transcripts in SNU761 cells (derived from a human hepatocellular carcinoma) were examined following exposure of the cells to different metabolic perturbations. SNU761 cells were cultured in the presence of various metabolic effectors for 24 hours after which time cell lysates were collected and the relative endogenous expression levels of SLC16A11 and SLC16A13 transcripts were assessed. The metabolic effectors included in the cell cultures included oleic acid (OA) at a low concentration (0.3 mM) or a high concentration (1.5 mM); insulin at a low concentration (100 nM) or a high concentration (500 nM) and glucagon at a low concentration (100 nM) and a high concentration (500 nM). Cells cultured in 2-FBS were used as a control. These metabolic effectors were found to alter the SLC16A11 and SLC16A13 transcripts at 17p13, with SLC16A13 transcript levels showing an increase at both the low and high concentrations of OA. (FIG. 22). Similarly, SNU761 cells were cultured in the presence or absence of low or high concentrations of pyruvate or lactate in the culture medium for 24 hours after which time cell lysates were analyzed. In the cultures, low (L) pyruvate concentration was 2 mM; high (H) pyruvate concentration was 10 mM, and low lactate concentration was 20 mM, while high lactate concentration was 100 mM. Pyruvate and lactate were found to alter transcripts at 17p13 at both low and high concentrations of pyruvate and lactate.

Figure 23:
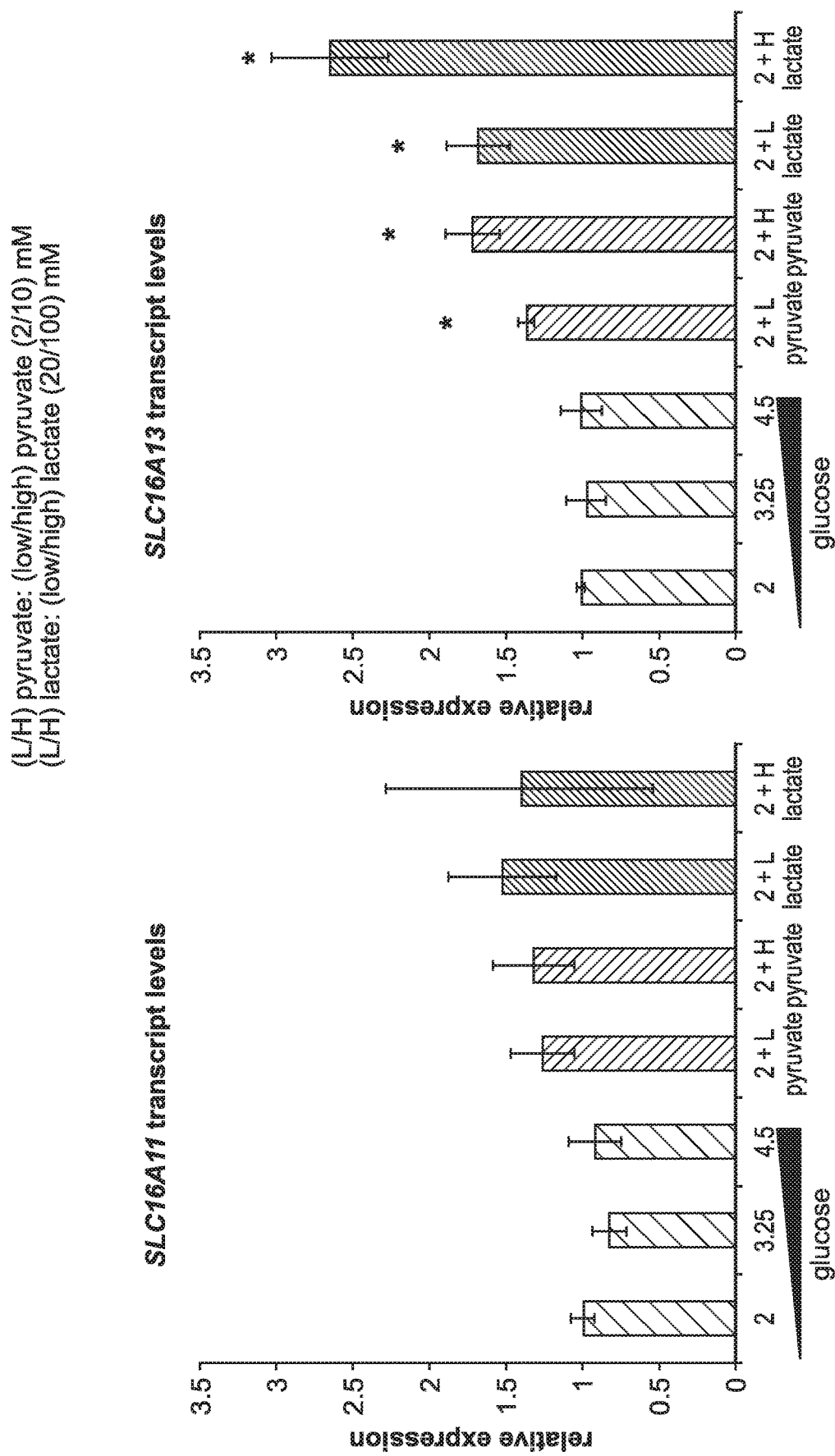
FIG. 23 provides bar graphs showing the effects of low and high concentrations of pyruvate or lactate on expression levels of SLC16A11 and SLC16A13 transcripts in SNU761 cells cultured for 24 hours in the presence of 2 mM pyruvate (low), 10 mM pyruvate (high), 20 mM lactate (low), or 100 mM lactate (high). Relative transcript levels of SLC16A11 and SLC16A13 are shown, compared with transcript levels in cell cultured in increasing concentrations of glucose. Altered levels of transcripts at 17p13 were seen at both low and high concentrations of pyruvate and lactate.

(FIG. 23). In particular, high concentrations of pyruvate and lactate increased the relative transcript levels of SLC16A13, as seen in FIG. 23.

The experiments and experimental results described in the Examples herein above were obtained using the methods and materials described below.

Integration of Data and Imputation

The cohorts, genotyping, and credible set analysis have been described previously (SIGMA T2D Consortium, 2014, Nature, 506:97-101; Estrada, K. et al., 2014, JAMA, 311 (22): 2305-2314). Briefly, for the credible set analysis, two datasets were built first (FIG. 1A). One dataset was comprised of 4,478 samples that had been genotyped by exome chip and OMNI 2.5. The other dataset comprised another subset of 3,732 samples genotyped by exome chip, OMNI2.5 and whole-exome sequencing. All the variants with minor allele frequency (MAF) higher than 0.001 for both datasets. Both datasets were phased with SHAPEIT26 (version 2.5). Next the 1000 G (phase 3, release June 2014) was imputed into both datasets separately. The whole-exome variants that were not imputable using 1000G phase 3 were also imputed into the samples that had not been ascertained by whole-exome sequencing. An impute 2 information score >0.8 was used as a post-imputation quality control. The association analysis was then performed separately in each cohort using SNP test adjusting for body mass index (BMI), age, sex and the first two principal components to adjust for population stratification. Both results were then meta-analyzed using Metal7.

The Genomics Platform at the Broad Institute (Cambridge, Mass.) received, QC'd and tracked DNA samples for Exome array processing. The samples were plated into 96-well plates that included a quality control sample for processing on the Illumina HumanExome BeadChip (Illumina, Inc. San Diego, Calif.) using manufacturer's protocols. The arrays were scanned using Illumina iScans. Genotypes were called using three different calling algorithms: Illumina GenCall, Z-call (Goldstein, J. I. et al., 2012, Bioinformatics, 28:2543-2545) and Birdsuite (http://www.broadinstitute.org/science/programs/medical-and-population-genetics/birdsuite/birdsuite-0).

Clusters were fit using the Birdseed algorithm to each genotyping plate independently. Genotypes with confidence below 99.9% were excluded from analysis (e.g., considered "missing" or "no-call" genotypes). Samples with low numbers of non-reference alleles (<~20,000, depending on the cohort), low call rate (<99.3%) or unusually high heterozygosity (>~0.05, depending on the cohort) were removed from subsequent analysis; thresholds were chosen based on visual inspection of the sample distributions. Variants with low call rate (<99.2%) or mean confidence for alternative genotype calls (<99%) were also excluded from subsequent analysis.

Integration of Data and Credible Set Analysis

For the credible set analysis, first two datasets were built (FIG. 1A). One dataset was comprised of 4,478 samples that had been genotyped by exome chip and OMNI 2.5 (Dataset 1) (SIGMA T2D Consortium et al., 2014, Nature, 506:97-101). The other dataset comprised another subset of 3,732 samples genotyped by exome chip, OMNI2.5, and whole-exome sequencing (Dataset 2) (Estrada, K. et al., 2014, JAMA, 311(22): 2305-2314). All the variants with MAF higher than 0.001 were retained for both datasets. Both datasets were phased with SHAPEIT2 (Delaneau, O. et al., 2013, Nat Meths, 10:5-6) (version 2.5) and then imputed the 1000 G (phase 3, release June 2014) into both datasets separately. Whole-exome variants that were not imputable using 1000G phase 3 were also imputed into samples that had not been ascertained by whole-exome sequencing (Dataset 1). Variants with impute 2 information score<0.8 were removed as a post-imputation quality control. The association analysis was then performed separately in each cohort using SNPtest adjusting for body mass index (BMI), age, sex and the first two principal components to adjust for population stratification. Both results were then meta-analyzed using Metal (Willer, C. J. et al., 2010, Bioinformatics, 26:2190-2191).

The credible set was constructed as previously described (Wakefield, J., 2007, Am J Hum Genet, 81:208-227). Briefly, for each association meta-analysis results, an approximate Bayes factor was computed for each variant with an r-squared greater than 0.1 with the top variant at the SLC16A11 locus using the formula:

$$abf = \frac{\sqrt{(1-r)}}{\exp\left(-r \times \frac{z^2}{2}\right)}$$

where $z = \text{beta}/se$ and $r = \frac{0.04}{se^2 + 0.04}$ under the assumption that the prior on beta is Gaussian with variance 0.04. The posterior probability for each variant was then computed by dividing the ABF by the total number of variants in the region. All variants were ranked by posterior probability and the minimal set of variants that resulted in a cumulative posterior probability of 0.99 was deemed the 99% credible set.

Association Analysis in MEDIA

The MEDIA dataset consists of meta-analysis results from 17 T2D studies (ARIC, CARDIA, CFS, CHS, FamHS, GeneSTAR, GENOA, HANDLS, Health ABC, HUFS, JHS, MESA, MESA Family, SIGNET-REGARDS, WFSM, FIND, and WHI) with up to 23,827 African American subjects (8,284 cases and 15,543 controls) (Ng, M.C. et al., 2014, PloS Genetics, 10:e1004517). The results of each study were imputed using the HapMap reference panel and meta-analyzed using inverse-variance fixed-effects meta-analysis using METAL.

Cell Culture

HEK293-T (human embryonic kidney) and HuH7 (Human Hepatoma) cell lines were cultured in Dulbecco's modified Eagle's medium (DMEM), supplemented with 10% Fetal Calf Serum (FCS), 100 ug/ml Streptomycin and 100U/ml Penicillin. Cells were grown in either 75 cm$^2$ or 175 cm$^2$ flasks, in a humidified $CO_2$ incubator, at 37° C.

Primary Human Hepatocytes

Primary human hepatocytes were purchased from Bioreclamation IVT. Lots heterozygous for the T2D risk haplotype include ACB, BEB, DSX, NQA, PAA, and QSK. Lots heterozygous for the African haplotype include AIH, FRY, GEB, JLP, KDD, NRE, ZBG, and ZXO. Genotyping at rs13342232 and rs75493593 from Bioreclamation IVT was used to infer heterozygosity for the T2D haplotype (heterozygous for the alternative allele at both SNPs) and the African haplotype (heterozygous for the alternative allele at rs13342232 and homozygous reference at rs75493593). Cells were thawed and immediately resuspended in CP medium (Bioreclamation IVT) with torpedo antibiotic (Bioreclamation IVT). Cell concentration and viability were assessed prior to use. For RNA isolation, cell pellets were frozen at −80° C. For ChIP-sequencing, 1×10$^6$ cells were cross-linked with 1% formaldehyde for 10 minutes at 37° C. prior to freezing in liquid nitrogen.

eQTL and Allele-Specific Expression Analyses

For the eQTL analyses, normalized gene expression counts were compared between individuals who carried 0, 1, or 2 copies of the T2D risk haplotype. Within each genotype, the mean count for each gene was calculated. Percent change and standard error mean were calculated for each pairwise comparison between genotypes. Statistical significance was assessed with a t-test. The analysis accounted for multiple hypothesis testing using a Bonferroni correction for the number of genes tested and the number of comparisons between genotypes.

Statistical significance was assessed by linear regression assuming an additive model for the SNP, and adjusting by age, sex, BMI, and T2D status. Multiple hypothesis testing was accounted for using a Bonferroni correction for the number of traits tested and the number of comparisons between genotypes.

For each heterozygote individual in the allele-specific expression analyses, the proportion of total SLC16A11 gene expression counts that originate from the T2D risk allele versus the reference allele was computed. The overall proportion and 95% confidence intervals from all the samples were calculated by meta-analyzing with inverse variance method after logit transformation using the 'meta' package (version 4.5-0). The statistical significance of the differences between the pooled proportion and the expected proportion under the null (0.5) was calculated by computing the Z-statistic from which the two-tailed p-value was derived.

Luciferase Reporter Assays and Analysis

Cells were plated into 96 well plates and after 24 hours were transfected with 150 ng of the appropriate firefly vector, 50 ng empty vector control pLX304, and 20 ng of the renilla vector pRL-CMV (Promega). After 48 hr, luminescence was detected using Dual-Glo® Luciferase Assay System (Promega) and a Synergy H4 microplate reader (BioTek). For each well, firefly luminescence was normalized by renilla luminescence. To combine data across experiments, the average value for a given construct in a given experiment was used and statistical significance was assessed using a t-test.

RNA-Sequencing and Analysis 250 ng total RNA was depleted for ribosomal RNA using NEBNext® rRNA Depletion Kit (New England BioLabs) according to the manufacturer's protocol. First strand synthesis was completed with Maxima Reverse Transcriptase using random hexamers (Thermo Fisher Scientific). Second strand synthesis was done with NEBNext® mRNA Second Strand Synthesis Module (New England BioLabs). Illumina library construction was performed with Nextera® XT DNA Library Preparation Kit (Illumina) according to the manufacturer's protocol with the following modification: 0.4 ng of dsDNA was tagmented at 55° C. for 10 min. Library quality was assessed with BioAnalyzer (Agilent) and concentration was determined by Qubit fluorometric quantification (Thermo Fischer Scientific). Libraries were sequenced on an Illumina NextSeq500, 75 bp paired end. Fastqc (http://www.bioinformatics.babraham.ac.uk/projects/fastqc/) was used to assess read quality. STAR (Dobin et al., 2012) was used to map reads to an index generated from GRCh38 and Gencode v24. RNA-SeQC (DeLuca et al., 2012) was used to assess overall quality of the RNA-sequencing experiment. FeatureCounts (Liao et al, 2014, Mol Cell Biol, 31:2591-2604) was used to summarize reads across genes. Finally, DESeq2 (Love et al., 2014) was used to perform differential expression analysis and GSEA PreRanked (http://software.broadinstitute.org/gsea/index.jsp) was used for pathway analysis.

Visceral Adipose and Liver Tissue Collection

Visceral adipose and liver samples were collected from subjects undergoing bariatric surgery for severe obesity (BMI greater than 40 kg/m2, or greater than 35 kg/m2 with comorbid entities) or elective surgery in nonobese patients. Patients were selected for bariatric surgery after 6 months of rigorous lifestyle intervention. All individuals were Mexican Mestizos older than 18 years, carefully selected from the Integral Clinic of Surgery for Obesity and Metabolic Diseases or General Surgery Department at the Tláhuac Hospital in Mexico City. Tissue samples were obtained at the beginning of the surgery with harmonic scalpel in all cases as follow: visceral fat was obtained from the greater omentum at the middle of the greater curvature of the stomach. Liver biopsy was obtained at the distal end of the left hepatic lobe, just above the spleen. VAT and liver samples were frozen immediately after removal. The protocol for collecting VAT and liver samples was approved by the respective local research and ethics committees and all patients signed an informed consent.

For genotyping, genomic DNA was purified from whole blood samples using a modified salting-out precipitation method (Gentra Puregene, Qiagen Systems, Inc., Valencia, Calif., USA). Genotyping of the rs149483638 variant was performed using a custom TaqMan SNP Genotyping Assay (Applied Biosystems, Foster City, Calif., USA) and genotype of each sample was assigned automatically by SDS 2.3 software (Applied Biosystems, Foster City, Calif., USA). Genotyping of variants rs13342692 (Assay ID: C_25760519_10) and rs13342232 (Assay ID: C_31793671_10) were performed using TaqMan SNP Genotyping Assay (Applied Biosystems, Foster City, Calif., USA). Five previously genotyped samples were added in all plates as positive controls.

RNA Isolation

Total RNA was extracted from cells using the RNeasy Mini Kit (Qiagen) according to the manufactures protocol. RNA was isolated from frozen tissue samples by the Broad Institute's Genomics Platform using the miRNEasy Mini Kit from Qiagen.

siRNA Treatment

The following siRNAs were ordered from GE Dharmacon: Accell Human SLC16A11 siRNA SMARTpool (E-007404-00-0050) and Accell Non-targeting Pool (D-001910-10-50). siRNAs were reconstituted in PBS at 100 μM. Hepatocytes were plated into 24 well plates (Corning, 354408) at a density of 350,000 cells per well. After 4 hours, cells were washed once with HI media (Bioreclamation IVT) and siRNAs in HI media were added at a final concentration of 1 μM. After 24 hours, fresh CP media was added. Hepatocytes were grown for an additional 24 hours.

Droplet Digital PCR (ddPCR)

Total RNA was extracted using miRNeasy Mini Kits or RNeasy Mini Kits (Qiagen). RNA was DNase treated and converted into cDNA using the High-Capacity RNA-to-cDNA kit (Thermo Fisher Scientific). The following FAM-labeled, TaqMan Real-Time PCR assays (Thermo Fisher Scientific) were used to quantify gene expression: RNASEK (Hs00947009_m1 and Hs00947010_g1), BCL6B (Hs00394655_m1 and Hs00960914_g1), SLC16A13 (Hs00416832_m1 and Hs00914030_m1), SLC16A11 (Hs00601062_g1 and Hs01558330_g1), and CLEC10A (Hs00924864_g1 and Hs00197107_m1). VIC-labeled probes for TBP (Hs00427620_m1) and HPRT1 (Hs02800695_m1) were used for normalization. For allele-specific expression experiments, ddPCR assays (Fwd primer: 5'-AGGCAGCCAGCCC-3' (SEQ ID NO: 83); Rev primer: 5'-CCGAGGTAGAGATGCAG-3'(SEQ ID NO: 84) that distinguish the SLC16A11 reference (5'-TTTCGCCAGCGATCTG-3' (SEQ ID NO: 85); HEX-labeled probe) and T2D risk (5'-TCGCCAGCGGTCTG-3' (SEQ ID NO: 86); FAM-labeled probe) alleles at rs13342692 were custom designed by BioRad. Droplets were generated and analyzed using a QX200 Droplet Generator and Reader system (BioRad). Data were extracted using QuantaSoft (BioRad) and analyzed using Microsoft Excel.

ChIP-Sequencing and Analysis

Chromatin immunoprecipitation (ChIP)-sequencing for H3K27ac, H3K4me1, and H3K4me3 were performed on primary human hepatocytes (lots ACB, DSX, and QSK). Cross-linked pellets were lysed for 10 min on ice and chromatin fragmented using a Branson 250 digital sonifier. Each ChIP was performed as described previously (Bernstein et al., 2005, Cell, 120:169-181) with 1 mg of antibody, incubated overnight at 4° C. The following antibodies were used for ChIP: H3K27ac (Active Motif 39133), H3K4me1 (Cell Signaling Technologies 5326BF), and H3K4me3 (Cell Signaling Technologies 9751BF). A 50/50 slurry of protein A and protein G Dynabeads was used to capture enriched chromatin, which was then washed before reverse-crosslinking and proteinase K digestion at 65° C. AMPure XP beads were used to clean up and isolate ChIP DNA for subsequent library construction. Illumina sequencing library construction was performed as previously described (Mikkelsen et al., 2007, Nature, 448:553-560) and sequenced on an Illumina NextSeq500, 150 bp paired end.

Reads for immunoprecipitated H3K27ac, H3K4me1, H3K4me3, and input DNA were mapped to GRCh37 using Bowtie2 (Langmead and Salzberg, 2012, Nat Methods, 9:357-359). Peaks were called using HOMER (Heinz, S. et al., 2010, Mol. Cell., 38:576-589). Alignments were processed using WASP to adjust for reference-mapping bias (van de Geijn, B. et al., 2015, Nat Methods, 12:1061-1063). Evidence of the risk SNP was not detected at rs4630597, rs78972129, and rs76070643 in lot QSK and, consequently, removed these variants in this donor from further analyses. For each variant in each sample, a binomial test was performed in order to detect a skew in reference versus alternate (T2D risk) allele read counts. P-values across samples were combined using Fisher's method and accounted for multiple hypothesis testing using a Bonferroni correction for the number of variants and histone modifications tested. A histone modification at a variant was considered significantly skewed if it met the selected Bonferroni-corrected significance threshold and if the direction of the allelic imbalance was consistent across all donors.

ChIP-PCR and Analysis 5 ng of input and histone modification ChIP libraries were PCR amplified using PrimeSTAR HS DNA polymerase (Clontech) with primers spanning T2D risk credible set variants. A second PCR was performed to add indices and adapters compatible with Illumina next-generation sequencing (Nextera® XT Index Kit, Illumina). PCR amplicons were purified using a QIAquick PCR Purification Kit (Qiagen). Library concentration was determined by Qubit fluorometric quantification (Thermo Fischer Scientific). Libraries were then sequenced on an Illumina MiSeq, 155 bp single end.

At the genomic location corresponding to each T2D risk credible set variant, we computed the proportion of total read counts that originate from the T2D risk allele versus the reference allele. Allele-specific analyses were then performed as described in the eQTL section.

Preparation of Reagents for Microinjection in Mouse Zygotes

The following guides were used for generating the Slc16a11 and Slc16a13 knockout mice respectively: 5' AGTCCTAACCTCGCTTGGCT-3' (SEQ ID NO: 87) and 5'-GCAGCCCAATACTCAGGTAT-3' (SEQ ID NO: 88). DNA oligos encoding the guides placed downstream of a T7 promoter and upstream of the tracrRNA sequence were ordered from Integrated DNA Technologies. An oligo encoding the reverse complement of the T7 promoter was also synthesized. The long DNA oligos were annealed by placing at 95° C. for 5 min followed by slow cooling to 4° C. sgRNAs were in vitro transcribed using the Standard RNA Synthesis kit (New England BioLabs, E2040) following the manufacturer's guidelines. sgRNAs were then purified with the MEGAclear Kit Purification for Large Scale Transcription Reactions kit (Thermo Fischer Scientific, AM1908) according to the manufacturer's guidelines. We included the DNase treatment step. sgRNAs targeting Slc16a11 or Slc16a13 and Cas9 mRNA (in the form of hspCas9 SmartNuclease mRNA: CAS500A-1 from System Biosciences) were delivered to the Genome Modification Facility at Harvard University, where they were microinjected into C57BL/6J mouse zygotes.

Next-Generation Sequencing for Genotyping Mice and Data Analysis gDNA was extracted from tails using standard protocols. About 100 ng of gDNA was PCR amplified using PrimeSTAR HS DNA polymerase (Clontech) with primers spanning the targeted site. A second PCR was performed to add indices and adapters compatible with Illumina next-generation sequencing (Nextera® XT Index Kit, Illumina). PCR amplicons were purified using a QIAquick PCR Purification Kit (Qiagen). Library concentration was determined by Qubit fluorometric quantification (Thermo Fischer Scientific). Libraries were then sequenced on an Illumina MiSeq, 150 bp paired end. Given that a range of indels were expected in the mice born from the sgRNA and Cas9 microinjections, custom scripts were used to compare the sequences of mutant mice obtained from next-generation sequencing to the wild-type sequence. After colonies of mice were established, we used PCR based methods for genotyping.

RNA-Sequencing and Analysis 300 ng total RNA was depleted for ribosomal RNA using NEBNext® rRNA Depletion Kit (New England BioLabs) according to the manufacturer's protocol. First strand synthesis was completed with Maxima Reverse Transcriptase using random hexamers (Thermo Fisher Scientific). Second strand synthesis was done with NEBNext® mRNA Second Strand Synthesis Module (New England BioLabs). Illumina library construction was performed with Nextera® XT DNA Library Preparation Kit (Illumina) according to the manufacturer's protocol with the following modification: 0.4 ng of dsDNA was tagmented at 55° C. for 10 min. Library quality was assessed with BioAnalyzer (Agilent) and concentration was determined by Qubit fluorometric quantification (Thermo Fischer Scientific). Libraries were sequenced on an Illumina NextSeq 500, 75bp paired end. Fastqc (http://www.bioinformatics.babraham.ac.uk/projects/fastqc/) was used to assess read quality. STAR (Dobin et al., 2012) was used to map reads to an index generated from GRCm38 and Gencode vM9. RNA-SeQC (DeLuca et al., 2012) was used to assess overall quality of the RNA-sequencing experiment. FeatureCounts (Liao et al, 2014, Mol Cell Biol, 31:2591-2604) was used to summarize reads across genes. Finally, DESeq2 (Love et al., 2014) was used to perform differential expression analysis and GSEA PreRanked (http://software.broadinstitute.org/gsea/index.jsp) was used for pathway analysis.

CRISPR Transactivation Assay

Cell lines derived from HEK293-T cells were established by lentivirus infection resulting in stable integration of two components of the SAM system namely dCas9-VP64 and MS2-p65-HSF1. The resulting stable cell lines were then plated into 96 well plates and left overnight. The next day, cells were transfected with the guide RNAs (pHKO23), the final component of the SAM system. After an additional 48 hours, cells were harvested for gene expression analyses.

Plasmids

Plasmids encoding C-terminus, V5-tagged human wild-type (reference) and T2D risk SLC16A11 (SLC16A11$^{REF}$ and SLC16A11$^{T2D}$, respectively) were generated through synthesis of the open reading frames and subcloning into the pLX304 lentiviral vector (Genscript). K7A and P2D variants of SLC16A11 were introduced through site-directed mutagenesis (Agilent). The AltM variant of SLC16A11 was generated by PCR amplifying the shorter protein with attB1 and attB2 sites and then Gateway® recombination-mediated replacement of the ccdB gene in pLX304. SLC16A11 tagged with a N-terminus V5 epitope in pLX304 was generated using standard cloning techniques by inserting a V5 tag in front of the SLC16A11 initiator methionine and a stop codon before the V5 tag encoded by pLX304. SLC16A13 and BSG pLX304 expression plasmids were obtained from the Genetic Perturbation Platform at the Broad Institute. SLC16A1 pLX304 has been described previously (SIGMA T2D Consortium et al., 2014, Nature, 506:97-101). Empty vector control pLX304 was generated by Gateway® recombination-mediated replacement of the ccdB gene with a multiple cloning site. Plasmids encoding SLC16A11 tagged with a C-terminus HA epitope in pLX304 were generated using standard cloning techniques by inserting a HA tag and a stop codon before the V5 tag encoded by pLX304. Pyronic was a gift from Luis Felipe Barros (Addgene plasmid #51308) (San Martin, A. et al., 2014, PLoS One, 9:e85780). For CRISPR/Cas9-mediated genome editing, two guide sequences targeting human BSG (5'-TGGATGTTGGCCGTGCCCAT-3' (SEQ ID NO: 89) and 5'-CACCTGTCACTGACTGGGCC-3' (SEQ ID NO: 90) were cloned into LentiCRISPRv2 (a gift from Feng Zhang), as described (Sanjana, N. E. et al., 2014, Nat Methods, 11:783-784; Shalem, O. et al., 2014, Science, 343:84-87).

The pHKO23 plasmid (similar to pLentiCRISPRv2) was used for CRISPR/Cas9-mediated genome engineering in cells. Plasmids used for Cas9-transactivation are available from Addgene (https://www.addgene.org/browse/article/9503/) and include lenti-sgRNA(MS2)_Zeo, lenti dCAS-VP64, and lenti sgRNA(MS2)_Zeo.

Transient Transfections

Transient plasmid transfections were performed using lipofectamine 2000 (for HEK-293T cells) or Lipofectamine 3000 (for HuH7 cells), 48 hours prior to experiments, according to the guidelines provided by the manufacturer (Invitrogen or Thermo Fisher Scientific).

Lentivirus Generation

HEK293-T cells ($3 \times 10^6$) were platted into 10 cm plates and left overnight. The next day, cells were transfected with 12 ug pHKO23, 9 ug PAX2, and 3 ug VSVG using Transit according to the manufacturer's protocol. After 24 hours, medium was changed to media supplemented with 30% FBS in phenol free DMEM. After an additional 24 hours, lentivirus was harvested and cellular debris was removed using a 0.45 um filter and lentivirus was concentrated with a 100 KDa spin column according to the manufacturer's protocol.

Lentiviral Transduction

The Genetic Perturbation Platform at the Broad Institute generated lentivirus carrying SLC16A11 variants from pLX304 plasmids. To generate lentivirus for CRISPR/Cas9-mediated knockout, HEK293T cells were plated at a density of $3 \times 10^6$ cells per 10 cm plate. The next day, cells were transfected with 12 µg LentiCRISPRv2 plasmid carrying guides targeting human BSG, 9 µg PAX2, and 3 µg VSVG using TransIT (Mirus Bio). After 24 hr, medium was replaced with medium supplemented with 30% FBS in phenol-free DMEM. Twenty-four hours later, lentivirus was harvested and cellular debris removed by filtration through a 0.45 µm filter (Millipore). Lentivirus was concentrated with a 100 kDa spin column (Millipore).

For viral transduction, HEK293T, HuH7, or U2OS MEM-EA cells were spin-infected for 1 hr at 800 g at 31° C. with lentivirus and 8 µg/mL polybrene. Transduced cells were selected with either 3 µg/mL puromycin or 5 µg/mL of blasticidin (Thermo Fisher Scientific) for at least 7 days to establish stable cell lines.

Western Blot Analyses

Total protein concentration was measured using a BCA assay (Thermo Fisher Scientific) and equal quantities of protein were loaded on each gel. Lysates were prepared for western blotting by adding LDS sample buffer (Thermo Fisher Scientific) and either NuPage reducing reagent (Thermo Fisher Scientific) or 5% beta-mercaptoethanol. Samples were denatured by incubation at 42° C. for 10 min prior to analysis by SDS-PAGE and immunoblotting. Nitrocellulose membranes were blocked for 15 min with 5% milk in TBST and then incubated with primary antibody in blocking solution overnight at 4° C. Primary antibodies are detailed below. Higher antibody dilutions were used to detect immunoprecipitated proteins. Signals were detected with HRP-conjugated secondary antibodies, followed by chemiluminescent detection and autoradiography.

| Primary Antibodies used in Western Blot Analysis | | | |
|---|---|---|---|
| Protein | Dilution | Product Number | Company |
| V5 epitope | 1:1,000-1:15,000 | #13202 D3H8Q | Cell Signaling |
| HA epitope | 1:1,000-1:20,000 | #3724 C29F4 | Cell Signaling |
| BSG | 1:750-1:2,500 | #12314 | Cell Signaling |
| Na/KATPase | 1:20,000 | ab7671 | Abcam |
| Caleuxin | 1:10,000 | #2433 | Cell Signaling |
| Tubulin | 1:10,000 | ab21058 | Abcam |
| Vinculin | 1:10,000 | ab129002 | Abcam |

For membrane fractionation experiments, autoradiographs were scanned and densitometry quantified with ImageJ. Data was exported to Excel and SLC16A11-V5 levels in plasma membrane fractions were normalized to SLC16A11-V5 levels in the intracellular membrane fraction. Data from independent experiments was combined by dividing each normalized value in a given experiment by the average of the normalized values obtained for SLC16A11$^{REF}$ in that experiment. The relative amount of SLC16A11 at the plasma membrane was then calculated by averaging across these values and statistical significance was assessed with a t-test.

Analysis of SLC16 Protein Levels

For evaluation of SLC16 family member and SLC16A11 variant levels by western blot analysis, cell lysates were collected 48 hr after transfection. For protein stability experiments, HEK293T cells transfected with SLC16 family members were treated with 10 mg/mL cycloheximide (Cayman Chemical, 14126) for 10 min, 30 min, 1 hr, 2 hr, or 4 hr prior to collection of protein lysates. For evaluation of proteasomal degradation, HuH7 cells stably transduced with SLC16A11$^{REF}$-V5 and stably expressing SLC16A11 were treated with 5 µM MG132 (Cayman Chemical, 10012628) for 3 hours prior to collection of protein lysates. Protein lysates were collected in lysis buffer containing 1% NP40, 0.1% SDC, 150 mM NaCl, 50 mM TrisHCl pH 7.5, and 1 mM EDTA with protease inhibitors (Roche). Lysates were rotated for 30 min at 4° C. Supernatant was collected following centrifugation for 10 min at 14,000 g at 4° C.

Metabolomics and Data Analysis

HuH7 cells were plated in 6-well plates at a density of 400,000 per well. After 24 hours, cells were transfected with 1.5 µg of SLC16A11$^{REF}$ or controls. After 24 hours, media was changed. After an additional 48 hours, intracellular metabolites and media were harvested as previously described in SIGMA T2D Consortium et al., 2014, Nature, 506:97-101. Within each experiment, metabolite-profiling data was first total signal normalized. Individual metabolite values were flagged as outliers and removed if they were more than 3 standard deviations from the mean value within a sample type (where sample types were overexpression of SLC16A11$^{REF}$ or controls). Additionally all metabolite values within a sample type were removed if they had a coefficient of variation greater than 0.5. For each experiment, metabolite values were log transformed and normalized by the mean value for that metabolite within all sample types as previously described in SIGMA T2D Consortium et al., 2014, Id. This enabled aggregation of data across the 2 experiments. Fold-changes for each metabolite were calculated by dividing the median value of the SLC16A11$^{REF}$ treatments by the median value of the control treatments. Significance was computed using a Wilcoxon test between the two sample types.

For the primary human hepatocyte experiments, intracellular metabolites were harvested as previously described in SIGMA T2D Consortium et al., 2014, Id. For the overexpression experiments ion chromatography/mass spectrometry was used for metabolite profiling. For the knockdown experiments liquid chromatography/mass spectrometry was used.

The over-expression and knock-down experiments in primary human hepatocytes were analyzed as follows. Within each experiment, metabolite-profiling data was first total signal normalized. Individual metabolite values were flagged as outliers and removed if they were more than 2 standard deviations from the mean value within a sample type (where sample types are SLC16A11 siRNA or negative control siRNA treatment). For each experiment, metabolite values were normalized by the mean value for that metabolite within the negative control siRNA treatments to enable aggregation of data across all 3 experiments. The additional data in the combined dataset allowed for improved ability to detect outliers. Outlier values were identified and removed if they were more than 2 standard deviations from the mean value within a sample type. Fold-changes for each metabolite were calculated by dividing the median value of the SLC16A11 siRNA treatments by the median value of the negative control siRNA treatments. Significance was computed using a Wilcoxon test between the two sample types.

For mouse experiments, livers and plasma from 5 weeks old female Slc16a11 KO and their wild-type controls on a high fat diet for one week were collected after 2 hours fast. Liver samples were snap-frozen in liquid nitrogen at the time of collection and a liver powder as obtained using a Covaris LE220 according to the manufacture's guidelines. For metabolite profiling, about 80 mg of powder liver and 100 µL of plasma were used. Processed metabolomics data was analyzed by first normalizing by the average of the wild-type mice within a litter. Fold-changes were computed by dividing the mean of normalized values for knockout mice by the corresponding values for wild-type mice. Statistical significance was assessed using a t-test.

Metabolite enrichment analysis was computed as previously described in SIGMA T2D Consortium et al., 2014, Nature, 506:97-101.

Membrane Fractionation

Plasma membranes were separated from intracellular membranes using a Plasma Membrane Protein Extraction Kit (Abcam ab65400) with minor modifications to the manufacturer's protocol. Briefly, a 15 cm plate of HEK293T cells transfected with SLC16A11$^{REF}$ or SLC16A11$^{T2D}$ was harvested in 1 mL homogenization buffer prior to Dounce homogenization. The plasma membrane fraction was resuspended in 33 µL lysis buffer. The cytoplasmic and intracellular membrane fractions were diluted by adding 75 µL lysis buffer to 25 µL of each fraction prior to quantification. Equal quantities of protein from each fraction were used in western blot analyses.

PathHunter® MEM-EA Pharmacotrafficking Assay and Data Analysis

SLC16A11$^{REF}$ or SLC16A11$^{T2D}$ with a C-terminal V5 tag were cloned into ProLink2 (DiscoveRx) for the PathHunter® MEM-EA Pharmacotrafficking assays (DiscoveRx) using standard cloning techniques. U2OS MEM-EA cells (DiscoverX) were plated into 96-well plates at a density of 8,000 per well. After 24 hours, cells were transfected with 200 ng of the appropriate SLC16A11 construct using Lipofectamine 2000. Medium was changed 24 hours after transfection. Luminescence was measured 24 hours later using the PathHunter® Detection kit (DiscoveRx) and an EnVision plate reader according to the manufacturer's protocol. Data were analyzed in Excel. Background from empty vector controls was subtracted from SLC16A11 signal. To combine data across different experiments, each data within an experiment was normalized to the average value of the variants in that experiment. Statistical significance was assessed by a t-test across the combined data.

Immunoprecipitations for Protein-Protein Interactions

HEK293T cells plated onto 15 cm plates were transfected with 40 µg plasmid encoding SLC16A11$^{REF}$ or SLC16A11$^{T2D}$ and/or BSG or empty vector control. After 48 hours, protein lysates were harvested in lysis buffer. Lysates were passed through a 20 G syringe and rotated for 30 min at 4° C., Supernatant was collected following a 10 min spin at 14,000 g at 4° C., and total protein concentration was measured using a BCA assay (Thermo Fisher Scientific).

For proteomics analysis, 20 µg total protein lysate was incubated with 100 mL of anti-V5 conjugated agarose beads (SIGMA, A7345) for 3 hr at 4° C. Beads were then washed once with lysis buffer and three times with wash buffer. After the last wash, residual wash buffer was removed, 10 µL fresh wash buffer was added, and beads were stored at −80° C. until analysis by the Proteomics Platform at the Broad Institute, as detailed in the "Proteomics Methods for SLC16A11 Protein Interaction Studies" below.

For co-immunoprecipitation analysis, 5-10 µg total protein lysates were incubated with 50 µL anti-V5 or anti-HA conjugated agarose beads (SIGMA, A7345 and A2095, respectively). Beads were washed three times with lysis buffer and once with wash buffer. Immunoprecipitated proteins were eluted off beads with 50 μL LDS sample buffer (Thermo Fisher Scientific) diluted in wash buffer and either NuPage reducing reagent (Thermo Fisher Scientific) or 5% beta-mercaptoethanol. Samples were incubated at 42° C. for 15 min and then 70° C. for 1 minute.

Live Cell Imaging

Cells were transferred onto glass cover slips in 60 mm tissue culture dishes 72 hr prior to the experiment. For pyruvate transport assays, HEK293T cells were co-transfected 24 hr after plating with 2 μg pyronic and 2 μg empty pLX304, SLC16A11$^{REF}$-pLX304 or SLC16A11$^{T2D}$-pLX304. Ten minutes prior to imaging, cells were equilibrated in physiological Ringer's solution (140 mM NaCl, 2 mM KCl, 1.5 mM Na2HPO4, 1 mM MgSO4, 2 mM CaCl2, and 10 mM D-glucose in 10 mM HEPES buffer; pH 7.4), following which cells were mounted onto a Ludin chamber (Life Imaging Services) for imaging. Pyruvate uptake was initiated by switching the buffer in the chamber to Ringer's solution containing 0.4 mM pyruvate at the indicated time point. The slopes immediately following addition and withdrawal of pyruvate indicate rates of pyruvate influx and efflux. Cytoplasmic pH changes, indicative of H$^+$ transport, were determined in cells loaded with 1 μM BCECF-AM (Rink, T. J. et al., 1982, J Cell Biol, 95:189-196), a pH sensitive dye. Proton uptake was initiated by adding 0.4 mM pyruvate. Rates of proton influx and efflux were calculated as the slopes immediately following addition and withdrawal of pyruvate, after correcting for baseline drift. Baseline drift due to fluorescence bleaching is calculated during the initial 50 seconds of each trace prior to addition of pyruvate. Linear regression of initial rates was calculated in Kaleidograph (Synergy Software) and normalized to empty vector controls.

Microscopy

The imaging system consisted of a Zeiss Cell Observer microscope (Zeiss), an X-Cite 120LED illumination system (Lumen Dynamics) and a Hamamatsu Orca-Flash4.0 digital CMOS camera (Hamamatsu).

Pyronic was excited using a 436/20 nm band-pass filter; emission was collected through a 540/40 band-pass filter nm with a 510 nm dichroic mirror for venus, and a 480/40 band-pass filter with a 455 nm dichroic mirror, for mTFP.

BCECF-AM was excited using a 436/20 nm band-pass filter for λ1, and a 495/10 nm band-pass filter for λ2; emission was collected through a 540/40 band-pass filter nm with a 510 nm dichroic mirror. Fluorescent imaging measurements were acquired (every 5 seconds) with the ZEN software (Zeiss) and analyzed using Microsoft excel (Microsoft), and Kaleidograph (Synergy Software).

Phenotype Microarrays and Data Analysis

HepG2 cells were plated into 10 cm plates at a density of 1.8×10$^6$ cells. After 24 hours, cells were transfected with 9 μg of SLC16A11$^{REF}$ or empty control vector. After 48 hours, cell viability was assessed and HepG2 cells were re-plated at a density of 10,000 cells per well into PM-M1 MicroPlate™ Carbon and Energy Sources (Biolog, 13101). Cells were plated in the minimal media MC-0 that was prepared according to the manufacturer's guideline with the modification that dialyzed FBS (Thermo Fischer Scientific) was used in place of FBS. After 24 hours, energy status was monitored using an OmniLog PM System.

Sequence Alignment and Three Dimensional Homology Modeling

Sequences of SLC16 family members (obtained from Uniprot) were aligned using the multiple sequence alignment program Clustal Omega (Sievers, F. et al., 2011, Mol Syst Biol, 7:539). A three-dimensional structural model of SLC16A11 was generated by homology modeling (von Grotthuss, M. et al., 2003, Proteins 53 Suppl 6:418-423). A template for the modeling was obtained using the GeneSilico Metaserver (Kurowski and Bujnicki, 2003, Nucl Acids Res, 31:3305-3307). The crystal structure of bacterial Glycerol-3-phosphate transporter, GlpT (1PW4) was ranked first by several different fold recognition methods, and was therefore chosen as a high confidence homologue. The SLC16A11 model was created using MODELLER (Sali, A. and Blundell, T. L., 1993, J Mol Biol, 234:779-815) based on the alignment provided by the profile-profile FFAS method (Rychlewski, L. et al., 2000, Protein Sci, 9:232-241).

Co-Immunoprecipitations

Protein lysate supernatant was harvested and total protein concentration was measured using BCA as described in the Western blot analysis section. About 20 mg total protein for the protein-protein interaction dataset and 5-10 mg total protein for addition IPs was added to anti-V5 or anti-HA conjugated to agarose beads (SIGMA). Protein lysates were rotated head-over-head for 3 hr at 4° C. Beads were then washed once with the lysis buffer (1% NP40, 0.1% SDC) and three times with a wash buffer (lysis buffer without any detergents). After the last wash, any residual wash buffer was removed with an insulin syringe, 10 μL of wash buffer was then added and beads were stored at −80° C. until proteomics analysis or Western blot analysis.

Proteomics Methods for SLC16A11 and T2D Risk (QNT) Protein Interaction Studies On-Bead Digest:

The beads from immunopurification were washed once with IP lysis buffer, then three times with PBS, the three different lysates of each replicate were resuspended in 90 uL digestion buffer (2M Urea, 50 mM Tris HCl), 2 ug of sequencing grade trypsin added, 1 hour shaking at 700 rpm. The supernatant was removed and placed in a fresh tube. The beads were then washed twice with 50 uL digestion buffer and combined with the supernatant. The combined supernatants were reduced (2 uL 500 mM DTT, 30 minutes, RT), alkylated (4 uL 500 mM IAA, 45 minutes, dark) and a longer overnight digestion performed: 2 ug (4 uL) trypsin, shake o/n, The samples were then quenched with 20 uL 10% FA and desalted on 10 mg SepPak columns.

iTRAQ Labeling of Peptides and Strong Cation Exchange (scx) Fractionation

Desalted peptides were labelled with iTRAQ reagents according to the manufacturer's instructions (AB Sciex, Foster City, Calif.). Peptides were dissolved in 30 μl of 0.5 M TEAB pH 8.5 solution and labeling reagent was added in 70 ul of ethanol. After 1 h incubation the reaction was stopped with 50 mM Tris/HCl pH 7.5. Differentially labelled peptides were mixed and subsequently desalted on 10 mg SepPak columns.

|  | iTRAQ labeling | | | |
| --- | --- | --- | --- | --- |
|  | 114 | 115 | 116 | 117 |
| Rep1 | WT | T2Drisk (QNT) | Empty vector Control1 | Empty vector Control 2 |
| Rep2 | WT | T2Drisk (QNT) | Empty vector Control1 | Empty vector Control 2 |

SCX fractionation of the differentially labelled and combined peptides was done as described in Rappsilber et al., (2007, Nat Protoc., 2(8):1896-1906), with 6 pH steps (buffers—all contain 25% acetonitrile) as below:

1: ammonium acetate 50 mM, pH 4.5,
2: ammonium acetate 50 mM, pH 5.5,
3: ammonium acetate 50 mM, pH 6.5,
4: ammonium bicarbonate 50 mM. pH 8,
5: ammonium hydroxide 0.1%, pH 9,
6: ammonium hydroxide 0.1%, pH 11.
Empore SCX disk used to make StageTips as described in the Rappsilber et al. publication, supra.

MS Analysis

Reconstituted peptides were separated on an online nano-flow EASY-nLC 1000 UHPLC system (Thermo Fisher Scientific) and analyzed on a benchtop Orbitrap Q Exactive Plus mass spectrometer (Thermo Fisher Scientific). The peptide samples were injected onto a capillary column (Picofrit with 10 μm tip opening/75 μm diameter, New Objective, PF360-75-10-N-5) packed in-house with 20 cm C18 silica material (1.9 μm ReproSil-Pur C18-AQ medium, Dr. Maisch GmbH, r119.aq). The UHPLC setup was connected with a custom-fit microadapting tee (360 μm, IDEX Health & Science, UH-753), and capillary columns were heated to 50° C. in column heater sleeves (Phoenix-ST) to reduce backpressure during UHPLC separation. Injected peptides were separated at a flow rate of 200 nL/min with a linear 80 min gradient from 100% solvent A (3% acetonitrile, 0.1% formic acid) to 30% solvent B (90% acetonitrile, 0.1% formic acid), followed by a linear 6 min gradient from 30% solvent B to 90% solvent B. Each sample was run for 120 min, including sample loading and column equilibration times. The Q Exactive instrument was operated in the data-dependent mode acquiring HCD MS/MS scans (R=17,500) after each MS1 scan (R=70,000) on the 12 top most abundant ions using an MS1 ion target of $3 \times 10^6$ ions and an MS2 target of $5 \times 10^4$ ions. The maximum ion time utilized for the MS/MS scans was 120 ms; the HCD-normalized collision energy was set to 27; the dynamic exclusion time was set to 20 s, and the peptide match and isotope exclusion functions were enabled.

Quantification and Identification of Peptides and Proteins

All mass spectra were processed using the Spectrum Mill software package v6.0 pre-release (Agilent Technologies) which includes modules developed by us for iTRAQ-based quantification. Precursor ion quantification was done using extracted ion chromatograms (XIC's) for each precursor ion. The peak area for the XIC of each precursor ion subjected to MS/MS was calculated automatically by the Spectrum Mill software in the intervening high-resolution MS1 scans of the LC-MS/MS runs using narrow windows around each individual member of the isotope cluster. Peak widths in both the time and m/z domains were dynamically determined based on MS scan resolution, precursor charge and m/z, subject to quality metrics on the relative distribution of the peaks in the isotope cluster vs theoretical. Similar MS/MS spectra acquired on the same precursor m/z in the same dissociation mode within +/-60 sec were merged. MS/MS spectra with precursor charge>7 and poor quality MS/MS spectra, which failed the quality filter by not having a sequence tag length>1 (i.e., minimum of 3 masses separated by the in-chain mass of an amino acid) were excluded from searching.

For peptide identification MS/MS spectra were searched against human Uniprot database to which a set of common laboratory contaminant proteins was appended as well as the sequence for V5-tagged SLC16A11 (also called SLC16A11$^{REF}$, WT, wild-type, throughout the proteomics datasets) and T2D risk (also called QNT throughout the proteomics datasets). Search parameters included: ESI-QEXACTIVE-HCD scoring parameters, trypsin enzyme specificity with a maximum of two missed cleavages, 40% minimum matched peak intensity, +/-20 ppm precursor mass tolerance, +/-20 ppm product mass tolerance, and carbamidomethylation of cysteines and iTRAQ labeling of lysines and peptide n-termini as fixed modifications. Allowed variable modifications were oxidation of methionine, N-terminal acetylation, Pyroglutamic acid (N-termQ), Deamidated (N), Pyro Carbamidomethyl Cys (N-termC), with a precursor MH+ shift range of −18 to 64 Da. Identities interpreted for individual spectra were automatically designated as valid by optimizing score and delta rank1-rank2 score thresholds separately for each precursor charge state in each LC-MS/MS while allowing a maximum target-decoy-based false-discovery rate (FDR) of 1.0% at the spectrum level.

In calculating scores at the protein level and reporting the identified proteins, redundancy is addressed in the following manner: the protein score is the sum of the scores of distinct peptides. A distinct peptide is the single highest scoring instance of a peptide detected through an MS/MS spectrum. MS/MS spectra for a particular peptide may have been recorded multiple times, (i.e. as different precursor charge states, isolated from adjacent SCX fractions, modified by oxidation of Met) but are still counted as a single distinct peptide. When a peptide sequence >8 residues long is contained in multiple protein entries in the sequence database, the proteins are grouped together and the highest scoring one and its accession number are reported. In some cases when the protein sequences are grouped in this manner there are distinct peptides which uniquely represent a lower scoring member of the group (isoforms or family members). Each of these instances spawns a subgroup and multiple subgroups are reported and counted toward the total number of proteins. iTRAQ ratios were obtained from the protein-comparisons export table in Spectrum Mill. To obtain iTRAQ protein ratios the median was calculated over all distinct peptides assigned to a protein subgroup in each replicate. To assign interacting proteins the Limma package in the R environment was used to calculate moderated t-test p, as described previously by Udeshi, N. D. et al., 2012, Mol. Cell Proteomics, 11:148-159) and added Blandt-Altman testing to filter out proteins for which the CI for reproducibility was below 95%.

BSG CRISPR/Cas9-Knockout Cells

BSG knockout HEK-293T cell lines were generated by transduction with lentivirus encoding spCas9 and guide RNAs targeting BSG. The following target sequences were cloned into the pHKO23 plasmid (F. Zhang) for generation of two, independent BSG knockout cell lines: TGGATGTTGGCCGTGCCCAT (SEQ ID NO: 91) and CACCTGTCACTGACTGGGCC (SEQ ID NO: 92).

Generation of Slc16a11 and Slc16a13 Knockout Mice with CRISPR/Cas9

CRISPR knockout mice were generated by co-injection of the necessary CRISPR/Cas9 mRNA components into zygotes. For Slc16a11, the sequence targeted in the mouse genome was: AGTCCTAACCTCGCTTGGCT (SEQ ID NO: 93). For Slc16a13, the sequence targeted in the genome was GCAGCCCAATACTCAGGTAT (SEQ ID NO: 94). DNA oligos were ordered from IDT encoding: 1) T7 promoter, spacer, and tracrRNA and 2) complementary sequence to the T7 promoter. DNA oligos were annealed and in vitro transcribed using the T7 High Yield RNA Synthesis Kit (New England BioLabs) according to the manufacture's protocol. The reaction was then DNAse I treated and purified with the MEGAclear Purification for Large Scale Transcription Reactions Kit (Ambion). Purified spacer-tracrRNA and hspCas9 SmartNuclease mRNA (System Biosciences) were injected into zygotes by the Gene Modification Facility at Harvard University.

For metabolite profiling and RNA-sequencing experiments, Slc16a11 wild-type and knockout mice were placed on a high fat diet (RDI, D12492i) for 1 week, and then euthanized for collection of liver and plasma. Liver was homogenized prior to analyses using a Covaris tissue Tube pulverizer.

Knockdown of SLC16A11 for Metabolite Profiling

The following siRNAs were ordered from GE Dharmacon: Accell Human SLC16A11 siRNA SMARTpool (E-007404-00-0050) and Accell Non-targeting Pool (D-001910-10-50). siRNAs were reconstituted in PBS at 100 µM. Hepatocytes were plated into collagen coated 24 well plates (Corning, 354408) at a density of 350,000 cells per well. After 4 hours, cells were washed once with HI media (Bioreclamation IVT) and siRNAs in HI media were added at a final concentration of 1 µM. After 24 hours, fresh CP medium was added. Hepatocytes were grown for an additional 24 hours. The samples consisted of 8 or 12 biological replicates of hepatocytes treated either with pooled siRNAs targeting SLC16A11 or negative controls across 2 or 3 replicate experiments. Lysates were collected for profiling 48 hours after siRNA knockdown. Due to the media change, differences in extracellular metabolites reflect changes accumulated during the 24 hour period prior to sample collection.

Primary human hepatocytes were removed from the incubator and immediately placed on ice. 500 µL of media was collected from the hepatocytes and put aside. Hepatocytes were then washed with 1 mL PBS. Lipids were extracted from hepatocytes by scraping in 250 µL of isopropanol (HPLC Grade; Honeywell) containing 1,2-didodecanoyl-sn-glycero-3-phosphocholine (Avanti Polar Lipids; Alabaster, Ala.). Polar metabolites were extracted by scraping in 250 µL of 80% methanol (VWR) containing 0.05 ng/µL inosine-15N4, 0.05 ng/µL thymine-d4, and 0.1 ng/µL glycocholate-d4 as internal standards (Cambridge Isotope Laboratories). Medium was centrifuged at 600 g at 4° C. for 5 min to remove any debris. Media metabolites for lipid analyses were precipitated by taking 10 µL and adding 190 µL isopropanol. Media metabolites for HLIC-neg were precipitated with 30 µL media+120 µL extraction solution (0.05 ng/µL Inosine-15N4, 0.05 ng/µL Thymine-d4, 0.1 ng/µL Glycocholate-d4 in 80% Methanol). Finally, media metabolites for HILIC-pos were precipitated with 10 µL media+90 µL extraction solution consisting of Acetonitrile: Methanol: Formic acid (75:25, 0.2 v:v:v) with a nominal concentration of 0.2 µg/mL valine-d8 (Sigma) and phenylalaine-d8 (Cambridge Isotopes Laboratories).

Metabolomics and Data Analysis

Analyses of lipids were conducted using an LC-MS system comprised of a Shimadzu Nexera X2 U-HPLC (Shimadzu Corp.; Marlborough, Mass.) coupled to an Exactive Plus orbitrap mass spectrometer (Thermo Fisher Scientific; Waltham, Mass.). Lipid extracts were injected onto an ACQUITY BEH C8 column (100×2.1 mm, 1.7 µm; Waters, Milford, Mass.). The column was eluted isocratically with 80% mobile phase A (95:5:0.1 vol/vol/vol 10 mM ammonium acetate/methanol/formic acid) for 1 minute followed by a linear gradient to 80% mobile-phase B (99.9:0.1 vol/vol methanol/formic acid) over 2 minutes, a linear gradient to 100% mobile phase B over 7 minutes, then 3 minutes at 100% mobile-phase B. MS data were acquired using electrospray ionization in the positive ion mode over 200-1100 µm/z and at 70,000 resolution. Other MS settings were: sheath gas 50, in source CID 5 eV, sweep gas 5, spray voltage 3 kV, capillary temperature 300° C., S-lens RF 60, heater temperature 300° C., microscans 1, automatic gain control target 1e6, and maximum ion time 100 ms. Raw data data were processed using TraceFinder 3.3 (Thermo Fisher Scientific; Waltham, Mass.) and Progenesis QI (Nonlinear Dynamics; Newcastle upon Tyne, UK) software for detection and integration of LC-MS peaks. Lipid identities were determined based on comparison to reference standards and reference plasma extracts and were denoted by total number of carbons in the lipid acyl chain(s) and total number of double bonds in the lipid acyl chain(s). Samples for negative and positive ion mode analyses of polar metabolites were achieved using the HILIC (hydrophilic interaction chromatography) method under basic conditions as described previously in SIGMA T2D Consortium et al., 2014, Nature, 506:97-101.

Within each experiment, metabolite-profiling data was first total signal normalized. Individual metabolite values were flagged as outliers and removed if they were more than 2 standard deviations from the mean value within a sample type (where sample types are SLC16A11 siRNA or negative control siRNA treatment). For each experiment, metabolite values were normalized by the mean value for that metabolite within the negative control siRNA treatments to enable aggregation of data across all 3 experiments. The additional data in the combined dataset allowed for improved ability to detect outliers. Outlier values were identified and removed if they were more than 2 standard deviations from the mean value within a sample type. Fold-changes for each metabolite were calculated by dividing the median value of the SLC16A11 siRNA treatments by the median value of the negative control siRNA treatments. Significance was computed using a Wilcoxon test between the two sample types.

To identify metabolite changes at the pathway level, a strategy that is commonly used for analysis of gene expression data was applied, namely, gene-set enrichment analysis (GSEA). Pathway enrichment was computed using the GSEA PreRanked tool, as implemented at http://software-.broadinstitute.org/gsea/index.jsp, using an unweighted enrichment score and 1,000 permutations. The log 2 transformed fold-changes between SLC16A11 knockdown and control were used as input, along with curated sets of KEGG pathways from the human reference set and 15 additional classes of metabolites covering lipid sub-types and carnitines. Only metabolite pathways and classes with at least 5 members measured in our dataset were considered.

Metabolic Profiling on HuH7 Cell Extracts

HuH7 cells were plated in 6 well plates and then transiently transfected with expression plasmids encoding C-terminus, V5-tagged SLC16A11 and control proteins (BFP, GFP, HcRed, and Luciferase). The day after transfection, the medium was removed and fresh medium was added to the cells. Two days later (after 3 days of gene expression), cellular metabolites were extracted in 80% methanol containing inosine-$^{15}$N4, thymine-d4 and glycocholate-d4 internal standards (Cambridge Isotope Laboratories; Andover, Mass.). (FIGS. 19-21).

HILIC-neg—Hydrophilic interaction liquid chromatography/negative ion mode MS detection to measure polar metabolites. HILIC analyses of water soluble metabolites in the negative ionization mode were conducted using an LC-MS system comprised of a Shimadzu Nexera X2 U-HPLC (Shimadzu Corp.; Marlborough, Mass.) coupled to a Q Exactive Plus hybrid quadrupole orbitrap mass spectrometer (Thermo Fisher Scientific; Waltham, Mass.). Cellular extracts were injected directly onto a 150×2.0 mm Luna NH2 column (Phenomenex; Torrance, Calif.) that was eluted at a flow rate of 400 μL/min with initial conditions of 10% mobile phase A (20 mM ammonium acetate and 20 mM ammonium hydroxide in water) and 90% mobile phase B (10 mM ammonium hydroxide in 75:25 v/v acetonitrile/ methanol) followed by a 10 min linear gradient to 100% mobile phase A. MS analyses were carried out using electrospray ionization in the negative ion mode using full scan analysis over 70-750 μm/z at 70,000 resolution and 3 Hz data acquisition rate. Other MS settings were: sheath gas 55, sweep gas 10, spray voltage −3 kV, capillary temperature 350° C., S-lens RF 50, heater temperature 325° C., microscans 1, automatic gain control target 1e6, and maximum ion time 250 ms. Metabolite identities were confirmed using authentic reference standards. Raw data were processed using TraceFinder software (version 3.3; Thermo Fisher Scientific; Waltham, Mass.) and Progenesis QI (Nonlinear Dynamics; Newcastle upon Tyne, UK).

Metabolic Profiling on Mouse Plasma and Liver

HILIC-neg—Hydrophilic interaction liquid chromatography/negative ion mode MS detection to measure polar metabolites. HILIC analyses of water soluble metabolites in the negative ionization mode were conducted using an LC-MS system comprised of a Shimadzu Nexera X2 U-HPLC (Shimadzu Corp.; Marlborough, Mass.) coupled to a Q Exactive Plus hybrid quadrupole orbitrap mass spectrometer (Thermo Fisher Scientific; Waltham, Mass.). Plasma or tissue homogenate (at a 4-to-1 uL water to mg tissue) (30 μL) was extracted using 120 μL of 80% methanol containing inosine-$^{15}$N4, thymine-d4 and glycocholate-d4 internal standards (Cambridge Isotope Laboratories; Andover, Mass.). The samples were centrifuged (10 min, 9,000×g, 4° C.) and supernatants were injected directly onto a 150×2.0 mm Luna NH2 column (Phenomenex; Torrance, Calif.) that was eluted at a flow rate of 400 μL/min with initial conditions of 10% mobile phase A (20 mM ammonium acetate and 20 mM ammonium hydroxide in water) and 90% mobile phase B (10 mM ammonium hydroxide in 75:25 v/v acetonitrile/methanol) followed by a 10 min linear gradient to 100% mobile phase A. MS analyses were carried out using electrospray ionization in the negative ion mode using full scan analysis over 70-750 μm/z at 70,000 resolution and 3 Hz data acquisition rate. Other MS settings were: sheath gas 55, sweep gas 10, spray voltage −3 kV, capillary temperature 350° C., S-lens RF 50, heater temperature 325° C., microscans 1, automatic gain control target 1e6, and maximum ion time 250 ms. Metabolite identities were confirmed using authentic reference standards. Raw data were processed using TraceFinder software (version 3.3; Thermo Fisher Scientific; Waltham, Mass.) and Progenesis QI (Nonlinear Dynamics; Newcastle upon Tyne, UK).

HILIC-pos—Hydrophilic interaction liquid chromatography/positive ion mode MS detection to measure polar metabolites. HILIC analyses of water soluble metabolites in the positive ionization mode were conducted using an LC-MS system comprised of a Shimadzu Nexera X2 U-HPLC (Shimadzu Corp.; Marlborough, Mass.) coupled to a Q Exactive hybrid quadrupole orbitrap mass spectrometer (Thermo Fisher Scientific; Waltham, Mass.). Plasma or tissue homogenate (at a 4-to-1 uL water to mg tissue) (10 μL) were prepared via protein precipitation with the addition of nine volumes of 74.9:24.9:0.2 v/v/v acetonitrile/methanol/formic acid containing stable isotope-labeled internal standards (valine-d8, Sigma-Aldrich; St. Louis, Mo.; and phenylalanine-d8, Cambridge Isotope Laboratories; Andover, Mass.). The samples were centrifuged (10 min, 9,000×g, 4° C.), and the supernatants were injected directly onto a 150×2 mm, 3 μm Atlantis HILIC column (Waters; Milford, Mass.). The column is eluted isocratically at a flow rate of 250 μL/min with 5% mobile phase A (10 mM ammonium formate and 0.1% formic acid in water) for 0.5 minute followed by a linear gradient to 40% mobile phase B (acetonitrile with 0.1% formic acid) over 10 minutes. MS analyses were carried out using electrospray ionization in the positive ion mode using full scan analysis over 70-800 μm/z at 70,000 resolution and 3 Hz data acquisition rate. Other MS settings were: sheath gas 40, sweep gas 2, spray voltage 3.5 kV, capillary temperature 350° C., S-lens RF 40, heater temperature 300° C., microscans 1, automatic gain control target 1e6, and maximum ion time 250 ms. Metabolite identities were confirmed using authentic reference standards. Raw data were processed using TraceFinder software (version 3.3; Thermo Fisher Scientific; Waltham, Mass.) and Progenesis QI (Nonlinear Dynamics; Newcastle upon Tyne, UK).

C8-pos—Reversed-phase C8 chromatography/positive ion mode MS detection to measure lipids. Analyses of polar and non-polar plasma lipids were conducted using an LC-MS system comprised of a Shimadzu Nexera X2 U-HPLC (Shimadzu Corp.; Marlborough, Mass.) coupled to an Exactive Plus orbitrap mass spectrometer (Thermo Fisher Scientific; Waltham, Mass.). Plasma or tissue homogenate (at a 4-to-1 uL water to mg tissue) (10 μL) were extracted for lipid analyses using 190 μL of isopropanol containing 1,2-didodecanoyl-sn-glycero-3-phosphocholine (Avanti Polar Lipids; Alabaster, Ala.). After centrifugation, supernatants were injected directly onto a 100×2.1 mm, 1.7 μm ACQUITY BEH C8 column (Waters; Milford, Mass.). The column is eluted isocratically with 80% mobile phase A (95:5:0.1 vol/vol/vol 10 mM ammonium acetate/methanol/formic acid) for 1 minute followed by a linear gradient to 80% mobile-phase B (99.9:0.1 vol/vol methanol/formic acid) over 2 minutes, a linear gradient to 100% mobile phase B over 7 minutes, then 3 minutes at 100% mobile-phase B. MS analyses were carried out using electrospray ionization in the positive ion mode using full scan analysis over 200-1100 μm/z at 70,000 resolution and 3 Hz data acquisition rate. Other MS settings were: sheath gas 50, in source CID 5 eV, sweep gas 5, spray voltage 3 kV, capillary temperature 300° C., S-lens RF 60, heater temperature 300° C., microscans 1, automatic gain control target 1e6, and maximum ion time 100 ms. Lipid identities were determined based on comparison to reference plasma extracts and were denoted by total number of carbons in the lipid acyl chain(s) and total number of double bonds in the lipid acyl chain(s). Raw data were processed using TraceFinder software (version 3.3; Thermo Fisher Scientific; Waltham, Mass.) and Progenesis QI (Nonlinear Dynamics; Newcastle upon Tyne, UK).

C18-neg—Reversed-phase C18 chromatography/negative ion mode MS detection to measure free fatty acids, bile acids, and metabolites of intermediate polarity. Analyses of free fatty acids and bile acids were conducted using an LC-MS system comprised of a Shimadzu Nexera X2 U-HPLC (Shimadzu Corp.; Marlborough, Mass.) coupled to a Q Exactive hybrid quadrupole orbitrap mass spectrometer (Thermo Fisher Scientific; Waltham, Mass.)). Plasma or tissue homogenate (at a 4-to-1 uL water to mg tissue) (30 μL) were extracted using 90 uL of methanol containing PGE$_2$-d4 (Cayman Chemical Co.; Ann Arbor, Mich.) and centrifuged (10 min, 9,000×g, 4° C.). The samples were injected onto a 150×2 mm ACQUITY BEH C18 column (Waters; Milford, Mass.). The column is eluted isocratically at a flow rate of 450 μL/min with 20% mobile phase A (0.01% formic acid in water) for 3 minutes followed by a linear gradient to 100% mobile phase B (acetonitrile with 0.01% acetic acid) over 12 minutes. MS analyses were carried out in the negative ion mode using electrospray ionization, full scan MS acquisition over 70-850 μm/z, and a resolution setting of 70,000. Metabolite identities were confirmed using authentic reference standards. Other MS settings were: sheath gas 45, sweep gas 5, spray voltage −3.5 kV, capillary temperature 320° C., S-lens RF 60, heater temperature 300° C., microscans 1, automatic gain control target 1e6, and maximum ion time 250 ms. Raw data were processed using TraceFinder software (version 3.3; Thermo Fisher Scientific; Waltham, Mass.) and Progenesis QI (Nonlinear Dynamics; Newcastle upon Tyne, UK).

Metabolite Profiling Analysis

Metabolite data from different experiments were independently total signal normalized; media data was not normalized. Outlier data were discarded within individual experiments based on the following criteria: 1) an individual metabolite value that was more than 3 standard deviations from the mean values for that metabolite within a sample type, 2) metabolite values within a sample type that had a coefficient of variation greater than 50%, and 3) any metabolite value associated with a sample that was more than 3 standard deviations from the mean correlation for all samples of a given sample type. Data were then log-transformed. Subtracting from each metabolite value the mean value of that metabolite across all samples in that experiment combined data from different experiments. Fold changes (FC) were then computed by comparing the median value of each metabolite in one sample type to the median value in another sample type and the Wilcox test was then applied to test whether the two distributions were equal.

Constructing the SLC16A11 Gene Expression Signature

Gene RPKM values from 119 human liver samples were downloaded from the Genotype-Tissue Expression project (GTEx) portal at http://www.gtexportal.org/home/datasets/. The file used was GTEx_Analysis_v6_RNA-seq_RNA-SeQCv1.1.8_gene_rpkm.gct. All genes were ranked by their Spearman correlation to SLC16A11 expression across the samples. We took the 50, 100, and 150 of the most positively and negatively correlated genes, that were measured in the LINCS dataset, and used them to generate to construct 3 SLC16A11 gene expression signatures.

Mining the LINCS Dataset

The SLC16A11 gene expression signatures were used to search the entire space of profiles in the LINCS dataset. The query was performed using the Clue App query found at https://clue.io/query. Connections made to compounds were extracted and further analyzed.

Cell Culture

SNU761 (human hepatocellular carcinoma) and NCIH716 (human cecum adenocarcinoma) were cultured in RPMI Medium 1640 supplemented with 10% Fetal Bovine Serum (FBS), 100 μg/ml Streptomycin and 100 U/ml Penicillin. Cells were grown in a humidified $CO_2$ incubator, at 37° C.

Primary human hepatocytes were purchased from Bioreclamation IVT. Hepatocyte lot used was BHL. Cells were thawed and immediately resuspended in CP media (Bioreclamation IVT) supplemented with torpedo antibiotic (Bioreclamation IVT). Cell concentration and viability were assessed prior to use. Cells were grown in a humidified $CO_2$ incubator, at 37° C.

Compound Treatments

KU-0063794 (Cayman Chemical, 13597), AZD-8055 (Cayman Chemical, 16978), and methotrexate (Cayman Chemical, 13960) stock solutions were prepared in DMSO. For the unbiased approach taken to investigate the compounds that connected to the SLC16A11 gene expression signature, compounds were obtained from compound management at the Broad Institute.

SNU761 and NCIH716 cells were plated into 96 well plates at a density of 20,000 cells per well. Hepatocytes were plated into collagen coated 96 well plates (Corning, 354408) at a density of 50,000 cells per well. After 24 hours, cells were treated with compounds at a final concentration of 10 μM or vehicle control for the appropriate amount of time.

RNA Isolation

At the time of collection, cells in 96 well plates were lysed by directly adding 50 μL of RLT buffer (Qiagen). 75 μL of AMPure XP beads, diluted by a factor of 5 in polyethylene glycol, were then added to bind nucleic acids. One wash with polyethylene glycol was then performed. DNase treatment (Qiagen) was carried out according to the manufacturer's protocol in a final volume of 50 μL. 100 μL of polyethylene glycol was added after the DNase treatment to crowd nucleic acids back onto the beads. Two washes with 80% ethanol were performed and residual ethanol was removed. RNA was then eluted in water.

Droplet Digital PCR (ddPCR)

RNA was DNase treated and converted into cDNA using the High-Capacity RNA-to-cDNA kit (Thermo Fisher Scientific). The following FAM-labeled TaqMan Real-Time PCR assays (Thermo Fisher Scientific) were used to quantify gene expression: SLC16A11 (Hs00601062_g1), SLC16A13 (Hs00416832_m1), SLC16A1 (Hs01560299_m1). The VIC-labeled TaqMan Real-Time assays TBP (Hs00427620_m1) or HPRT1 (Hs02800695_m1) were used for normalization. Droplets were generated and analyzed using a QX200 Droplet Generator and Reader system (BioRad). Data was extracted using QuantaSoft (BioRad) and analyzed using Microsoft Excel.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for increasing the expression of a SLC16A11 polypeptide or a polynucleotide encoding said polypeptide in a cell of a subject selected as a carrier of a SLC16A11 risk haplotype, the method comprising:
contacting a cell of a subject who is selected as a carrier of a SLC16A11 risk haplotype with a small molecule chemical compound that inhibits mechanistic target of rapamycin (mTOR), or a small molecule chemical compound that inhibits a checkpoint 1 or 2 kinase; wherein the small molecule mTOR inhibitor is selected from the group consisting of [5-[2-(2,6-dimethylmorpholin-4-yl)-4-morpholin-4-ylpyrido[2,3-d]pyrimidin-7-yl]-2-methoxyphenyl]methanol (KU-0063794), [5-[2,4-Bis((3S)-3-methylmorpholin-4-yl)pyrido[2,3-d]pyrimidin-7-yl]-2-methoxyphenyl]methanol (AZD-8055), 2-methyl-2-[4-(3-methyl-2-oxo-8-quinolin-3-ylimidazo[4,5-c]quinolin-1-yl)phenyl]propanenitrile (NVP-BEZ235), 3-(6-morpholin-4-yl-8-oxa-3,5,10-triazatricyclo[7.4.0.0$^{2,7}$]trideca-1(9),2(7)3,5,10,12-hexaen-4-yl)phenol (PI-103), methyl 4-[6-[4-(methoxycarbonylamino)phenyl]-4-morpholin-4-ylpyrazolo[3,4-d]pyrimidin-1-yl]piperidine-1-carboxylate (WYE-354), trans-4-[4-amino-5-(7-methoxy-1H-indol-2-yl)imidazo[5,1-f][1,2,4]triazin-7-yl]-cyclohexanecarboxylic acid (OSI-027), and deforolimus; and the small molecule checkpoint 1 or 2 kinase inhibitor is selected from the group consisting of 3-[(aminocarbonyl) amino]-5-(3-fluorophenyl)-N-(3S)-3-piperidinyl-2-thiophenecarboxamide (AZD-7762), 4-[(3S)-1-azabicyclo[2.2.2]oct-3-ylamino]-3-(1H-benzimidazol-2-yl)-6-chloro-2(1H)-quinolinone (CHIR-124), N-[5-Bromo-4-methyl-2-[(2S)-2-morpholinylmethoxy)phenyl]-N'-(5-methyl-2-pyrazinyl) urea (LY2603618), 6-bromo-3-(1-methyl-1H-pyrazol-4-yl)5-(3R)-3-piperidinyl-pyrazolo[1,5-a]pyrimidin-7-amine (MK-8776/SCH 900776), or (R)-α-Amino-N-[5,6-dihydro-2-(1-methyl-1H-pyrazol-4-yl]-6-oxo-1H-pyrrolo[4,3,2-ef][2,3]benzodiazepin-8-yl]-cyclohexaneacetamide (PF-477736): wherein the small molecule chemical compound increases SLC16A11 transcript levels by at least about 2-fold or 3-fold in the contacted cell; and wherein the SLC16A11 risk haplotype comprises a SLC16A11 polynucleotide variant encoding a polypeptide comprising an amino acid alteration selected from the group consisting of V113I, D127G, L187L, G340S, P443T, and a combination thereof, thereby increasing the expression of the SLC16A11 polypeptide or the polynucleotide encoding said polypeptide in the subject's cell.

2. A method for increasing the expression of a SLC16A11 polypeptide or a polynucleotide encoding said polypeptide, the method comprising:
contacting an adipocyte or hepatocyte of a subject who is selected as a carrier of a SLC16A11 risk haplotype with an agent selected from the group consisting of [5-[2-(2,6-dimethylmorpholin-4-yl)-4-morpholin-4-ylpyrido[2,3-d]pyrimidin-7-yl]-2-methoxyphenyl]methanol (KU-0063794), [5-[2,4-Bis((3S)-3-methylmorpholin-4-yl)pyrido[2,3-d]pyrimidin-7-yl]-2-methoxyphenyl]methanol (AZD-8055), 2-methyl-2-[4-(3-methyl-2-oxo-8-quinolin-3-ylimidazo[4,5-c]quinolin-1-yl)phenyl]propanenitrile (NVP-BEZ235), 3-(6-morpholin-4-yl-8-oxa-3,5,10-triazatricyclo[7.4.0.0$^{2,7}$]trideca-1(9),2(7),3,5,10,12-hexaen-4-yl)phenol (PI-103), methyl 4-[6-[4-(methoxycarbonylamino)phenyl]-4-morpholin-4-ylpyrazolo[3,4-d]pyrimidin-1-yl]piperidine-1-carboxylate (WYE-354), trans-4-[4-amino-5-(7-methoxy-1H-indol-2-yl)imidazo[5,1-f][1,2,4]triazin-7-yl]-cyclohexanecarboxylic acid (OSI-027), and deforolimus; wherein the agent increases SLC16A11 transcript levels by at least about 2-fold or 3-fold in the contacted cell; and wherein the SLC16A11 risk haplotype comprises a SLC16A11 polynucleotide variant encoding a polypeptide comprising an amino acid alteration selected from the group consisting of V113I, D127G, L187L, G340S, P443T, and a combination thereof, thereby increasing the expression of the SLC16A11 polypeptide or the polynucleotide encoding said polypeptide in the subject's cell.

3. The method of claim 1, wherein the small molecule chemical compound that inhibits mTOR is KU-0063794 or AZD-8055.

4. The method of claim 2, wherein the method inhibits mTOR in a cell.

5. The method of claim 1, wherein the cell is a hepatocyte, adipocyte, thyroid cell, or salivary gland cell.

6. The method of claim 1, wherein the cell is in vitro or in vivo.

7. The method of claim 6, wherein the cell is present in a diabetic subject.

8. The method of claim 7, wherein the small molecule chemical compound inhibits mTOR in the diabetic subject.

9. The method of claim 7, wherein the method treats or prevents type 2 diabetes in the subject.

10. The method of claim 1, wherein the small molecule chemical compound that inhibits a checkpoint 1 or 2 kinase is 3-[(aminocarbonyl) amino]-5-(3-fluorophenyl)-N-(3S)-3-piperidinyl-2-thiophenecarboxamide (AZD-7762).

11. The method of claim 1, wherein the small molecule chemical compound increases SLC16A11 transcript levels by at least about 4-fold or 5-fold in the contacted cell.

12. The method of claim 1, wherein the subject is identified as having a SCL16A11 protein comprising V113I, D127G, L187L, G340S, and P443T amino acid alterations.

13. A method for increasing the expression of a SLC16A11 polypeptide or a polynucleotide encoding said polypeptide in a cell having a SLC16A11 risk haplotype, the method comprising:
identifying a cell as having a SLC16A11 risk haplotype; and
contacting the cell identified as having a SLC16A11 risk haplotype with a small molecule chemical compound that inhibits mechanistic target of rapamycin (mTOR); or a small molecule chemical compound that inhibits a checkpoint 1 or 2 kinase; wherein the small molecule chemical compound mTOR inhibitor is selected from the group consisting of [5-[2-(2,6-dimethylmorpholin-4-yl)-4-morpholin-4-ylpyrido[2,3-d]pyrimidin-7-yl]-2-methoxyphenyl]methanol (KU-0063794), [5-[2,4-Bis((3S)-3-methylmorpholin-4-yl)pyrido[2,3-d]pyrimidin-7-yl]-2-methoxyphenyl]methanol (AZD-8055), 2-methyl-2-[4-(3-methyl-2-oxo-8-quinolin-3-ylimidazo[4,5-c]quinolin-1-yl)phenyl]propanenitrile (NVP-BEZ235), 3-(6-morpholin-4-yl-8-oxa-3,5,10-triazatricyclo[7.4.0.0$^{2,7}$]trideca-1(9),2(7)3,5,10,12-hexaen-4-yl)phenol (PI-103), methyl 4-[6-[4-(methoxycarbonylamino)phenyl]-4-morpholin-4-ylpyrazolo[3,4-d]pyrimidin-1-yl]piperidine-1-carboxylate (WYE-354), trans-4-[4-amino-5-(7-methoxy-1H-indol-2-yl)imidazo[5,1-f][1,2,4]triazin-7-yl]-cyclohexanecarboxylic acid (OSI-027), and deforolimus; and the small molecule checkpoint 1 or 2 kinase inhibitor is selected from the group consisting of 3-[(aminocarbonyl) amino]-5-(3-fluorophenyl)-N-(3S)-3-piperidinyl-2-thiophenecarboxamide (AZD-7762), 4-[(3S)-1-azabicyclo[2.2.2]oct-3-ylamino]-3-(1H-benzimidazol-2-yl)-6-chloro-2(1H)-quinolinone (CHIR-124), N-[5-Bromo-4-methyl-2-[(2S)-2-morpholinylmethoxy)phenyl]-N'-(5-methyl-2-pyrazinyl) urea (LY2603618), 6-bromo-3-(1-methyl-1H-pyrazol-4-yl)5-(3R)-3-piperidinyl-pyrazolo[1,5-a]pyrimidin-7-amine (MK-8776/SCH 900776), or (R)-α-Amino-N-[5,6-dihydro-2-(1-methyl-1H-pyrazol-4-yl]-6-oxo-1H-pyrrolo[4,3,2-ef][2,3]benzodiazepin-8-yl]-cyclohexaneacetamide (PF-477736); wherein the SLC16A11 risk haplotype comprises a SLC16A11 polynucleotide variant encoding a polypeptide comprising an amino acid alteration selected from the group consisting of V113I, D127G, L187L, G340S, P443T, and a combination thereof, thereby increasing the expression of the SLC16A11 polypeptide or the polynucleotide encoding said polypeptide in the cell.

14. The method of claim 13, further wherein the small molecule chemical compound that inhibits mTOR is selected from the group consisting of N-[4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl]-N'-methyl-urea (WYE-125132); 9-(6-Amino-3-pyridinyl)-1-[3-(trifluoromethyl)phenyl]-benzo[h]-1,6-naphthyridin-2(1H)-one (torin- 2), 1-(4-(4-propionylpiperazin-1-yl)-3-(trifluoromethyl) phenyl)-9-(quinolin-3-yl)benzo[h][1,6]naphthyridin-2(1H)-one (torin-1), and sirolimus.

15. The method of claim 13, wherein the small molecule chemical compound increases SLC16A11 transcript levels by at least about 2-fold or 3-fold in the contacted cell.

16. The method of claim 13, wherein the cell is identified as having a SCL16A11 protein comprising one or more amino acid alterations selected from the group consisting of V113I, D127G, L187L, G340S and P443T.

17. The method of claim 13, wherein the cell has a SCL16A11 risk haplotype SNP selected from the group consisting of rs77086571, rs74577409 and rs2292351.

18. The method of claim 13, wherein the cell is a cell of a subject having or at risk of developing type 2 diabetes (T2D).

19. The method of claim 13, wherein the cell is selected from the group consisting of a hepatocyte, an adipocyte, a thyroid cell and a salivary gland cell.

20. The method of claim 13, wherein the small molecule chemical compound increases SLC16A11 transcript levels by at least about 4-fold or 5-fold in the contacted cell.

21. The method of claim 2, wherein the cell is a hepatocyte, adipocyte, thyroid cell, or salivary gland cell.

22. The method of claim 2, wherein the cell is in vitro or in vivo.

23. The method of claim 2, wherein the cell is present in a diabetic subject and/or wherein the method treats or prevents type 2 diabetes in the subject.

24. The method of claim 2, wherein the small molecule chemical compound increases SLC16A11 transcript levels by at least about 4-fold or 5-fold in the contacted cell.

25. The method of claim 2, wherein the subject is identified as having a SCL16A11 protein comprising V113I, D127G, L187L, G340S, and P443T amino acid alterations.

26. The method of claim 1, further wherein the small molecule chemical compound that inhibits mTOR is selected from the group consisting of N-[4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl]-N'-methyl-urea (WYE-125132); 9-(6-Amino-3-pyridinyl)-1-[3-(trifluoromethyl)phenyl]-benzo[h]-1,6-naphthyridin-2(1H)-one (torin-2), 1-(4-(4-propionylpiperazin-1-yl)-3-(trifluoromethyl) phenyl)-9-(quinolin-3-yl)benzo[h][1,6]naphthyridin-2(1H)-one (torin-1), and sirolimus.

27. The method of claim 1, wherein the cell has a SCL16A11 risk haplotype SNP selected from the group consisting of rs77086571, rs74577409 and rs2292351.

28. The method of claim 1, further wherein the cell identified as having a SLC16A11 risk haplotype is contacted with a small molecule compound that is an inhibitor of mTOR selected from the group consisting of tipifarnib-P2, calpeptin, MEK1-2-inhibitor, Fostamatinib, PP-30, PD-0325901, PIK-90, BMS-536924, PI-828, PI-103, KIN001-244, serdemetan, PP-2, WYE-354, methotrexate, U0126, U-0126, NU-7026, Selumetinib, PAC-1, Apitolisib (GDC-0980, RG7422), BGT226 (NVP-BGT226), CC-223, Chrysophanic acid, CH5132799, CZ415, Everolimus (RAD001), ETP-46464, GDC-0349, Gedatolisib (PF-05212384, PKI-587), GSK1059615, INK 128 (MLN0128), Omipalisib (GSK2126458, GSK458), Palomid 529 (P529), PF-04691502, PI-103, PP121, Tacrolimus (FK506), Temsirolimus (CCI-779, NSC 683864), Torkinib (PP242), Vistusertib (AZD-2014), Voxtalisib (XL765, SAR245409), WAY-600, WYE-687, XL388, and Zotarolimus (ABT-578).

29. The method of claim 2, wherein the cell has a SCL16A11 risk haplotype SNP selected from the group consisting of rs77086571, rs74577409 and rs2292351.

30. The method of claim 13, further wherein the cell identified as having a SLC16A11 risk haplotype is contacted with a small molecule compound that is an inhibitor of mTOR selected from the group consisting of tipifarnib-P2, calpeptin, MEK1-2-inhibitor, Fostamatinib, PP-30, PD-0325901, PIK-90, BMS-536924, PI-828, PI-103, KIN001-244, serdemetan, PP-2, WYE-354, methotrexate, U0126, U-0126, NU-7026, Selumetinib, PAC-1, Apitolisib (GDC-0980, RG7422), BGT226 (NVP-BGT226), CC-223, Chrysophanic acid, CH5132799, CZ415, Everolimus (RAD001), ETP-46464, GDC-0349, Gedatolisib (PF-05212384, PKI-587), GSK1059615, INK 128 (MLN0128), Omipalisib (GSK2126458, GSK458), Palomid 529 (P529), PF-04691502, PI-103, PP121, Tacrolimus (FK506), Temsirolimus (CCI-779, NSC 683864), Torkinib (PP242), Vistusertib (AZD-2014), Voxtalisib (XL765, SAR245409), WAY-600, WYE-687, XL388, and Zotarolimus (ABT-578).

31. The method of claim 2, wherein the adipocyte or N-[4-[1-(1,4-dioxaspiro[4.5]dec-8-yl)-4-(8-oxa-3-azabicyclo[3.2.1]oct-3-yl)-1H-pyrazolo[3,4-d]pyrimidin-6-yl]phenyl]-N'-methyl- urea (WYE-125132); 9-(6-Amino-3-pyridinyl)-1-[3-(trifluoromethyl)phenyl]-benzo[h]-1,6-naphthyridin-2(1H)-one (torin-2), 1-(4-(4-propionylpiperazin-1-yl)-3-(trifluoromethyl)phenyl)-9-(quinolin-3-yl)benzo[h][1,6]naphthyridin-2(1H)-one (torin-1), and sirolimus.

32. The method of claim 2, wherein the adipocyte or hepatocyte of the subject is contacted with a small molecule chemical compound that inhibits a checkpoint 1 or 2 kinase and is selected from one or more of 3-[(aminocarbonyl) amino]-5-(3-fluorophenyl)-N-(3S)-3-piperidinyl-2-thiophenecarboxamide (AZD-7762), 4-[(3S)-1-azabicyclo [2.2.2]oct-3-ylamino]-3-(1H-benzimidazol-2-yl)-6-chloro-2 (1H)-quinolinone (CHIR-124), N-[5-Bromo-4-methyl-2-[(2S)-2-morpholinylmethoxy)phenyl]-N'-(5-methyl-2-pyrazinyl)urea (LY2603618), 6-bromo-3-(1-methyl-1H-pyrazol-4-yl)-5-(3R)-3-piperidinyl-pyrazolo[1,5-a] pyrimidin-7-amine (MK-8776/SCH 900776), or (R)-α-Amino-N-[5,6-dihydro-2-(1-methyl-1H-pyrazol-4-yl)-6-oxo-1H-pyrrolo[4,3,2-ef][2,3]benzodiazepin-8-yl]-cyclohexaneacetamide (PF-477736).

33. The method of claim 32, wherein the small molecule chemical compound that inhibits a checkpoint 1 or 2 kinase is 3-[(aminocarbonyl) amino]-5-(3-fluorophenyl)-N-(3S)-3-piperidinyl-2-thiophenecarboxamide (AZD-7762).

34. The method of claim 2, wherein the small molecule chemical compound that inhibits mTOR is KU-0063794 or AZD-8055.

35. The method of claim 13, wherein the small molecule chemical compound that inhibits mTOR is KU-0063794 or AZD-8055.

36. The method of claim 13, wherein the small molecule chemical compound that inhibits a checkpoint 1 or 2 kinase is 3-[(aminocarbonyl) amino]-5-(3-fluorophenyl)-N-(3S)-3-piperidinyl-2-thiophenecarboxamide (AZD-7762).

* * * * *